US009949979B2

United States Patent
Cooke et al.

(10) Patent No.: US 9,949,979 B2
(45) Date of Patent: Apr. 24, 2018

(54) USE OF INHIBITORS OF THE ACTIVITY OR FUNCTION OF PI3K

(71) Applicant: NOVARTIS AG, Basel (CH)

(72) Inventors: Nigel Graham Cooke, Oberwil (CH); Paulo Antonio Fernandes Gomes Dos Santos, Basel (CH); Pascal Furet, Thann (FR); Christina Hebach, Muenchenstein (CH); Klemens Hoegenauer, Oberwil (CH); Gregory Hollingworth, Kent (GB); Christoph Kalis, Gundelfingen (DE); Ian Lewis, Riehen (CH); Alexander Baxter Smith, Niffer (FR); Nicolas Soldermann, Village-Neuf (FR); Frederic Stauffer, Hesingue (FR); Ross Strang, Hagenthal le Bas (FR); Frank Stowasser, Murg (DE); Nicola Tuffilli, Moehlin (CH); Anette Von Matt, Biel-Benken (CH); Romain Wolf, Schlierbach (FR); Frederic Zecri, Brookline, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/365,512

(22) PCT Filed: Dec. 14, 2012

(86) PCT No.: PCT/IB2012/057332
§ 371 (c)(1),
(2) Date: Jun. 13, 2014

(87) PCT Pub. No.: WO2013/088404
PCT Pub. Date: Jun. 20, 2013

(65) Prior Publication Data
US 2015/0342951 A1   Dec. 3, 2015

Related U.S. Application Data

(60) Provisional application No. 61/576,194, filed on Dec. 15, 2011.

(51) Int. Cl.
*A61K 31/519* (2006.01)
*A61K 31/5377* (2006.01)
*A61K 31/541* (2006.01)
*A61K 31/517* (2006.01)
*A61K 31/551* (2006.01)
*C07D 401/14* (2006.01)
*C07D 413/14* (2006.01)
*C07D 401/04* (2006.01)
*C07D 403/04* (2006.01)
*C07D 239/74* (2006.01)
*C07D 487/08* (2006.01)

(52) U.S. Cl.
CPC .......... *A61K 31/519* (2013.01); *A61K 31/517* (2013.01); *A61K 31/5377* (2013.01); *A61K 31/541* (2013.01); *A61K 31/551* (2013.01); *C07D 239/74* (2013.01); *C07D 401/04* (2013.01); *C07D 401/14* (2013.01); *C07D 403/04* (2013.01); *C07D 413/14* (2013.01); *C07D 487/08* (2013.01)

(58) Field of Classification Search
None
See application file for complete search history.

(56) References Cited

U.S. PATENT DOCUMENTS

| 6,150,372 A | 11/2000 | Palanki et al. | |
|---|---|---|---|
| 8,653,092 B2 * | 2/2014 | Cooke | C07D 471/04 514/264.1 |
| 2009/0203678 A1 * | 8/2009 | Mazier | A61K 31/335 514/218 |

FOREIGN PATENT DOCUMENTS

| DE | 2057 225 | 6/1971 |
|---|---|---|
| JP | 2007-524673 A | 8/2005 |
| JP | 2008-546639 A | 12/2008 |
| WO | 1994/24132 A1 | 10/1994 |
| WO | 2002/20496 A1 | 3/2002 |
| WO | 2004/058756 A1 | 7/2004 |
| WO | 2005/086814 A2 | 9/2005 |
| WO | 2005/121142 A1 | 12/2005 |
| WO | 2006/062981 A2 | 6/2006 |
| WO | 2006/071095 A1 | 7/2006 |
| WO | 2006/119504 A2 | 11/2006 |
| WO | 2007/071055 A1 | 6/2007 |
| WO | 2008/009077 A2 | 1/2008 |
| WO | 2008/012326 A1 | 1/2008 |
| WO | 2008/015001 A1 | 2/2008 |
| WO | 2008/123963 A1 | 10/2008 |
| WO | 2008/130481 A1 | 10/2008 |
| WO | 2008/144463 A1 | 11/2008 |

(Continued)

OTHER PUBLICATIONS

Arevalo et al., Ocular Toxoplasmosis in the Devloping World, International Ophthalmology Clinics. 2010; 50(2): 57-69.
Bottieau et al., Therapy of vector-borne protozoan infections in nonendemic settings. Expert Reviews, Anti Infect. Ther. ; May 2011, 9(5): 583-608.
Dil et al, Role of phosphoinositide 3-kinase p110δ in TLR4- and TLR9-mediated B cell cytokine production and differentiation. Molecular Immunology. Apr. 2009; 46: 1970-1978.
Durand et al., Phosphoinositide 3-Kinase p110δ Regulates Natural Antibody Production, Marginal Zone and B-1 B Cell Function, and Autoantibody Responses. The Journal of Immunology. Nov. 2009; 183 (9): 5673-5684.

(Continued)

*Primary Examiner* — Jeffrey S Lundgren
*Assistant Examiner* — Stephanie K Springer
(74) *Attorney, Agent, or Firm* — David Kurlandsky

(57) ABSTRACT

The invention relates to new uses of PI3K inhibitors, wherein said inhibitors have an inhibitory action on the PI3K isoform delta for the treatment of immunopathology in a subject suffering from a disease or disorder selected from malaria, leishmaniasis, trypanosomiasis, toxoplasmosis and/or neurocysticercosis, via functional inhibition of TLR9 of the infected subject.

9 Claims, 5 Drawing Sheets

(56) References Cited

FOREIGN PATENT DOCUMENTS

| WO | 2008/150827 A1 | 12/2008 |
|---|---|---|
| WO | 2008/157191 A2 | 12/2008 |
| WO | 2009/019656 A1 | 2/2009 |
| WO | 2009/047255 A1 | 4/2009 |
| WO | 2009/058361 A1 | 5/2009 |
| WO | 2009/123967 A1 | 10/2009 |
| WO | 2010/036908 A1 | 4/2010 |
| WO | 2010/110747 A1 | 9/2010 |
| WO | 2010/120991 A1 | 10/2010 |
| WO | 2010/129816 A2 | 11/2010 |
| WO | 2011/001112 A1 | 1/2011 |
| WO | 2011/001113 A2 | 1/2011 |
| WO | 2011/055320 A1 | 5/2011 |
| WO | 2012/004299 A1 | 1/2012 |
| WO | 2013/057711 A1 | 4/2013 |
| WO | 2013/088404 A1 | 6/2013 |

OTHER PUBLICATIONS

Franklin et al, Therapeutic targeting of nucleic acid-sensing Toll-like receptors prevents experimental cerebral malaria. PNAS. Feb. 2011; 108(9): 3689-3694.

Gowda et al, The Nuclesome (Histone-DNA Complex) Is the TLR9-Specific Immunostimulatory Component of Plasmodium falciparum That Activates DCs. PLoS. One. Jun. 2011; 6,(6): 1-13.

Hawlisch et al, C5a Negatively Regulates Toll-like Receptor 4-Induced Immune Responses. Immunity. Apr. 2005; 22; 415-426.

Hawlisch et al, Complement and Toll-like receptors: Key regulators of adaptive immune responses. Molecular Immunology. Jan. 2006: 43; 13-21.

Hedayat et al, Targeting of Toll-like receptors: a decade of progress in combating infectious diseases. Lancet Infect. Diseases. Jun. 2011; 11: 702-712.

Higgins et al, Immunopathogenesis of falciparum malaria: implications for adjunctive therapy in the management of severe and cerebral malaria. Expert Reviews, Anti Infect. Ther. 2011; 9(9): 803-819.

Kawai et al, Toll-like Receptors and Their Crosstalk with Other Innate Receptors in Infection and Immunity. May 2011; 34: 637-650.

Marone R. et al, Targeting phosphoinositide 3-kinase—Moving towards therapy. Biochimica et Biophysica Acta. Jan. 2008; 1784: 159-185.

Mishra et al., Toll-Like Receptors in CNS Parasitic Infections, T. Kielian, Toll-like Receptors: Roles in Infection and Neuropathology. 2009. 83-104.

Peixoto-Rangel et al, Candidate gene analysis of ocular toxoplasmosis in Brazil, evidence for a role for toll-like receptor 9 (TLR9) Mem Inst Oswaldo. Dec. 2009; 104(8): 1187-1190.

Pellegrini et al, The role of Toll-like receptors and adaptive immunity in the development of protective or pathological immune response triggered by the Trypnosoma cruzi protozoan. Future Microbiol. Jun. 2011; 6(12): 1521-1533.

Schofield et al., Immunological Processes in Malaria Pathogenesis. Nature Reviews Immunol. Sep. 2005; 5:722-735.

Schofield, Intravascular infiltrates and organ-specific inflammation in malaria pathogenesis. Immunology and Cell Biology. Mar. 2007; 85: 130-137.

Shio et al, Innate inflammatory response to the malarial pigment hemozoin. Microbes and Infection. Jul. 2010; 12: 889-899.

Simone et al, TLRs innate immunereceptors and Plasmodium falciparum erythrocyte membrane protein 1 (PfEMP1), CIDR1α-driven human polyclonal B-cell activation. Acta Tropica. May 2011; 119: 144-150.

Vaid et al, PfPI3K, a phosphatidylinositol-3 kinase from Plasmodium falciparum, is exported to the host erythrocyte and is involved in hemoglobin trafficking. Blood. Jan. 2010; 115: 2500-2507.

Zauner et al., TLR9 triggering in Burkitt's lymphoma cell lines suppresses the EBV BZLF1 transcription via histone modification. Oncogene. May 2010; 29: 4588-4598.

Vaid, Ankush et al.: "PfPI3K, a phosphatidylinositol-3-kinase from Plasmodium falciparum, is exported to the host erythrocyte and is involved in hemoglobin trafficking", Blood, Mar. 25, 2010, vol. 115, No. 2, pp. 2500-2508.

Xu, H. et al.: "Anti-malarial agent artesunate inhibits TNF-α-induced production of proinflammatory cytokines via inhibition of Ne-κB and PI3 kinase/Akt signal pathway in human rheumatoid arthritis fibroblast-like synoviocytes", Rheumatology 2007, vol. 46, pp. 920-926.

Derbyshire, Emily R. et al.: "Chemical Interrogation of the Malaria Kinome", ChemBioChem, Sep. 2014, pp. 1-12.

* cited by examiner

USE OF INHIBITORS OF THE ACTIVITY OR FUNCTION OF PI3K

This application is a U.S. National Phase filing of International Application No. PCT/IB2012/057332 filed Dec. 14, 2012, which claims priority to U.S. Application No. 61/576,194 filed Dec. 15, 2011, the contents of which are incorporated herein by reference in their entirety.

FIELD OF THE INVENTION

The invention relates to new uses of inhibitors of the activity or function of the phosphoinositide 3' OH kinase family (hereinafter PI3K inhibitors), wherein said inhibitors have an inhibitory action on the PI3K isoform delta and/or pharmaceutically acceptable salts and/or solvates thereof. The invention relates further to new uses of tetrahydro-pyrido-pyrimidine derivatives as drug candidates in free form or in pharmaceutically acceptable salt form with valuable druglike properties, such as e.g. metabolic stability and suitable pharmacokinetics, form for the modulation, notably the inhibition of PI3K, wherein the activity or function of PI3K isoform delta is inhibited.

BACKGROUND OF THE INVENTION

Parasitic infections still represent one of the most important causes of morbidity and mortality worldwide. Among the parasites that cause human and animal pathology the phylum apicomplexa comprises a group of vector-borne parasites that is responsible for a wide variety of serious illnesses including but not limited to malaria, leishmaniasis and trypanosomiasis. Malaria alone infects 5-10% of humanity and causes around two milion deaths per year. [Schofield et al, "*Immunological processes in malaria pathogenesis*", *Nat Rev Imm* 2005], [Schofiled L, "*Intravascular infiltrates and organ-specific inflammation in malaria pathogenesis*], [Mishra et al, "*TLRs in CNS Parasitic infections*", *Curr Top Micro Imm* 2009], [Bottieau et al, "*Therapy of vector-borne protozoan infections in nonendemic settings*", *Expert Rev. Anti infect. Ther.*, 2011].

Toll-like receptors (TLRs) are germ-line encoded, phylogenetically ancient molecules that recognize evolutionary conserved structural relevant molecules (known as pathogen—associated molecular patterns (PAMPs)) within microbial pathogens. Various different cell types including cells of the immune system express TLRs and are thereby able to detect the presence of PAMPs. Sofar 10 functional TLR family members (TLR1-10) have been described in humans, all of which recognize specific PAMP molecules. Following recognition of these specific PAMPs TLRs induce and orchestrate the immuneresponse of the host to infections with bacteria, viruses, fungi and parasites. [Hedayat et al, "*Targeting of TLRs: a decade of progress in combating infectious disease*", review, *Lancet Infectious disease* 2011], [Kwai et al, "*TLRs and their crosstalk with other innate receptors in infection and immunity*", review, *Immunity* May-2011].

The immune system of the infected host responds to infection with the TLR induced production of pro-inflammatory cytokines mainly of the T-helper 1 type (Th1). While adequate amounts of these cytokines are beneficial and required to clear the infection an overproduction of these mediators is harmful to the host and associated with immune mediated pathology including neuropathology and tissue damage with severe and often fatal consequences. One prominent and highly relevant example of such immune mediated pathology is acute and cerebral malaria (CM) which causes severe clinical symptoms and is often fatal. [Schofield et al, "*Immunological processes in malaria pathogenesis*" *Nat Rev Imm* 2005], [Schofiled L, "*Intravascular infiltrates and organ-specific inflammation in malaria pathogenesis*], [Mishra et al, "*TLRs in CNS Parasitic infections*", *Curr Top Micro Imm* 2009], [Bottieau et al, "*Therapy of vector-borne protozoan infections in nonendemic settings*", *Expert Rev. Anti infect. Ther.*, 2011] [Hedayat et al, "*Targeting of TLRs: a decade of progress in combating infectious disease*", review, *Lancet Infectious disease* 2011]. Despite progress made in treatment and eradication of malaria, the mortality rate that is associated with severe malaria, including CM remains unacceptably high. Strategies directed solely at the eradication of the parasite in the host might therefore not be sufficient to prevent neurological complications and death in all cases of CM. Development of new innovative adjunct therapeutic strategies to efficiently reduce the CM-associated mortality and morbidity that is caused, in part, by host-mediated immunopathology remains therefore an urgent medical need [Higgins et al, "*Immunopathogenesis of falciparum malaria: implications for adjunctive therapy in the management of severe and cerebral malaria*", *Expert Rev. Anti Infect. Ther.* 2011].

Recently further evidence has been provided that TLR9 plays a key role in the recognition and response to parasites including but not limited to *Plasmodium, Leishmania, Trypanosoma* and *Toxoplasma* [Gowda et al, "*The Nucleosome is the TLR9-specific Immunostimulatory component of plasmodium falciparum that activates DCs*", *PLoS ONE*, June 2011], [Peixoto-Rangel et al, "*Candidate gene analysis of ocular toxoplasmosis in Brazil: evidence for a role for TLR9*", *Mem Inst Oswaldo Cruz* 2009], [Pellegrini et al, "*The role of TLRs and adoptive immunity in the development of protective or pathological immune response triggered by the Trypanosoma cruzi protozoan*", *Future Microbiol* 2011] and that interference with the activation of TLRs including TLR9 represents a promising strategy to prevent the deleterious inflammatory responses in severe and cerebral malaria [Franklin et al, "*Therapeutical targeting of nucleic acid-sensing TLRs prevents experimental cerebral malaria*", *PNAS* 2011]

Malaria is an infectious disease caused by four protozoan parasites: *Plasmodium falciparum; Plasmodium vivax; Plasmodium ovale*; and *Plasmodium malaria*. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas. There are four main forms of Leishmaniasis. Visceral leishmaniasis, also called kala-azar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal. The drugs currently available for treating Chagas disease are Nifurtimox and benznidazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

Toxoplasmosis is endemic through most of the world, which can infect a large proportion of the adult population. However, its prevalence differs in different countries. It is estimated to infect at least 10% of adults in northern temperate countries and more than half of adults in Mediterranean and tropical countries. *Toxoplasma gondii* is a ubiquitous, obligate intracellular protozoan and is considered to be the most common cause of infective retinitis in humans, which depends on a variety of factors, including climate, hygiene, and dietary habits. The course of disease in immunocompetent adults is usually asymptomatic and self-limiting. As soon as infection has occurred, the parasite forms latent cysts in the retina and in other organs of the body, which can reactivate years after the initial infection giving rise to acute retinochoroiditis and the formation of new retinochoroidal lesions. [Arevalo et al, "Ocular Toxoplasmosis in the developing world", Internat. Ophthal. Clin 2010]

Neurocysticercosis is the most common parasitic disease of the CNS (incidence ~2.5 million worldwide) caused by the larvae of *Taenia solium*. The disease has a long asymptomatic phase in humans characterized by the absence of a detectable inflammatory response surrounding the parasite. The overall immune response during the asymptomatic phase is of the Th2 phenotype. However, the destruction of larvae by therapeutic treatment or by normal parasite attrition causes a strong inflammatory response, often consisting of a chronic granulomatous reaction and manifestation of typical symptoms of the disease. The immune response in the CNS of symptomatic patients consists of an overt Th1 phenotype or a mixed Th1, Th2, and Th3 response, depending upon the absence or presence of granulomas. The hyperinflammatory response prevailing during the symptomatic phase in the CNS is responsible for the severe neuropathology and mortality associated with neurocysticercosis [Mishra et al, "TLRs in CNS Parasitic infections", Curr Top Micro Imm 2009].

In view of the foregoing there is a strong need for the development of novel effective treatment options for the management of parasitic diseases including the diseases mentioned above, addressing especially the associated immunopathology.

SUMMARY OF THE INVENTION

It has been found that PI3K inhibitors, wherein said inhibitors have an inhibitory action on the PI3K isoform delta, and/or pharmaceutically acceptable salts and/or solvates thereof exhibit anti-inflammatory properties including functional inhibition of TLR9 and are suitable for the treatment of diseases or disorders that are caused by or related to TLR9 mediated immunopathology or TLR9 mediated disbalance of pro- and anti-inflammatory responses.

The invention therefore provides a PI3K inhibitor, wherein said inhibitor has an inhibitory action on the PI3K isoform delta, and/or pharmaceutically acceptable salts and/or solvates thereof for use in the treatment of a condition, a disease or disorder caused by a parasite selected from a parasite of the *Plasmodium* genus, for example *Plasmodium falciparum, Plasmodium vivax, Plasmodium ovale* or *Plasmodium malaria*; a parasite of the *Trypanosoma* genus, for example *Trypanosoma cruzi*; a parasite of the *Leishmania* genus, for example *Leishmania donovani*; a parasite of the *Toxoplasma* genus, for example *Toxoplasma gondii* or a Helminth, for example *Taenia solium*, via functional inhibition of TLR9 of the infected subject.

The invention further provides a PI3K inhibitor, wherein said inhibitor has an inhibitory action on the PI3K isoform delta, and/or pharmaceutically acceptable salts and/or solvates thereof for use in the treatment of immunopathology in a subject suffering from a disease or disorder selected from malaria, leishmaniasis, trypanosomiasis, toxoplasmosis and/or neurocysticercosis; especially acute and cerebral malaria and/or Chagas disease, via functional inhibition of TLR9 of the infected subject.

The invention further provides a method for the treatment of a condition, disease or disorder caused by a parasite selected from a parasite of the *Plasmodium* genus, for example *Plasmodium falciparum, Plasmodium vivax, Plasmodium ovale* or *Plasmodium malaria*; a parasite of the *Trypanosoma* genus, for example *Trypanosoma cruzi*; a parasite of the *Leishmania* genus, for example *Leishmania donovani*; a parasite of the *Toxoplasma* genus, for example *Toxoplasma gondii* or a Helminth, for example *Taenia solium*, via functional inhibition of TLR9 of the infected subject, comprising administration of a therapeutically effective amount of a PI3K inhibitor, wherein said inhibitor has an inhibitory action on the PI3K isoform delta, and/or pharmaceutically acceptable salts and/or solvates thereof, to a subject, e.g. a human subject, in need of such treatment.

The invention further provides a method for the treatment of immunopathology in a subject suffering from a disease or disorder selected from malaria, leishmaniasis, trypanosomiasis, toxoplasmosis and/or neurocysticercosis; especially acute and cerebral malaria and/or Chagas disease, via functional inhibition of TLR9 of the infected subject, comprising administration of a therapeutically effective amount of a PI3K inhibitor, wherein said inhibitor has an inhibitory action on the PI3K isoform delta, and/or pharmaceutically acceptable salts and/or solvates thereof, to a subject, e.g. a human subject, in need of such treatment.

The invention further provides the use of a PI3K inhibitor, wherein said inhibitor has an inhibitory action on the PI3K isoform delta, and/or pharmaceutically acceptable salts and/or solvates thereof for the manufacture of a medicament for the treatment of a condition, disease or disorder caused by a parasite selected from a parasite of the *Plasmodium* genus, for example *Plasmodium falciparum*, *Plasmodium vivax*, *Plasmodium ovale* or *Plasmodium malaria*; a parasite of the *Trypanosoma* genus, for example *Trypanosoma cruzi*; a parasite of the *Leishmania* genus, for example *Leishmania donovani*; a parasite of the *Toxoplasma* genus, for example *Toxoplasma gondii* or a Helminth, for example *Taenia solium*, via functional inhibition of TLR9 of the infected subject.

The invention further provides the use of a PI3K inhibitor, wherein said inhibitor has an inhibitory action on the PI3K isoform delta, and/or pharmaceutically acceptable salts and/or solvates thereof for the manufacture of a medicament for the treatment of immunopathology in a subject suffering from a disease or disorder selected from malaria, leishmaniasis, trypanosomiasis, toxoplasmosis and/or neurocysticercosis; especially acute and cerebral malaria and/or Chagas disease, via functional inhibition of TLR9 of the infected subject.

The invention further provides the use of a PI3K inhibitor, wherein said inhibitor has an inhibitory action on the PI3K isoform delta, and/or pharmaceutically acceptable salts and/or solvates thereof for the treatment of a condition, disease or disorder caused by a parasite selected from a parasite of the *Plasmodium* genus, for example *Plasmodium falciparum*, *Plasmodium vivax*, *Plasmodium ovale* or *Plasmodium malaria*; a parasite of the *Trypanosoma* genus, for example *Trypanosoma cruzi*; a parasite of the *Leishmania* genus, for example *Leishmania donovani*; a parasite of the *Toxoplasma* genus, for example *Toxoplasma gondii* or a Helminth, for example *Taenia solium*, via functional inhibition of TLR9 of the infected subject.

The invention further provides the use of a PI3K inhibitor, wherein said inhibitor has an inhibitory action on the PI3K isoform delta, and/or pharmaceutically acceptable salts and/or solvates thereof for the treatment of immunopathology in a subject suffering from a disease or disorder selected from malaria, leishmaniasis, trypanosomiasis, toxoplasmosis, and/or neurocysticercosis; especially acute and cerebral malaria and/or Chagas disease, via functional inhibition of TLR9 of the infected subject.

The invention further provides a pharmaceutical composition comprising a PI3K inhibitor, wherein said inhibitor has an inhibitory action on the PI3K isoform delta, and/or pharmaceutically acceptable salts and/or solvates thereof for use in the treatment of a condition, disease or disorder caused by a parasite selected from a parasite of the *Plasmodium* genus, for example *Plasmodium falciparum*, *Plasmodium vivax*, *Plasmodium ovale* or *Plasmodium malaria*; a parasite of the *Trypanosoma* genus, for example *Trypanosoma cruzi*; a parasite of the *Leishmania* genus, for example *Leishmania donovani*; a parasite of the *Toxoplasma* genus, for example *Toxoplasma gondii* or a Helminth, for example *Taenia solium*, via functional inhibition of TLR9 of the infected subject.

The invention further provides a pharmaceutical composition comprising a PI3K inhibitor, wherein said inhibitor has an inhibitory action on the PI3K isoform delta, and/or pharmaceutically acceptable salts and/or solvates thereof for the treatment of immunopathology in a subject suffering from a disease or disorder selected from malaria, leishmaniasis, trypanosomiasis, toxoplasmosis and/or neurocysticercosis; especially acute and cerebral malaria and/or Chagas disease, via functional inhibition of TLR9 of the infected subject.

DETAILED DESCRIPTION OF THE INVENTION

Figure 1:
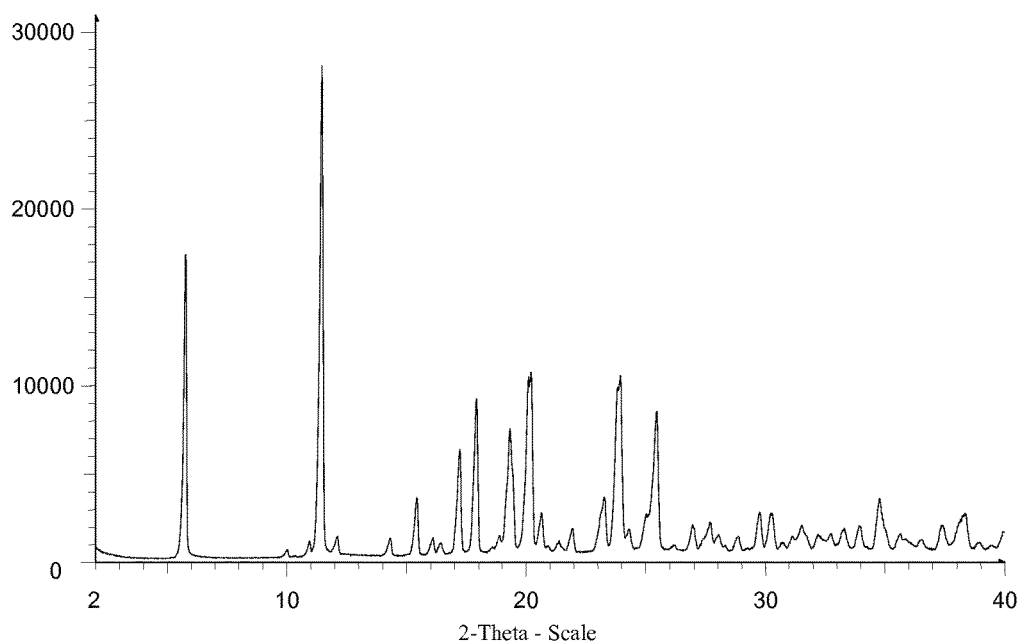
FIG. 1 discloses the X-ray Powder Diffraction Pattern of Example 1 citrate salt FIG. 2 discloses the X-ray Powder Diffraction Pattern of Example 1 fumarate salt FIG. 3 discloses the X-ray Powder Diffraction Pattern of Example 1 napadisylate salt FIG. 4 discloses the X-ray Powder Diffraction Pattern of Example 67 phosphate salt FIG. 5 discloses the X-ray Powder Diffraction Pattern of Example 67 HCl salt FIG. 6 discloses the X-ray Powder Diffraction Pattern of Example 67 hippurate salt FIG. 7 discloses the X-ray Powder Diffraction Pattern of Example 1 anhydrous form FIG. 8 discloses the X-ray Powder Diffraction Pattern of Example 1 trihydrate FIG. 9 discloses the X-ray Powder Diffraction Pattern of Example 67 anhydrous form
Figure 2:
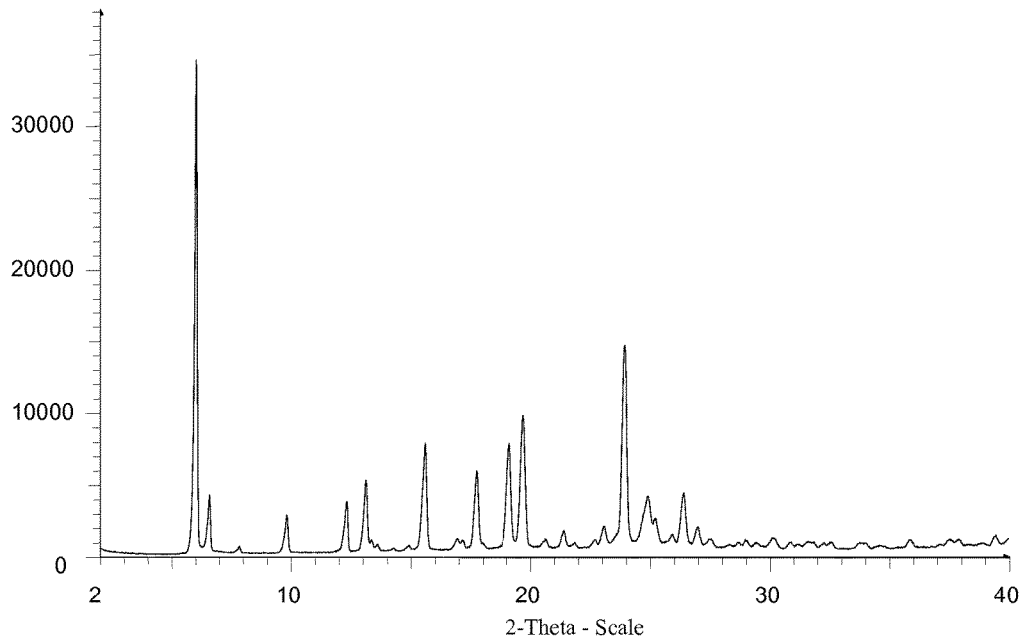
Figure 3:
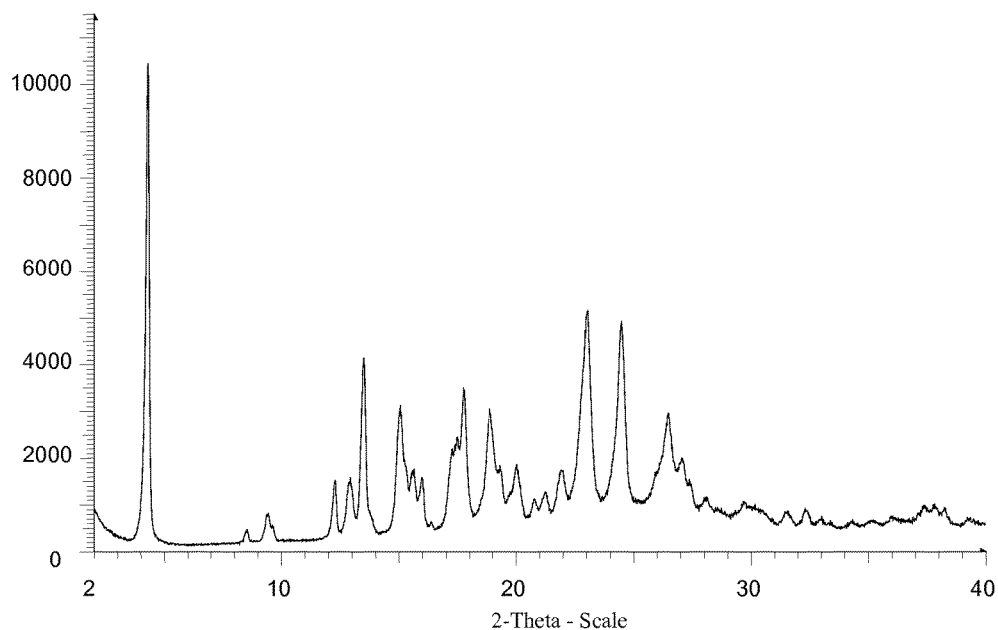
Figure 4:
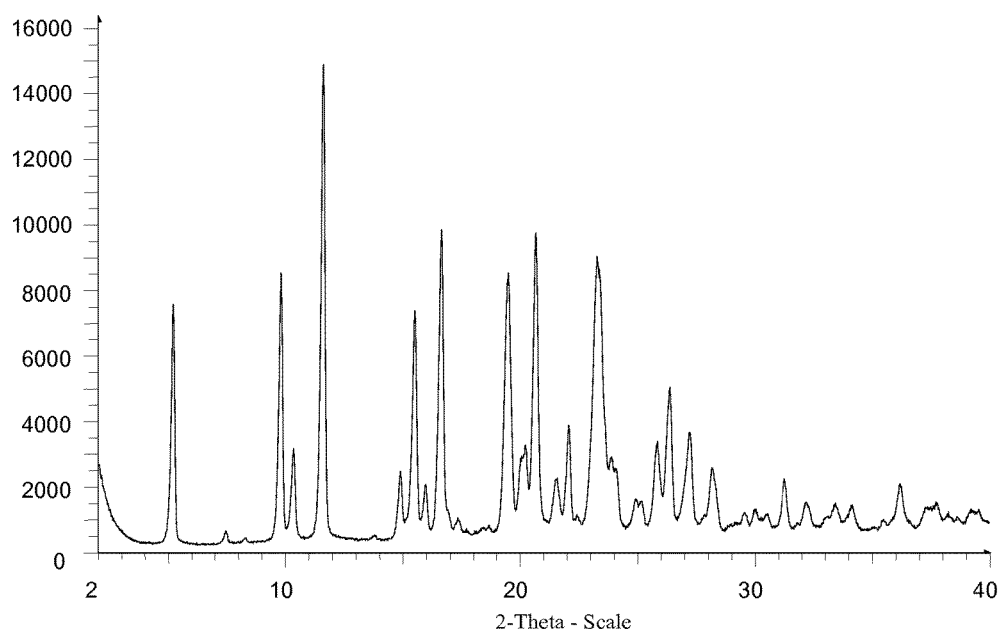
Figure 5:
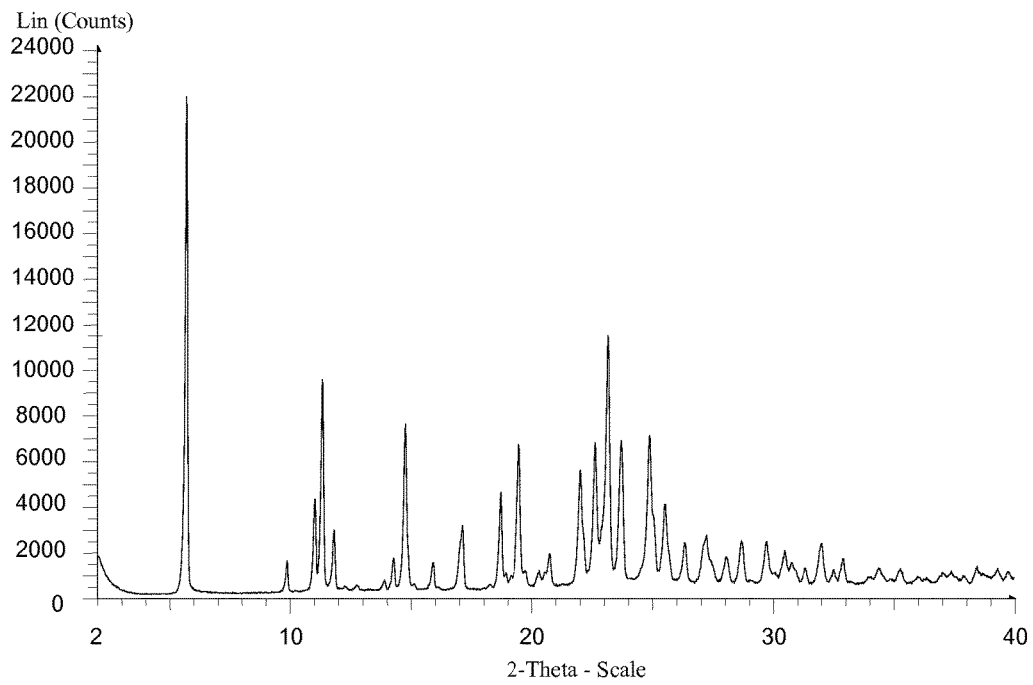
Figure 6:
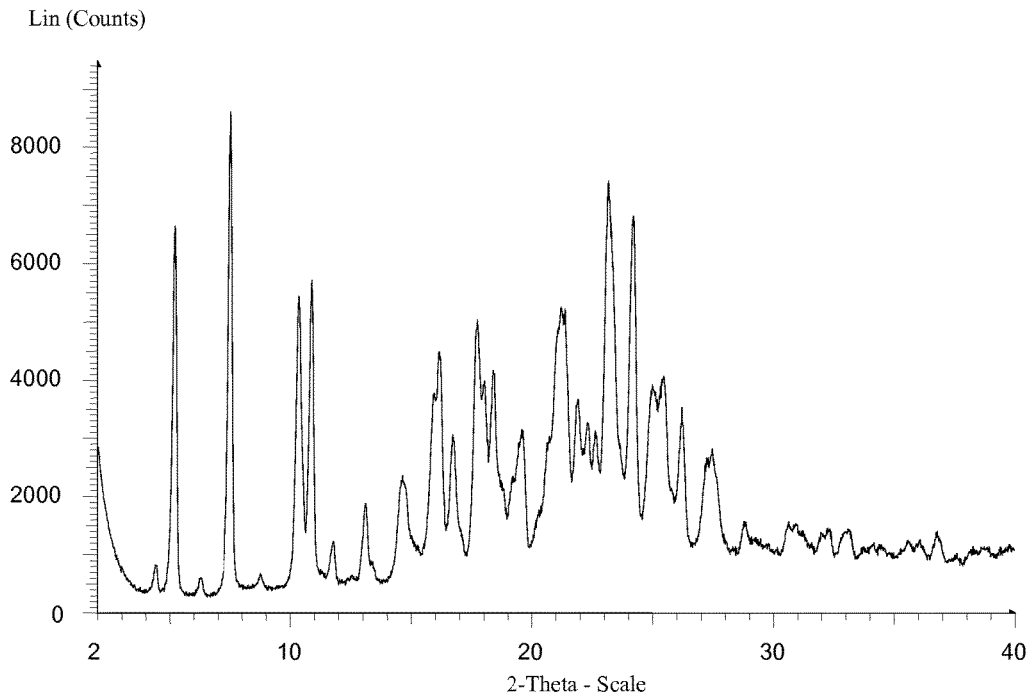
Figure 7:
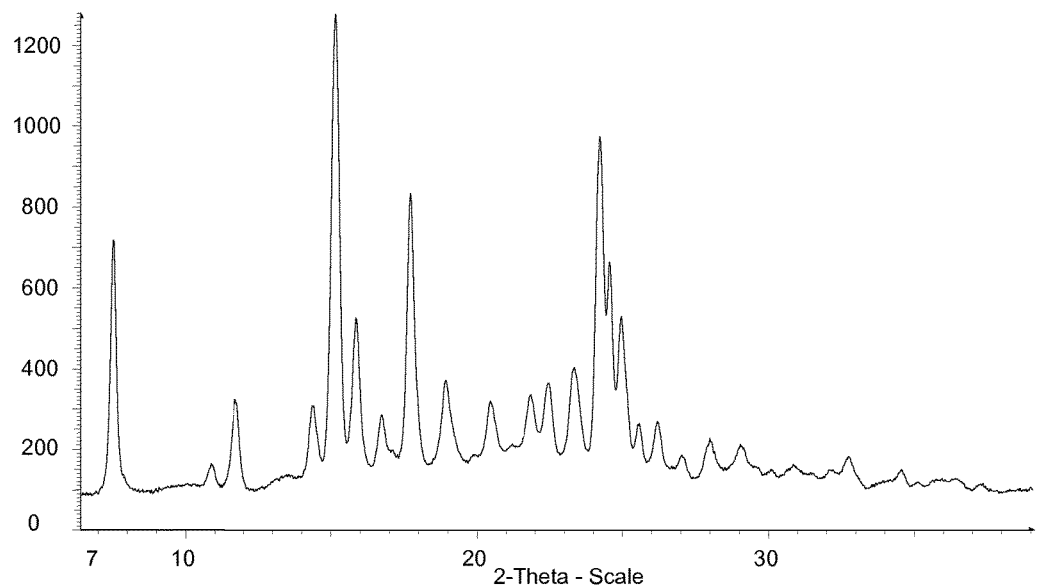
Figure 8:
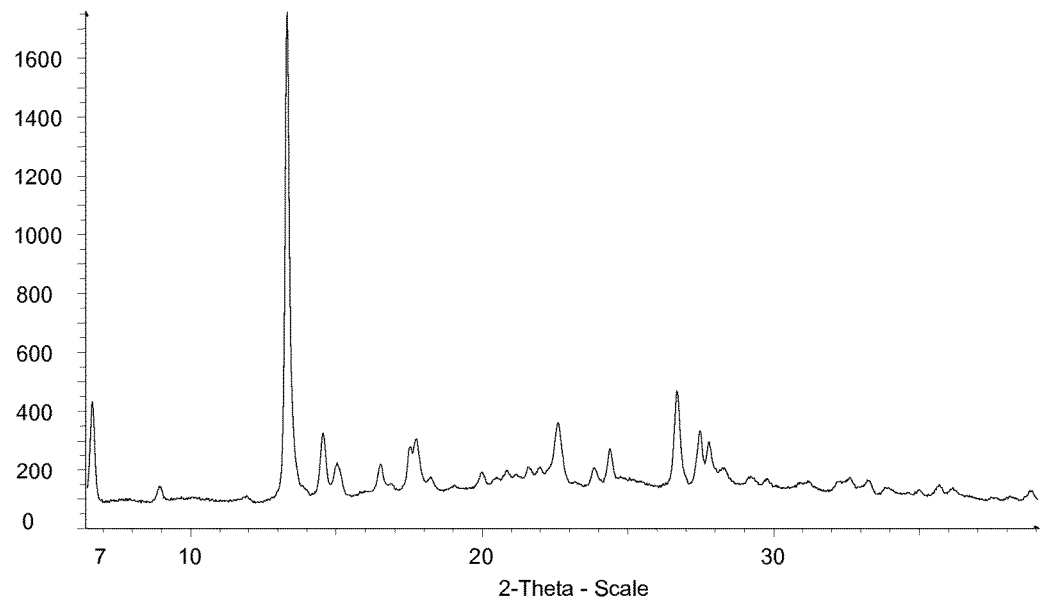
Figure 9:
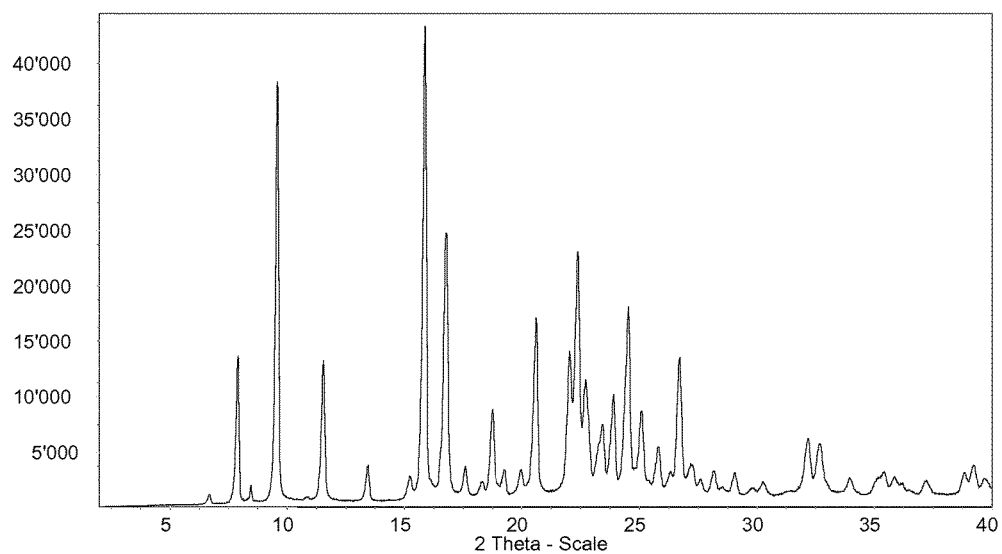

The methods and compositions of the present invention comprise a PI3K inhibitor, wherein said inhibitor has an inhibitory action on the PI3K isoform delta, or a pharmaceutically acceptable salt or ester thereof and/or pharmaceutically acceptable salts and/or solvates thereof. The PI3K inhibitor, wherein said inhibitor has an inhibitory action on the PI3K isoform delta, useful in the compositions of the present invention may be any PI3K inhibitor, wherein said inhibitor has an inhibitory action on the PI3K isoform delta known in the art.

For example, the PI3K inhibitor, wherein said inhibitor has an inhibitory action on the PI3K isoform delta may be chosen from those compounds described in WO1998023760, WO2001085986, WO2003035075, WO2005016348, WO2005016349, WO2005112935, WO2005113556, WO2008064018, WO2009064802, WO2010057048, WO2010123931, WO2010111432, WO2011011550, WO2011075628, WO2008118454, WO2008118455, WO2008118468, WO2010151740, WO2010151737, WO2010151735, WO2010151791, WO2009088990, WO2010036380, WO2010129816, WO2011008302, WO2010059593, WO2011075630, WO2011075643, WO2011008487, WO2006046031, WO2006046035, WO2007042810, WO2008125833, WO2008125835, WO2008125839, WO2008152387, WO2008152390, WO2008152394, WO2010138589 WO2010136491, WO2011101429, WO2010102958, WO2011067364, WO2011067365, WO2011067366, WO2011048111, WO2010005558, WO2011041399, WO2011055215, WO2011058149, WO2011021038, WO2009036768, WO2010065923, WO2011146882, WO2012097000, WO2012007493, WO2008000421, WO2011123751, WO2009046448, WO2010006086, WO2009120094, WO2002088112, WO2009011617, WO2007023186, WO2011135351, WO2010125082, WO2011130342, WO2012037226, WO2012037204, WO2009154741, WO2009147189, WO2009147190, WO2009147188, US20110312979, WO2012135175, WO2012126901, WO2012125629, WO2012146666, WO2012146667, WO2012135009, WO2012140419;

or described in

Knight Z A, Gonzalez B, Feldman M E, et al. A pharmacological map of the PI3-K family defines a role for p110alpha in insulin signaling. Cell 2006; 125(4):733-47;

Rommel C. Taking PI3Kdelta and PI3Kgamma one step ahead: dual active PI3Kdelta/gamma inhibitors for the treatment of immune-mediated inflammatory diseases. Curr Top Microbiol Immunol 2010; 346:279-99;

Liao C H, Pei-Yuan J S, Patel V, et al. RO2492, A phosphoinositide-288-kinase D inhibitor, shows inhibitory effects in a variety of human cell types and suppresses collagen-induced arthritis in mice. Arthritis Rheum 2010; 62(Suppl 10):288;

Sweeney Z K. Potent and highly selective benzimidazole inhibitors of PI3-Kinase delta. 242nd ACS National Meeting & Exposition 2011 MEDI15;

Safina B S. Discovery of potent and highly selective PI3-Kinase Delta inhibitors: Taming time-dependent inhibition. 242nd ACS National Meeting & Exposition 2011 MEDI10;

Viswanadha S, Prasanna R, Muthuppalaniappan M, et al. RP5237—a novel, selective, and potent inhibitor of PI3Kdelta with therapeutic potential in B-cell [abstract 1200]. Lymphomas European Multidisciplinary Cancer Congress; 23-27 Sep. 2011; Stockholm;

Routhu K, Varanasi K, Veeraraghavan S, et al. Pre-clinical efficacy of RP5090 in PI3K delta mediated airway disorders [abstract 4495]. European Respiratory Society Annual Congress; 24-28 Sep. 2011; Amsterdam Timothy D. Cushing, Daniela P. Metz, Douglas A. Whittington, and Lawrence R. McGee PI3Kδ and PI3Kγ as Targets for Autoimmune and Inflammatory Diseases. J. Med. Chem. 2012, 55(20), p 8559-8581

Specific compounds include for example:

GDC-0941, IC81174, IC-87114, CAL-101 (GS-1101), CAL-263, XL-499, D-121, CAL-120 (GS-9820), CAL-129, AMG-319, PIK-294, RO-2492, RP-5237, RP-5090, RP-5002, INK-1138, IPI-145, KAR-4139, XL-499, PIK-39, TG100-115, INK654, INK666, INK007, SW-13, SW-30, AS5, AS15 GSK-418, OXY-111A, RP-5264, KAR-4141, X-339 or

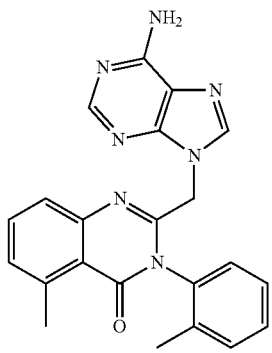

-continued

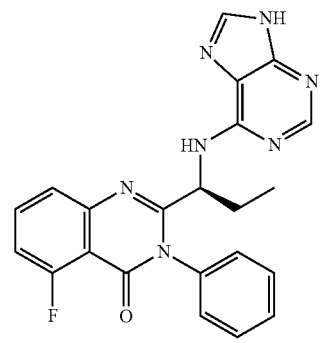

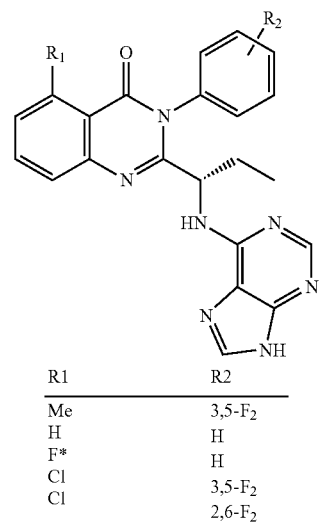

| R1 | R2 |
|----|----|
| Me | 3,5-F$_2$ |
| H | H |
| F* | H |
| Cl | 3,5-F$_2$ |
| Cl | 2,6-F$_2$ |

*CAL-101.

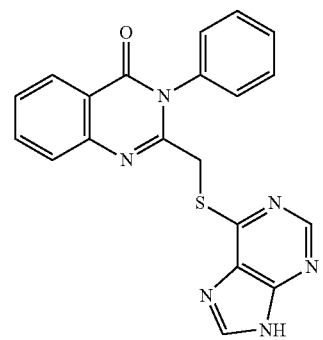

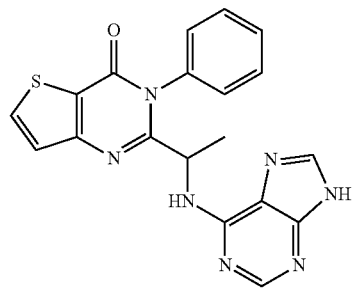

9
-continued
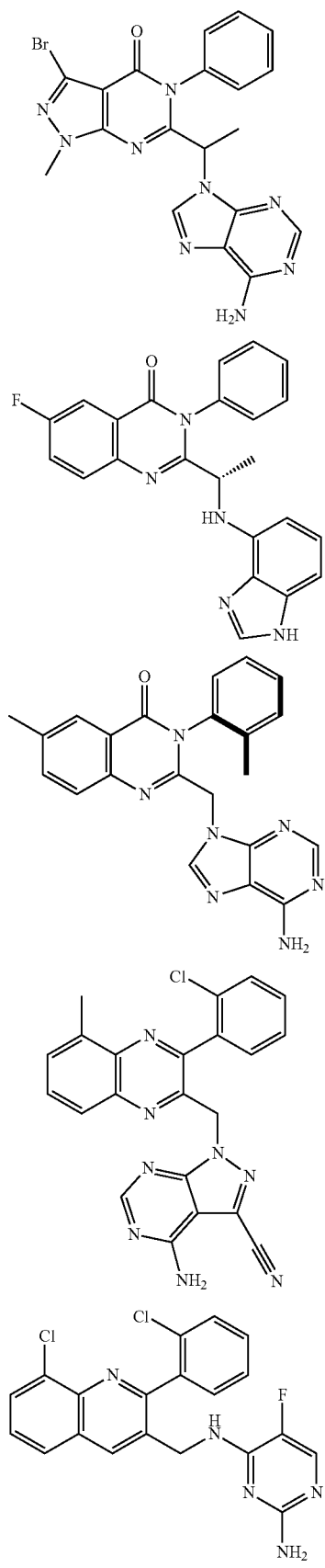
10
-continued
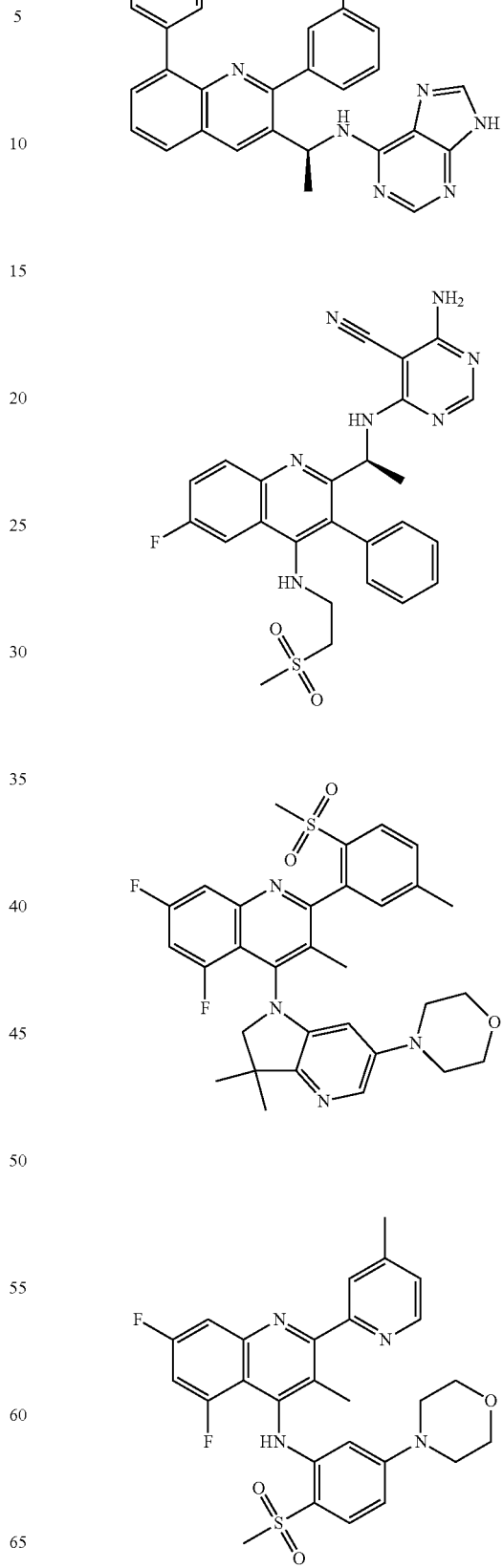

11
-continued
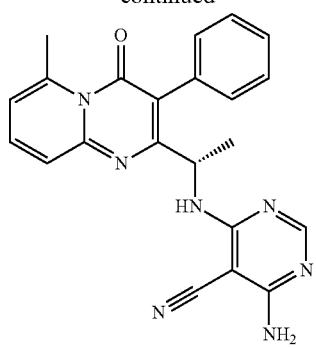
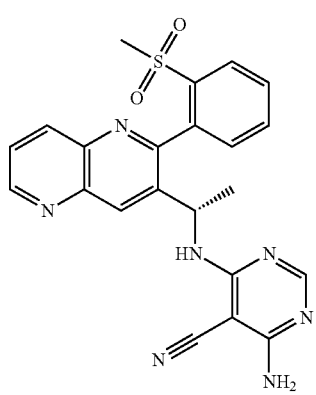
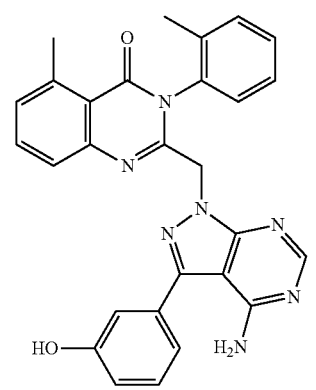
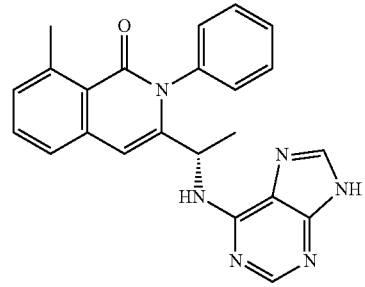
12
-continued
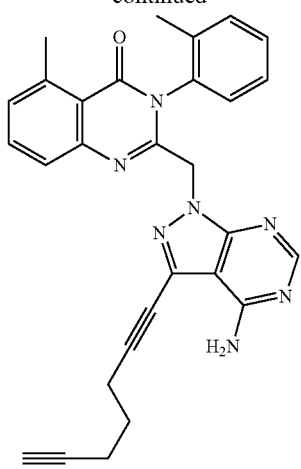

13
-continued
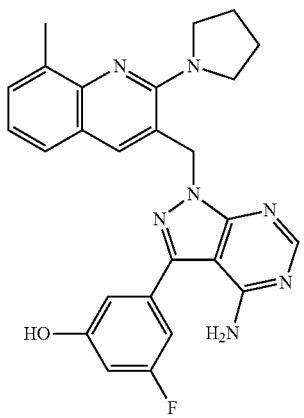
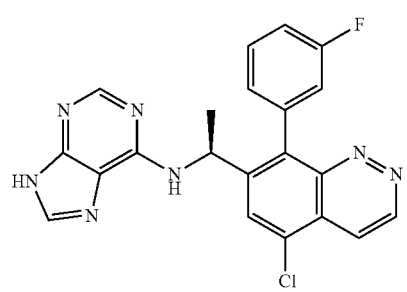
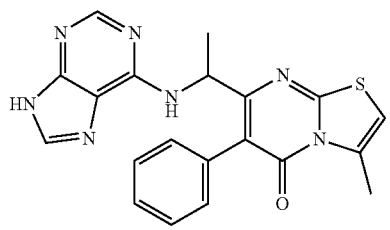
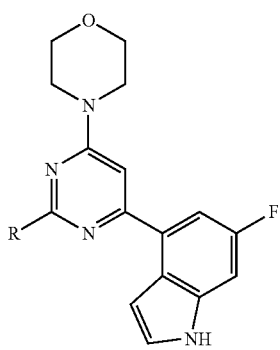
R =
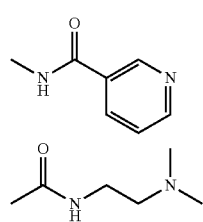
14
-continued
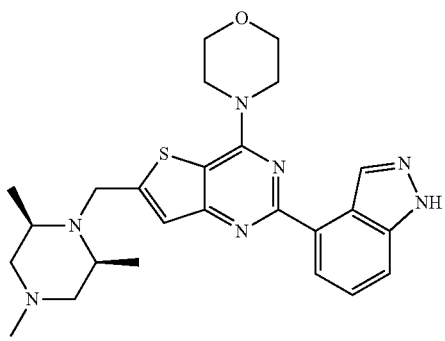
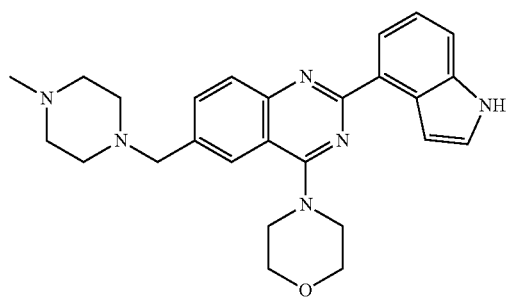
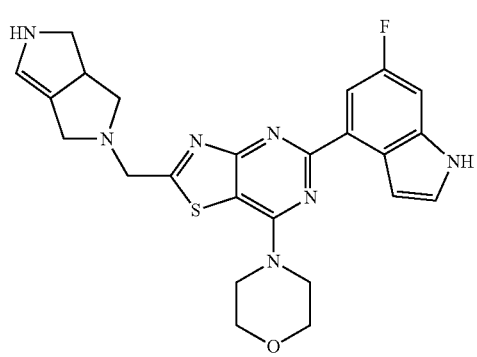
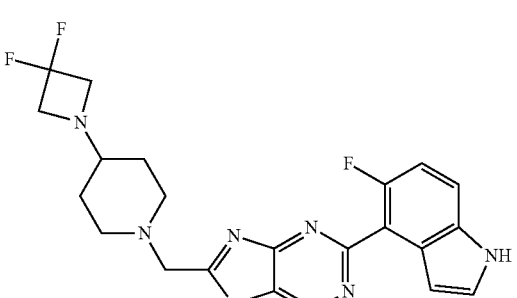
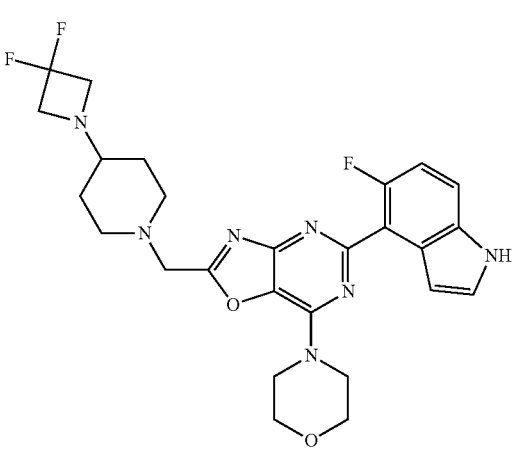

15
-continued
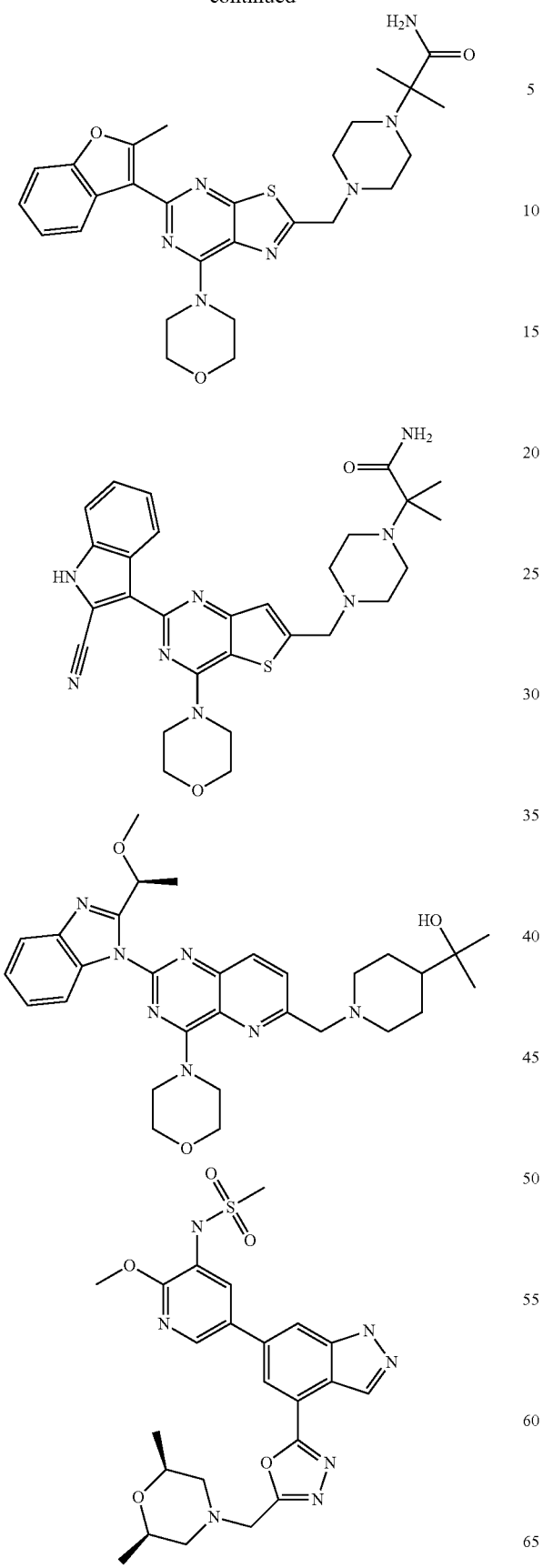
16
-continued
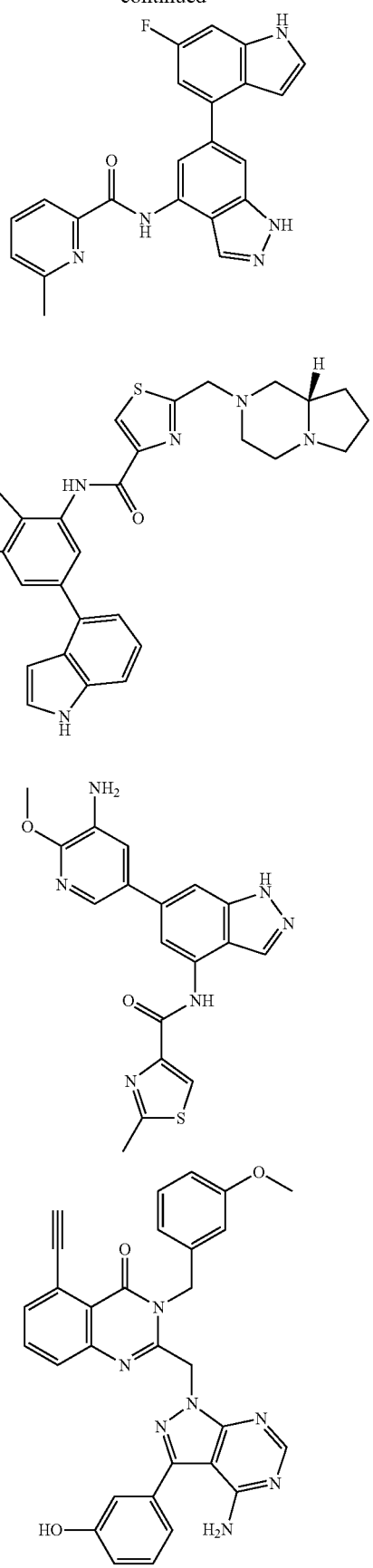

17
-continued
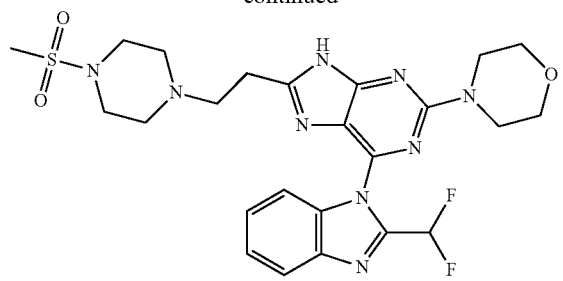
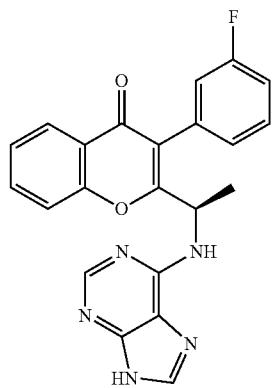
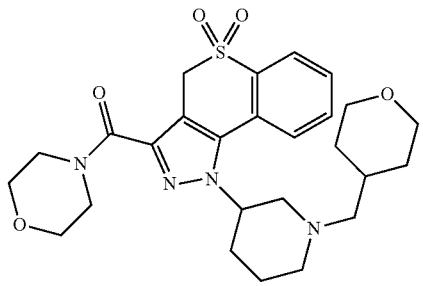
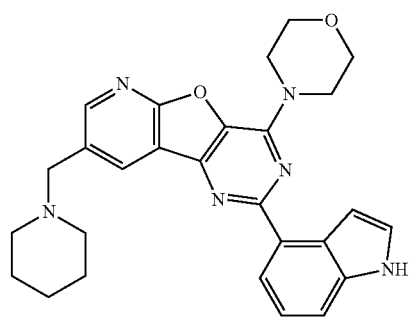
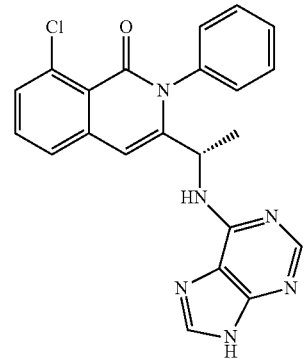
18
-continued
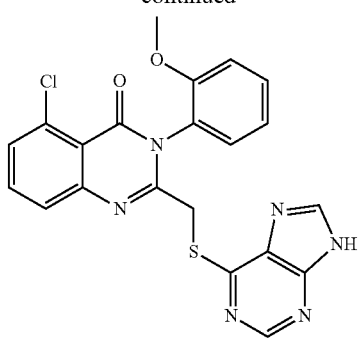
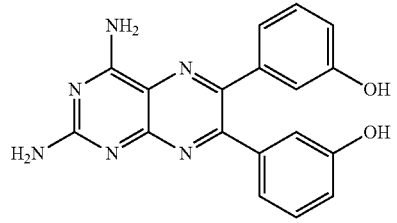
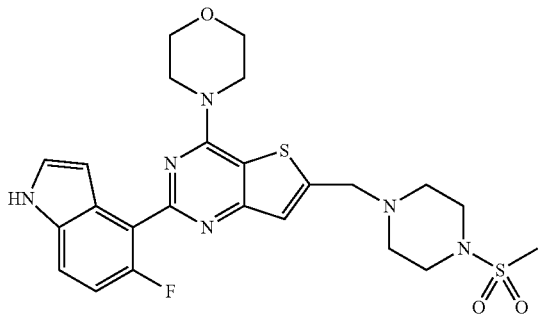
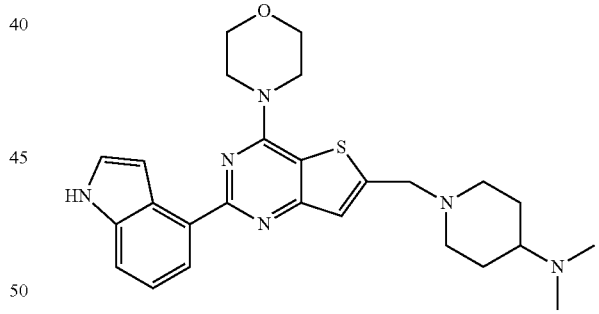
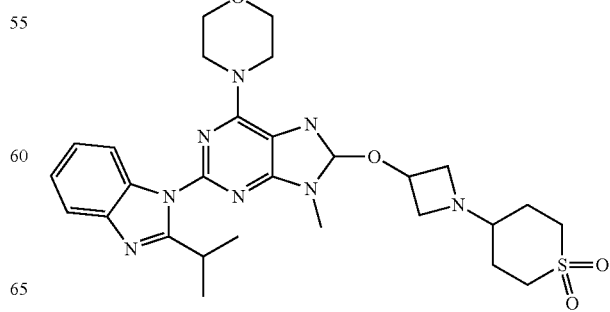

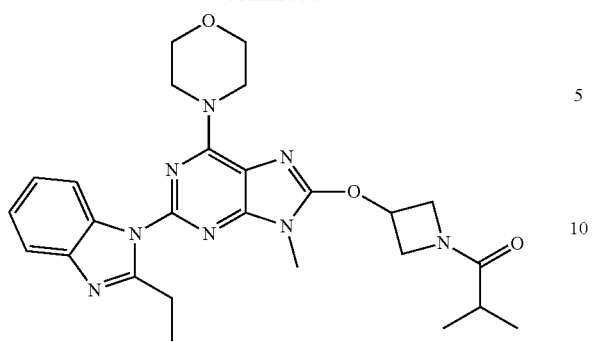
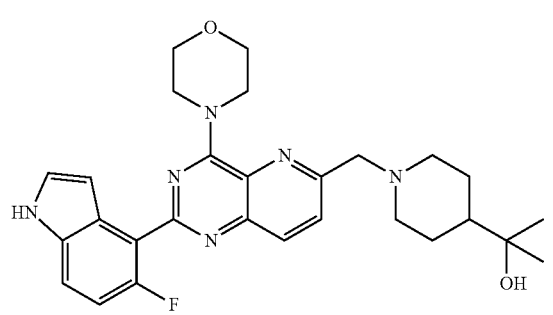
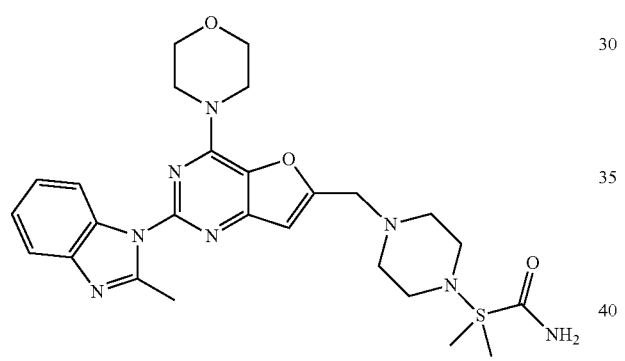
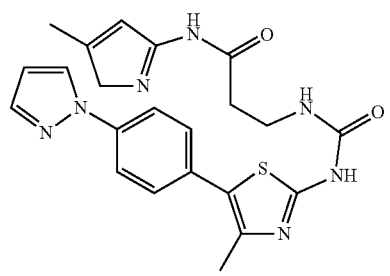
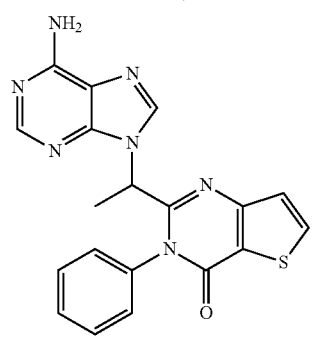
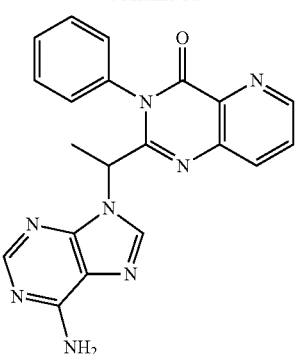
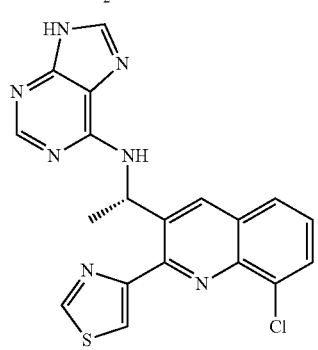
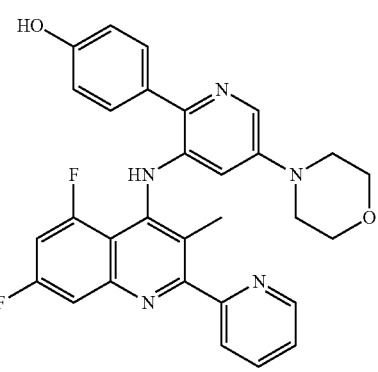
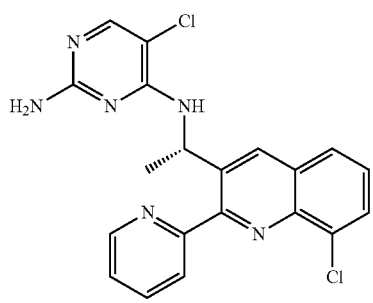
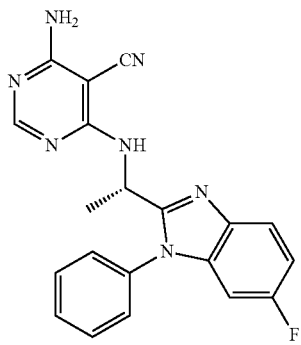

21
-continued
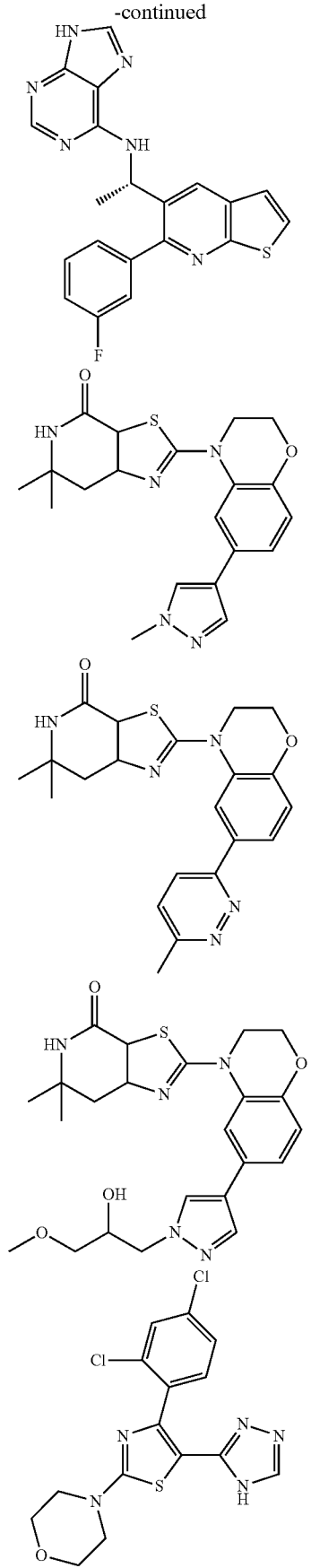
22
-continued
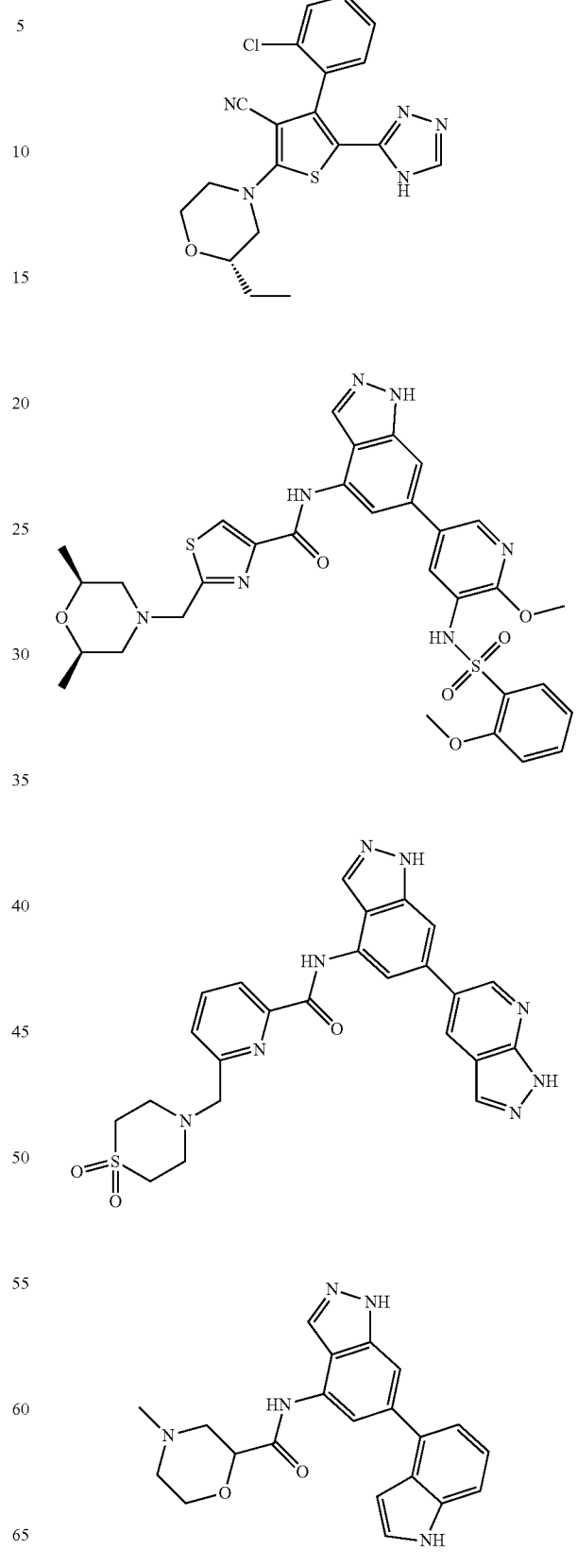

-continued
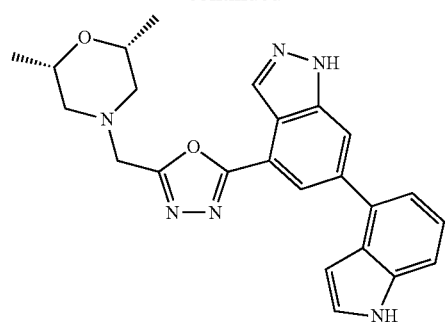
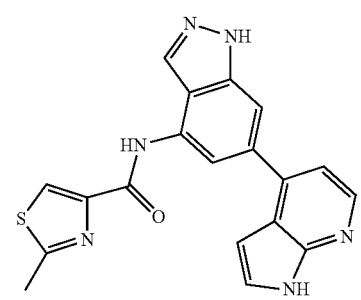
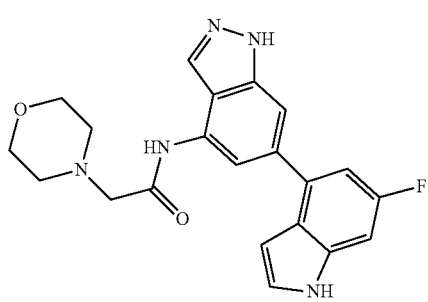
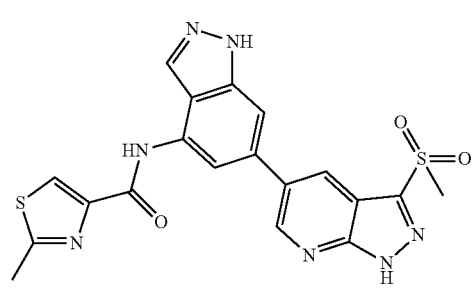
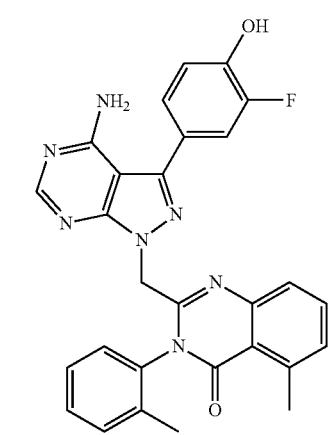
-continued
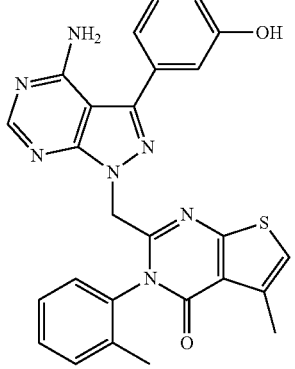
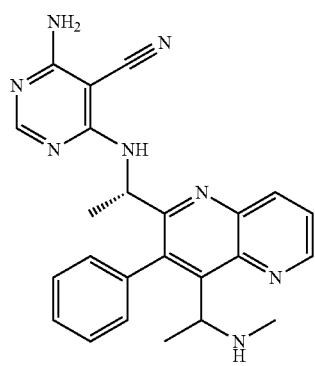
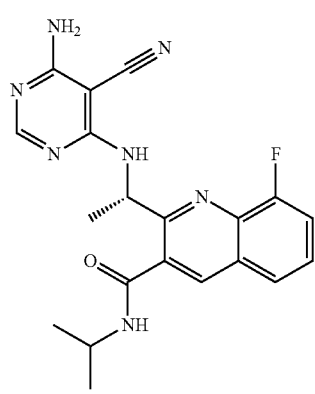
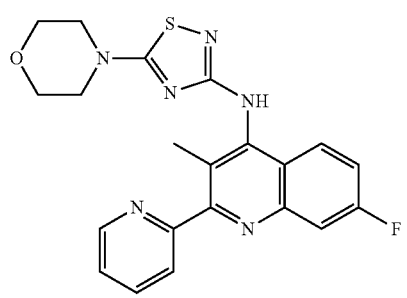

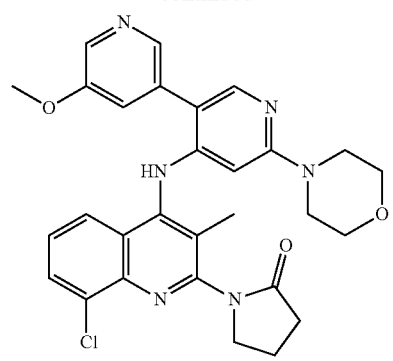
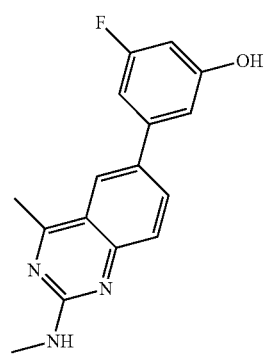
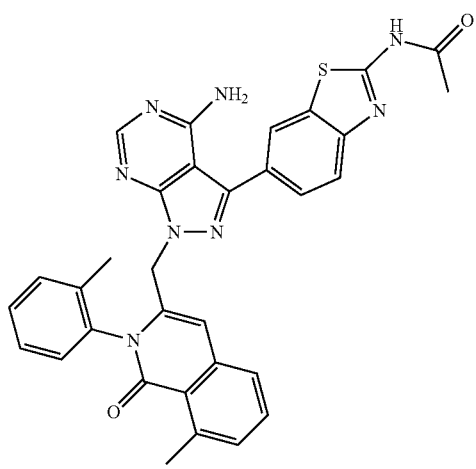
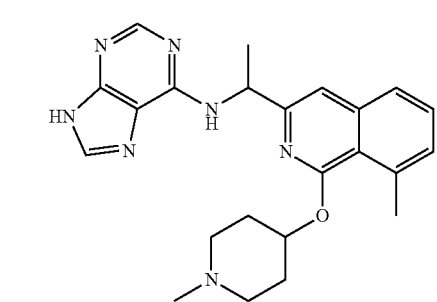
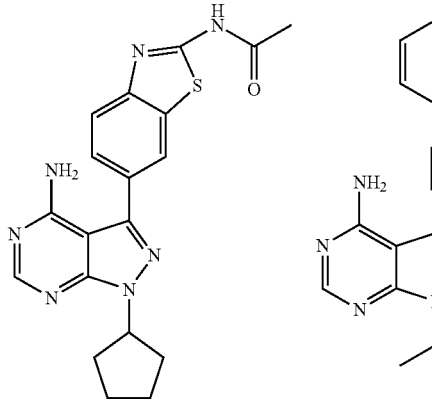
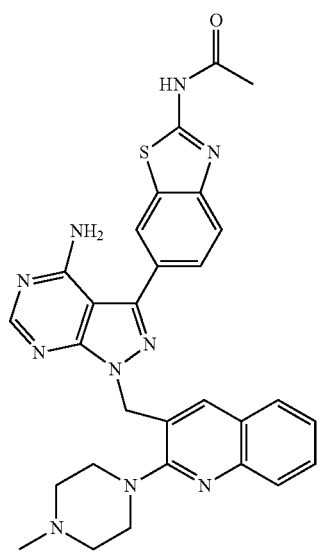
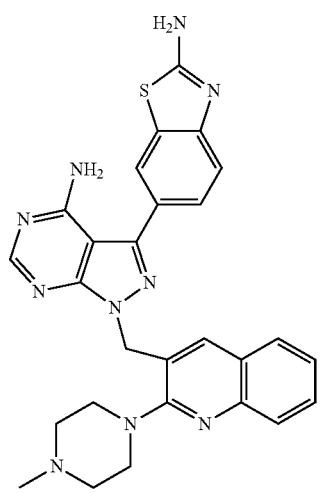

-continued
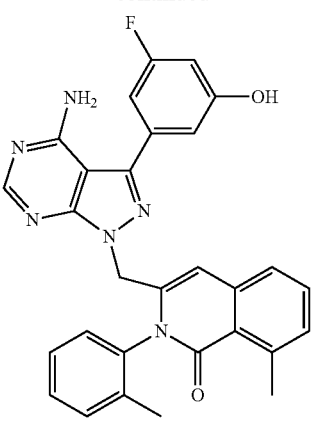
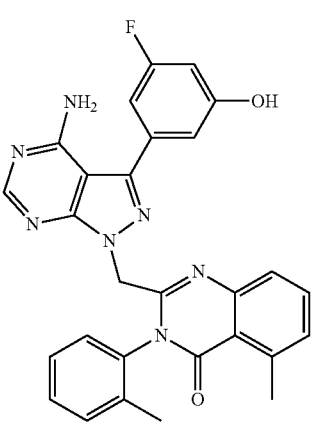
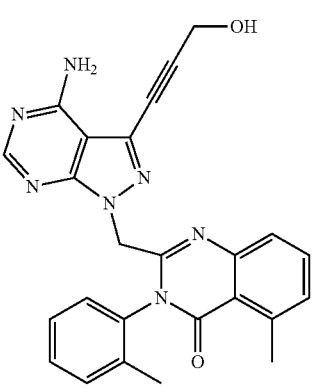
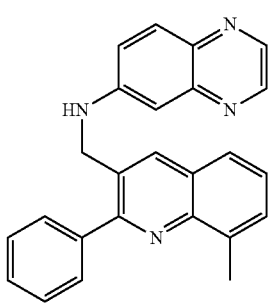
-continued
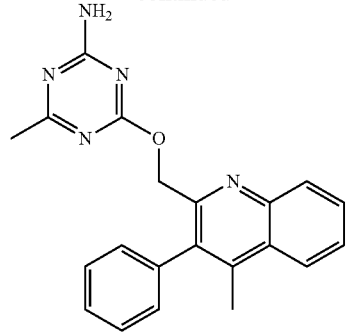
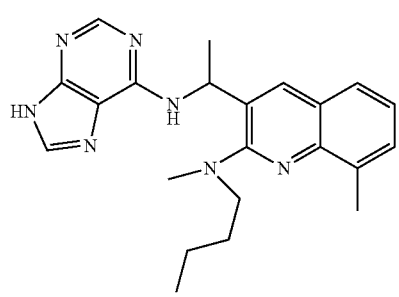
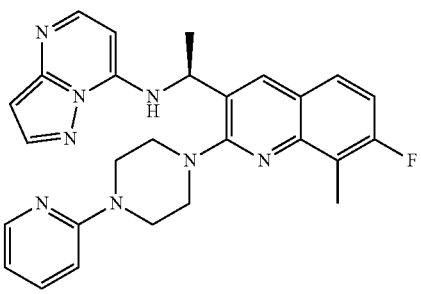
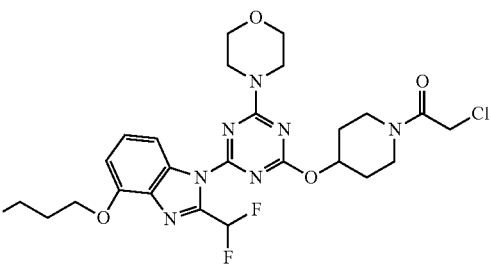
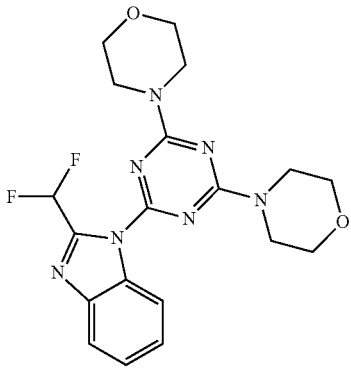

29
-continued
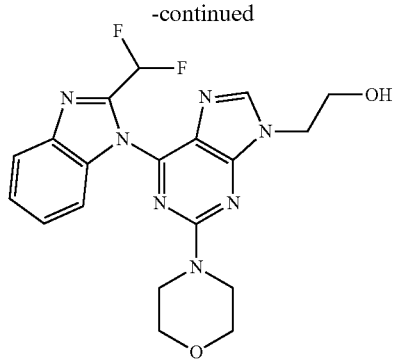
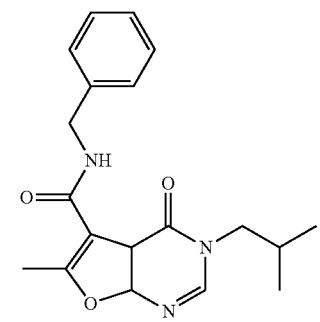
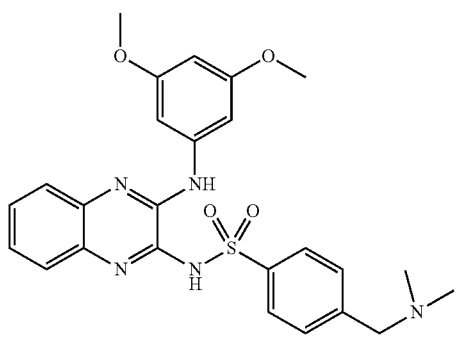
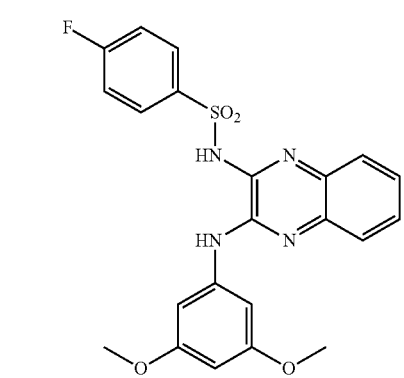
30
-continued
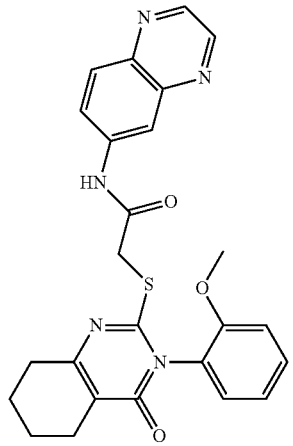
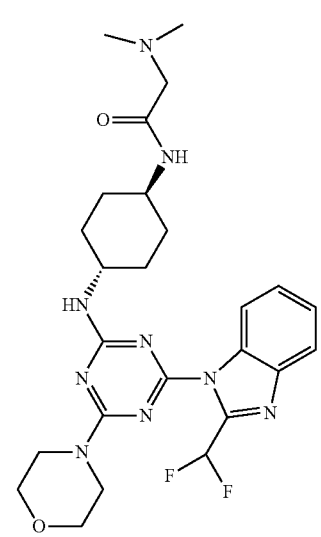
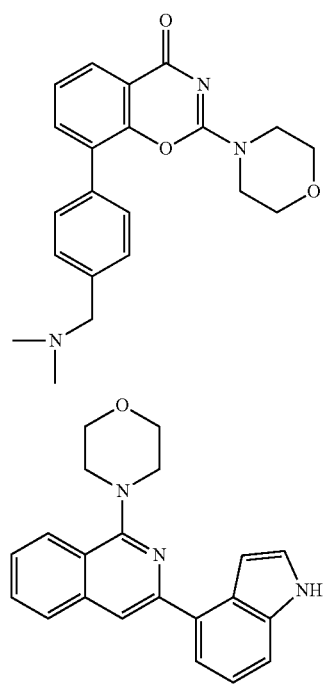

-continued
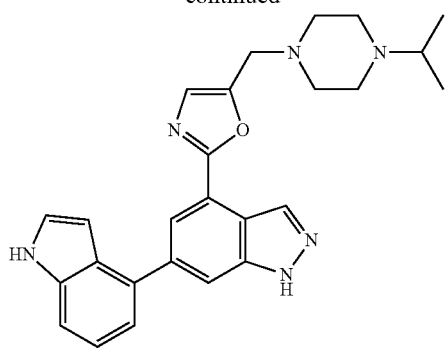
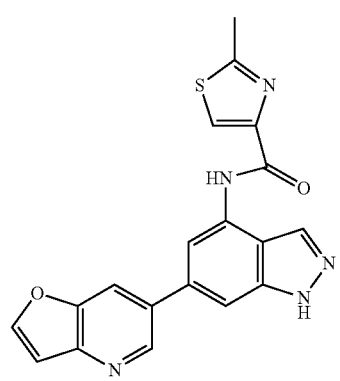
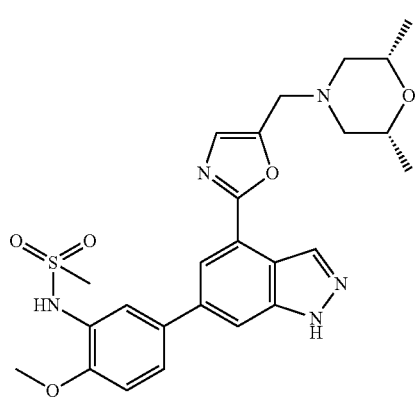
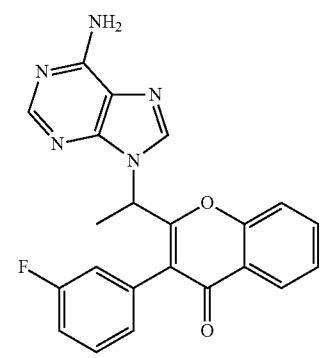
-continued
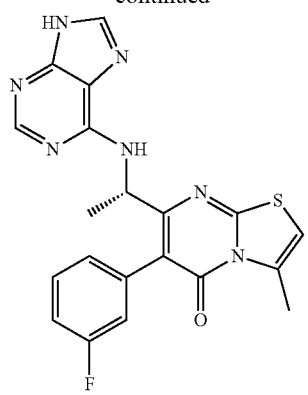
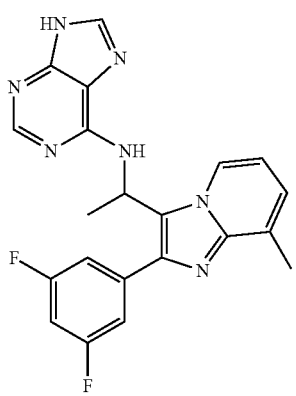
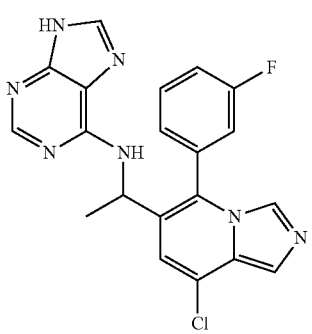
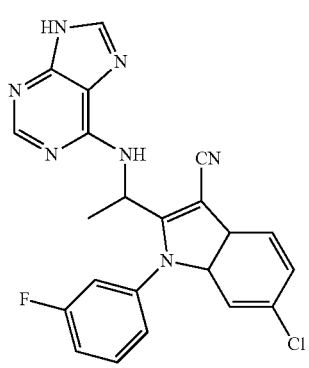

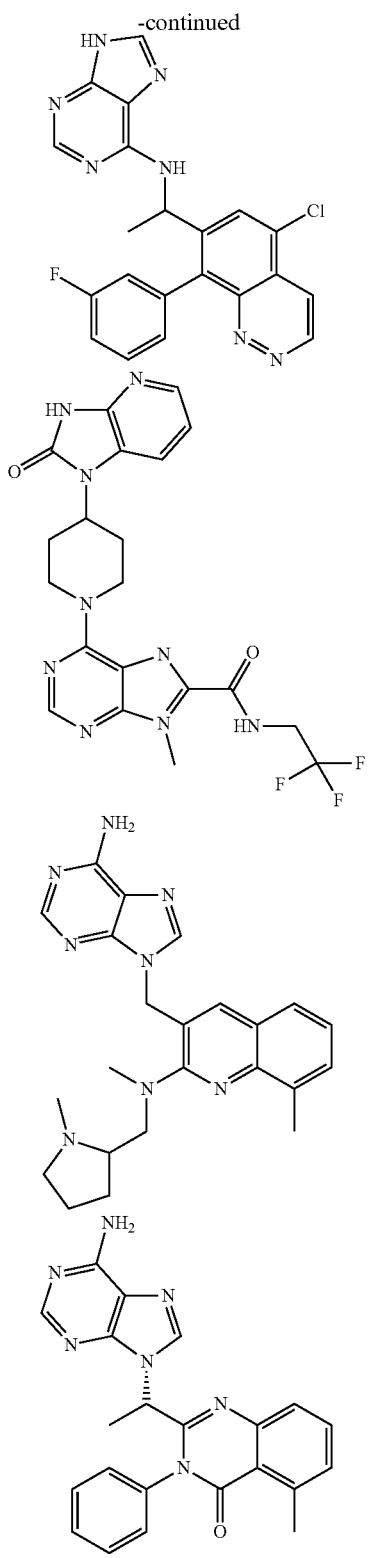

In one embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 1 nM and 500 nM.

In another embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 1 nM and 100 nM.

In another embodiment of the present invention, the PI3K inhibitor, wherein said inhibitor has an inhibitory action on the PI3K isoform delta, wherein the range of activity, expressed as $IC_{50}$, in the enzymatic PI3K delta assay is from is between 0.5 nM and 10 nM.

In one embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 1000 nM.

In another embodiment of the present invention, the PI3K inhibitor, wherein said inhibitor has an inhibitory action on the PI3K isoform delta, wherein the range of activity, expressed as $IC_{50}$, in the cellular PI3K delta assay is from is between 1 nM and 500 nM.

In another embodiment of the present invention, the PI3K inhibitor, wherein said inhibitor has an inhibitory action on the PI3K isoform delta where the inhibitor shows selectivity for the PI3K isoform delta over one or more of the other isoforms wherein this selectivity is at least 10 fold.

In another embodiment of the present invention, the PI3K inhibitor, wherein said inhibitor has an inhibitory action on the PI3K isoform delta where the inhibitor shows selectivity for the PI3K isoform delta over one or more of the other isoforms wherein this selectivity is at least 20 fold.

In another embodiment of the present invention, the PI3K inhibitor, wherein said inhibitor has an inhibitory action on the PI3K isoform delta where the inhibitor shows selectivity for the PI3K isoform delta over the different paralogs PI3K α and β, wherein this selectivity is at least 10 fold. Such a PI3K inhibitor is referred to as a PI3K delta inhibitor.

In another embodiment of the present invention, the PI3Kdelta inhibitor shows selectivity for the PI3K isoform delta over the different paralogs PI3K α and β, wherein this selectivity is at least 20 fold.

In another embodiment of the present invention, the PI3Kdelta inhibitor has an inhibitory action on the PI3K isoform delta, wherein the range of activity, expressed as $IC_{50}$, in the cellular PI3K delta assay is from is between 1 nM and 500 nM and shows a selectivity for the PI3K isoform delta over the different paralogs PI3K α and β, wherein this selectivity is at least 20 fold.

In another embodiment of the present invention, the PI3K inhibitor, wherein said inhibitor has an inhibitory action on the PI3K isoform delta, is a low molecular weight compound.

In another embodiment of the present invention, the PI3K inhibitor, wherein said inhibitor has an inhibitory action on the PI3K isoform delta, is a low molecular weight compound with a molecular weight of below 1000 daltons.

In one embodiment of the present invention, the PI3K inhibitor, wherein said inhibitor has an inhibitory action on the PI3K isoform delta, is disclosed in PCT/EP2011/061393, which is incorporated herein by reference in its entirety.

In one embodiment of the present invention, the PI3K inhibitor, wherein said inhibitor has an inhibitory action on the PI3K isoform delta, is a tetrahydro-pyrido-pyrimidine compound of the formula (I) and/or pharmaceutically acceptable salts and/or solvates thereof,

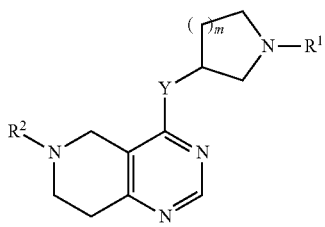

(I)

wherein
Y is selected from O or NR³;
R¹ is selected from phenyl, pyridyl, pyrimidinyl, pyrazinyl, pyridazinyl, 1,2,3-triazinyl, 1,2,4-triazinyl, 1,3,5-triazinyl,
or
—C(O)—R⁴
wherein
R⁴ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, $C_1$-$C_8$-alkyl-sulfonyl-$C_1$-$C_8$-alkyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
wherein '$C_1$-$C_8$-alkyl' in N—$C_1$-$C_8$-alkyl-amino and N,N-di-$C_1$-$C_8$-alkyl-amino may be unsubstituted or substituted by halogen, hydroxy or $C_1$-$C_4$-alkoxy;
wherein '$C_3$-$C_{12}$-cycloalkyl' in $C_3$-$C_{12}$-cycloalkyl and $C_3$-$C_{12}$-cycloalkyl-$C_1$-$C_8$-alkyl may be unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;
wherein 'heterocyclyl' is selected from oxiranyl, aziridinyl, oxetanyl, thiethanyl, acetitinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl, thiomorpholinyl, piperazinyl, azepanyl, thiepanyl or oxepanyl; each of which is unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;
wherein 'heterocyclyl' can be attached at a heteroatom or a carbon atom and where the N and/or S heteroatoms can also optionally be oxidized to various oxidation states;
wherein 'heteroaryl' is selected from
furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl, 1,3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl or 1,3,5-triazinyl; each of which is unsubstituted or substituted by 1-5 substituents independently selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;

R² is selected from phenyl, naphthyl, pyridyl, pyrimidinyl, pyrazinyl, pyridazinyl, quinolinyl or isoquinolinyl, each of which is unsubstituted or substituted by 1-5 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;

R³ is selected from H, $C_1$-$C_4$-alkyl or halo-$C_1$-$C_4$-alkyl; and
m is selected from 0 or 1.

In one embodiment of the present invention, the PI3K inhibitor, wherein said inhibitor has an inhibitory action on the PI3K isoform delta, is a quinazoline compound of the formula (II) and/or pharmaceutically acceptable salts and/or solvates thereof,

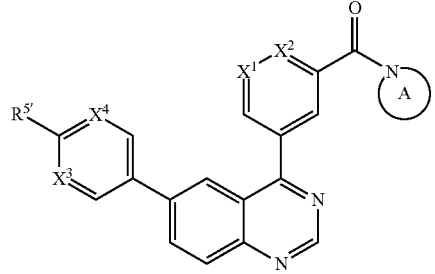

(II)

wherein
A is a saturated, 5-8 membered mono- or 6-12 membered bicyclic fused, bicyclic bridged or bicyclic spiro heterocyclic ring optionally containing 1-2 additional heteroatoms selected from N, O or S, wherein the heterocyclic ring is unsubstituted or substituted by 1-4 substituents selected from
hydroxy-
halo-
$C_1$-$C_7$-alkyl-
$C_1$-$C_7$-alkyl-carbonyl-
halo-$C_1$-$C_7$-alkyl-
halo-$C_1$-$C_7$-alkyl-carbonyl-
$C_1$-$C_7$-alkoxy-carbonyl-
oxo (O=);
$X^1$ and $X^2$ are CH, N, CR
wherein R is independently selected from
halogen-
halo-$C_1$-$C_7$-alkyl-
$C_1$-$C_7$-alkyl-
$C_1$-$C_7$-alkoxy-;
$X^3$ is CH, N, CR³' wherein $R^{3'}$ is selected from
cyano-
nitro-
halogen-
halo-$C_1$-$C_7$-alkyl-
$C_1$-$C_7$-alkyl-
$C_1$-$C_7$-alkoxy-
$C_1$-$C_{10}$-cycloalkyl-oxy-
phenyl-oxy-
benzyl-oxy-
$C_1$-$C_7$-alkoxy-$C_1$-$C_7$-alkoxy-
carboxyl-
$C_1$-$C_7$-alkoxy-carbonyl-
amino-carbonyl-
N—$C_1$-$C_7$-alkyl-amino-carbonyl-
N,N-di-$C_1$-$C_7$-alkyl-amino-carbonyl-amino-sulfonyl-
N—$C_1$-$C_7$-alkyl-amino-sulfonyl-
N,N-di-$C_1$-$C_7$-alkyl-amino-sulfonyl-
1-pyrrolidino-sulfonyl-
4-morpholino-sulfonyl-
$C_1$-$C_7$-alkyl-sulfonyl-
$C_1$-$C_7$-alkyl-sulfonyl-amino-;
$X^4$ is CH, N, $CR^{4'}$
wherein $R^{4'}$ is selected from
$F_3C$—;
$R^{5'}$ is selected from
hydrogen-
halogen-
hydroxy-
$C_1$-$C_7$-alkyl-
$C_1$-$C_7$-alkoxy-
halo-$C_1$-$C_7$-alkyl-
halo-$C_1$-$C_7$-alkyl-oxy-
amino-
N—$C_1$-$C_7$-alkyl-amino-
N,N-di-$C_1$-$C_7$-alkyl-amino-
$C_1$-$C_7$-alkyl-carbonyl-
$C_1$-$C_7$-alkyl-carbonyl-amino-
amino-sulfonyl-
$C_1$-$C_7$-alkyl-sulfonyl-amino-
1-pyrrolidinyl-
1-piperazinyl-
with the proviso that, if $X^4$ is CH, then $R^{3'}$ and $R^{5'}$ are not both methoxy.

Unless specified otherwise, the term "compounds of formula (I)" or "compounds of formula (II)" refers to compounds of formula (I) or formula (II), respectively, subformulae thereof, salts of the compound, hydrates or solvates of the compounds, as well as all stereoisomers (including diastereoisomers and enantiomers), tautomers and isotopically labeled compounds (including deuterium substitutions).

As used herein, the term "a", "an", "the" and similar terms used in the context of the present invention, especially in the context of the claims, are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language, e.g. "such as", provided herein is intended merely to better illuminate the invention and does not pose a limitation on the scope of the invention otherwise claimed.

The invention may be more fully appreciated by reference to the following description, including the following glossary of terms and the concluding examples. As used herein, the terms "including", "containing" and "comprising" are used herein in their open, non-limiting sense. Where compounds of formula (I) or compounds of formula (II) are mentioned, this is meant to include also the tautomers and N-oxides of the compounds of formula (I) or formula (II), respectively.

Tautomers, such as tautomers between keto- and enol form, lactam- and lactim form, amid form and imidic acid form or enamine form and imine form, can be present for example in the R1 or R2 portion of compounds of formula (I). The nitrogen atoms of the tetrahydro-pyrido-pyrimidine core of the compounds of formula (I) as well as nitrogen containing heterocyclyl and heteroaryl residues can form N-oxides.

Where the plural form is used for compounds, salts, and the like, this is taken to mean also a single compound, salt, or the like.

The general terms used hereinbefore and hereinafter preferably have within the context of this disclosure the following meanings, unless otherwise indicated:

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Typically, alkyl groups have 1-7, more preferably 1-4 carbons.

As used herein, the term "halo-alkyl" refers to an alkyl as defined herein, which is substituted by one or more halo groups as defined herein. The halo-alkyl can be mono-halo-alkyl, di-halo-alkyl or poly-halo-alkyl including per-halo-alkyl. A mono-halo-alkyl can have one iodo, bromo, chloro or fluoro within the alkyl group. Di-halo-alky and poly-halo-alkyl groups can have two or more of the same halo atoms or a combination of different halo groups within the alkyl. Typically the poly-halo-alkyl contains up to 12, or 10, or 8, or 6, or 4, or 3, or 2 halo groups. Non-limiting examples of halo-alkyl include fluoro-methyl, di-fluoro-methyl, tri-fluoro-methyl, chloro-methyl, di-chloro-methyl, tri-chloro-methyl, penta-fluoro-ethyl, hepta-fluoro-propyl, di-fluoro-chloro-methyl, di-chloro-fluoro-methyl, di-fluoro-ethyl, di-fluoro-propyl, di-chloro-ethyl and dichloro-propyl. A per-halo-alkyl refers to an alkyl having all hydrogen atoms replaced with halo atoms.

As used herein, for compounds of formula (I), the term "heterocyclyl" or "heterocyclic" refers to a 3 to 7 membered monocyclic or 7 to 10 membered saturated or partially saturated ring or ring system, which contains at least one heteroatom selected from N, O and S, where the N and S can also optionally be oxidized to various oxidation states. 'Heterocyclyl' can be attached at a heteroatom or a carbon atom. 'Heterocyclyl' can include fused or bridged rings as well as spirocyclic rings. Examples of heterocycles include oxiranyl, aziridinyl, oxetanyl, thiethanyl, acetitinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl thiomorpholinyl, piperazinyl, azepanyl, thiepanyl and oxepanyl.

As used herein, for compounds of formula (I), the term "heteroaryl" refers to a 4-, 5-, 6-, or 7-membered monocyclic, 7-, 8-, 9-, 10-, 11-, or 12-membered bicyclic or 10-, 11-, 12-, 13-, 14- or 15-membered tricyclic unsaturated ring or ring system—carrying the highest possible number of conjugated double bonds in the ring(s), which contains at least one heteroatom selected from N, O and S, wherein the N and S can also optionally be oxidized to various oxidation states. 'Heteroaryl' can be attached at a heteroatom or a carbon atom. 'Heteroaryl' can include fused or bridged rings as well as spirocyclic rings. Examples of heteroaryl include furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl, 1,3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl and 1,3,5-triazinyl.

As used herein, for compounds of formula (II), the term "saturated heterocyclyl" for A refers to a ring system, for example a 5-, 6-, 7- or 8-membered monocyclic or 6-, 7-, 8-, 9-, 10-, 11-, or 12-membered bicyclic system and contains at least one heteroatom selected from N which is the point of attachment to the rest of the molecule. The heterocyclic group can be attached at a heteroatom or a carbon atom. The heterocyclic ring may contain 1-2 additional heteroatoms selected from N, O or S. The heterocyclyl can include fused or bridged rings as well as spirocyclic rings. Examples of heterocycles A include but are not limited to

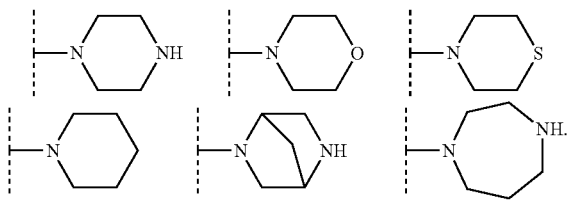

In another embodiment, examples of heterocycles A include but are not limited to

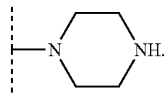

As used herein, the term "cycloalkyl" refers to saturated or partially unsaturated monocyclic, bicyclic or tricyclic hydrocarbon groups of 3-12 carbon atoms. Unless otherwise provided, cycloalkyl refers to cyclic hydrocarbon groups having between 3 and 10 ring carbon atoms or between 3 and 7 ring carbon atoms. Exemplary bicyclic hydrocarbon groups include octahydroindyl, decahydronaphthyl. Exemplary tricyclic hydrocarbon bicyclo[2.1.1]hexyl, bicyclo [2.2.1]heptyl, bicyclo[2.2.1]heptenyl, 6,6-dimethylbicyclo [3.1.1]heptyl, 2,6,6-trimethylbicyclo[3.1.1]heptyl, bicyclo [2.2.2]octy. Exemplary tetracyclic hydrocarbon groups include adamantyl.

As used herein, for compounds of formula (II), the term "cycloalkyl" preferably refers to cyclopropyl, cyclopentyl or cyclohexyl.

As used herein, the term "oxy" refers to an —O— linking group.

As used herein, the term "carboxy" or "carboxyl" is —COOH.

As used herein, all substituents are written in a way to show the order of functional groups (groups) they are composed of. The functional groups are defined herein above. The point of their attachment is indicated with a hyphen (-) or an equal sign (=), as appropriate for compounds of formula (II).

"Treatment" includes prophylactic (preventive) and therapeutic treatment as well as the delay of progression of a disease or disorder.

Various embodiments of the invention are described herein. It will be recognized that features specified in each embodiment may be combined with other specified features to provide further embodiments.

In one embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ia)

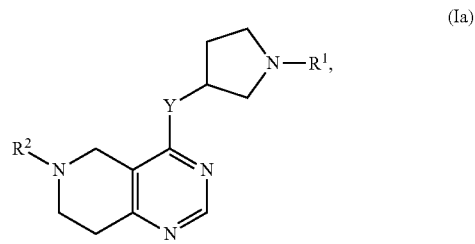

wherein $R^1$, $R^2$ and Y are as defined above.

In one embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ia')

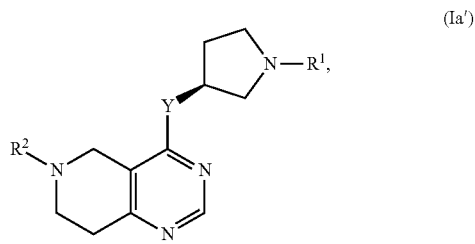

wherein $R^1$, $R^2$ and Y are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ib)

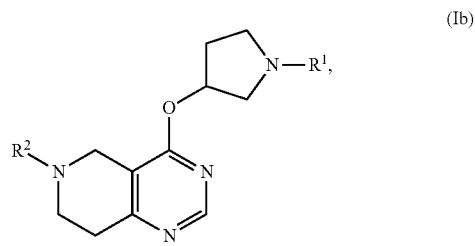

wherein $R^1$ and $R^2$ are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ib')

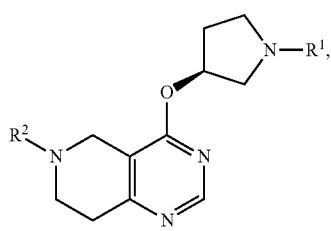

(Ib')

wherein R¹ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ic)

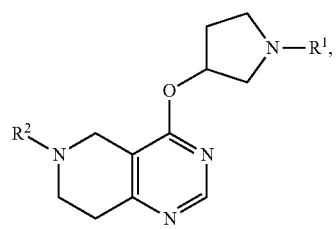

(Ic)

wherein R¹ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ic')

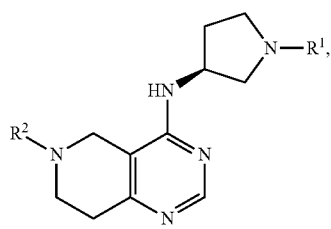

(Ic')

wherein R¹ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Id)

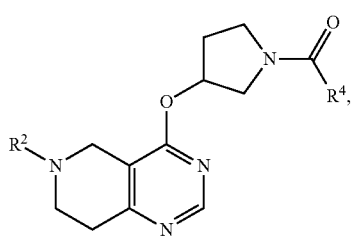

(Id)

wherein R⁴ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Id')

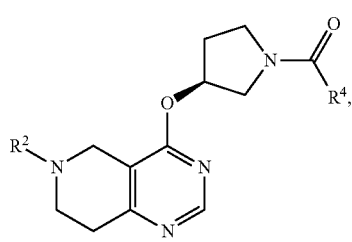

(Id')

wherein R⁴ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ie)

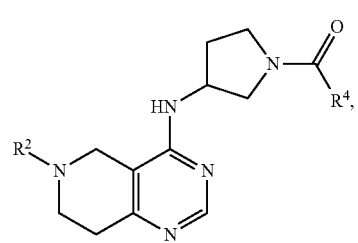

(Ie)

wherein R⁴ and R² are as defined above.

In another embodiment of the present invention, the PI3K inhibitor, wherein said inhibitor has an inhibitory action on the PI3K isoform delta, is a compound of the formula (I) and/or a pharmaceutically acceptable salt and/or a solvate thereof, selected from a compound of the formula (Ie')

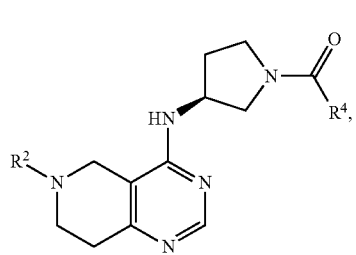

(Ie')

wherein R⁴ and R² are as defined above.

In another embodiment of the present invention, the PI3K inhibitor, wherein said inhibitor has an inhibitory action on the PI3K isoform delta, is a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein R² is selected from naphthyl, pyridyl or pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl.

In another embodiment of the present invention, the PI3K inhibitor, wherein said inhibitor has an inhibitory action on the PI3K isoform delta, is a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl, wherein one substituents is located in the para position relative to the point of connection of $R^2$ to the core of the compound.

In another embodiment of the present invention, the PI3K inhibitor, wherein said inhibitor has an inhibitory action on the PI3K isoform delta, is a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from halogen, cyano, $C_1$-$C_4$-alkyl, halo-$C_1$-$C_4$-alkyl, $C_1$-$C_4$-alkoxy or amino, wherein one substituents is located in the para position relative to the point of connection of $R^2$ to the core of the compound.

In another embodiment of the present invention, the PI3K inhibitor, wherein said inhibitor has an inhibitory action on the PI3K isoform delta, is a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of $R^2$ to the core of the compound.

In another embodiment of the present invention, the PI3K inhibitor, wherein said inhibitor has an inhibitory action on the PI3K isoform delta, is a compound of the formulae (I), (Ia) or (Ia') and/or a pharmaceutically acceptable salt and/or a solvate thereof, wherein $R^3$ is H.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') and/or a pharmaceutically acceptable salt and/or a solvate thereof, wherein $R^1$ is selected from phenyl, pyridyl, pyrimidinyl, pyrazinyl, pyridazinyl, 1,2,3-triazinyl, 1,2,4-triazinyl or 1,3,5-triazinyl.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') and/or a pharmaceutically acceptable salt and/or a solvate thereof, wherein $R^1$ is selected from pyridyl or pyrimidinyl.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') and/or a pharmaceutically acceptable salt and/or a solvate thereof, wherein
$R^1$ is —C(O)—$R^4$, wherein $R^4$ is as defined above.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') and/or a pharmaceutically acceptable salt and/or a solvate thereof, wherein
$R^1$ is —C(O)—$R^4$, wherein $R^4$ is as defined above.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein $R^4$ is selected from $C_1$-$C_8$-alkyl, $C_1$-$C_8$-alkoxy-$C_1$-$C_8$-alkyl, heterocyclyl, heterocyclyl-$C_1$-$C_8$-alkyl, $C_3$-$C_{12}$-cycloalkyl, heteroaryl, $C_1$-$C_8$-alkoxy or N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxy or $C_1$-$C_4$-alkoxy;

wherein '$C_3$-$C_{12}$-cycloalkyl' in $C_3$-$C_{12}$-cycloalkyl may be unsubstituted or substituted by 1-3 substituents independently selected from oxo, halogen, $C_1$-$C_8$-alkyl, hydroxyl, $C_1$-$C_8$-alkoxy, $C_1$-$C_8$-alkyl-carbonyl;

wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_8$-alkyl, hydroxyl, $C_1$-$C_8$-alkoxy, $C_1$-$C_8$-alkyl-carbonyl;

wherein 'heterocyclyl' can be attached at a heteroatom or a carbon atom and where the N and/or S heteroatoms can also optionally be oxidized to various oxidation states;

wherein 'heteroaryl' is selected from furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from halogen, $C_1$-$C_8$-alkyl, hydroxyl, $C_1$-$C_8$-alkoxy, $C_1$-$C_8$-alkyl-carbonyl;

wherein 'heteroaryl' can be attached at a heteroatom or a carbon atom and where the N and/or S heteroatoms can also optionally be oxidized to various oxidation states.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$—C(O)—$R^4$; or a compound of the formulae (Id), (Id'), (Ie) or (Ie') and/or a pharmaceutically acceptable salt and/or a solvate thereof, wherein $R^4$ is selected from heterocyclyl, $C_4$-$C_8$-cycloalkyl or heteroaryl;

wherein '$C_3$-$C_{12}$-cycloalkyl' may be unsubstituted or substituted by 1-3 substituents independently selected from fluoro, $C_1$-$C_4$-alkyl, hydroxyl, $C_1$-$C_4$-alkoxy;

wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;

wherein 'heterocyclyl' can be attached at a heteroatom or a carbon atom and where the N and/or S heteroatoms can also optionally be oxidized to various oxidation states;

wherein 'heteroaryl' is selected from furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from $C_1$-$C_4$-alkyl, hydroxyl;

wherein 'heteroaryl' can be attached at a heteroatom or a carbon atom and where the N and/or S heteroatoms can also optionally be oxidized to various oxidation states.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$—C(O)—$R^4$; or a compound of the formulae (Id), (Id'), (Ie) or (Ie') and/or a pharmaceutically acceptable salt and/or a solvate thereof, wherein $R^4$ is selected from heterocyclyl;

wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;

wherein 'heterocyclyl' can be attached at a heteroatom or a carbon atom and where the N and/or S heteroatoms can also optionally be oxidized to various oxidation states.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein $R^4$ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxy or $C_1$-$C_4$-alkoxy.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein $R^4$ is selected from $C_1$-$C_8$-alkyl.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of $R^2$ to the core of the compound and $R^4$ is selected from heterocyclyl;

wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;

wherein 'heterocyclyl' can be attached at a heteroatom or a carbon atom and where the N and/or S heteroatoms can also optionally be oxidized to various oxidation states.

In another embodiment of the present invention, the PI3K inhibitor, wherein said inhibitor has an inhibitory action on the PI3K isoform delta, is a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of $R^2$ to the core of the compound and $R^4$ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxy or $C_1$-$C_4$-alkoxy.

In one embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein A is a saturated heterocycle selected from

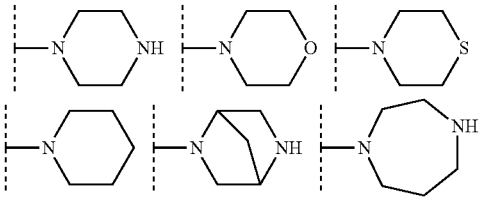

which is unsubstituted or substituted by 1-4 substituents selected from
hydroxy-
halo-
$C_1$-$C_7$-alkyl-
$C_1$-$C_7$-alkyl-carbonyl-
halo-$C_1$-$C_7$-alkyl-
halo-$C_1$-$C_7$-alkyl-carbonyl-
$C_1$-$C_7$-alkoxy-carbonyl-
oxo (O=).

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein A is a saturated heterocycle selected from

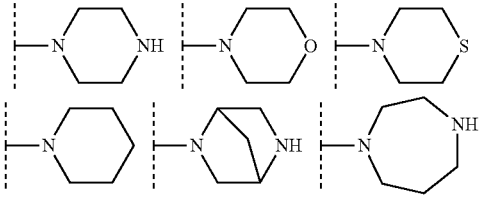

which is unsubstituted or substituted by 1-3 substituents selected from
hydroxy-
fluoro-
$C_1$-$C_4$-alkyl-
$C_1$-$C_4$-alkyl-carbonyl-
fluoro-$C_1$-$C_4$-alkyl-
oxo (O=).

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein A is a saturated heterocycle selected from

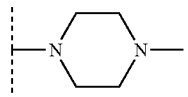

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
A is a saturated heterocycle selected from

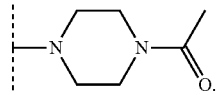

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^1$ is CH, N, $CR^{1'}$
wherein $R^1$ is selected from
halogen-
halo-$C_1$-$C_7$-alkyl-
$C_1$-$C_7$-alkyl-
$C_1$-$C_7$-alkoxy-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^1$ is CH, N, $CR^1$
wherein $R^1$ is selected from
fluoro-
$C_1$-$C_4$-alkyl-
fluoro-$C_1$-$C_4$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^1$ is CH.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^1$ is $CR^{1'}$
wherein $R^{1'}$ is selected from
fluoro-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^2$ is CH, N, $CR^{2'}$
wherein $R^{2'}$ is selected from
$C_1$-$C_7$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^2$ is CH, N, $CR^{2'}$
wherein $R^{2'}$ is selected from
$C_1$-$C_4$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^2$ is CH.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N; and
$R^{5'}$ is selected from
$C_1$-$C_7$-alkyl-
$C_1$-$C_7$-alkoxy-
halo-$C_1$-$C_7$-alkyl-oxy-
amino-
N—$C_1$-$C_7$-alkyl-amino-
N,N-di-$C_1$-$C_7$-alkyl-amino-
1-pyrrolidinyl-
1-piperazinyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N; and
$R^{5'}$ is selected from
methoxy-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
$C_1$-$C_7$-alkyl-
$C_1$-$C_7$-alkoxy-
halo-$C_1$-$C_7$-alkyl-oxy-
amino-
N—$C_1$-$C_7$-alkyl-amino-
N,N-di-$C_1$-$C_7$-alkyl-amino-
1-pyrrolidinyl-
1-piperazinyl-; and
$X^3$ is CH or $CR^{3'}$
wherein $R^{3'}$ is selected from
cyano-
halogen-
halo-$C_1$-$C_7$-alkyl-
$C_1$-$C_7$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
$C_1$-$C_4$-alkyl-
$C_1$-$C_4$-alkoxy-
fluoro-$C_1$-$C_4$-alkyl-oxy-
amino- N—$C_1$-$C_4$-alkyl-amino-
N,N-di-$C_1$-$C_4$-alkyl-amino-
1-pyrrolidinyl-
1-piperazinyl-; and
$X^3$ is CH or $CR^{3'}$
  wherein $R^{3'}$ is selected from
  cyano-
  fluoro-
  chloro-
  fluoro-$C_1$-$C_4$-alkyl-
  $C_1$-$C_4$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
methoxy-; and
$X^3$ is CH or $CR^{3'}$
  wherein $R^{3'}$ is selected from
  cyano-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
$C_1$-$C_7$-alkyl-
$C_1$-$C_7$-alkoxy-
halo-$C_1$-$C_7$-alkyl-oxy-
amino-
N—$C_1$-$C_7$-alkyl-amino-
N,N-di-$C_1$-$C_7$-alkyl-amino-
1-pyrrolidinyl-
1-piperazinyl-; and
$X^3$ is N.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
$C_1$-$C_4$-alkyl-
$C_1$-$C_4$-alkoxy-
fluoro-$C_1$-$C_4$-alkyl-oxy-
amino-
N—$C_1$-$C_4$-alkyl-amino-
N,N-di-$C_1$-$C_7$-alkyl-amino-
1-pyrrolidinyl-
1-piperazinyl-; and
$X^3$ is N.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
methoxy-; and
$X^3$ is N.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
hydrogen; and
$X^3$ is $CR^{3'}$
  wherein $R^{3'}$ is selected from
  N,N-di-$C_1$-$C_7$-alkyl-amino-carbonyl-
  N,N-di-$C_1$-$C_7$-alkyl-amino-sulfonyl-
  1-pyrrolidino-sulfonyl-
  4-morpholino-sulfonyl-
  $C_1$-$C_7$-alkyl-sulfonyl-
  $C_1$-$C_7$-alkyl-sulfonyl-amino-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is N;
$R^{5'}$ is selected from
hydrogen; and
$X^3$ is $CR^{3'}$
  wherein $R^{3'}$ is selected from
  $C_1$-$C_4$-alkyl-sulfonyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is CH;
$R^{5'}$ is selected from
$C_1$-$C_7$-alkyl-
$C_1$-$C_7$-alkoxy-
halo-$C_1$-$C_7$-alkyl-oxy-
amino-
N—$C_1$-$C_7$-alkyl-amino-
N,N-di-$C_1$-$C_7$-alkyl-amino-; and
$X^3$ is $CR^{3'}$
  wherein $R^{3'}$ is selected from
  cyano-
  halogen-
  halo-$C_1$-$C_7$-alkyl-
  $C_1$-$C_7$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is CH;
$R^{5'}$ is selected from
$C_1$-$C_4$-alkyl-
$C_1$-$C_4$-alkoxy-
fluoro-$C_1$-$C_7$-alkyl-oxy-
amino-
N—$C_1$-$C_4$-alkyl-amino-
N,N-di-$C_1$-$C_4$-alkyl-amino-; and
$X^3$ is $CR^{3'}$
  wherein $R^{3'}$ is selected from
  cyano-
  fluoro-
  chloro-fluoro-
  $C_1$-$C_4$-alkyl-
  $C_1$-$C_4$-alkyl-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is $CR^{4'}$
wherein $R^{4'}$ is selected from
$F_3C-$;
$R^{5'}$ is selected from
amino-sulfonyl-
$C_1$-$C_7$-alkyl-sulfonyl-amino-; and
$X^3$ is CH.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
$X^4$ is $CR^{4'}$
wherein $R^{4'}$ is selected from
$F_3C-$;
$R^{5'}$ is selected from
hydrogen-; and
$X^3$ is CH or $CR^{3'}$
wherein $R^{3'}$ is selected from
N,N-di-$C_1$-$C_7$-alkyl-amino-carbonyl-
N,N-di-$C_1$-$C_7$-alkyl-amino-sulfonyl-
1-pyrrolidino-sulfonyl-
4-morpholino-sulfonyl-
$C_1$-$C_7$-alkyl-sulfonyl-
$C_1$-$C_7$-alkyl-sulfonyl-amino-.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
A is a saturated heterocycle selected from

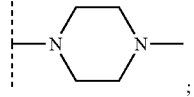

$X^1$ is CH;
$X^2$ is CH;
$X^4$ is N;
$R^5$ is selected from
methoxy-; and
$X^3$ is N.

In another embodiment of the present invention, the PI3K inhibitor, wherein said inhibitor has an inhibitory action on the PI3K isoform delta, is a compound of the formula (II) and/or a pharmaceutically acceptable salt and/or a solvate thereof, wherein
A is a saturated heterocycle selected from

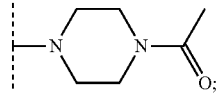

$X^1$ is $CR^1$
wherein $R^1$ is selected from fluoro-;
$X^2$ is CH;
$X^4$ is N;
$R^{5'}$ is selected from
methoxy-; and
$X^3$ is CH or $CR^{3'}$ wherein $R^{3'}$ is selected from
cyano-.

In another embodiment of the present invention, the PI3K inhibitor, wherein said inhibitor has an inhibitory action on the PI3K isoform delta, is a compound listed in the Examples section below.

In another embodiment of the present invention, the PI3K inhibitor, wherein said inhibitor has an inhibitory action on the PI3K isoform delta, is a compound of the formula (I), selected from
{(S)-3-[6-(6-Methoxy-5-methyl-pyridin-3-yl)-5,6,7,8-tetra-hydro-pyrido[4,3-d]pyrimidin-4-yloxy]-pyrrolidin-1-yl}-(tetrahydro-pyran-4-yl)-methanone;
{3-[6-(6-Methoxy-5-methyl-pyridin-3-yl)-5,6,7,8-tetra-hydro-pyrido[4,3-d]pyrimidin-4-yloxy]-pyrrolidin-1-yl}-(tetrahydro-pyran-4-yl)-methanone;
{(S)-3-[6-(2,4-Dimethoxy-pyrimidin-5-yl)-5,6,7,8-tetra-hydro-pyrido[4,3-d]pyrimidin-4-yloxy]-pyrrolidin-1-yl}-(tetrahydro-pyran-4-yl)-methanone;
{3-[6-(2,4-Dimethoxy-pyrimidin-5-yl)-5,6,7,8-tetrahydro-pyrido[4,3-d]pyrimidin-4-yloxy]-pyrrolidin-1-yl}-(tetra-hydro-pyran-4-yl)-methanone;
2-Methoxy-5-{4-[(S)-1-(tetrahydro-pyran-4-carbonyl)-pyr-rolidin-3-yloxy]-7,8-dihydro-5H-pyrido[4,3-d]pyrimidin-6-yl}-nicotinonitrile;
2-Methoxy-5-{4-[1-(tetrahydro-pyran-4-carbonyl)-pyrroli-din-3-yloxy]-7,8-dihydro-5H-pyrido[4,3-d]pyrimidin-6-yl}-nicotinonitrile;
1-{(S)-3-[6-(5,6-Dimethoxy-pyridin-3-yl)-5,6,7,8-tetra-hydro-pyrido[4,3-d]pyrimidin-4-yloxy]-pyrrolidin-1-yl}-propan-1-one;
1-{3-[6-(5,6-Dimethoxy-pyridin-3-yl)-5,6,7,8-tetrahydro-pyrido[4,3-d]pyrimidin-4-yloxy]-pyrrolidin-1-yl}-pro-pan-1-one;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(tetra-hydro-pyran-4-yl)-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-(tetra-hydro-pyran-4-yl)-methanone;
2-Amino-5-{4-[(S)-1-(tetrahydro-pyran-4-carbonyl)-pyrro-lidin-3-yloxy]-7,8-dihydro-5H-pyrido[4,3-d]pyrimidin-6-yl}-nicotinonitrile;
2-Amino-5-{4-[1-(tetrahydro-pyran-4-carbonyl)-pyrrolidin-3-yloxy]-7,8-dihydro-5H-pyrido[4,3-d]pyrimidin-6-yl}-nicotinonitrile;
(S)-(3-(6-(5-Fluoro-6-methoxypyridin-3-yl)-5,6,7,8-tetra-hydropyrido[4,3-d]pyrimidin-4-yloxy)pyrrolidin-1-yl) (tetrahydro-2H-pyran-4-yl)methanone;
(3-(6-(5-Fluoro-6-methoxypyridin-3-yl)-5,6,7,8-tetrahydro-pyrido[4,3-d]pyrimidin-4-yloxy)pyrrolidin-1-yl)(tetra-hydro-2H-pyran-4-yl)methanone;
(S)-2-Methoxy-5-(4-(1-(2-methoxyacetyl)pyrrolidin-3-yloxy)-7,8-dihydropyrido[4,3-d]pyrimidin-6(5H)-yl) nicotinonitrile;
2-Methoxy-5-(4-(1-(2-methoxyacetyl)pyrrolidin-3-yloxy)-7,8-dihydropyrido[4,3-d]pyrimidin-6(5H)-yl)nicotinoni-trile;
(S)-5-(4-(1-(Cyclopentanecarbonyl)pyrrolidin-3-yloxy)-7, 8-dihydropyrido[4,3-d]pyrimidin-6(5H)-yl)-2-methoxynicotinonitrile;
5-(4-(1-(Cyclopentanecarbonyl)pyrrolidin-3-yloxy)-7,8-di-hydropyrido[4,3-d]pyrimidin-6(5H)-yl)-2-methoxynico-tinonitrile;

(2,4-Dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

(2,4-Dimethyl-oxazol-5-yl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

(3-Methoxy-cyclobutyl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

(3-Methoxy-cyclobutyl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

({(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;

({3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;

1-(4-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;

1-(4-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;

5-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;

5-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;

(4,4-Difluoro-cyclohexyl)-{(S)-3-[6-(5,6-dimethoxy-pyridin-3-yl)-5,6,7,8-tetrahydro-pyrido[4,3-d]pyrimidin-4-yloxy]-pyrrolidin-1-yl}-methanone;

(4,4-Difluoro-cyclohexyl)-{3-[6-(5,6-dimethoxy-pyridin-3-yl)-5,6,7,8-tetrahydro-pyrido[4,3-d]pyrimidin-4-yloxy]-pyrrolidin-1-yl}-methanone;

2-Methoxy-5-{4-[(S)-1-(2-tetrahydro-pyran-4-yl-acetyl)-pyrrolidin-3-yloxy]-7,8-dihydro-5H-pyrido[4,3-d]pyrimidin-6-yl}-nicotinonitrile;

2-Methoxy-5-{4-[1-(2-tetrahydro-pyran-4-yl-acetyl)-pyrrolidin-3-yloxy]-7,8-dihydro-5H-pyrido[4,3-d]pyrimidin-6-yl}-nicotinonitrile;

5-{4-[(S)-1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;

5-{4-[1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;

5-{4-[(S)-1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;

5-{4-[1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
Isoxazol-3-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-3-yl-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-5-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-5-yl-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
2-Methoxy-5-{4-[(S)-1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-3-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-3-carbonyl)-pyrrolidin-3-yloxy]-7,8-dihydro-5H-pyrido[4,3-d]pyrimidin-6-yl}-nicotinonitrile;
(2,2-Dimethyl-tetrahydro-pyran-4yl)-{(S)-3-[6-(6-Methoxy-5-methyl-pyridin-3-yl)-5,6,7,8-tetrahydropyrido[4,3-d]pyrimidin-4-yloxy]-pyrrolidin-1-yl}-methanone;
(2,2-Dimethyl-tetrahydro-pyran-4yl)-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(S)-(2,4-Dimethyloxazol-5-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(2,4-Dimethyloxazol-5-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(thiazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(thiazol-5-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-pyrazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-pyrazol-5-yl)methanone;
4-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-3-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-3-yl)methanone;
(S)-(1H-Imidazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(1H-Imidazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
5-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
5-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(S)-(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;
(S)-(3-(6-(6-methoxy-5-(trifluoromethyl)pyridin-3-yl)-5,6,7,8-tetrahydropyrido[4,3-d]pyrimidin-4-yloxy)pyrrolidin-1-yl)(5-methyl-1,3,4-oxadiazol-2-yl)methanone;
(3-(6-(6-methoxy-5-(trifluoromethyl)pyridin-3-yl)-5,6,7,8-tetrahydropyrido[4,3-d]pyrimidin-4-yloxy)pyrrolidin-1-yl)(5-methyl-1,3,4-oxadiazol-2-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyrazin-2-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyrazin-2-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-imidazol-4-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-imidazol-4-yl)methanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone;

{(S)-3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

(S)-(3-(6-(6-Amino-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Amino-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-yloxy)azetidin-1-yl)(tetrahydro-2H-pyran-4-yl)methanone;

{(S)-3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

[(S)-3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone;

[3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(S)-1-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)-3,3-dimethylbutan-1-one;

1-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)-3,3-dimethylbutan-1-one;

1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one;

1-{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one;

2-Methoxy-5-[4-((S)-1-propionyl-pyrrolidin-3-yloxy)-7,8-dihydro-5H-pyrido[4,3-d]pyrimidin-6-yl]-nicotinonitrile;

2-Methoxy-5-[4-(1-propionyl-pyrrolidin-3-yloxy)-7,8-dihydro-5H-pyrido[4,3-d]pyrimidin-6-yl]-nicotinonitrile;

(S)-6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

(S)-6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

(S)-1-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)propan-1-one;

1-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)propan-1-one;

(S)-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(tetrahydro-2H-pyran-4-yl)methanone;

(S)-2-Methoxy-5-(4-(1-(tetrahydro-2H-pyran-4-carbonyl)pyrrolidin-3-ylamino)-7,8-dihydropyrido[4,3-d]pyrimidin-6(5H)-yl)nicotinonitrile;

2-Methoxy-5-(4-(1-(tetrahydro-2H-pyran-4-carbonyl)pyrrolidin-3-ylamino)-7,8-dihydropyrido[4,3-d]pyrimidin-6(5H)-yl)nicotinonitrile;

(S)-1-(4-(3-(6-(6-Methoxy-5-(trifluoromethyl)pyridin-3-yl)-5,6,7,8-tetrahydropyrido[4,3-d]pyrimidin-4-ylamino)pyrrolidine-1-carbonyl)piperidin-1-yl)ethanone;

1-(4-(3-(6-(6-Methoxy-5-(trifluoromethyl)pyridin-3-yl)-5,6,7,8-tetrahydropyrido[4,3-d]pyrimidin-4-ylamino)pyrrolidine-1-carbonyl)piperidin-1-yl)ethanone;

(2,2-Dimethyltetrahydro-2H-pyran-4-yl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(2,2-Dimethyltetrahydro-2H-pyran-4-yl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(S)-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(oxazol-5-yl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(oxazol-5-yl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

((1s,4R)-4-Hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1s,4R)-4-Hydroxycyclohexyl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1r,4S)-4-Hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1r,4S)-4-Hydroxycyclohexyl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;
(S)-(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;
(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;
(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;
(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;
(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;
(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;
(2,2-Dimethyltetrahydro-2H-pyran-4-yl)((S)-3-(6-(6-methoxy-5-methylpyridin-3-yl)-5,6,7,8-tetrahydropyrido[4,3-d]pyrimidin-4-ylamino)pyrrolidin-1-yl)methanone;
(2,2-Dimethyltetrahydro-2H-pyran-4-yl)(3-(6-(6-methoxy-5-methylpyridin-3-yl)-5,6,7,8-tetrahydropyrido[4,3-d]pyrimidin-4-ylamino)pyrrolidin-1-yl)methanone;
(S)-1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;
1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;
(S)-(3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;
(3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;
(S)-(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;
(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;
(Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone;
(Tetrahydro-pyran-4-yl)-{3-{6-(5-(trifluoromethyl)pyridin-3-yl)-5,6,7,8-tetrahydropyrido[4,3-d]pyrimidin-4-ylamino)pyrrolidin-1-yl}-methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;
(S)-(4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)—N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;
N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;
(S)-1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;
1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;
(S)-2-Methoxy-5-(4-(1-(morpholine-4-carbonyl)pyrrolidin-3-yloxy)-7,8-dihydropyrido[4,3-d]pyrimidin-6(5H)-yl)nicotinonitrile;
2-Methoxy-5-(4-(1-(morpholine-4-carbonyl)pyrrolidin-3-yloxy)-7,8-dihydropyrido[4,3-d]pyrimidin-6(5H)-yl)nicotinonitrile;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;
1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;
1-(4-{3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;
{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;
{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;
{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;
{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;
{(S)-3-[6-(6-Methoxy-pyridin-3-yl)-5,6,7,8-tetrahydro-pyrido[4,3-d]pyrimidin-4-yloxy)pyrrolidin-1-yl}-(tetrahydro-pyran-4-yl)-methanone; or
{3-[6-(6-Methoxy-pyridin-3-yl)-5,6,7,8-tetrahydropyrido[4,3-d]pyrimidin-4-yloxy)pyrrolidin-1-yl}-(tetrahydro-pyran-4-yl)-methanone.

In view of the close relationship between the compounds of the formula (I) or formula (II) in free form and those in the form of their salts, including those salts that can be used as intermediates, for example in the purification or identification of the novel compounds, any reference to the compounds or a compound of the formula (I) or formula (II) hereinbefore and hereinafter is to be understood as referring to the compound in free form and/or also to one or more salts thereof, as appropriate and expedient, as well as to one or more solvates, e.g. hydrates.

The compounds of formula (I) or formula (II) or salts thereof are prepared in accordance with processes known per se, though not previously described for the manufacture of the compounds of the formula (I) or formula (II), respectively.

As used herein, the term "pharmaceutically acceptable salts" refers to salts that retain the biological effectiveness and properties of the PI3K inhibitors, wherein said inhibitors have an inhibitory action on the PI3K isoform delta, and, which typically are not biologically or otherwise undesirable. In many cases, the PI3K inhibitors, wherein said inhibitors have an inhibitory action on the PI3K isoform delta, used in the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns 1 to 12 of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

For isolation or purification purposes it is also possible to use pharmaceutically unacceptable salts, for example picrates or perchlorates. For therapeutic use, only pharmaceutically acceptable salts or free compounds are employed.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the progression of the disease or disorder.

As used herein, a subject is "in need of" a treatment if such subject would benefit biologically, medically or in quality of life from such treatment.

The term "administration" or "administering" of the subject compound means providing a PI3K inhibitor, wherein said inhibitor has an inhibitory action on the PI3K isoform delta, to a subject in need of treatment. Administration "in combination with" one or more further therapeutic agents includes simultaneous (concurrent) and consecutive administration in any order, and in any route of administration.

The invention also provides the use of a pharmaceutical compositions comprising a PI3K inhibitor, wherein said inhibitors have an inhibitory action on the PI3K isoform delta. The invention thus provides the use of a pharmaceutical composition comprising a PI3K inhibitor, wherein said inhibitor has an inhibitory action on the PI3K isoform delta, and one or more carriers/excipients;

a pharmaceutical composition comprising a therapeutically effective amount of a PI3K inhibitor, wherein said inhibitor has an inhibitory action on the PI3K isoform delta, and one or more pharmaceutically acceptable carriers/excipients.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The present invention provides the use of a pharmaceutical composition comprising a PI3K inhibitor, wherein said inhibitor has an inhibitory action on the PI3K isoform delta, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art. Suitable compositions for oral administration include an effective amount of a PI3K inhibitor, wherein said inhibitor has an inhibitory action on the PI3K isoform delta, in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed.

Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a PI3K inhibitor, wherein said inhibitor has an inhibitory action on the PI3K isoform delta, with a suitable carrier. Carriers suitable for transdermal delivery include absorbable pharmacologically acceptable solvents to assist passage through the skin of the subject. For example, transdermal devices are in the form of a bandage comprising a backing member, a reservoir containing the PI3K inhibitor, wherein said inhibitor has an inhibitory action on the PI3K isoform delta, optionally with carriers, optionally a rate controlling barrier to deliver the PI3K inhibitor, wherein said inhibitor has an inhibitory action on the PI3K isoform delta, of the skin of the subject at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder, either alone, as a mixture, for example a dry blend with lactose, or a mixed component particle, for example with phospholipids, from a dry powder inhaler or an aerosol spray presentation from a pressurised container, pump, spray, atomizer or nebuliser, with or without the use of a suitable propellant.

The present invention further provides the use of anhydrous pharmaceutical compositions and dosage forms comprising the PI3K inhibitors, wherein said inhibitors have an inhibitory action on the PI3K isoform delta, as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers, e.g., vials, blister packs, and strip packs.

The invention further provides the use of pharmaceutical compositions and dosage forms that comprise one or more agents that reduce the rate by which the PI3K inhibitor, wherein said inhibitor has an inhibitory action on the PI3K isoform delta, as an active ingredient will decompose. Such agents, which are referred to herein as "stabilizers," include, but are not limited to, antioxidants such as ascorbic acid, pH buffers, or salt buffers, etc.

Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Suitable excipients/carriers may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The dosage of the active ingredient depends upon the disease to be treated and upon the species, its age, weight, and individual condition, the individual pharmacokinetic data, and the mode of administration. The amount of active ingredient in a formulation can vary within the full range employed by those skilled in the art.

Pharmaceutical compositions comprising a PI3K inhibitor, wherein said inhibitor has an inhibitory action on the PI3K isoform delta in association with at least one pharmaceutical acceptable carrier (such as excipient and/or diluent) may be manufactured in conventional manner, e.g. by means of conventional mixing, granulating, coating, dissolving or lyophilising processes.

The invention also relates to the use of combinations comprising a PI3K inhibitor, wherein said inhibitor has an inhibitory action on the PI3K isoform delta, and one or more additional active ingredients. The invention thus provides the use of

- a combination in particular a pharmaceutical combination, comprising a therapeutically effective amount of a PI3K inhibitor, wherein said inhibitor has an inhibitory action on the PI3K isoform delta, and one or more therapeutically active agents, for the treatment of malaria, leishmaniasis, toxoplasmosis, trypanosomiasis, and/or neurocysticercosis; especially acute and cerebral malaria and/or Chagas disease
- a combined pharmaceutical composition, adapted for simultaneous or sequential administration, comprising a therapeutically effective amount of a PI3K inhibitor, wherein said inhibitor has an inhibitory action on the PI3K isoform delta, as defined herein; therapeutically effective amount(s) of one or more combination partners for the treatment of malaria, leishmaniasis, toxoplasmosis, trypanosomiasis, and/or neurocysticercosis; especially acute and cerebral malaria and/or Chagas disease.

The term "a therapeutically effective amount" of a PI3K inhibitor, wherein said inhibitor has an inhibitory action on the PI3K isoform delta, refers to an amount of the PI3K inhibitor, wherein said inhibitor has an inhibitory action on the PI3K isoform delta, that will elicit the biological or medical response of a subject, for example, reduction or inhibition of an enzyme or a protein activity, or ameliorate symptoms, alleviate conditions, slow or delay disease progression, or prevent a disease, etc.

"Combination" refers to either a fixed combination in one dosage unit form, or a kit of parts for the combined administration where a PI3K inhibitor, wherein said inhibitor has an inhibitory action on the PI3K isoform delta, and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof, e.g. a patient, and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a PI3K inhibitor, wherein said inhibitor has an inhibitory action on the PI3K isoform delta, and a combination partner, are both administered to a patient simultaneously in the form of a single entity or dosage. The term "non-fixed combination" means that the active ingredients, e.g. a PI3K inhibitor, wherein said inhibitor has an inhibitory action on the PI3K isoform delta, and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The PI3K inhibitor, wherein said inhibitor has an inhibitory action on the PI3K isoform delta, may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, PI3K inhibitors, wherein said inhibitors have an inhibitory action on the PI3K isoform delta, may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt;

mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C(PNU 156804), [4-(4'-hydroxyphenyl)-amino-6,7-dimethoxyquinazoline](WHI-P131), [4-(3'-bromo-4'-hydroxylphenyl)-amino-6,7-dimethoxyquinazoline](WHI-P154), [4-(3',5'-dibromo-4'-hydroxylphenyl)-amino-6,7-dimethoxyquinazoline]WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

PI3K inhibitors, wherein said inhibitors has an inhibitory action on the PI3K isoform delta, may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPARγ agonist), activated charcoal, Erythropoietin, Levamisole, and pyronaridine.

PI3K inhibitors, wherein said inhibitors have an inhibitory action on the PI3K isoform delta, may also be used to advantage in combination with each other or in combination with other therapeutic agents, such as used for the treatment of Leishmaniosis, Trypanosomiasis, Toxoplasmosis and Neurocysticercosis. Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposomal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with s, wherein said inhibitor has an inhibitory action on the PI3K isoform delta, can be prepared and administered as described in the art, such as in the documents cited above.

PI3K inhibitors, wherein said inhibitors have an inhibitory action on the PI3K isoform delta, may also be used to advantage in combination with known therapeutic processes.

EXPERIMENTAL DETAILS

Insofar as the production of the starting materials is not particularly described, the compounds are known or may be prepared analogously to methods known in the art or as described hereafter.

The following examples are illustrative of the invention without any limitation.

Abbreviations:
Ar aryl
AcOH acetic acid
aq aqueous
Ar aryl
BOC tert-butyl-carbonate
BOP benzotriazol-1-yloxytris(dimethylamino)phosphonium hexafluorophosphate
br.s. broad singlet
BSA bovine serum albumin
$CDCl_3$ chloroform-d
CDI 1,1'-carbonyldiimidazole
$CH_2Cl_2$ dichloromethane
$CH_3CN$ acetonitrile
$Cs_2CO_3$ cesium carbonate
d doublet
dd doublet of doublets
DIPEA N-ethyldiisopropylamine
DME 1,4-dimethoxyethane
DMF N,N-dimethylformamide
DBU 1,8-diaza-7-bicyclo[5.4.0]undecene
DMSO dimethylsulfoxide
dt doublet of triplets
EDC 1-ethyl-3-(3-dimethylaminopropyl)carbodiimide hydrochloride
eq. equivalent
EtOAc ethyl acetate
FCC flash column chromatography
h hour
HBTU (2-(1H-benzotriazole-1-yl)-1,1,3,3-tetramethyluronium hexafluorophosphate
HCl hydrochloric acid
HOBT benzotriazol-1-ol
HPLC high pressure liquid chromatography
HT high throughput
$H_2O$ water
Hyflo Hyflo Super Cel Medium
IFN Interferon (e.g. IFN-α=Interferon-α)
IL Interleukin (e.g. IL-6=Interleukin-6)
Isolute®SCX-2 polymer supported sulfonic acid macroporous polystyrene
K kelvin
$K_2CO_3$ potassium carbonate
LC liquid chromatography
M molar
MeCN acetonitrile
MeOD methanol-d4
MeOH methanol
2-Me-THF 2-methyltetrahydrofuran MgSO$_4$ magnesium sulfate
MHz mega herz
MS mass spectroscopy
m multiplet
mBar millibar
mL milliliter
mm millimeter
mM millimolar
min. minute
mw microwave
NaOH sodium hydroxide
Na$_2$SO$_4$ sodium sulfate
NaHCO$_3$ sodium hydrogen carbonate
NaO$^t$Bu sodium tert-butoxide
NEt$_3$ triethylamine
NH$_3$ ammonia
NH$_4$OH concentrated solution of ammonia in water possessing a specific gravity of 0.88
NMP N-methylpyrrolidinone
NMR nuclear magnetic resonance
OBD optimum bed density
Pd(OAc)$_2$ palladium acetate
Pd(OH)$_2$/C palladium hydroxide on carbon
Pd$_2$(dba)$_3$ tris(dibenzylideneacetone)dipalladium
Pd$_2$(dba)$_3$.CHCl$_3$ tris(dibenzylideneacetone)dipalladium chloroform complex
PL-HCO$_3$ MP polymer supported hydrogen carbonate macroporous polystyrene
PL-SO$_3$H MP polymer supported sulfonic acid macroporous polystyrene
rt room temperature
Rt retention time
s singulet
SCX-2 polymer supported sulfonic acid macroporous polystyrene
t triplet
TBME tert-butylmethyl ether
tBuOK potassium tert-butoxide
tert-BuONa sodium tert-butoxide
TFA trifluoroacetic acid
THF tetrahydrofuran
UPLC ultra performance liquid chromatography
X-Phos dicyclohexyl(2',4',6'-triisopropylbiphenyl-2-yl)phosphine
Microwave equipment used is a Biotage Initiator®
All compounds are named using AutoNom.
LCMS Methods Used:

LC Method 1 (Rt$^{(1)}$): The retention times (Rt) were obtained on a Agilent HPLC system with an Ascentis®Express column C18 30×2.1 mm, 2.7 µm (Supelco) applying a gradient (H$_2$O+0.05% formic acid+3.75 mM Ammonium acetate)/(CH$_3$CN+0.04% formic acid) 90/10 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC Method 2 (Rt$^{(2)}$): The retention times (Rt) were obtained on a Agilent HPLC system with an Ascentis®Express column C18 30×2.1 mm, 2.7 µm (Supelco) applying a gradient (H$_2$O+0.05% formic acid+3.75 mM Ammonium acetate)/(CH$_3$CN+0.04% formic acid) 95/5 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC Method 3 (Rt$^{(3)}$): The retention times (Rt) were obtained on a Agilent HPLC system with an Ascentis®Express column C18 30×2.1 mm, 2.7 µm (Supelco) applying a gradient (H$_2$O+0.05% formic acid+3.75 mM Ammonium acetate)/(CH$_3$CN+0.04% formic acid) 99/1 over 0.5 min and 1.2 mL/min as solvent flow then 99/1 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC Method 4 (Rt$^{(4)}$): The retention times (Rt) were obtained on a Agilent HPLC system with an Ascentis®Express column C18 30×2.1 mm, 2.7 µm (Supelco) applying a gradient (H$_2$O+0.05% formic acid+3.75 mM Ammonium acetate)/(CH$_3$CN+0.04% formic acid) 90/10 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC Method 5 (Rt$^{(5)}$): The retention times (Rt) were obtained on a Agilent HPLC system with an Ascentis®Express column C18 30×2.1 mm, 2.7 µm (Supelco) applying a gradient (H$_2$O+0.05% TFA)/(CH$_3$CN+0.04% TFA) 95/5 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC Method 6 (Rt$^{(6)}$): The retention times (Rt) were obtained on a Agilent HPLC system with an Ascentis®Express column C18 30×2.1 mm, 2.7 µm (Supelco) applying a gradient (H$_2$O+TFA)/(CH$_3$CN+0.04% TFA) 99/1 over 0.5 min and 1.2 mL/min as solvent flow then 99/1 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC Method 7 (Rt$^{(7)}$): The retention times (Rt) were obtained on a Waters Agilent HPLC system with an Ascentis®Express column C18 30×2.1 mm, 2.7 µm (Supelco) applying a gradient (H$_2$O+0.05% TFA)/(CH$_3$CN+0.04% TFA) 90/10 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC Method 8 (Rt$^{(8)}$): The retention times (Rt) were obtained on a Waters HPLC alliance-HT system with an XTerra column MS C18, 50×4.6 mm, 5 µm, reverse phase, applying a gradient (H$_2$O+0.1% TFA)/(CH$_3$CN+0.1% TFA) 95/5 to 0/100 over 8.0 min and 2.0 mL/min as solvent flow and 45° C. for the oven temperature. Detection method UV 220-400 nm-MS.

LC Methode 1' (Rt$^{(1')}$): The retention times (Rt) were obtained on a Waters HPLC alliance-HT system with a XBridge MS column C18 30/3.0 2.5 m applying a gradient H$_2$O (+0.1% formic acid)/CH$_3$CN (+0.1% formic acid) 90/10 to 5/95 over 1.7 minutes and 1.2 mL/min. as solvent flow and 40° C. for the oven temperature.

LC Methode 2' (Rt$^{(2')}$): The retention times (Rt) were obtained on a Waters HPLC alliance-HT system with a XBridge MS column C18 30/3.0 2.5 m applying a gradient H$_2$O (+0.1% TFA)/CH$_3$CN (+0.1% TFA) 90/10 to 5/95 over 1.7 minutes and 1.2 mL/min. as solvent flow and 40° C. for the oven temperature.

LC Methode 3' (Rt$^{(3')}$): The retention times (Rt) were obtained on a Waters HPLC alliance-HT system with a XBridge MS column C18 30/3.0 2.5 m applying a gradient H$_2$O (+0.1% TFA)/CH$_3$CN (+0.1% TFA) 95/5 to 5/95 over 3.7 minutes and 1.2 mL/min. as solvent flow and 40° C. for the oven temperature.

LC Methode 4' (Rt$^{(4')}$): The retention times (Rt) were obtained on a Waters HPLC alliance-HT system with a SunFire column C18 20×4.6 mmm applying a gradient H$_2$O (+0.1% TFA)/CH$_3$CN (+0.1% TFA) 95/5 to 0/100 over 4 minutes and 1 mL/min. as solvent flow and 45° C. for the oven temperature.

LC Method 5' (Rt$^{(5')}$): The retention times (Rt) were obtained on a Waters UPLC-MS system with a Acquity UPLC BEH C18 50×2.1 mm, 1.7 um column applying a gradient H$_2$O (+0.1% formic acid)/CH$_3$CN (+0.1% formic acid) 95/5 to 10/90 over 4 minutes and 0.7 mL/min. as solvent flow and 30° C. for the oven temperature.

LC Method 6' (Rt$^{(6')}$): The retention times (Rt) were obtained on a Waters UPLC-MS system with a Acquity UPLC BEH C18 50×2.1 mm, 1.7 um column applying a gradient H$_2$O (+0.1% formic acid)/CH$_3$CN (+0.1% formic acid) 80/20 to 5/95 over 4.2 minutes and 0.7 mL/min. as solvent flow and 30° C. for the oven temperature.

LC Method 7' (Rt$^{(7')}$): The retention times (Rt) were obtained on a Waters HPLC alliance-HT system with a XBridge MS column C18 30/3.0 2.5 m applying a gradient H$_2$O (+0.1% formic acid)/CH$_3$CN (+0.1% formic acid) 95/5 to 5/95 over 3.7 minutes and 1.2 mL/min. as solvent flow and 40° C. for the oven temperature.

LC Method 8' (Rt$^{(8')}$): The retention times (Rt) were obtained on a Waters HPLC alliance-HT system with a XBridge MS column C18 30/3.0 2.5 m applying a gradient H$_2$O (+0.1% formic acid)/CH$_3$CN (+0.1% formic acid) 99/1 to 5/95 over 2.2 minutes and 1.2 mL/min. as solvent flow and 40° C. for the oven temperature.

LC Method 9' (Rt$^{(9')}$): The retention times (Rt) were obtained on a Waters HPLC alliance-HT system with a XBridge MS column C18 30/3.0 2.5 m applying a gradient H$_2$O (+0.1% TFA)/CH$_3$CN (+0.1% TFA) 99/1 to 5/95 over 2.2 minutes and 1.2 mL/min. as solvent flow and 40° C. for the oven temperature.

LC Method 10' (Rt$^{(10')}$): The FIA-MS (MS) were obtained on a Waters HPLC-MS instrument.

Purification Method:
Preparative Reverse Phase Gilson HPLC
  Method A: Column SunFire prep C18 OBD 5 µm, 30×100 mm from WATERS, with H$_2$O+0.1% TFA and Acetonitrile+0.1% TFA as mobile phase. Detection method UV 220-400 nm
  Method B: Column Atlantis prep T3 OBD 5 µm, 30×150 mm from WATERS, with H$_2$O+0.1% TFA and Acetonitrile+0.1% TFA as mobile phase. Detection method UV 220-400 nm
  Method C: Column XTerra RP18 OBD 5 µm, 19×50 mm from WATERS, with H$_2$O+0.1% TFA and Acetonitrile+0.1% TFA as mobile phase. Detection method UV 220-400 nm X-Ray Powder Diffraction
Instrumentation:

| Method X1 | |
|---|---|
| Instrument | Bruker AXS, D8 Advance |
| Irradiation | CuKα (30 kV, 40 mA) |
| Detector | PSD (Vantec) detector |
| Scan range | 2°-40° (2 theta value) |

| Method X2 | |
|---|---|
| Instrument | Bruker D8 GADDS Discover |
| Irradiation | CuKα (40 kV, 40 mA) |
| Detector | HI-STAR Area detector |
| Scan range | 6°-40° (2 theta value) |

Preparation of Intermediate Compounds

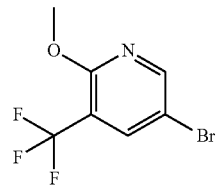

Intermediate 1

5-Bromo-2-methoxy-3-trifluoromethyl-pyridine

To 2-methoxy-3-(trifluoromethyl)pyridine (20.0 g, 113.0 mmol) and 1,3-dibromo-5,5-dimethylimidazolidine-2,4-dione (43.6 g, 152.0 mmol) was added TFA (80 mL) and the resulting mixture stirred at rt for 18 h under argon. The TFA was removed in vacuo (50 mbar, 45° C.) and the residue suspended in tert-butyl methyl ether (200 mL). The resulting colourless solid was removed by filtration and washed with tert-butyl methyl ether (50 mL). The filtrate was concentrated in vacuo and suspended in EtOAc (50 mL) The insoluble colourless solid was removed by filtration and washed with EtOAc (50 mL). The filtrate was concentrated in vacuo, diluted with heptane/tert-butyl methyl ether (5/1, 20 mL) and the insoluble colourless solid was removed by filtration. The filtrate was purified by column chromatography on silica gel with heptane/EtOAc, 100/0 to 90/10. The crude product was filtered through a plug of NaHCO$_3$ (20 g) and the filtrate evaporated in vacuo to give a golden oil (27.9 g). The oil was dissolved in heptanes (20 mL) and purified by filtered through a plug of silica gel (80 g), eluting with heptane to give 5-bromo-2-methoxy-3-(trifluoromethyl) pyridine as a colourless oil (22.5 g, 74% yield). $^1$H-NMR (400 MHz, DMSO-d$_6$, 298 K): δ ppm 4.03 (s, 3H) 7.95 (d, 1H) 8.4 (d, 1H).

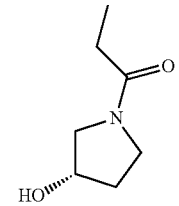

Intermediate 2

1-((S)-3-Hydroxy-pyrrolidin-1-yl)-propan-1-one (S)-Pyrrolidin-3-ol (10.0 g, 81.0 mmol), triethylamine (23.6 mL, 170.0 mmol) and CH$_2$Cl$_2$ (150 mL) were combined in a pear-shaped flask to give a beige suspension. The mixture was cooled to −10° C. and propionyl chloride (7.06 mL, 81.0 mmol) was added dropwise over 15 min, maintaining the temperature between −10 to 0° C. The resulting beige suspension was stirred for 2 h at 0° C. MeOH (9.8 mL) was added and the mixture allowed to warm to room temperature then stirred for 1 h to give a brown solution. The mixture was evaporated in vacuo to give a beige residue which was stirred in diethylether (200 mL) and filtered. The filtrate was evaporated in vacuo to give 1-((S)-3-hydroxy-pyrrolidin-1-yl)-propan-1-one as a yellow oil (11.23 g, 95% yield). $^1$H-NMR (400 MHz, DMSO-$d_6$, 298 K): δ ppm 0.92-1.02 m, 3H) 1.67-1.97 (m, 2H) 2.13-2.28 (m, 2H) 3.18-3.52 (m, 4H) 4.17-4.32 (m, 1H) 4.85-4.97 (m, 1H). LCMS: [M+H]+=144.0

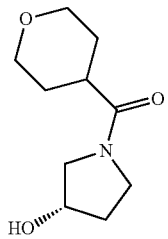

Intermediate 3

((S)-3-Hydroxy-pyrrolidin-1-yl)-(tetrahydro-pyran-4-yl)-methanone

The (S)-pyrrolidin-3-ol hydrochloride (3.69 g, 29.9 mmol) and triethylamine (6.65 g, 9.16 mL, 65.7 mmol) were put in $CH_2Cl_2$ (15 mL). The suspension was cooled at ~3° C. To this mixture, a solution of tetrahydro-pyran-4-carbonyl chloride (4.67 g, 29.9 mmol) in $CH_2Cl_2$ (15 mL) was added slowly. Then the resulting reaction mixture was stirred for 1.5 h at 3-10° C. The reaction mixture was then concentrated to give a powder. To this powder, addition of EtOAc (100 mL). The solid was filtered and washed with EtOAc. The recovered filtrate was then concentrated to give ((S)-3-hydroxy-pyrrolidin-1-yl)-(tetrahydro-pyran-4-yl)-methanone as beige powder. (6.77 g, 98% yield). $^1$H-NMR (400 MHz, Methanol-$d_4$, 298 K): δ ppm 1.59-2.15 (m, 6H) 2.69-2.86 (m, 1H) 3.43-3.75 (m, 6H) 3.94-4.00 (m, 2H) 4.37-4.48 (m, 1H). LCMS: [M+H]+=199.9, $Rt^{(6)}$=0.86 min

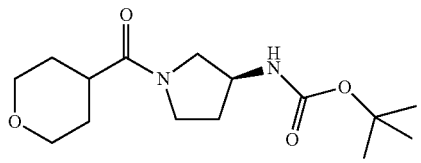 [SMILES: CC(C)(C)OC(=O)N[C@H]1CCN(C(=O)C2CCOCC2)C1]

Intermediate 4

[(S)-1-(Tetrahydro-pyran-4-carbonyl)-pyrrolidin-3-yl]-carbamic acid tert-butyl ester To a vigorously stirring solution of tetrahydro-2H-pyran-4-carbonyl chloride (0.455 g, 3.06 mmol) in $CH_2Cl_2$ (10 mL) was added simultaneously portionwise sat. $NaHCO_3$ (aq) (10 mL) and a solution of the (S)-pyrrolidin-3-yl]-carbamic acid tert-butyl ester (570 mg, 3.06 mmol) at rt. The resulting biphasic mixture was stirred vigorously at rt for 3 h. The organic layer was separated by filtration through a phase separation tube, concentrated in vacuo and purified by flash chromatography on silica gel with $CH_2Cl_2$/MeOH to give [(S)-1-(tetrahydro-pyran-4-carbonyl)-pyrrolidin-3-yl]-carbamic acid tert-butyl ester as a colourless gum (0.623 g, 68% yield) LCMS: [M+H]+=299.6, $Rt^{(7)}$=0.73 min.

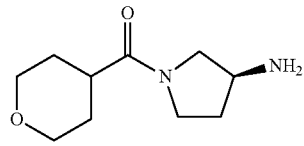 [SMILES: N[C@H]1CCN(C(=O)C2CCOCC2)C1]

Intermediate 5

(S)-3-Amino-pyrrolidin-1-yl-(tetrahydro-pyran-4-yl)-methanone

To (S)-1-(tetrahydro-pyran-4-carbonyl)-pyrrolidin-3-yl]-carbamic acid tert-butyl ester (intermediate 4) (0.623 g, 2.09 mmol) in $CH_2Cl_2$ (2.0 mL) was added TFA (2.0 mL) and the resulting mixture stood at rt for 8 h. Evaporated in vacuo and eluted through an Isolute® SCX-2 cartridge, eluting with methanol, then with 2M ammonia in methanol. Basic fractions were concentrated in vacuo to give [(S)-3-amino-pyrrolidin-1-yl-(tetrahydro-pyran-4-yl)-methanone as a colourless solid (0.34 g, 82% yield) LCMS: [M+H]+=199.0, $Rt^{(3)}$=0.1 min.

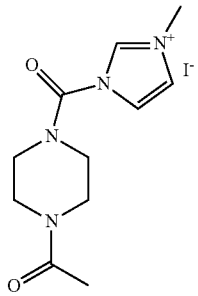 [SMILES: CC(=O)N1CCN(C(=O)n2cc[n+](C)c2)CC1 ; [I-]]

Intermediate 6

3-(4-Acetyl-piperazine-1-carbonyl)-1-methyl-3H-imidazol-3-ium iodide 1-(Piperazin-1-yl)ethanone (143 mg, 1.12 mmol) and CDI (199 mg, 1.23 mmol) were refluxed in THF (10 mL) under argon overnight. Cooled to room temperature, diluted with $CH_2Cl_2$ (20 mL) and water (5 mL) and the organic layer filtered through a phase separation tube and concentrated in vacuo. Dissolved in acetonitrile (5 mL) in a glass vial and methyl iodide (0.279 mL, 4.46 mmol) was added. The vial was capped and stood at room temperature for 24 h. The solvent was evaporated in vacuo and the residue triturated with heptane/EtOAc, 10/1 (10 mL) to give 3-(4-acetyl-piperazine-1-carbonyl)-1-methyl-3H-imidazol-3-ium iodide as a colourless gum (400 mg) which was used without further purification.

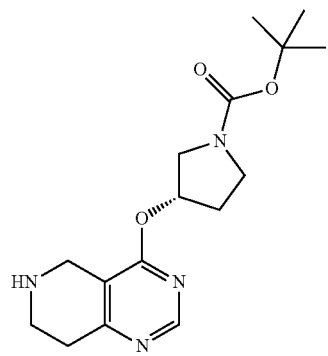 [SMILES: CC(C)(C)OC(=O)N1CC[C@H](Oc2ncnc3c2CNCC3)C1]

Intermediate 7

(S)-3-(5,6,7,8-Tetrahydro-pyrido[4,3-d]pyrimidin-4-yloxy)-pyrrolidine-1-carboxylic acid tert-butyl ester Pd(OH)$_2$/C (1.2 g, 1.71 mmol) was flushed with argon, (S)-3-(6-Benzyl-5,6,7,8-tetrahydro-pyrido[4,3-d]pyrimidin-4-yloxy)-pyrrolidine-1-carboxylic acid tert-butyl ester (10.95 g, 26.7 mmol) dissolved in methanol (25 mL) was added followed by the addition of ammonium formate (1.68 g, 26.7 mmol). The reaction mixture was refluxed for 1 h, cooled down to room temperature, filtered through a celite pad and concentrated under vacuum. Purification by flash chromatography on silica gel (CH$_2$Cl$_2$ then TBME then TBME/MeOH 100/0 to 90/10 then TBME/MeOH/NH$_4$OH 85/15/5) gave (S)-3-(5,6,7,8-tetrahydro-pyrido[4,3-d]pyrimidin-4-yloxy)-pyrrolidine-1-carboxylic acid tert-butyl ester (7.39 g, 87% yield) as a yellow sticky oil. $^1$H NMR (400 MHz, methanol-d4, 298K) δ ppm 1.46-1.46 (m, 9 H) 2.10-2.30 (m, 2 H) 2.78-2.83 (m, 2 H) 3.11-3.14 (m, 2 H) 3.41-3.60 (m, 3 H) 3.65-3.72 (m, 1 H) 3.78 (s, 2 H) 5.68 (m, 1 H) 8.52 (s, 1 H). LCMS: [M+H]$^+$=321.2, Rt$^{(2)}$=0.87 min Alternative synthesis for intermediate 7:

Pd(OH)$_2$/C (1.54 g, 2.2 mmol) was flushed with nitrogen, (S)-3-(6-benzyl-5,6,7,8-tetrahydro-pyrido[4,3-d]pyrimidin-4-yloxy)-pyrrolidine-1-carboxylic acid tert-butyl ester (8.5 g, 20.67 mmol) dissolved in methanol (50 mL) was added followed by the addition of triethylammonium formate (7.9 g, 53.7 mmol). The reaction mixture was refluxed for 1 h, cooled down to room temperature, filtered through a celite pad and the filtrate was partitioned between 2-Me-THF (50 mL) and water (20 mL). The upper organic phase was collected and the bottom aqueous phase was re-extracted with 2-Me-THF (10 mL). All the organic layers were combined and concentrated under vacuum to provide (S)-3-(5,6,7,8-tetrahydro-pyrido[4,3-d]pyrimidin-4-yloxy)-pyrrolidine-1-carboxylic acid tert-butyl ester (6.2 g, 94% yield) as a yellow gum.

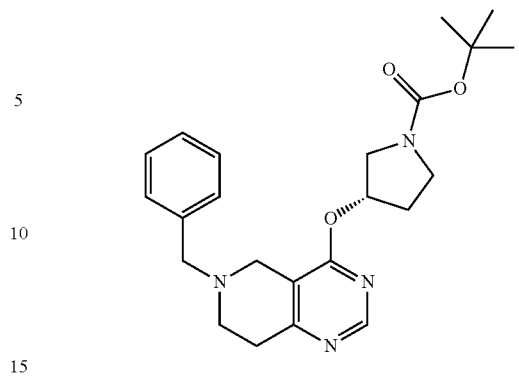

(S)-3-(6-Benzyl-5,6,7,8-tetrahydro-pyrido[4,3-d]pyrimidin-4-yloxy)-pyrrolidine-1-carboxylic acid tert-butyl ester To a solution of (S)-3-hydroxypyrrolidine-1-carboxylic acid tert-butyl ester (0.94 g, 5.01 mmol) in THF (20 mL) was added under argon NaH (0.23 g, 5.78 mmol). The mixture was stirred at rt for 25 min., then 6-benzyl-4-chloro-5,6,7,8-tetrahydro-pyrido[4,3-d]pyrimidine (1 g, 3.85 mmol) was added and stirring continued at rt for 4 h. The mixture was quenched with H$_2$O, extracted with CH$_2$Cl$_2$. The organic layer was filtered and evaporated to dryness. Purification by flash chromatography on silica gel (heptanes/ethyl acetate, 1/1) gave the (S)-3-(6-benzyl-5,6,7,8-tetrahydro-pyrido[4,3-d]pyrimidin-4-yloxy)-pyrrolidine-1-carboxylic acid tert-butyl ester (1.35 g, 85% yield) as a yellow gum. $^1$H NMR (400 MHz, DMSO-d6, 298K) δ ppm 1.39 (s, 9 H) 2.00-2.20 (m, 2 H) 2.35-2.81 (m, 4 H) 3.36-3.63 (m, 6 H) 3.70 (br.s, 2 H) 5.50-5.59 (m, 1 H) 7.25-7.37 (m, 5H) 8.56 (s, 1 H). LCMS: [M+H]+=411.6, Rt$^{(7)}$=1.00 min

Alternative synthesis for (S)-3-(6-Benzyl-5,6,7,8-tetrahydro-pyrido[4,3-d]pyrimidin-4-yloxy)-pyrrolidine-1-carboxylic acid tert-butyl ester To a solution of (S)-3-hydroxypyrrolidine-1-carboxylic acid tert-butyl ester (6.21 g, 33.16 mmol) and 6-benzyl-4-chloro-5,6,7,8-tetrahydro-pyrido[4,3-d]pyrimidine (9 g, 34.65 mmol) in 2-Me-THF (100 mL) was added under nitrogen tBuOK (8.17 g, 72.95 mmol). The mixture was stirred at rt for 25 min. The mixture was quenched with H$_2$O. The organic layer was washed with brine. The resulting organic solution was concentrated in vacuo to provide (S)-3-(6-benzyl-5,6,7,8-tetrahydro-pyrido[4,3-d]pyrimidin-4-yloxy)-pyrrolidine-1-carboxylic acid tert-butyl ester (12.6 g, 89% yield) as a yellow gum.

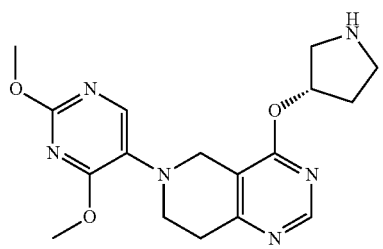 [SMILES: COc1ncc(N2CCc3ncnc(O[C@H]4CCNC4)c3C2)c(OC)n1]

Intermediate 8

6-(2,4-Dimethoxy-pyrimidin-5-yl)-4-((S)-pyrrolidin-3-yloxy)-5,6,7,8-tetrahydro-pyrido[4,3-d]pyrimidine 5-Bromo-2,4-dimethoxy-pyrimidine (89 mg, 0.41 mmol), X-Phos (46 mg, 0.09 mmol) bis(dibenzylideneacetone)palladium(0) (29 mg, 0.03 mmol), cesium carbonate (203 mg, 0.62 mmol) were combined and flushed 10 min with Argon. To this mixture was added (S)-3-(5,6,7,8-tetrahydro-pyrido[4,3-d]pyrimidin-4-yloxy)-pyrrolidine-1-carboxylic acid tert-butyl ester (intermediate 7) (100 mg, 0.31 mmol) in dioxane (4 mL), the vial was capped and the reaction mixture was stirred at 120° C. for 4.5 h. The mixture was allowed to cool to rt and filtered through a celite pad. The filtrate was diluted with EtOAc (20 mL) and washed with sat. NaHCO₃(aq) (10 mL), brine (10 mL), dried (Na₂SO₄) and concentrated in vacuo. Dissolved in dioxane (4 mL) and added to a glass vial containing 5-bromo-2,4-dimethoxy-pyrimidine (89 mg, 0.41 mmol), X-Phos (46 mg, 0.09 mmol) tris(dibenzylideneacetone)dipalladium(0) (29 mg, 0.03 mmol), cesium carbonate (203 mg, 0.62 mmol). The vial was capped and the reaction mixture was stirred at 120° C. for 4.5 h. The mixture was allowed to cool to rt and filtered through a celite pad. The filtrate was diluted with EtOAc (20 mL) and washed with sat. NaHCO₃(aq) (10 mL) then brine (10 mL), dried (Na₂SO₄) and concentrated in vacuo to give (S)-3-(6-(2,4-dimethoxy-pyrimidin-5-yl)-5,6,7,8-tetrahydropyrido[4,3-d]pyrimidin-4-yloxy)pyrrolidine-1-carboxylic acid tert-butyl ester which was used without further purification. (S)-3-(6-(2,4-dimethoxy-pyrimidin-5-yl)-5,6,7,8-tetrahydropyrido[4,3-d]pyrimidin-4-yloxy)pyrrolidine-1-carboxylic acid tert-butyl ester was dissolved in CH₂Cl₂ (2.0 mL) and TFA added (1 mL). The resulting mixture was stirred for 30 min. at room temperature. The reaction mixture was concentrated in vacuo. Purification by preparative reverse phase Gilson HPLC and subsequent neutralization of the combined fractions by PL-HCO3 cartridge & lyophilisation gave 6-(2,4-dimethoxy-pyrimidin-5-yl)-4-((S)-pyrrolidin-3-yloxy)-5,6,7,8-tetrahydro-pyrido[4,3-d]pyrimidine as a yellow powder (11 mg, 10% yield over 2 steps). LCMS: [M+H]+=359.1, Rt$^{(2)}$=0.79 min

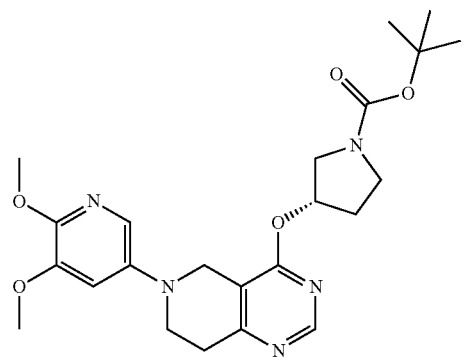

Intermediate 9

2-Amino-5-[4-((S)-pyrrolidin-3-yloxy)-7,8-dihydro-5H-pyrido[4,3-d]pyrimidin-6-yl]nicotinonitrile (S)-3-(5,6,7,8-Tetrahydro-pyrido[4,3-d]pyrimidin-4-yloxy)-pyrrolidine-1-carboxylic acid tert-butyl ester (intermediate 7) (84 mg, 0.263 mmol), imidodicarbonic acid, 2-[5-bromo-3-(cyano)-2-pyridinyl]-, 1,3-bis(1,1-dimethylethyl)ester (115 mg, 0.289 mmol), X-Phos (376 mg, 0.079 mmol), tris(dibenzylideneacetone)dipalladium(0) (24 mg, 0.026 mmol), cesium carbonate (171 mg, 0.526 mmol) were combined in a glass vial and flushed 10 min with Argon. To this mixture was added dioxane (4.0 mL), the vial was capped and the reaction mixture stirred at 120° C. for 1.5 h. The reaction was allowed to cool to rt and filtered through a celite pad, The filtrate was diluted with EtOAc (20 mL) and washed with sat. NaHCO₃(aq) (10 mL) and brine (10 mL), dried (Na₂SO₄) and concentrated in vacuo to give (S)-tert-butyl 3-(6-(6-(bis(tert-butoxycarbonyl)amino)-5-(cyano)pyridin-3-yl)-5,6,7,8-tetrahydropyrido[4,3-d]pyrimidin-4-yloxy)pyrrolidine-1-carboxylate which was used without further purification. (S)-tert-butyl 3-(6-(6-(bis(tert-butoxycarbonyl)amino)-5-(cyano)pyridin-3-yl)-5,6,7,8-tetrahydropyrido[4,3-d]pyrimidin-4-yloxy)pyrrolidine-1-carboxylate was dissolved in CH₂Cl₂ (2.0 mL) and TFA added (1 mL). The resulting mixture was stirred for 30 min at room temperature. The reaction mixture was concentrated in vacuo. Purification by preparative reverse phase Gilson HPLC and subsequent neutralization of the combined fractions by PL-HCO3 cartridge & lyophilisation gave 2-amino-5-[4-((S)-pyrrolidin-3-yloxy)-7,8-dihydro-5H-pyrido[4,3-d]pyrimidin-6-yl]nicotinonitrile as a yellow powder (17 mg, 19% yield over 2 steps). LCMS: [M+H]+=338.3, Rt$^{(3)}$=1.16 min.

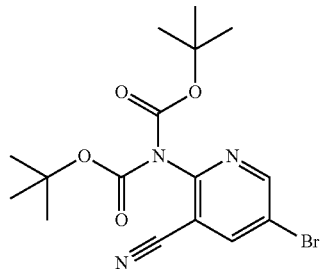

Imidodicarbonic acid, 2-[5-bromo-3-(cyano)-2-pyridinyl]-,1,3-bis(1,1-dimethylethyl)ester To 2-amino-5-bromonicotinonitrile (0.785 g, 3.96 mmol), triethylamine (0.553 mL, 3.96 mmol) and 4-dimethylaminopyridine (20 mg, 0.164 mmol) in CH₂Cl₂ (25 mL) was added di-tert-butyl-dicarbonate (2.16 g, 9.91 mmol) and the resulting mixture stirred at room temperature for 18 h. Evaporated to dryness in vacuo and triturated in heptane (25 mL) for 72 h. The resulting precipitate was filtered and washed with heptane (10 mL) to give imidodicarbonic acid, 2-[5-bromo-3-(cyano)-2-pyridinyl]-,1,3-bis(1,1-dimethylethyl)ester as a beige solid (1.1 g, 70% yield). ¹H NMR (400 Mhz, CDCl₃, 298K) 1.51 (s, 18H) 8.16 (d, 1H) 8.77 (d, 1H). LCMS: [M+H]+=398/400.1, Rt$^{(4)}$=1.43 min.

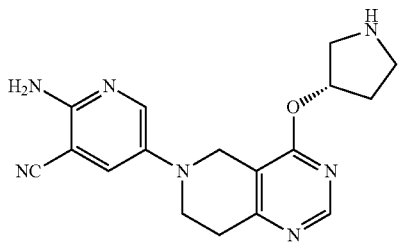 [SMILES: N#Cc1cc(N2CCc3ncnc(O[C@H]4CCNC4)c3C2)cnc1N]

Intermediate 10

(S)-3-[6-(5,6-Dimethoxy-pyridin-3-yl)-5,6,7,8-tetra-hydro-pyrido[4,3-d]pyrimidin-4-yloxy]-pyrrolidine-1-carboxylic acid tert-butyl ester To a glass vial was added (S)-3-(5,6,7,8-tetrahydro-pyrido [4,3-d]pyrimidin-4-yloxy)-pyrrolidine-1-carboxylic acid tert-butyl ester (intermediate 7) (1.00 g, 3.12 mmol), 5-bromo-2,3-dimethoxypyridine (0.82 g, 3.75 mmol), sodium tert-butoxide (0.46 g, 4.68 mmol), tris(dibenzylideneacetone)dipalladium(0) (0.11 g, 0.13 mmol), 2-di-t-butylphosphino-2'-(N,N-dimethylamino)biphenyl (0.06 g, 0.18 mmol) and anhydrous toluene (10 mL). The vial was flushed with a stream of argon for 15 sec and capped. The mixture was heated with stirring for 18 h at 80° C. Allowed to cool and filtered through a celite pad. The filtrate was diluted with EtOAc (50 mL) and washed with brine (20 mL). The organic layer was separated, dried (Na₂SO₄) and concentrated in vacuo. Purified by flash column chromatography on silica gel with EtOAc/MeOH, 98/2 to 92/18 to give (S)-3-[6-(5, 6-dimethoxy-pyridin-3-yl)-5,6,7,8-tetrahydro-pyrido[4,3-d] pyrimidin-4-yloxy]-pyrrolidine-1-carboxylic acid tert-butyl ester as a pale yellow foam (1.05 g, 74% yield). LCMS: [M+H]+=458.1, Rt$^{(4)}$=1.02 min.

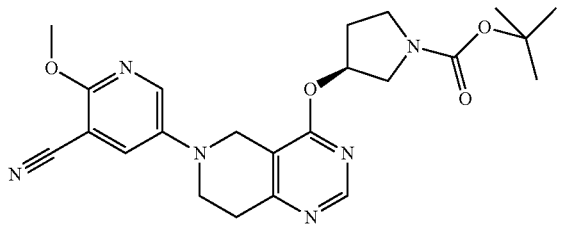 [SMILES: COc1ncc(N2CCc3ncnc(O[C@H]4CCN(C(=O)OC(C)(C)C)C4)c3C2)cc1C#N]

Intermediate 11

(S)-3-[6-(5-Cyano-6-methoxy-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido [4,3-d]pyrimidin-4-yloxy)-pyrrolidine-1-carboxylic acid tert-butyl ester (intermediate 7) (630 mg, 1.97 mmol), 5-bromo-2-methoxynicotinonitrile (419 mg, 1.97 mmol), cesium carbonate (1281.0 mg, 3.93 mmol), tris(dibenzylideneacetone)dipalladium(0) (180 mg, 0.20 mmol), X-Phos (319 mg, 0.67 mmol) and anhydrous dioxane (10.0 mL). The vial was flushed with a stream of argon for 15 sec and capped. The mixture was heated with stirring for 1 h at 110° C. and then stirred at room temperature for 18 h. Diluted with CH₂Cl₂ (100 mL) and water (30 mL) and filtered through a celite pad. The organic phase was separated by filtering through a phase separation tube and concentrated in vacuo. Purified by flash chromatography on silica gel with heptanes/EtOAc, 80/20 to 0/100 to give (S)-3-[6-(5-cyano-6-methoxy-pyridin-3-yl)-5,6,7,8-tetrahydro-pyrido[4,3-d] pyrimidin-4-yloxy]-pyrrolidine-1-carboxylic acid tert-butyl ester as a brown gum (350 mg, 39% yield) LCMS: [M+H]+=453.6, Rt$^{(7)}$=1.29 min.

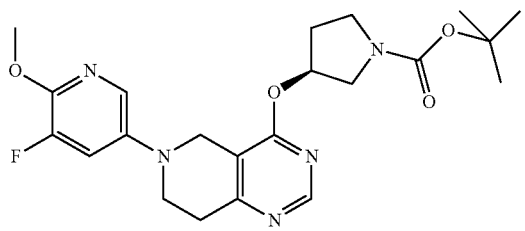 [SMILES: COc1ncc(N2CCc3ncnc(O[C@H]4CCN(C(=O)OC(C)(C)C)C4)c3C2)cc1F]

Intermediate 12

(S)-3-[6-(5-Fluoro-6-methoxy-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido [4,3-d]pyrimidin-4-yloxy)-pyrrolidine-1-carboxylic acid tert-butyl ester (intermediate 7) (150 mg, 0.47 mmol), 5-bromo-3-fluoro-2-methoxypyridine (96 mg, 0.47 mmol), cesium carbonate (305 mg, 0.94 mmol), tris(dibenzylideneacetone)dipalladium(0) (43 mg, 0.05 mmol), X-Phos (76 mg, 0.16 mmol) and anhydrous dioxane (2.0 mL). The vial was flushed with a stream of argon for 15 sec and capped. The mixture was heated with stirring for 1.5 h at 110° C. and then stirred at room temperature for 18 h. Diluted with CH₂Cl₂ (25 mL), filtered through a celite pad and concentrated in vacuo. Purified by reverse phase Gilson HPLC (Method A) to give (S)-3-[6-(5-fluoro-6-methoxy-pyridin-3-yl)-5,6,7,8-tetrahydro-pyrido[4,3-d]pyrimidin-4-yloxy]-pyrrolidine-1-carboxylic acid tert-butyl ester trifluoroacetate as a brown gum (45 mg, 17% yield) LCMS: [M+H]+=446.4, Rt$^{(4)}$=1.41 min.

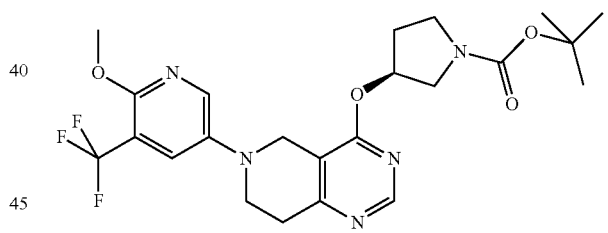

Intermediate 13

(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido [4,3-d]pyrimidin-4-yloxy)-pyrrolidine-1-carboxylic acid tert-butyl ester (intermediate 7) (150 mg, 0.47 mmol) 5-bromo-2-methoxy-3-(trifluoromethyl)pyridine (intermediate 1) (120 mg, 0.47 mmol), cesium carbonate (305 mg, 0.94 mmol), tris(dibenzylideneacetone)dipalladium(0) (43 mg, 0.05 mmol), X-Phos (76 mg, 0.16 mmol) and anhydrous dioxane (2.0 mL). The vial was flushed with a stream of argon for 15 sec and capped. The mixture was heated with stirring for 1 h at 110° C. and then stirred at room temperature for 18 h. Diluted with CH₂Cl₂ (10 mL) and water (2 mL), filtered through a celite pad. The organic phase was separated by filtering through a phase separation tube and concentrated in vacuo. Purified by reverse phase Gilson HPLC (Method A) to give (S)-tert-butyl 3-(6-(6-methoxy-5-(trifluoromethyl)pyridin-3-yl)-5,6,7,8-tetrahydropyrido[4,3-d]pyrimidin-4-yloxy)pyrrolidine-1-carboxylate trifluoroacetate (S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester trifluoroacetate as a brown gum (90 mg, 32% yield) LCMS: [M+H]+=496.5, Rt$^{(7)}$=1.43 min.

C. then allowed to cool to room temperature and stirred at rt for 5 days. Diluted with CH$_2$Cl$_2$ (10 mL) and water (2 mL), filtered through a celite pad. The organic phase was separated by filtering through a phase separation tube and concentrated in vacuo. Purified by flash chromatography on silica gel with heptane/EtOAc 100/0 to 0/100 to give 6-(5-chloro-6-methoxy-pyridin-3-yl)-4-methoxy-5,6,7,8-tetrahydro-pyrido[4,3-d]pyrimidine as a yellow solid (95 mg, 19% yield) LCMS: [M+H]+=307.0/308.9, Rt$^{(3)}$=1.62 min.

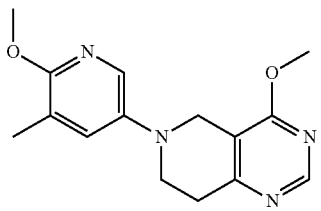 [SMILES: COc1ncc(N2CCc3ncnc(OC)c3C2)cc1C]

Intermediate 14

4-Methoxy-6-(6-methoxy-5-methyl-pyridin-3-yl)-5,6,7,8-tetrahydro-pyrido[4,3-d]pyrimidine To a glass vial was added 4-methoxy-5,6,7,8-tetrahydro-pyrido[4,3-d]pyrimidine (WO 2008/130481, p 47) (0.570 g, 3.45 mmol), 5-bromo-2-methoxy-3-methylpyridine (0.697 g, 3.45 mmol), cesium carbonate (2.25 g, 6.90 mmol), tris(dibenzylideneacetone)dipalladium(0) (0.316 g, 0.345 mmol), X-Phos (0.493 g, 1.04 mmol) and anhydrous dioxane (5 mL). The vial was flushed with a stream of argon for 15 sec and capped. The mixture was heated with stirring for 1 h 45 min at 110° C. then allowed to cool to room temperature and stirred at RT for 3 days. The reaction mixture was filtered through a celite pad and concentrated in vacuo. Purified by flash chromatography on silica gel with heptane/EtOAc, 100/0 to 0/100 then EtOAc/MeOH, 90/10 to give 4-methoxy-6-(6-methoxy-5-methyl-pyridin-3-yl)-5,6,7,8-tetrahydro-pyrido[4,3-d]pyrimidine as a brown gum (0.36 g, 36% yield) LCMS: [M+H]+=287.0, Rt$^{(7)}$=0.80 min.

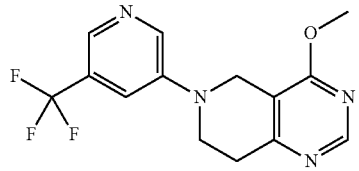

Intermediate 16

4-Methoxy-6-(5-trifluoromethyl-pyridin-3-yl)-5,6,7,8-tetrahydro-pyrido[4,3-d]pyrimidine To a glass vial was added 4-methoxy-5,6,7,8-tetrahydro-pyrido[4,3-d]pyrimidine (0.273 g, 1.65 mmol), 3-bromo-5-(trifluoromethyl)pyridine (0.373 g, 1.65 mmol), cesium carbonate (1.08 g, 3.31 mmol), tris(dibenzylideneacetone) dipalladium(0) (0.076 g, 0.083 mmol), X-Phos (0.079 g, 0.165 mmol) and anhydrous dioxane (5 mL). The vial was flushed with a stream of argon for 15 sec and capped. The mixture was heated with stirring for 1.5 h at 110° C. Filtered through a celite pad, concentrated in vacuo and purified by flash chromatography on silica gel with heptanes/EtOAc, 100/0 to 0/100 to give 4-methoxy-6-(5-trifluoromethyl-pyridin-3-yl)-5,6,7,8-tetrahydro-pyrido[4,3-d]pyrimidine as an orange gum (195 mg, 34% yield) $^1$H NMR (DMSO-d6, 298K) 2.95 (t, 2H) 3.77 (t, 2H) 4.02 (s, 3H) 4.37 (s, 2H) 7.67-7.71 (m, 1H) 8.30-8.34 (m, 1H) 8.63 (s, 1H) 8.67-8.71 (1H, m) LCMS: [M+H]+=311.2, Rt$^{(4)}$=0.94 min.

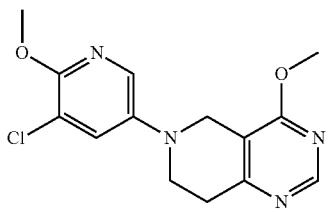 [SMILES: COc1ncc(N2CCc3ncnc(OC)c3C2)cc1Cl]

Intermediate 15

6-(5-Chloro-6-methoxy-pyridin-3-yl)-4-methoxy-5,6,7,8-tetrahydro-pyrido[4,3-d]pyrimidine To a glass vial was added 4-methoxy-5,6,7,8-tetrahydro-pyrido[4,3-d]pyrimidine (WO 2008/130481, p 47) (0.273 g, 1.65 mmol), 5-bromo-3-chloro-2-methoxypyridine (0.368 g, 1.65 mmol), sodium tert-butoxide (318 mg, 3.31 mmol), diacetoxypalladium (0.037 g, 0.17 mmol), X-Phos (0.079 g, 0.17 mmol) and anhydrous toluene/tert-butanol, 5/1 (6 mL). The vial was flushed with a stream of argon for 15 sec and capped. The mixture was heated with stirring for 2 h at 110°

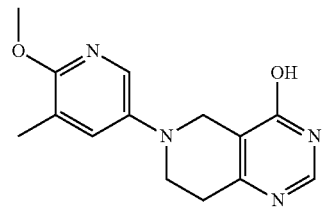

Intermediate 17

6-(6-Methoxy-5-methyl-pyridin-3-yl)-5,6,7,8-tetrahydro-pyrido[4,3-d]pyrimidin-4-ol To 4-methoxy-6-(6-methoxy-5-methyl-pyridin-3-yl)-5,6,7,8-tetrahydro-pyrido[4,3-d]pyrimidine (intermediate 14) (360 mg, 1.26 mmol) in MeOH (2.0 mL) in a glass vial was added 2M NaOH(aq) (2.0 mL). The vial was capped and heated at 90° C. for 24 h. Acidified with glacial AcOH to pH 6, evaporated in vacuo and the residue extracted with CH$_2$Cl$_2$ (2×30 mL). With each extraction, the CH$_2$Cl$_2$ layer was decanted from the solid residue. The CH$_2$Cl$_2$ layers were combined and eluted through an Isolute® SCX-2 cartridge, eluting with methanol, then with 2M ammonia in methanol. Basic fractions were concentrated in vacuo to give 6-(6-methoxy-5-trifluoromethyl-pyridin-3-yl)-5,6,7,8-tetrahydropyrido[4,3-d]pyrimidin-4-ol as a brown gum (260 mg, 76% yield) LCMS: [M+H]+=273.1, Rt$^{(3)}$=1.33 min.

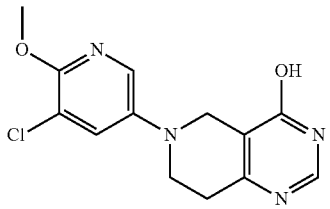 [SMILES: COc1ncc(N2CCc3ncnc(O)c3C2)cc1Cl]

Intermediate 18

6-(5-Chloro-6-methoxy-pyridin-3-yl)-5,6,7,8-tetrahydro-pyrido[4,3-d]pyrimidin-4-ol To 6-(5-chloro-6-methoxy-pyridin-3-yl)-4-methoxy-5,6,7,8-tetrahydro-pyrido[4,3-d]pyrimidine (intermediate 15) (95 mg, 0.31 mmol) in MeOH (5.0 mL) in a glass vial was added 2M NaOH(aq) (3.0 mL). The vial was capped and heated at 90° C. for 24 h. Acidified with glacial AcOH to pH 6, evaporated in vacuo and the residue extracted with CH$_2$Cl$_2$ (1×50 mL with stirring). With each extraction, the CH$_2$Cl$_2$ layer was decanted from the solid residue. The CH$_2$Cl$_2$ layers were combined. The solid residue was then washed with water (10 mL) and filtered. This filtered solid was combined with the CH$_2$Cl$_2$ layers and evaporated in vacuo to give 6-(5-chloro-6-methoxy-pyridin-3-yl)-5,6,7,8-tetrahydro-pyrido[4,3-d]pyrimidin-4-ol as a yellow solid (90 mg, 107% yield) LCMS: [M+H]+=293.0/294.8, Rt$^{(3)}$=1.38 min.

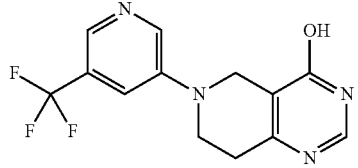 [SMILES: Oc1ncnc2c1CN(c1cncc(C(F)(F)F)c1)CC2]

Intermediate 19

6-(5-Trifluoromethyl-pyridin-3-yl)-5,6,7,8-tetrahydro-pyrido[4,3-d]pyrimidin-4-ol To 4-methoxy-6-(5-trifluoromethyl-pyridin-3-yl)-5,6,7,8-tetrahydro-pyrido[4,3-d]pyrimidine (intermediate 16) (190 mg, 0.612 mmol) in MeOH (2.0 mL) in a glass vial was added 2M NaOH(aq) (2.0 mL). The vial was capped and heated at 90° C. for 24 h. Acidified with glacial AcOH to pH 6, evaporated in vacuo and the residue extracted with CH$_2$Cl$_2$ (2×30 mL with sonication). With each extraction, the CH$_2$Cl$_2$ layer was decanted from the solid residue. The CH$_2$Cl$_2$ layers were combined and eluted through an Isolute® SCX-2 cartridge, eluting with methanol, then with 2M ammonia in methanol. Basic fractions were concentrated in vacuo to give 6-(5-(trifluoromethyl-pyridin-3-yl)-5,6,7,8-tetrahydro-pyrido[4,3-d]pyrimidin-4-ol as a yellow solid (167 mg) LCMS: [M+H]+=297.2, Rt$^{(4)}$=0.69 min.

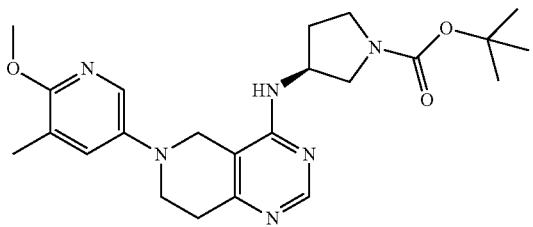 [SMILES: COc1ncc(N2CCc3ncnc(N[C@H]4CCN(C(=O)OC(C)(C)C)C4)c3C2)cc1C]

Intermediate 20

(S)-3-[6-(6-Methoxy-5-methyl-pyridin-3-yl)-5,6,7,8-tetrahydro-pyrido[4,3-d]pyrimidin-4-ylamino)-pyrrolidine-1-carboxylic acid tert-butyl ester To 6-(6-methoxy-5-trifluoromethyl-pyridin-3-yl)-5,6,7,8-tetrahydro-pyrido[4,3-d]pyrimidin-4-ol (intermediate 17) (178 mg, 0.654 mmol) in acetonitrile (2.0 mL) was added BOP (376 mg, 0.854 mmol) and DBU (0.197 mL, 1.31 mmol). The resulting solution was stood at rt for 2 min then added (S)-tert-butyl 3-aminopyrrolidine-1-carboxylate (365 mg, 1.96 mmol) in acetonitrile (2.0 mL) and heated the mixture at 75° C. for 72 h. The reaction mixture was evaporated in vacuo and purified by reverse phase Gilson HPLC (Method A) to give (S)-3-[6-(6-methoxy-5-methyl-pyridin-3-yl)-5,6,7,8-tetrahydro-pyrido[4,3-d]pyrimidin-4-ylamino)-pyrrolidine-1-carboxylic acid tert-butyl ester trifluoroacetate (60 mg, 17% yield) as a brown gum. LCMS: [M+H]+=441.2, Rt$^{(3)}$=1.50 min

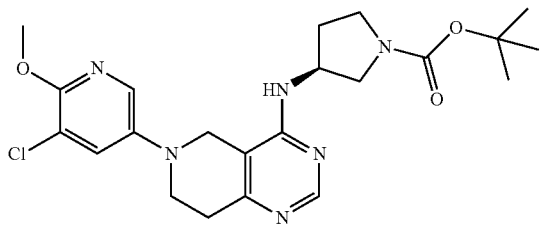 [SMILES: COc1ncc(N2CCc3ncnc(N[C@H]4CCN(C(=O)OC(C)(C)C)C4)c3C2)cc1Cl]

Intermediate 21

(S)-3-[6-(5-Chloro-6-methoxy-pyridin-3-yl)-5,6,7,8-tetrahydro-pyrido[4,3-d]pyrimidin-4-ylamino]-pyrrolidine-1-carboxylic acid tert-butyl ester To 6-(5-chloro-6-methoxypyridin-3-yl)-5,6,7,8-tetrahydro-pyrido[4,3-d]pyrimidin-4-ol (intermediate 18) (90 mg, 0.31 mmol) in acetonitrile (3.0 mL) was added BOP (177 mg, 0.40 mmol) and DBU (0.15 mL, 0.99 mmol). The resulting solution was stood at rt for 2 min then added (S)-tert-butyl 3-aminopyrrolidine-1-carboxylate (0.17, 0.93 mmol) and heated the mixture at 70° C. for 96 h. The reaction mixture was evaporated in vacuo and purified by reverse phase Gilson HPLC (Method A) to give (S)-3-[6-(5-chloro-6-methoxy-pyridin-3-yl)-5,6,7,8-tetrahydro-pyrido[4,3-d]pyrimidin-4-ylamino]-pyrrolidine-1-carboxylic acid tert-butyl ester trifluoroacetate (50 mg, 35% yield) as a brown gum. LCMS: [M+H]+=461.1/463.0, Rt$^{(4)}$=0.93 min.

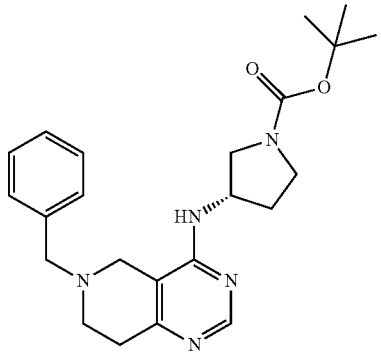 [SMILES: CC(C)(C)OC(=O)N1CC[C@H](Nc2ncnc3c2CN(Cc2ccccc2)CC3)C1]

Intermediate 22

(S)-3-(6-Benzyl-5,6,7,8-tetrahydro-pyrido[4,3-d]pyrimidin-4-ylamino)-pyrrolidine-1-carboxylic acid tert-butyl ester 6-Benzyl-4-chloro-5,6,7,8-tetrahydro-pyrido[4,3-d]pyrimidine (5.0 g, 19.06 mmol), (S)-tert-butyl 3-aminopyrrolidine-1-carboxylate (4.11 g, 20.96 g) and triethylamine (3.98 mL, 28.6 mmol) were heated in a sealed vial at 120° C. for 42 h. The mixture was allowed to cool, diluted with tert-butyl methyl ether (100 mL) and the resulting suspension stirred for 10 min. The mixture was diluted with water (50 mL) and the organic layer separated. The organic layer was washed with brine (20 mL), dried (Na$_2$SO$_4$) and evaporated in vacuo to give a brown gum. The residue was purified by column chromatography on silica gel with EtOAc/MeOH, 98/2 to 82/18 to give (S)-3-(6-benzyl-5,6,7,8-tetrahydro-pyrido[4,3-d]pyrimidin-4-ylamino)-pyrrolidine-1-carboxylic acid tert-butyl ester as a pale yellow foam (7.36 g, 93% yield). $^1$H-NMR (400 MHz, CDCl$_3$, 298 K): δ ppm 1.48 (s, 9H) 2.10-2.31 (m, 2H) 2.80-2.96 (m, 4H) 3.15-3.87 (m, 8H) 4.44-4.77 (m, 1H) 5.62-5.73 (m, 1H) 7.29-7.45 (m, 5H) 8.50 (s, 1H). LCMS: [M+H]+=410.0, Rt$^{(6)}$=1.39 min.

Alternative synthesis for intermediate 22:

(S)-tert-Butyl-3-aminopyrrolidine-1-carboxylate (50 g, 192.5 mmol) was added to 6-benzyl-4-chloro-5,6,7,8-tetrahydro-pyrido[4,3-d]pyrimidine (39.440 g, 211.8 mmol) in NMP (200 mL) solution followed by the addition of K$_2$CO$_3$ (39.9 g, 288.8 mmol). The mixture was heated to 120° C. for 20 h. The mixture was allowed to cool, partitioned between water (300 mL) and ethylacetate (500 mL). the bottom aqueous phase was discarded and the upper organic phase was washed with brine (150 mL) and concentrated in vacuo to provide crude (S)-3-(6-benzyl-5,6,7,8-tetrahydro-pyrido[4,3-d]pyrimidin-4-ylamino)-pyrrolidine-1-carboxylic acid tert-butyl ester as a pale yellow foam (76.44 g, 97% yield).

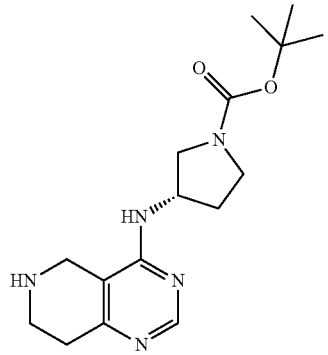 [SMILES: CC(C)(C)OC(=O)N1CC[C@H](Nc2ncnc3c2CNCC3)C1]

Intermediate 23

(S)-3-(5,6,7,8-Tetrahydro-pyrido[4,3-d]pyrimidin-4-ylamino)-pyrrolidine-1-carboxylic acid tert-butyl ester To a solution of (S)-3-(6-benzyl-5,6,7,8-tetrahydro-pyrido[4,3-d]pyrimidin-4-ylamino)-pyrrolidine-1-carboxylic acid tert-butyl ester (intermediate 22) (30.1 g, 73.5 mmol) in MeOH (100 mL) was added 20% palladium hydroxide on carbon (3.3 g) then ammonium formate (4.63 g, 73.5 mmol) and the mixture heated at reflux for 1 h. Added ammonium formate (0.38 g, 6.02 mmol) and continued heating at reflux for 30 min. The reaction mixture was allowed to cool and filtered through a celite pad, washing with MeOH (50 mL) then CH$_2$Cl$_2$ (50 mL). The filtrate was evaporated in vacuo to give a brown oil. Dissolved in CH$_2$Cl$_2$ (100 mL), added solid NaHCO$_3$ (10 g) and filtered through a celite pad. The filtrate was evaporated in vacuo to give a brown oil. Dissolved in EtOAc (50 mL) and a solid precipitated which was filtered to give (S)-3-(5,6,7,8-tetrahydro-pyrido[4,3-d]pyrimidin-4-ylamino)-pyrrolidine-1-carboxylic acid tert-butyl ester as a beige solid (15.55 g, 66% yield). $^1$H-NMR (400 MHz, DMSO-d$_6$, 298 K): δ ppm 1.40 (s, 9H) 1.81-1.98 (m, 1H) 2.05-2.17 (m, 1H) 2.92 (t, 2H) 3.10-3.46 (m, 5H) 3.49-3.63 (m, 3H) 4.47-4.63 (m, 1H) 6.46 (d, 1H, N—H) 8.25 (s, 1H). LCMS: [M+H]+=320.0, Rt$^{(6)}$=1.29 min.

Alternative synthesis for intermediate 23:

Pd(OH)$_2$/C (6.60 g, 5.3 mmol) was flushed with nitrogen, (S)-3-(6-benzyl-5,6,7,8-tetrahydro-pyrido[4,3-d]pyrimidin-4-ylamino)-pyrrolidine-1-carboxylic acid tert-butyl ester (intermediate 22) dissolved in methanol (164 mL) was added followed by the addition of triethylammonium formate (28.4 g, 188.0 mmol). The reaction mixture was refluxed for 1 h, cooled down to room temperature, filtered through a celite pad and the filtrate was concentrated under vacuum. the residue was recrystallized with methyl tert-butyl ether (200 mL) and heptanes (50 mL) to provide (S)-3-(5,6,7,8-tetrahydro-pyrido[4,3-d]pyrimidin-4-ylamino)-pyrrolidine-1-carboxylic acid tert-butyl ester as a beige solid (25.7 g, 85% yield).

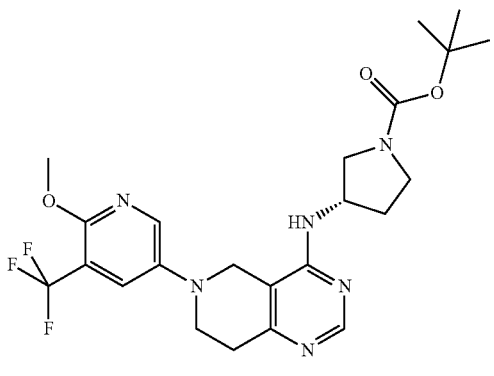 [SMILES: COc1ncc(N2CCc3ncnc(N[C@H]4CCN(C(=O)OC(C)(C)C)C4)c3C2)cc1C(F)(F)F]

Intermediate 24

(S)-3-[6-(6-Methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester To a glass vial was added (S)-3-(5,6,7,8-tetrahydro-pyrido[4,3-d]pyrimidin-4-ylamino)-pyrrolidine-1-carboxylic acid tert-butyl ester (intermediate 23) (3.5 g, 10.96 mmol), 5-bromo-2-methoxy-3-(trifluoromethyl)pyridine (intermediate 1) (3.09 g, 12.05 mmol), sodium tert-butoxide (1.58 g, 16.44 mmol), tris(dibenzylideneacetone)dipalladium(0) (0.502 g, 0.548 mmol), 2-di-t-butylphosphino-2'-(N,N-dimethylamino)biphenyl (0.225 g, 0.657 mmol) and anhydrous tert-butanol (6 mL). The vial was flushed with a stream of argon for 15 sec and capped. The mixture was heated with stirring for 5 h at 100° C. Allowed to cool and partitioned between EtOAc (100 mL) and water (20 mL) and filtered the biphasic mixture through a celite pad. The organic layer was separated, dried (MgSO4) and concentrated in vacuo. Purified by flash column chromatography through Biotage® amino silica gel eluting with heptane/EtOAc, 100/0 to 0/100 then EtOAc/MeOH (90/10) to give (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester as a yellow foam (4.00 g, 74% yield). LCMS: [M+H]+=495.2, Rt(3)=1.59 min.

Alternative synthesis for intermediate 24:

To a glass flask was added (S)-3-(5,6,7,8-tetrahydro-pyrido[4,3-d]pyrimidin-4-ylamino)-pyrrolidine-1-carboxylic acid tert-butyl ester (intermediate 23) (6.331 g, 15.86 mmol), 5-bromo-2-methoxy-3-(trifluoromethyl)pyridine (intermediate 1) (4.465 g, 17.442 mmol), sodium tert-butoxide (2.29 g, 23.78 mmol), tris(dibenzylideneacetone)dipalladium(0) (0.726 g, 0.793 mmol), di-tert-butyl(2'-methylbiphenyl-2-yl)phosphine (0.297 g, 0.951 mmol) and anhydrous tert-butanol (30 mL). The flask was flushed with a stream of nitrogen for 15 sec and capped. The mixture was heated with stirring for 4 h under reflux. The mixture was allowed to cool to rt and partitioned between EtOAc (100 mL) and water (20 mL). The biphasic mixture was filtered the through a celite pad. The organic layer was separated and concentrated in vacuo to give crude (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester as a yellow foam (7.46 g, 95% yield).

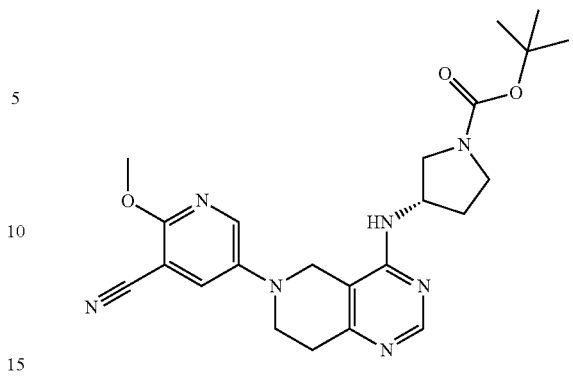

Intermediate 25

(S)-3-[6-(5-Cyano-6-methoxy-pyridin-3-yl)-5,6,7,8-tetrahydro-pyrido[4,3-d]pyrimidin-4-ylamino]-pyrrolidine-1-carboxylic acid tert-butyl ester To a glass vial was added (S)-3-(5,6,7,8-tetrahydro-pyrido[4,3-d]pyrimidin-4-ylamino)-pyrrolidine-1-carboxylic acid tert-butyl ester (intermediate 23) (566 mg, 1.77 mmol), 5-bromo-2-methoxynicotinonitrile (453 mg, 2.13 mmol), cesium carbonate (1155 mg, 3.54 mmol), tris(dibenzylideneacetone)dipalladium(0) (162 mg, 0.18 mmol), X-Phos (287 mg, 0.60 mmol) and anhydrous tert-butanol (5 mL). The vial was flushed with a stream of argon for 15 sec and capped. The mixture was heated with stirring for 18 h at 110° C. Allowed to cool and partitioned between CH2Cl2 (20 mL) and water (10 mL) and filtered the biphasic mixture through a celite pad. The organic layer was separated by filtering through a phase separation tube and concentrated in vacuo. Purified by flash column chromatography on silica gel with heptane/EtOAc, 100/0 to 0/100 then EtOAc/MeOH (90/10) to give (S)-3-[6-(5-cyano-6-methoxy-pyridin-3-yl)-5,6,7,8-tetrahydro-pyrido[4,3-d]pyrimidin-4-ylamino]-pyrrolidine-1-carboxylic acid tert-butyl ester as a brown gum (234 mg, 29% yield). LCMS: [M+H]+=452.1, Rt(4)=0.90 min.

Intermediate 1'

5-Bromo-2-methoxy-3-trifluoromethyl-pyridine

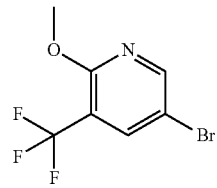

2-Methoxy-3-trifluoromethyl-pyridine (2.7 g, 14.79 mmol) and 1,3-dibromo-5,5-dimethylhydantoin (5.28 g, 18.48 mmol) were placed in a round-bottom flask. To this mixture was slowly added 40 ml TFA. The mixture was stirred overnight at ambient temperature (16 h). After completion of the reaction, TFA solvent was evaporated in vacuo and the resulting residue was neutralized to pH6-7 by the addition of saturated NaHCO3. The aqueous layer was extracted with DCM two times and the combined extract was washed with brine, dried over magnesium sulfate and concentrated in vacuo to give a mixture of oil and white solid. The residue was redissolved into 20% Ethylacetate/Heptane (50 ml) and the insoluble white solid was filtered off. The filtrate was concentrated and then purified by Flash-chromatography on silica gel (EtOAc/Heptane 5/95) to give 5-Bromo-2-methoxy-3-trifluoromethyl-pyridine as a colorless liquid (2.08 g, 52% yield).

$^1$H-NMR (400 MHz, DMSO-d$_6$, 298 K): δ ppm 4.03 (s, 3H) 7.95 (d, 1H) 8.4 (d, 1H).

2-Methoxy-3-trifluoromethyl-pyridine

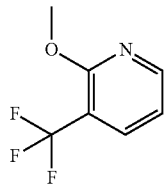

2-Chloro-3-trifluoromethyl-pyridine (3 g, 16.53 mmol) was dissolved in 30 ml of a solution of sodium methoxide (5.4M) in methanol. The mixture was stirred at ambient temperature for 2 days. After this period of time, the reaction was taken into ice and extracted with DCM three times. The combined extract was washed with brine, dried over magnesium sulfate and concentrated in vacuo to give 2-methoxy-3-trifluoromethyl-pyridine as a light liquid (2.7 g, 89% yield). $^1$H-NMR (400 MHz, DMSO-d$_6$, 298 K): δ ppm 3.98 (s, 3H) 7.2 (dd, 1H) 8.11 (d, 1H) 8.45 (d, 1H). MS: 178.1 [M+1]$^+$, Rt$^{(1)}$=1.29 min.

Intermediate 2'

5-Bromo-2-ethoxy-3-trifluoromethyl-pyridine

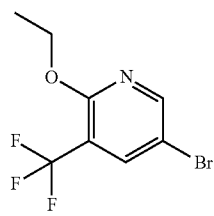

Intermediate 2' was prepared according the procedure described for intermediate 1' using a solution of sodium ethoxyde in ethanol instead of a solution of sodium methoxide. $^1$H-NMR (400 MHz, DMSO-d$_6$, 298 K): δ ppm 1.33 (t, 4 H) 4.45 (q, 3 H) 8.31 (s, 1 H) 8.58 (s, 1 H).

Intermediate 3'

1-[4-(5-Bromo-2-methyl-benzoyl)-piperazin-1-yl]-ethanone

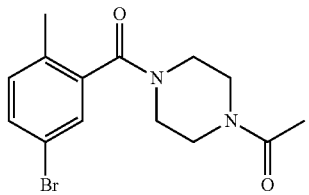 [SMILES: CC(=O)N1CCN(C(=O)c2cc(Br)ccc2C)CC1]

To a mixture of 5-bromo-2-methylbenzoic acid (2.0 g, 9.30 mmol) in DCM (25 mL) was added DIPEA (3.25 mL, 18.60 mmol) and HBTU (4.23 g, 11.16 mmol) at rt. The reaction mixture was stirred at rt for 20 min. To the mixture was then added 1-(piperazin-1-yl)ethanone (1.311 g, 10.23 mmol) and the reaction mixture was stirred at rt for 1 hour. The reaction was quenched with a saturated aqueous solution of NaHCO$_3$ and extracted with DCM. The organic layer was washed twice with brine, dried by passing through a phase separating cartridge and evaporated. Purification by Flash chromatography using Biotage Isolera system (amine functionalized silica KP-NH, eluting with Cyclohexane/EtOAc 0 to 100%) gave the title compound (2.475 g, 82% yield) as a white foam. MS: 325.4 [M+1], Rt$^{(2)}$=0.94 min.

Intermediate 4'

1-[4-(3-Bromo-5-trifluoromethyl-benzoyl)-piperazin-1-yl]-ethanone

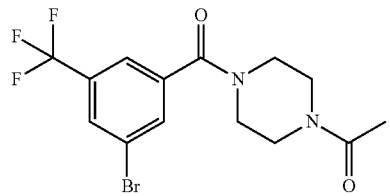 [SMILES: CC(=O)N1CCN(C(=O)c2cc(Br)cc(C(F)(F)F)c2)CC1]

Intermediate 4' was prepared according the procedure described for intermediate 3' using 3-bromo-5-trifluoromethylbenzoic acid instead of 5-bromo-2-methylbenzoic acid. MS: 379.3-381.3 [M+H]$^+$, Rt$^{(2)}$=1.129 min.

Intermediate 5'

1-[4-(3-Bromo-5-methoxy-benzoyl)-piperazin-1-yl]-ethanone

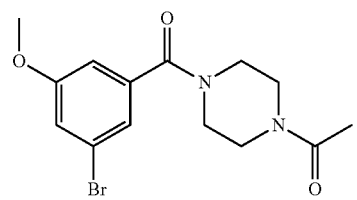 [SMILES: COc1cc(Br)cc(C(=O)N2CCN(C(C)=O)CC2)c1]

Intermediate 5' was prepared according the procedure described for intermediate 3' using 3-bromo-5-methoxybenzoic acid (intermediate 17) instead of 5-bromo-2-methylbenzoic acid. MS: 343.2 [M+H]$^+$, Rt$^{(2)}$=1.02 min.

Intermediate 6'

1-[4-(3-Bromo-5-methyl-benzoyl)-piperazin-1-yl]-ethanone

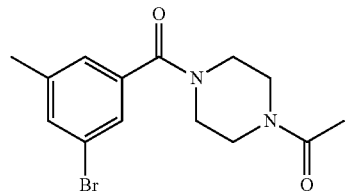 [SMILES: CC(=O)N1CCN(C(=O)c2cc(C)cc(Br)c2)CC1]

Intermediate 6' was prepared according the procedure described for intermediate 3' using 3-bromo-5-methoxybenzoic acid (intermediate 17) instead of 5-bromo-2-methylbenzoic acid. MS: 325.2-327.1 [M+H]+, Rt$^{(2)}$=0.98 min.

Intermediate 7'

1-[4-(3-Bromo-5-chloro-benzoyl)-piperazin-1-yl]-ethanone

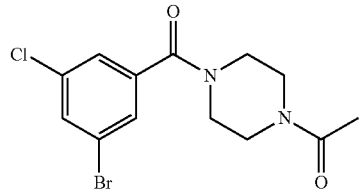 [SMILES: CC(=O)N1CCN(C(=O)c2cc(Cl)cc(Br)c2)CC1]

Intermediate 7' was prepared according the procedure described for intermediate 3' using 3-bromo-5-methoxybenzoic acid (intermediate 17) instead of 5-bromo-2-methylbenzoic acid. MS: 345.2-347.1-349.0 [M+H]+, Rt$^{(2)}$=1.02 min.

Intermediate 8'

N-(4-bromo-2-(trifluoromethyl)phenyl)methanesulfonamide

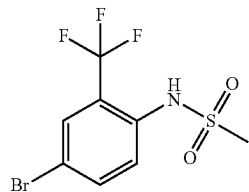 [SMILES: CS(=O)(=O)Nc1ccc(Br)cc1C(F)(F)F]

To a mixture of 2-amino-5-bromobenzotrifluoride (1.0 g, 4.17 mmol) in DCM (10 mL) at 0-5° C. was added NEt$_3$ (1.16 mL, 8.33 mmol), then methanesulfonyl chloride (0.389 mL, 5 mmol) dropwise. The reaction mixture was stirred at rt for 4 days. After 2 days, more NEt$_3$ was added (1.16 mL, 8.33 mmol). As there was no evolution after 3 days, more NEt$_3$ (0.580 mL, 4.17 mmol) and methanesulfonyl chloride (0.324 mL, 4.17 mmol) were added. The reaction was not completed, so the reaction mixture was then heated in a microwave oven at 110° C. for 20 min. There was no evolution, so the reaction was stopped. The reaction mixture was diluted with water and DCM. Layers were separated. The organic layer was washed with water, dried over MgSO$_4$ and evaporated. Purification by Flash chromatography using CombiFlash Companion ISCO system (Redisep silica 40 g column, eluting with Cyclohexane/EtOAc 100:0 to 70:30) did not give the pure compound. Purification by prep HPLC using Gilson system (SunFire C18 column, eluting with H$_2$O+0.1% TFA/CH$_3$CN 20% to 85%) gave the title compound (404 mg, 31% yield) as a white solid. $^1$H-NMR (400 MHz, DMSO-d$_6$, 298 K): δ ppm 3.12 (s, 3H) 7.55 (d, 1H) 7.91 (d, 1H) 7.92 (s, 1H) 9.56 (s, 1H). MS$^{(10)}$: 316.3-318.2 [M−1]−.

Intermediate 9'

N-(3-bromo-5-(trifluoromethyl)phenyl)methanesulfonamide

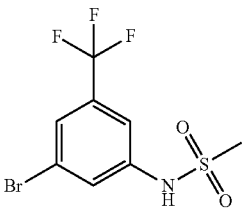 [SMILES: CS(=O)(=O)Nc1cc(Br)cc(C(F)(F)F)c1]

To a mixture of 3-amino-5-bromobenzotrifluoride (1.0 g, 4.17 mmol) in pyridine (10 mL) at 0-5° C. was added dropwise methanesulfonyl chloride (0.389 mL, 5 mmol). The reaction mixture was stirred at rt for 4 days. As the reaction was not completed, the reaction mixture was then heated in a microwave oven at 150° C. for 15 min. There was no evolution, so the reaction was stopped. The reaction mixture was concentrated until dryness, and the residue was co-evaporated with toluene. The residue was then diluted with a saturated aqueous solution of NaHCO$_3$ and extracted with DCM. The organic layer was dried over MgSO$_4$ and evaporated. Purification by Flash chromatography using CombiFlash Companion ISCO system (Redisep silica 12 g column, eluting with Cyclohexane/EtOAc 100:0 to 70:30) gave the title compound (1.05 g, 79% yield) as a white solid. $^1$H-NMR (400 MHz, DMSO-d$_6$, 298 K): δ ppm 3.14 (s, 3H) 7.48 (s, 1H) 7.64 (s, 1H) 7.68 (s, 1H) 10.42 (s, 1H). MS$^{(10)}$: 316.3-318.2 [M−1]−.

Intermediate 10'

2-Difluoromethoxy-5-(4,4,5,5-tetramethyl-[1,3,2]dioxaborolan-2-yl)-pyridine

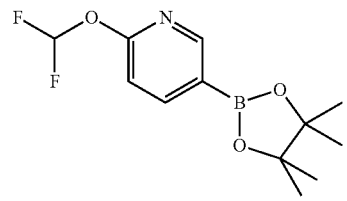 [SMILES: CC1(C)OB(c2ccc(OC(F)F)nc2)OC1(C)C]

In a sealed tube was added 2-hydroxy-5-(4,4,5,5-tetramethyl-1,3,2-dioxaborolan-2-yl)pyridine (300 mg, 1.357 mmol), sodium chlorodifluoroacetate (320 mg, 2.036 mmol) in acetonitrile (5 mL). This suspension was heated to 80° C. and stirred overnight. The reaction mixture was cooled down to rt, diluted with EtOAc, washed with an aqueous solution of NaHCO$_3$ and brine. The organic layer dried over MgSO$_4$, filtered and evaporated. Purification by flash chromatography on silica gel (CH2Cl2/MeOH, 95/5) gave the title compound (197 mg, 53% yield). MS: 272.8 [M+H]+, Rt$^{(6)}$=3.12 min.

Intermediate 11'

6,6-Difluoro-[1,4]diazepane

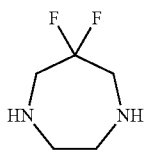

The compound was prepared following literature procedure: Wellner, E.; Sandin, H.; *Synthesis;* 2002; 2; 223-226. $^1$H-NMR (400 MHz, DMSO-d$_6$, 298 K): δ ppm 3.47 (s, 4H) 3.89 (t, 4H)

The boronic acids or boronic esters described herein are prepared according the general procedure described below.

Scheme 1'

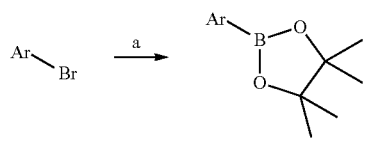

a) Bis-(pinacolato)-diboron, PdCl$_2$(dppf)-CH$_2$Cl$_2$, KOAc, dioxane, 80° C., 16 h.

Intermediate 12'

2-Methoxy-5-(4,4,5,5-tetramethyl-[1,3,2]dioxaborolan-2-yl)-nicotinonitrile

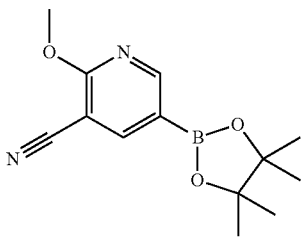 [SMILES: COc1ncc(B2OC(C)(C)C(C)(C)O2)cc1C#N]

Solution A: PdCl$_2$(dppf)-CH$_2$Cl$_2$ (0.958 g, 1.174 mmol), KOAc (6.91 g, 70.4 mmol) and Bis-(pinacolato)-diboron (7.15 g, 28.2 mmol) were placed into a 250 mL flask and degassed. Solution B: In a separate vial, 5-bromo-2-methoxy nicotinitrile (5 g, 23.47 mmol) was dissolved in 100 mL of anhydrous dioxane. Solution B was added to solution A, and the reaction mixture heated to 80° C. for 16 h. The mixture was cooled down to rt, diluted with EtOAc and the remaining solid filtered off. The filtrate was evaporated under vacuum to yield a black oil. Purification by flash chromatography on silica gel (CH$_2$Cl$_2$/MeOH, 95/5) gave the title compound (5.7 g, 89% yield) as a beige powder. $^1$H-NMR (400 MHz, DMSO-d$_6$, 298 K): δ ppm 1.31 (s, 12H) 4.03 (s, 3H) 8.31 (s, 1H) 8.62 (s, 1H). MS: 261.5 [M+1]$^+$, Rt$^{(2)}$=1.47 min.

Intermediate 13' to 22', were prepared using procedures analogous to those used for intermediate 12', using the corresponding Aryl bromide as starting materials.

| Intermediate | Structure | Rt (min.) | MS(ES): [M + H]$^+$ |
|---|---|---|---|
| Intermediate 13' | 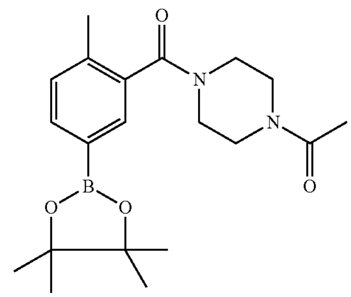 [SMILES: CC(=O)N1CCN(C(=O)c2cc(B3OC(C)(C)C(C)(C)O3)ccc2C)CC1] | 1.10 $^{(1)}$ | 373.2 |
| Intermediate 14' | 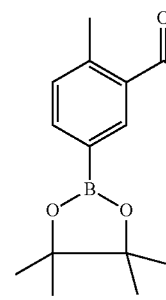 | 1.36 $^{(1)}$ | 263.1 |
| Intermediate 15' | 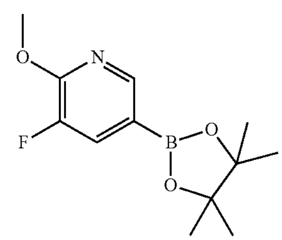 [SMILES: COc1ncc(B2OC(C)(C)C(C)(C)O2)cc1F] | 1.53 $^{(1)}$ | 254.1 |
| Intermediate 16' | 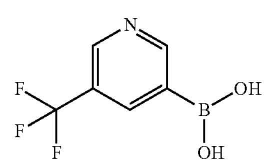 [SMILES: OB(O)c1cncc(C(F)(F)F)c1] | 0.64 $^{(1)}$ | 191.9 |
| Intermediate 17' | 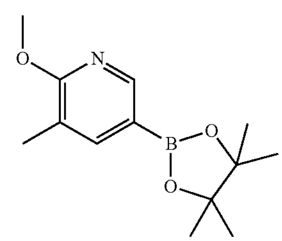 | 1.58 $^{(1)}$ | 250.1 |
| Intermediate 18' | 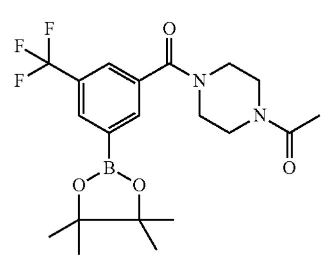 [SMILES: CC(=O)N1CCN(C(=O)c2cc(B3OC(C)(C)C(C)(C)O3)cc(C(F)(F)F)c2)CC1] | 1.29 $^{(1)}$ | 427.3 |

-continued

| Intermediate | Structure | Rt (min.) | MS(ES): [M + H]+ |
|---|---|---|---|
| Intermediate 19' | 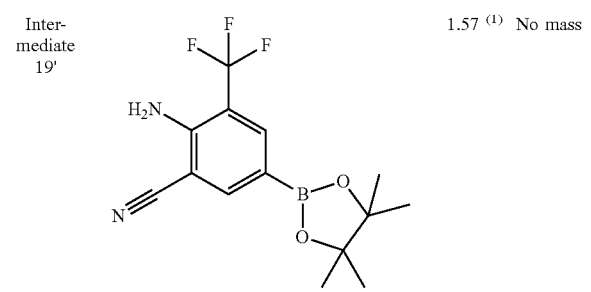 | 1.57 (1) | No mass |
| Intermediate 20' | 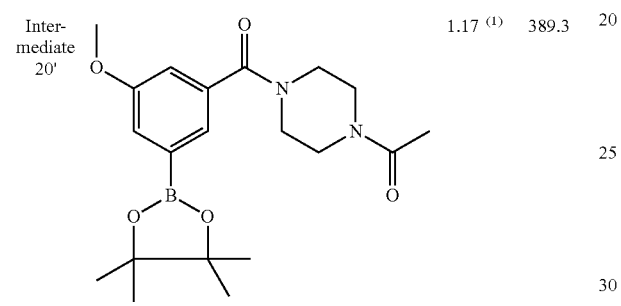 | 1.17 (1) | 389.3 |
| Intermediate 21' | 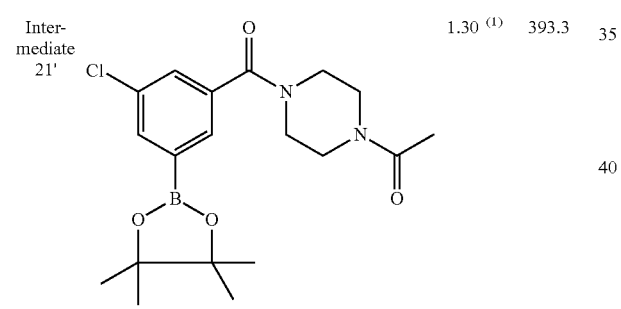 | 1.30 (1) | 393.3 |

| Intermediate | Structure | Rt (min.) | MS(ES): [M + H]+ |
|---|---|---|---|
| Intermediate 22' | 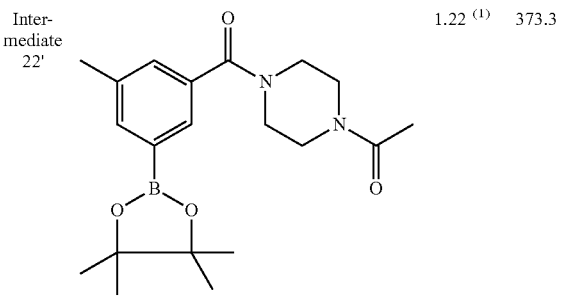 | 1.22 (1) | 373.3 |

(1) LC methode 1, (2) LC medthode 2

Intermediate 23'

3-Bromo-5-methoxybenzoic acid

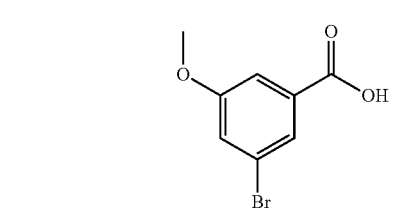

To a vigorously stirred mixture of 1-Bromo-3-methoxy-5-methylbenzene (1 g, 4.97 mmol), Pyridine (3.22 mL, 39.8 mmol) and Water (8 ml) was added in small portions KMnO$_4$ (3.14 g, 19.89 mmol) at 105° C. The mixture which turned to a black suspension was stirred 24 hours at 105° C., then cooled down to RT and filtered over Hyflo. The black residue was washed several times with EtOAc. The filtrate was then diluted in EtAOc and washed with a 2M solution of HCl. The organic layer was dried over sodium sulfate, filtered and concentrated to afford the title compound (281 mg, 24% yield) as a white solid. MS: 229.1 [M+H]+, Rt$^{(1)}$=1.18 min.

Preparation of Examples

Scheme 1

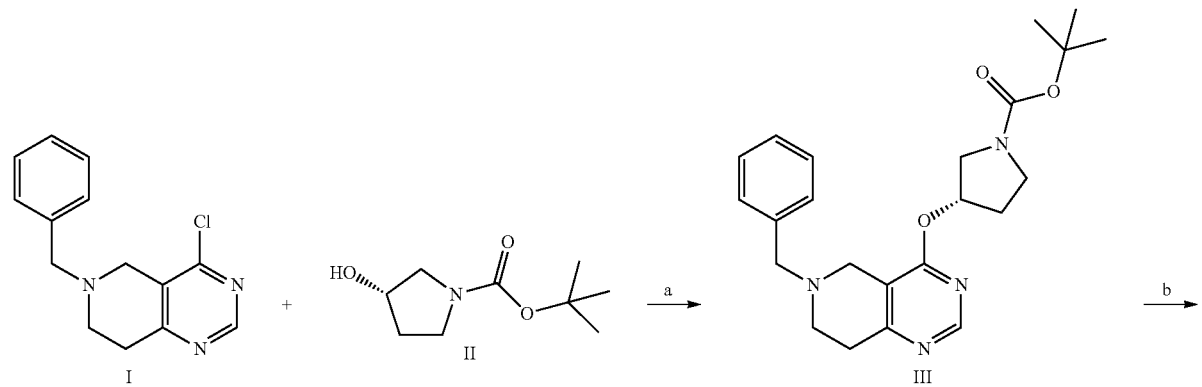

-continued

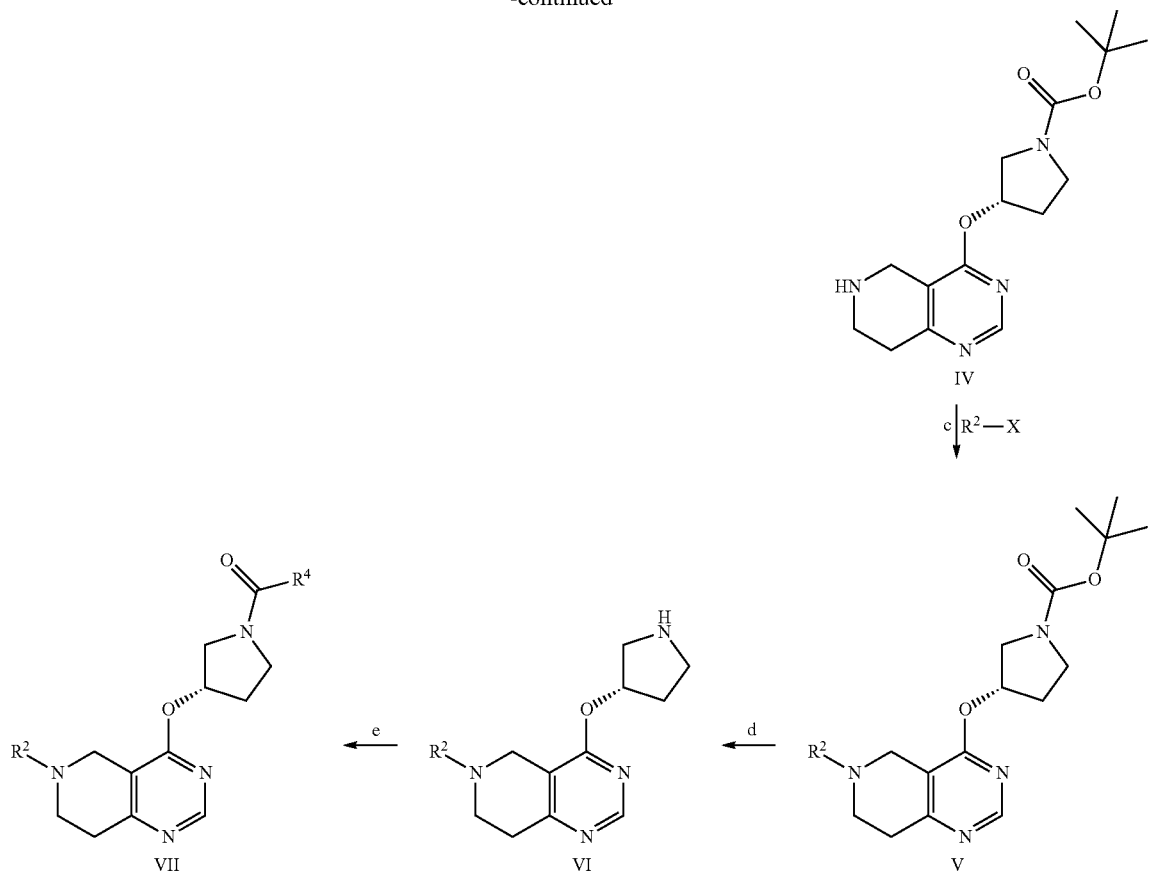

a) (S)-3-(6-Benzyl-5,6,7,8-tetrahydro-pyrido[4,3-d]pyrimidin-4-yloxy)-pyrrolidine-1-carboxylic acid tert-butyl ester III is firstly prepared by reacting 6-benzyl-4-chloro-5,6,7,8-tetrahydro-pyrido[4,3-d]pyrimidine with (S)-3-hydroxy-pyrrolidine-1-carboxylic acid tert-butyl ester in the presence of a suitable base such as sodium hydride (NaH) and polar organic solvent such as THF or dioxane under inert gas conditions at room temperature. b) N-debenzylation is performed under customary transfer hydrogenation conditions, using among the possible palladium catalysts, preferably palladium hydroxide on carbon Pd(OH)$_2$/C and among the possible formate salt preferably ammonium formate and organic solvent such as preferably methanol. The reaction is preferably carried out under refluxing conditions. c) Buchwald-Hartwig cross coupling between (S)-3-(5,6,7,8-tetrahydro-pyrido[4,3-d]pyrimidin-4-yloxy)-pyrrolidine-1-carboxylic acid tert-butyl ester IV and aryl bromide of the general formula $R^2$—X where X=Bromo or Iodo is performed under customary Buchwald-Hartwig conditions using such a ligand such as X-Phos or 2-di-t-butylphosphino-2'-(N,N-dimethylamino)biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with X-Phos, base such as preferably Cs$_2$CO$_3$ or preferably tert-BuONa, and organic solvent such as preferably dioxane or preferably THF. The reaction is preferably stirred at a temperature of approximately 80-120° C., preferably 120° C. The reaction may preferably carry out under an inert gas such as nitrogen or argon. d) N—BOC deprotection is performed under customary BOC deprotection conditions using among the possible acid preferably trifluoroacetic acid or HCl and suitable organic solvent such as CH$_2$Cl$_2$ or diethyl ether. The reaction is preferably performed at room temperature. e)

Reaction of compounds of general formula VI with an acid chloride of formula $R^4$C(O)Cl or carboxylic acid of formula $R^4$C(O)OH. Those skilled in the art will appreciate that there are many known ways of preparing amides. For example, see Mantalbetti, C. A. G. N and Falque, V., Amide bond formation and peptide coupling, Tetrahedron, 2005, 61(46), pp 10827-10852 and references cited therein. The examples provided herein are thus not intended to be exhaustive, but merely illustrative.

The following general methods i-v have been used.

i. To a vigorously stirring solution of the acid chloride (1.3 eq.) in CH$_2$Cl$_2$ was added simultaneously portionwise excess sat. NaHCO$_3$(aq) and a solution of the amine of general formula VI (1.0 eq.) in CH$_2$Cl$_2$ at rt. The resulting biphasic mixture was stirred vigorously at rt for 2 h. The organic layer was separated, dried (MgSO$_4$), concentrated in vacuo and purified by either reverse phase chromatography, normal phase chromatography or crystallisation.

ii. To the amine of general formula VI (1.0 eq.) in CH$_2$Cl$_2$ was added the acid chloride (1.1 eq.) and triethylamine (3.0 eq.) at rt. The reaction mixture was stirred at room temperature for 1 h. The reaction mixture was concentrated under vacuum and subsequently partitioned between water and a suitable organic solvent and purified either reverse phase chromatography, normal phase chromatography or crystallisation.

iii. To the carboxylic acid (1.0 eq.) and HBTU (1.2 eq.) in DMF was added triethylamine (4.0 eq.). The mixture was stirred for 20 min and then the amine of general formula VI (1.0 eq.) in DMF was added. The mixture was allowed to stir overnight at room temperature and subsequently partitioned between water and a suitable organic solvent. The organic phase was separated, dried (MgSO$_4$), concentrated in vacuo and purified by either reverse phase chromatography, normal phase chromatography or crystallisation.

iv. To the carboxylic acid (1.0 eq.) and the amine general formula VI (1.0 eq.) in DMF was added DCC (1.2 eq.) in DMF. The reaction mixture was stirred at rt for 18 h and concentrated in vacuo and purified by either reverse phase chromatography, normal phase chromatography or crystallisation.

v. To the carboxylic acid (1.1 eq.) and the amine general formula VI (1.0 eq.) in CH$_2$Cl$_2$ was added benztriazol-1-ol (1.1 eq.) and EDC (1.6 eq.). The reaction mixture was stirred at rt for 18 h and subsequently partitioned between water and a suitable organic solvent. The organic phase was separated, dried (MgSO$_4$), concentrated in vacuo and purified by either reverse phase chromatography, normal phase chromatography or crystallization.

Scheme 2

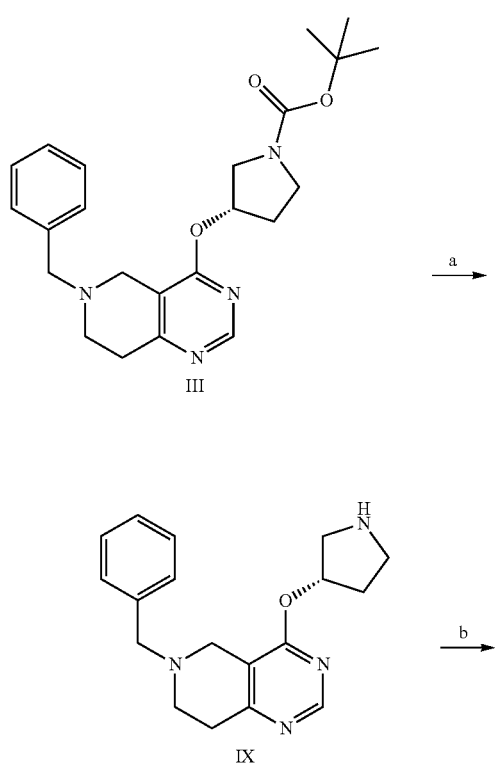

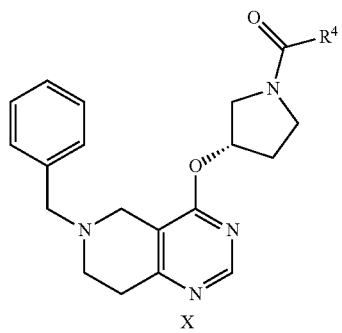

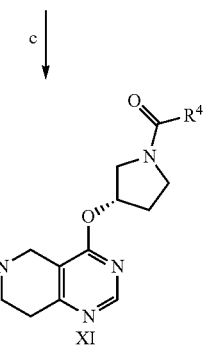

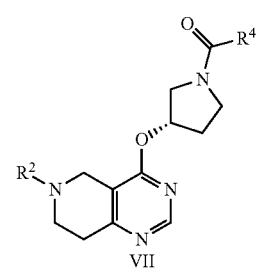

a) N—BOC deprotection is performed under customary BOC deprotection conditions using among the possible acid preferably trifluoro-actetic acid and organic solvent preferably CH$_2$Cl$_2$. The reaction is preferably performed at room temperature. b) Reaction of compound of general formula IX with an acid chloride of formula R$^4$C(O)Cl or carboxylic acid of formula R$^4$C(O)OH using general methods i-v as described in Scheme 1, step e. Those skilled in the art will appreciate that there are many known ways of preparing amides. For example, see Mantalbetti, C. A. G. N and Falque, V., Amide bond formation and peptide coupling, Tetrahedron, 2005, 61(46), pp 10827-10852 and references cited therein. The examples provided herein are thus not intended to be exhaustive, but merely illustrative.

c) Removal of the benzyl protecting group is performed using standard methodology as described in "Protecting groups in Organic Synthesis" by T. W. Greene and P. Wutz, 3$^{rd}$ edition, 1999, John Wiley and Sons. Typical conditions comprise of 1.0 eq. of compound of general formula X (8.0 eq. of ammonium formate and 20% (w/w) palladium hydroxide Pd(OH)$_2$/C (catalyst) heated under reflux in methanol. d) Buchwald-Hartwig cross coupling between compound of general formula XI and compounds of general formula R$^2$—X where X=Bromo or Iodo is performed under customary Buchwald-Hartwig conditions using such a ligand such as X-Phos or 2-di-t-butylphosphino-2'-(N,N-dimethylamino)biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with X-Phos, base such as preferably Cs$_2$CO$_3$ or preferably tert-BuONa, and organic solvent such as preferably dioxane or preferably THF. The reaction is preferably stirred at a temperature of approximately 80-150° C., preferably 120° C. The reaction may preferably be carried out under an inert gas such as nitrogen or argon.

Scheme 3
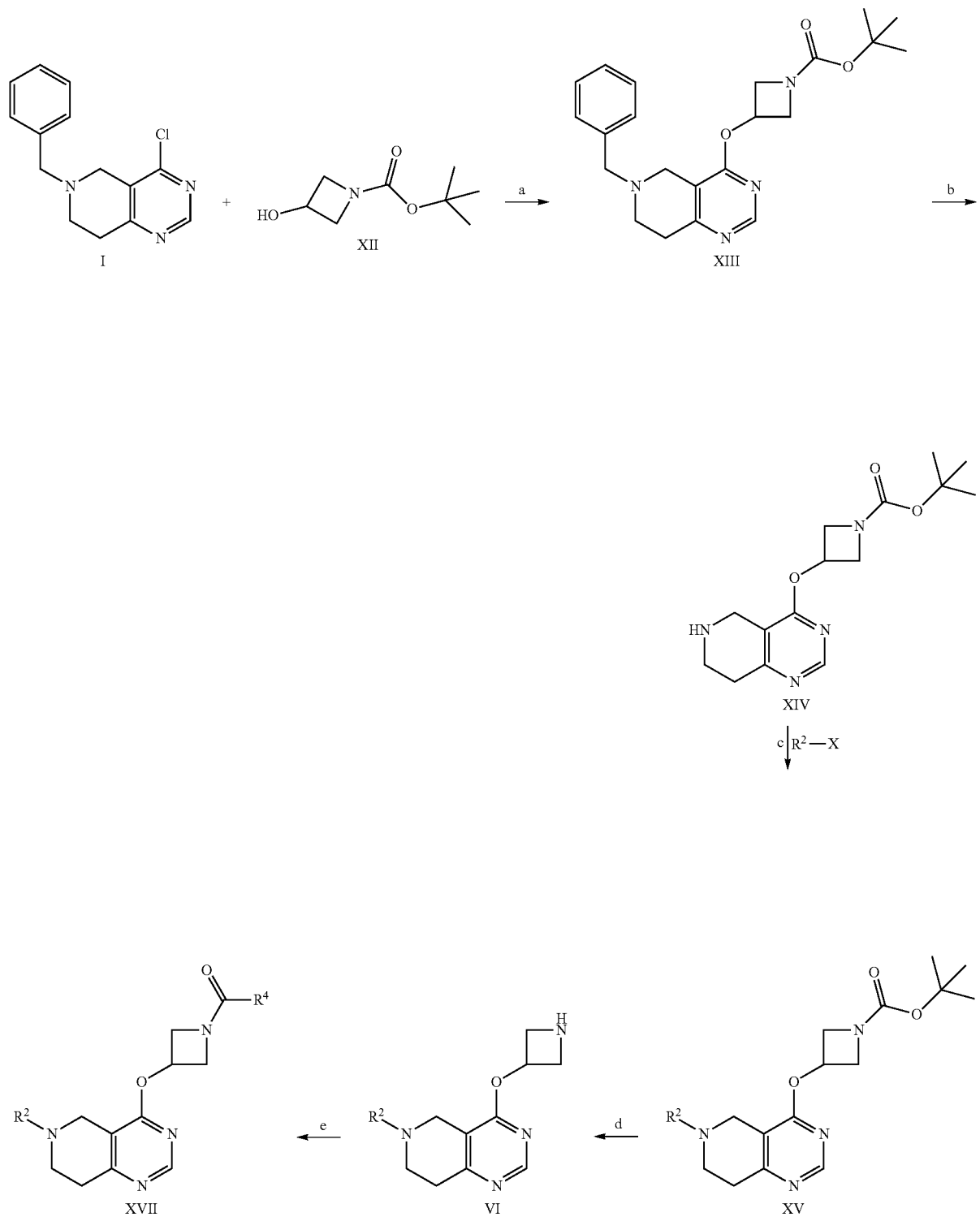
Compounds of general formula XVII can be prepared in a similar manner as described for steps a-e in Scheme 1, starting from 6-benzyl-4-chloro-5,6,7,8-tetrahydro-pyrido[4,3-d]pyrimidine (I) and tert-butyl 3-hydroxyazetidine-1-carboxylate (XII).

Scheme 4

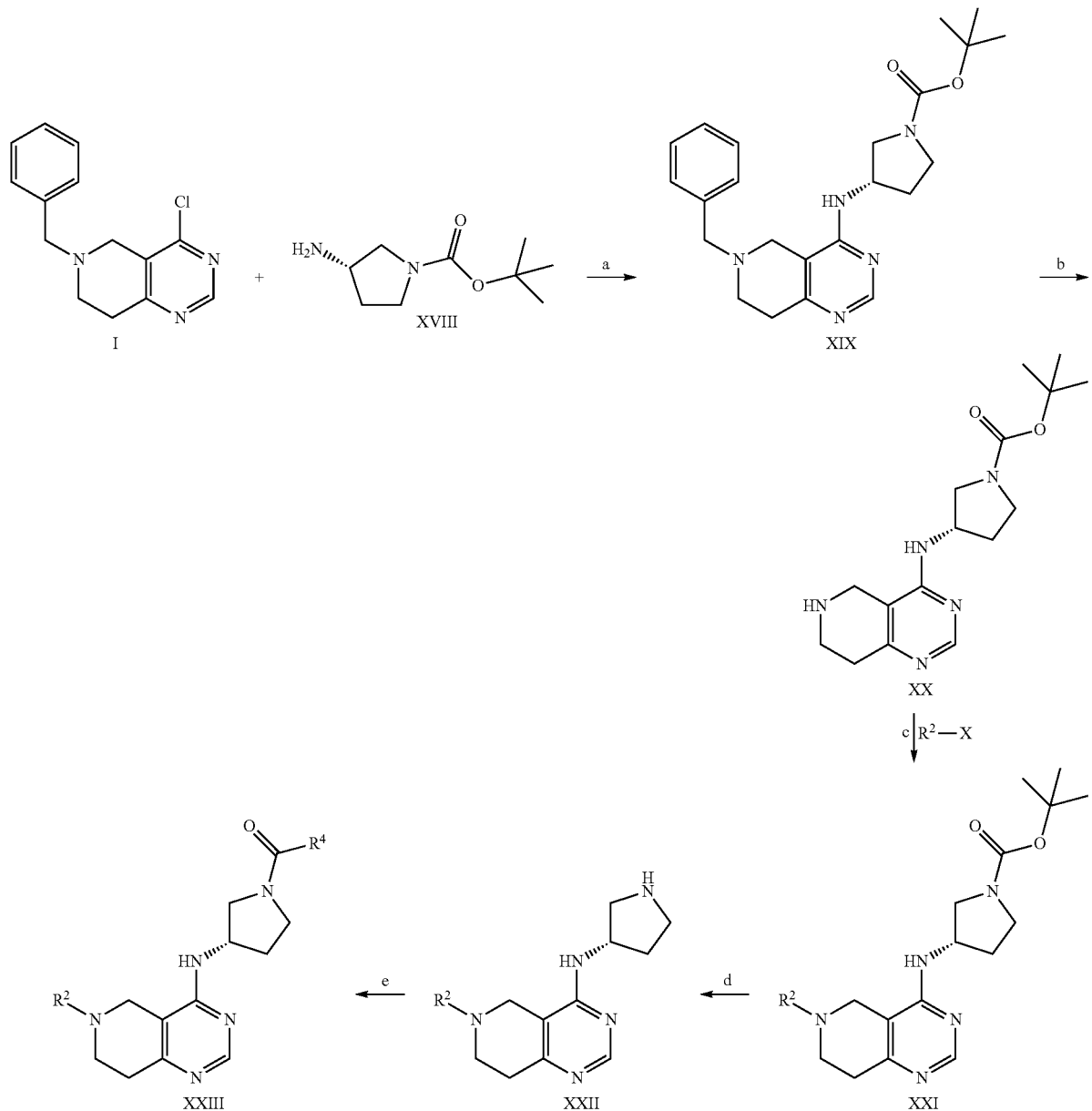

a) (S)-3-(6-Benzyl-5,6,7,8-tetrahydro-pyrido[4,3-d]pyrimidin-4-yloxy)-pyrrolidine-1-carboxylic acid tert-butyl ester XIX is firstly prepared by reacting 6-benzyl-4-chloro-5,6,7,8-tetrahydro-pyrido[4,3-d]pyrimidine with (S)-3-Amino-pyrrolidine-1-carboxylic acid tert-butyl ester in the presence of a suitable base such as triethylamine or N,N-diisopropylethylamine at elevated temperature (e.g. 120° C.) for 24-48 h. Typical conditions comprise of 1.0 eq. of 6-benzyl-4-chloro-5,6,7,8-tetrahydro-pyrido[4,3-d]pyrimidine, 1.0 eq. of (S)-3-amino-pyrrolidine-1-carboxylic acid tert-butyl ester and 1.5 eq. of triethylamine at 120° C. for 48 h. b) Removal of the benzyl protecting group is performed using standard methodology as described in "Protecting groups in Organic Synthesis" by T. W. Greene and P. Wutz, 3$^{rd}$ edition, 1999, John Wiley and Sons. Typical conditions comprise of 1.0 eq. of (S)-3-(6-benzyl-5,6,7,8-tetrahydro-pyrido[4,3-d]pyrimidin-4-yloxy)-pyrrolidine-1-carboxylic acid tert-butyl ester XIX, 1.1-8.0 eq. of ammonium formate and 20% (w/w) palladium hydroxide Pd(OH)$_2$/C (catalyst) heated under reflux in methanol. c) (S)-3-(5,6,7,8-Tetrahydro-pyrido[4,3-d]pyrimidin-4-yloxy)-pyrrolidine-1-carboxylic acid tert-butyl ester XX is reacted with halide R$^2$—X (where R2 is defined above and X is halo and preferably bromo or iodo), in the presence of a suitable base such as sodium tert-butoxide or cesium carbonate and a suitable catalyst system such as Pd$_2$(dba)$_3$ with 2-di-t-butyl-phosphino-2'-(N,N-dimethylamino)biphenyl or Pd$_2$(dba)$_3$ with X-Phos in a suitable solvent such as anhydrous tert-butanol or anhydrous dioxane, heated at elevated temperature (e.g. 100° C.). The reaction may preferably be carried out under an inert gas such as nitrogen or argon. Typical conditions comprise of 1 eq. of (S)-3-(5,6,7,8-tetrahydropyrido[4,3-d]pyrimidin-4-yloxy)-pyrrolidine-1-carboxylic acid tert-butyl ester XX, 1-1.5 eq. of R2-X, 1.5-2.0 eq. of sodium tert-butoxide, 5-10 mol % $Pd_2(dba)_3$ and 5-10 mol % 2-di-t-butylphosphino-2'-(N,N-dimethylamino)biphenyl in anhydrous tert-butanol at 100° C. for 5-24 hours under an atmosphere of argon. d) N-Boc deprotection is performed under customary Boc deprotection conditions with a suitable acid such as trifluoroactetic acid in a suitable solvent such as $CH_2Cl_2$ at room temperature. Typical conditions comprise of 1 eq. of compound of general formula XII in excess trifluoroacetic acid in $CH_2Cl_2$ at room temperature for 1-3 h. e) Reaction of compounds of general formula XXII with an acid chloride of formula $R^4C(O)Cl$ or carboxylic acid of formula $R^4C(O)OH$ using general methods i-v as described in Scheme 1, step e. Those skilled in the art will appreciate that there are many known ways of preparing amides. For example, see Mantalbetti, C. A. G. N and Falque, V., Amide bond formation and peptide coupling, Tetrahedron, 2005, 61(46), pp 10827-10852 and references cited therein. The examples provided herein are thus not intended to be exhaustive, but merely illustrative.

1-1.5 eq. of R2-X, 1.5-2.0 eq. of cesium carbonate, 5-10 mol % $Pd_2(dba)_3$ and 5-10 mol % X-Phos in dioxane at 110° C. for 5-24 hours under an atmosphere of argon. b) Compounds of general formula XXV is reacted with aqueous sodium hydroxide in a suitable solvent such as methanol or dioxane at elevated temperature (e.g. 100° C.) for 18-24 h. Typical conditions comprise of 1 eq. of compounds of general formula XXV in excess 2N sodium hydroxide(aq) in methanol at 100° C. for 18 h. c) Compounds of general formula XXI can be prepared using a base promoted phosphonium coupling reaction whereby compounds of general formula XXVI in a suitable solvent such as acetonitrile is reacted with a phosphonium salt such as benzotriazol-1-yloxytris (dimethylamino)phosphonium hexafluorophosphate (BOP) in the presence of a base such as 1,8-diaza-7-bicyclo[5.4.0] undecene (DBU) followed by addition of (S)-tert-butyl 3-aminopyrrolidine-1-carboxylate. The reaction mixture is preferably stirred at a temperature of 20° C. to 90° C. for 18-72 h. The reaction may preferably be carried out under an inert gas, e.g. nitrogen or argon. Typical conditions comprise of 1 equivalent of compounds of general formula XXVI, 1.0-1.5 eq. of BOP, 2.0-4.0 eq. of DBU and 2.0-3.0 eq. of

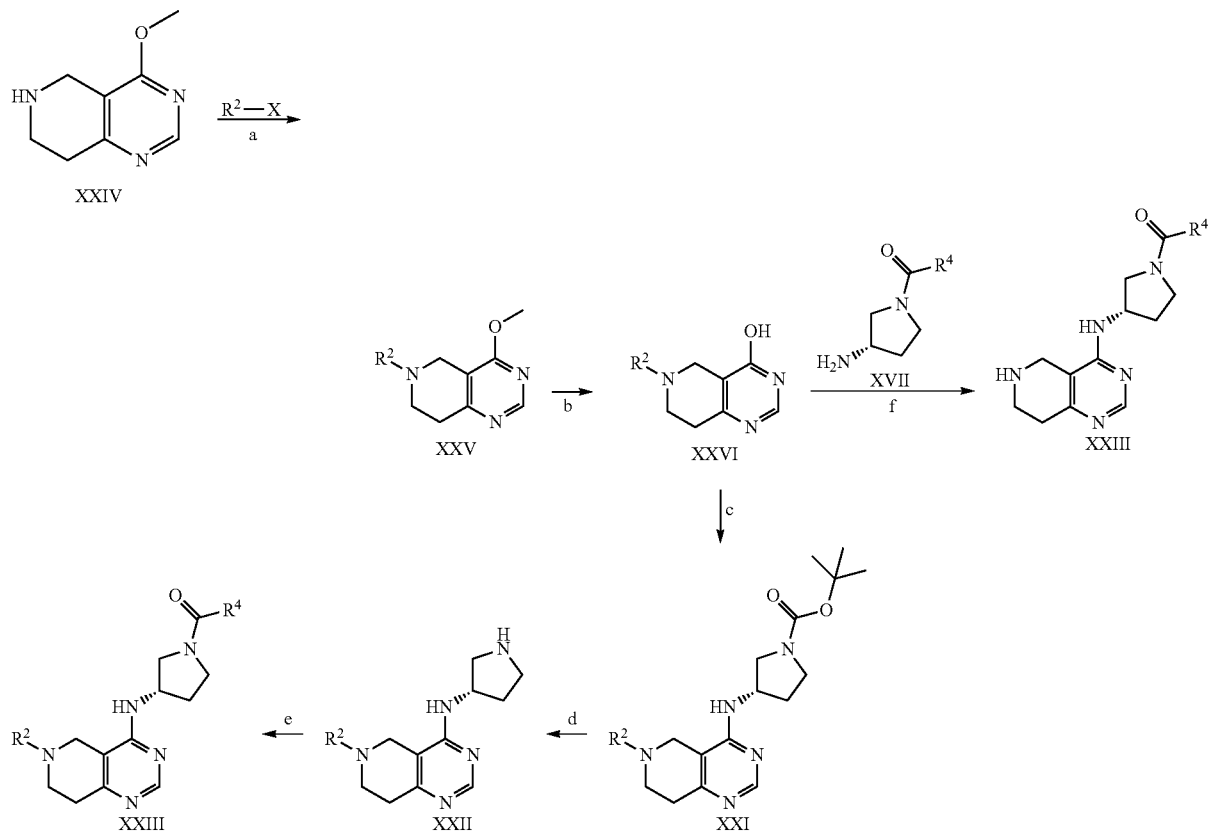

a) 4-Methoxy-5,6,7,8-tetrahydro-pyrido[4,3-d]pyrimidine (WO 2008/130481, p 47) is reacted with halide $R^2$—X (where R2 is defined above and X is halo and preferably bromo or iodo), in the presence of a suitable base such as cesium carbonate or sodium tert-butoxide and a suitable catalyst system such as $Pd_2(dba)_3$ with X-Phos or $Pd(OAc)_2$ with X-Phos in a suitable solvent such as dioxane or THF, heated at elevated temperature (e.g. 110° C.). The reaction may preferably be carried out under an inert gas such as nitrogen or argon. Typical conditions comprise of 1 eq. of 4-methoxy-5,6,7,8-tetrahydro-pyrido[4,3-d]pyrimidine, (S)-tert-butyl 3-aminopyrrolidine-1-carboxylate in acetonitrile at 65° C. for 72 hours under argon. Steps d) and e) can be carried out in a similar manner described for steps d) and e) in Scheme 1. Step f) can be carried out using a base promoted phosphonium coupling reaction in a similar manner as step c) in Scheme 5. Typical conditions comprise of 1 eq. of compounds of general formula XXVI, 1.0-1.5 eq. of BOP, 2.0-4.0 eq. of DBU and 2.0-3.0 eq. of amine of general formula XVII in acetonitrile at 90° C. for 24 hours under argon.

Scheme 6

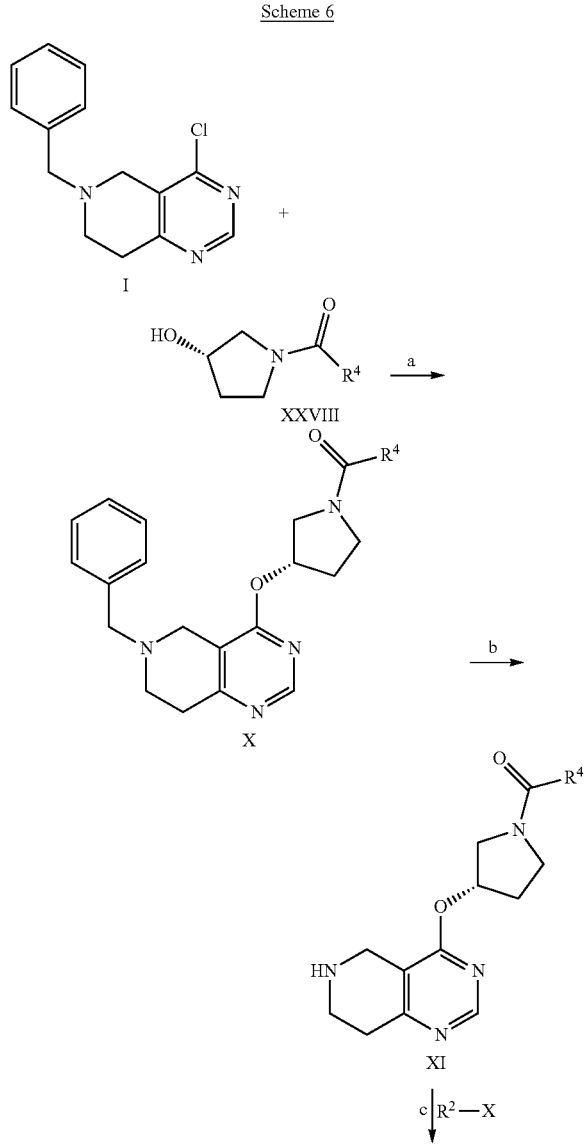

a) Alcohol of general formula XXVIII is reacted with the 6-benzyl-4-chloro-5,6,7,8-tetrahydro-pyrido[4,3-d]pyrimidine under customary conditions by deprotonation of the secondary alcohol using sodium hydride (NaH) and organic solvent THF under inert gaz conditions at room temperature.
b) N-debenzylation is performed under customary transfer hydrogenation conditions, using among the possible palladium catalysts, preferably palladium hydroxide Pd(OH)$_2$ and among the possible formate salt preferably ammonium formate and organic solvent such as preferably methanol. The reaction is preferably carried out under refluxing conditions. c) Buchwald-Hartwig cross coupling between compound of general formula XI and compounds of general formula R$^2$—X is performed under customary Buchwald-Hartwig conditions using such a ligand such as X-Phos or 2-di-t-butylphosphino-2'-(N,N-dimethylamino)biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with X-Phos, base such as preferably Cs$_2$CO$_3$ or preferably tert-BuONa, and organic solvent such as preferably dioxane or preferably THF. The reaction is preferably stirred at a temperature of approximately 80-150° C., preferably 120° C. The reaction may preferably carried out under an inert gas such as nitrogen or argon.

Scheme 7

-continued

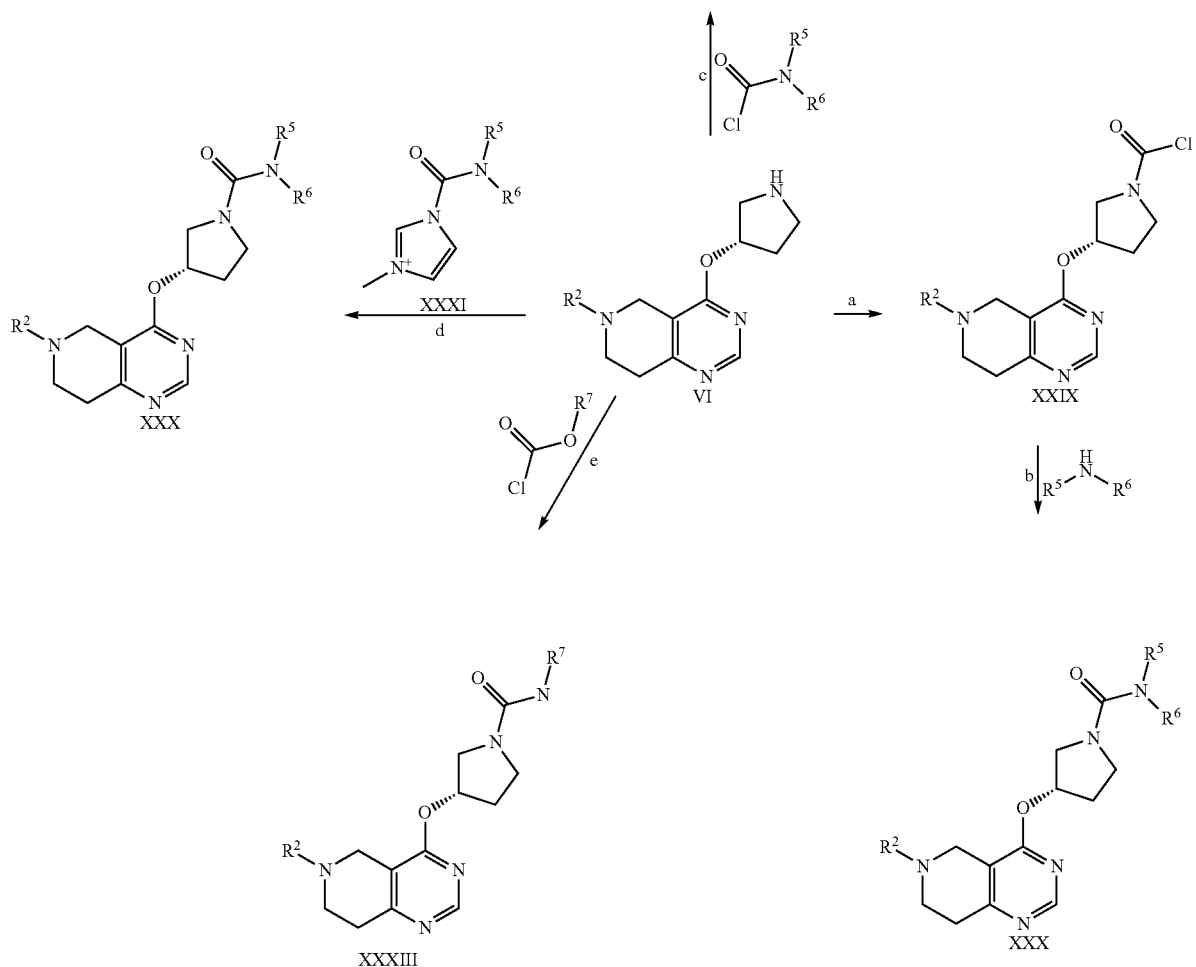

a) Compounds of general formula VI is reacted with phosgene in a suitable solvent such as $CH_2Cl_2$ in the presence of a suitable base such as triethylamine or N,N-diisopropylethylamine at a temperature of 0° C. to 25° C. for 1-2 hours. The reaction may preferably be carried out under an inert gas such as nitrogen or argon. Typical conditions comprise 1.0 eq. of compound of general formula VI, 1.0-5.0 eq. of phosgene, 3.0-4.0 eq. of triethylamine in $CH_2Cl_2$ under argon for 1 hour. b) Compound of general formula XXIX is reacted with amine R5R6NH in the presence of a suitable base such as triethylamine or N,N-diisopropylethylamine in a suitable solvent such as $CH_2Cl_2$ or N,N-dimethylformamide at a temperature of 10° C. to 30° C. for 1-18 h. The reaction may preferably be carried out under an inert gas such as nitrogen or argon. Typical conditions comprise 1.0 eq. of compound of general formula XXIX, 1.0-1.2 eq. of $R^5R^6NH$, 3.0-4.0 eq. of triethylamine in $CH_2Cl_2$ under argon for 2 hours. c) Compounds of general formula VI is reacted with carbamoyl chloride $R^5R^6NCOCl$ in the presence of a suitable base such as triethylamine or N,N-diisopropylethylamine in a suitable solvent such as $CH_2Cl_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of $R^5R^6NCOCl$, 3.0-4.0 eq. of triethylamine in $CH_2Cl_2$ under argon for 18 hours. d) Compounds of general formula VI is reacted with compounds of general formula XXXI in the presence of a suitable base such as triethylamine or N,N-diisopropylethylamine in a suitable solvent such as $CH_2Cl_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of compound of general formula XXXI, 1.0-2.0 eq. of triethylamine in $CH_2Cl_2$ under argon for 18 hours. e) Compounds of general formula VI is reacted with compounds of formula $R^7OCOCl$ in the presence of a suitable base such as triethylamine or N,N-diisopropylethylamine in a suitable solvent such as $CH_2Cl_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of compounds of general formula $R^7OCOCl$, 3.0-4.0 eq. of triethylamine in $CH_2Cl_2$ under argon for 18 hours.

Scheme 8

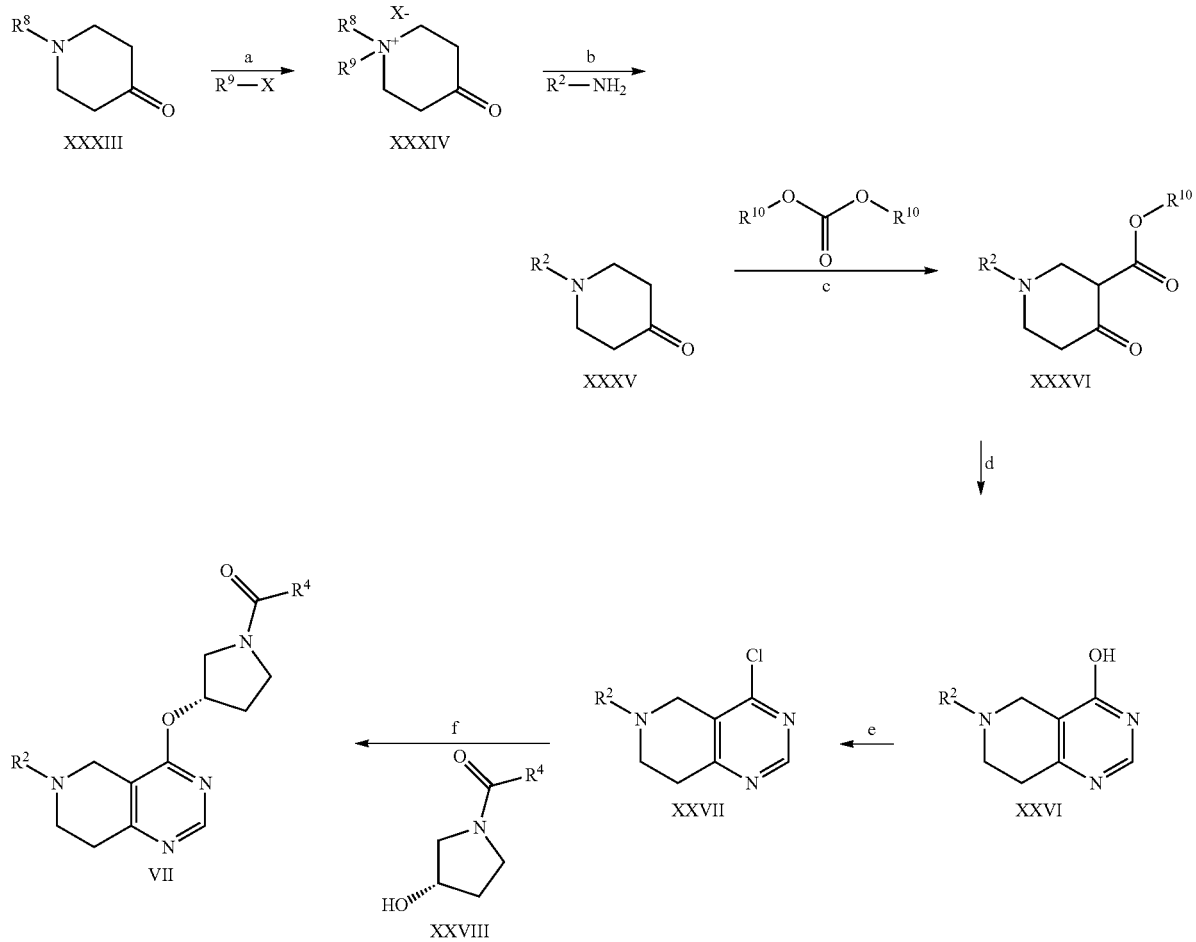

a) Quaternarization of the tertiary amine of general formula XXXIII (where $R^8$=alkyl e.g. benzyl) with compound of general formula $R^9$—X (where $R^9$=alkyl e.g. methyl and X=Bromo or Iodo) under customary conditions using in particular acetone as organic solvent. b) Alkylation of amine of general formula $R^2$—NH2 with quaternary amine XXXIV was performed by using base such a in particular $K_2CO_3$ and organic solvent such as in particular a 2/1 mixture of ethanol and water and heating the reaction mixture at 80-100° C., in particular 80° C. c) Compound of general formula XXXV was reacted with base such as in particular NaH and compound of general formula $(R^{10}O)_2CO$ (where $R^{10}$=alkyl e.g. carbonic acid dimethyl ester). The reaction mixture is stirred under high temperature (90° C.). d) Pyrimidine ring formation was obtained by reacting the compound of general formula XXXVI with formamidine acetate with a base such as sodium methoxide and organic solvent such as methanol at elevated temperature such as 90° C. for 2-18 h. e) Compound of general formula XXVI was reacted with phosphoryl chloride in presence of base such as triethylamine in organic solvent such as toluene at elevated temperature such as 100° C. for 12-18 h. f) Alcohol of general formula XXVIII is reacted with Compound of general formula XXXVII under customary conditions by deprotonation of the secondary alcohol using sodium hydride (NaH) and organic solvent THF under inert gas conditions at room temperature.

Where it is stated that compounds were prepared in the manner described for an earlier example, the skilled person will appreciate that reaction times, number of equivalents of reagents and reaction temperatures may be modified for each specific reaction, and that it may nevertheless be necessary or desirable to employ different work-up or purification conditions.

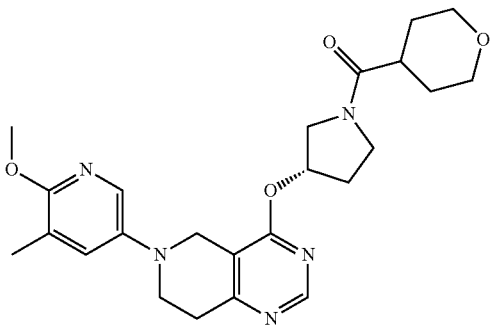 [SMILES: COc1ncc(N2CCc3ncnc(O[C@H]4CCN(C(=O)C5CCOCC5)C4)c3C2)cc1C]

Example 1

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone Synthesis of Example 1

Method 1a (According to Scheme 8)

Sodium hydride (60% in dispersion oil, 17.88 mg, 0.447 mmol) was added under argon to a solution of intermediate 3 (75 mg, 0.378 mmol) in 2 mL of dry THF. The suspension was stirred under an atmosphere of argon at ambient temperature for 15 min. 4-Chloro-6-(6-methoxy-5-methyl-pyridin-3-yl)-5,6,7,8-tetrahydro-pyrido[4,3-d]pyrimidine (100 mg, 0.344 mmol) was added and stirred at rt for an additional 3 hours. The reaction mixture was quenched with H$_2$O, extracted with CH$_2$Cl$_2$. The organic layer was washed with brine, dried over Na$_2$SO$_4$, filtered and evaporated to dryness. Purification by flash-chromatography on silica gel (CH$_2$Cl$_2$/MeOH 95/5) gave {(S)-3-[6-(6-methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone as a light yellow gum (115 mg, 74% yield). $^1$H-NMR (400 MHz, methanol-d4, 298K) δ ppm 1.59-1.87 (m, 4H) 2.20 (s, 3H) 2.27-2.43 (m, 2H) 2.74-2.91 (m, 1H) 2.97-3.03 (m, 2H) 3.42-4.14 (m, 15H) 5.75-5.86 (m, 1H) 7.39-7.43 (m, 1H) 7.63-7.68 (m, 1H) 8.57-8.61 (m, 1H). LCMS: [M+H]$^+$=454.2, Rt$^{(3)}$=1.46 min.

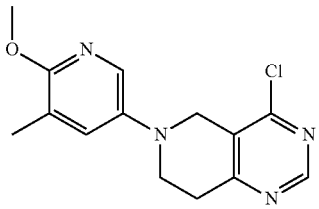 [SMILES: COc1ncc(N2CCc3ncnc(Cl)c3C2)cc1C]

4-Chloro-6-(6-methoxy-5-methyl-pyridin-3-yl)-5,6,7,8-tetrahydro-pyrido[4,3-d]pyrimidine A mixture of 6-(6-methoxy-5-methyl-pyridin-3-yl)-5,6,7,8-tetrahydro-pyrido[4,3-d]pyrimidin-4-ol (650 mg, 2.387 mmol), phosphoroxy chloride (0.334 mL, 3.58 mmol), triethylamine (0.665 mL, 4.77 mmol) and toluene (12 mL) was heated at 100° C. for 16 h. The mixture was neutralized with the addition of solid sodium bicarbonate, filtered and the solution was concentrated in vacuum. The remaining black residue was taken up in CH$_2$Cl$_2$ and water, the layers were separated and the organic phase washed with brine, dried over sodium sulfate, filtered and concentrated to give a dark brown solid. The solid was triturated in ethylacetate, filtered and dried under high vacuum to yield 4-chloro-6-(6-methoxy-5-methyl-pyridin-3-yl)-5,6,7,8-tetrahydro-pyrido[4,3-d]pyrimidine (630 mg, 91% yield) as a tan solid. $^1$H-NMR (400 MHz, DMSO-d6, 298K) δ ppm 2.15 (s, 3H) 3.03 (t, 2H) 3.53 (t, 2H) 3.82 (s, 3H) 4.26 (s, 2H) 7.49 (dd, 1H) 7.74 (d, 1H) 8.85 (s, 1H). LCMS: [M+H]$^+$=291.1, Rt$^{(4)}$=0.97 min.

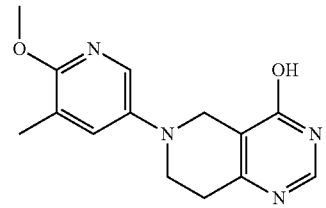 [SMILES: COc1ncc(N2CCc3ncnc(O)c3C2)cc1C]

6-(6-Methoxy-5-methyl-pyridin-3-yl)-5,6,7,8-tetrahydro-pyrido[4,3-d]pyrimidin-4-ol A mixture of 6'-methoxy-5'-methyl-4-oxo-3,4,5,6-tetrahydro-2H-[1,3']bipyridinyl-3-carboxylic acid methyl ester (900 mg, 3.23 mmol), formamidine acetate (521 mg, 4.85 mmol), sodium methoxide (5.4 Molar) in methanol (2.395 mL, 12.94 mmol) and methanol (4 mL) was heated to 90° C. for 3 h. The mixture was allowed to cool down to rt, diluted in CH$_2$Cl$_2$, neutralized with acetic acid (0.741 mL, 12.94 mmol) and quenched with H$_2$O. The layers were separated and aqueous was washed twice with CH$_2$Cl$_2$, organics were combined, washed with brine, dried over sodium sulfate, filtered and evaporated to give a yellow solid. The solid was triturated in ethylacetate to yield 6-(6-methoxy-5-methyl-pyridin-3-yl)-5,6,7,8-tetrahydro-pyrido[4,3-d]pyrimidin-4-ol (669 mg, yield 76%) as a white powder. $^1$H-NMR (400 MHz, DMSO-d6, 298K) δ ppm 2.14 (s, 3H) 2.72 (t, 2H) 3.39 (t, 2H) 3.81 (s, 3H) 3.90 (s, 2H) 7.42 (d, 1H) 7.67 (d, 1H) 8.07 (s, 1H) 12.46 (br.s., 1H). LCMS: [M+H]$^+$=273.1, Rt$^{(3)}$=1.30 min.

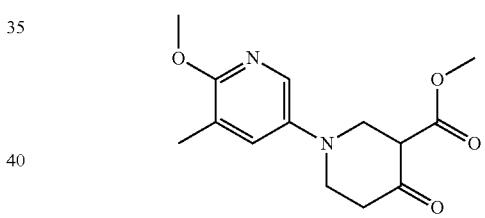

6'-Methoxy-5'-methyl-4-oxo-3,4,5,6-tetrahydro-2H-[1,3']bipyridinyl-3-carboxylic acid methyl ester To a stirred suspension of sodium hydride (60%, 153 mg, 6.36 mmol) in dimethyl carbonate (3.82 mL, 45.4 mmol) at room temperature was slowly added 6'-methoxy-5'-methyl-2,3,5,6-tetrahydro-[1,3']bipyridinyl-4-one (1 g, 4.54 mmol). The reaction mixture was heated to reflux (90° C.) for 1 h and then cooled to room temperature. The mixture was partitioned between CH$_2$Cl$_2$ and water and a solution of 1N HCl was added cautiously. The aqueous layer was separated and washed with an addition portion of CH$_2$Cl$_2$. The combined organic extracts were washed with brine, dried over sodium sulfate, filtered and evaporated to give the crude product, which was purified by flash-chromatography on silica gel (heptane/ethylacetate 3/1) to afford 6'-methoxy-5'-methyl-4-oxo-3,4,5,6-tetrahydro-2H-[1,3']bipyridinyl-3-carboxylic acid methyl ester (975 mg, yield 77%) as a white solid. $^1$H-NMR (400 MHz, DMSO, 298K) (mixture of keto and enol tautomers observed) δ ppm 2.12 (s, 6H) 2.36-2.69 (m, 4H) 3.26-3.96 (m, 20H) 7.34-7.77 (m, 4H) 11.84 (s, 1H). LCMS: [M+H]$^+$=279.1, Rt$^{(3)}$=1.51 min (tautomer 1) and 1.70 min (tautomer 2).

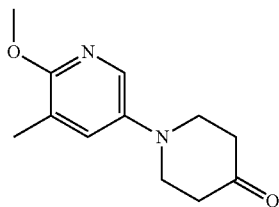 [SMILES: COc1ncc(N2CCC(=O)CC2)cc1C]

6'-Methoxy-5'-methyl-2,3,5,6-tetrahydro-[1,3']bi-pyridinyl-4-one

A slurry of iodide salt 1-benzyl-1-methyl-4-oxo-piperidinium (Ref: Tortolani, R.; Org. Lett., Vol. 1, No 8, 1999) (3.61 g, 10.86 mmol) in water (10 mL) was added slowly to a refluxing solution of 2-methoxy-5-amino-3-picolin (1 g, 7.24 mmol) and potassium carbonate (0.140 g, 1.013 mmol) in ethanol (20 mL). The reaction mixture was heated to reflux for an additional 3 h. The reaction mixture was cooled to rt and partitioned between $CH_2Cl_2$ and water. The organic layer was separated and washed with an addition portion of $CH_2Cl_2$. The combined organic layers were washed with brine, dried over sodium sulfate, filtered and concentrated to give the crude product which was purified by flash-chromatography on silica gel (heptane/ethylacetate 1/1) to afford 6'-methoxy-5'-methyl-2,3,5,6-tetrahydro-[1,3']bipyridinyl-4-one (1.15 g, yield 72%) as a light yellow gum. $^1$H-NMR (400 MHz, DMSO, 298K) δ ppm 2.12 (s, 3H) 2.42 (t, 4H) 3.46 (t, 4H) 3.80 (s, 3H) 7.40 (d, 1H) 7.71 (d, 1H). LCMS: [M+H]$^+$=221.1, Rt$^{(3)}$=1.41 min.

Synthesis of Example 1

Method 1b (According to Scheme 1)

Step 3
To a mixture 6-(6-methoxy-5-methyl-pyridin-3-yl)-4-((S)-pyrrolidin-3-yloxy)-5,6,7,8-tetrahydro-pyrido[4,3-d]pyrimidine (639 mg, 1.87 mmol) in $CH_2Cl_2$ (5 mL) was added the acid chloride tetrahydro-2H-pyran-4-carbonyl chloride (306 mg, 2.06 mmol) and triethylamine (0.522 mL, 3.74 mmol) at rt. The reaction mixture was stirred at rt for 10 min. The reaction mixture was concentrated under vacuum. Purification by preparative reverse phase Gilson HPLC and subsequent neutralization of the combined fractions by extraction with $CH_2Cl_2$/1N NaOH, separation of the organic phase through a phase separation tube and evaporated gave {(S)-3-[6-(6-methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone (432 mg, 51% yield) as a white powder. $^1$H-NMR (400 MHz, DMSO-d6, 298K) δ ppm 1.50-1.65 (m, 4H) 2.10-2.32 (m, 5H) 2.62-2.78 (m, 1H) 2.85-2.95 (m, 2H) 3.30-3.95 (m, 13H) 4.0-4.20 (m, 2H) 5.61-5.72 (m, 1H) 7.42 (br, 1H) 7.68 (m, 1H) 8.60-8.61 (m, 1H). LCMS: [M+H]$^+$=454.2, Rt$^{(1)}$=1.42 min.

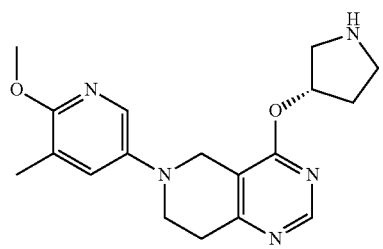 [SMILES: COc1ncc(N2CCc3ncnc(O[C@H]4CCNC4)c3C2)cc1C]

6-(6-Methoxy-5-methyl-pyridin-3-yl)-4-((S)-pyrrolidin-3-yloxy)-5,6,7,8-tetrahydro-pyrido[4,3-d]pyrimidine Step 2
(S)-3-[6-(6-Methoxy-5-methyl-pyridin-3-yl)-5,6,7,8-tetrahydro-pyrido[4,3-d]pyrimidin-4-yloxy]-pyrrolidine-1-carboxylic acid tert-butyl ester (2.05 g, 4.63 mmol) was dissolved in TFA/$CH_2Cl_2$ (½) and stirred at rt for 1 h. The reaction mixture was concentrated under vacuum, the residue was diluted with $CH_2Cl_2$, the organic layer washed with NaOH 1N then brine, dried over $Na_2SO_4$, filtered and evaporated to give 6-(6-methoxy-5-methyl-pyridin-3-yl)-4-((S)-pyrrolidin-3-yloxy)-5,6,7,8-tetrahydro-pyrido[4,3-d]pyrimidine. $^1$H NMR (400 MHz, CDCl$_3$, 298K) δ ppm 2.20-2.30 (m, 2H), 2.22 (s, 3H), 3.00-3.06 (t, 2H), 3.09-3.18 (m, 1H), 3.22-3.37 (m, 3H), 3.45-3.50 (t, 2H), 3.95 (s 3H), 4.10 (s, 2H), 4.20-4.65 (br.s 1 H), 5.63-5.69 (m, 1H), 7.21-7.252 (m, 1H), 7.70-7.74 (m, 1H), 8.60 (s, 1H). LCMS: [M+H]$^+$=341.9, Rt$^{(7)}$=0.61 min.

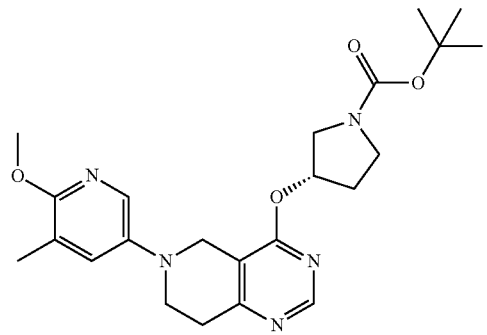 [SMILES: COc1ncc(N2CCc3ncnc(O[C@H]4CCN(C(=O)OC(C)(C)C)C4)c3C2)cc1C]

(S)-3-[6-(6-Methoxy-5-methyl-pyridin-3-yl)-5,6,7,8-tetrahydro-pyrido[4,3-d]pyrimidin-4-yloxy]-pyrrolidine-1-carboxylic acid tert-butyl ester Step 1
X-Phos (0.96 g, 2.01 mmol, 0.3 eq.), Pd$_2$(dba)$_3$ (0.615 g, 0.672 mmol, 0.1 eq.), Cs$_2$CO$_3$ (4.38 g, 13.44 mmol, 2 eq.) were combined and flushed 10 min with Argon. To this mixture, a solution of (S)-3-(5,6,7,8-tetrahydro-pyrido[4,3-d]pyrimidin-4-yloxy)-pyrrolidine-1-carboxylic acid tert-butyl ester (intermediate 7) (2.15 g, 6.72 mmol) in dioxane (6 mL) and 5-bromo-2-methoxy-3-methylpyridine (1.76 g, 8.73 mmol) were added at rt and the reaction mixture was stirred at 120° C. for 2 h. The reaction was cooled down to rt, the reaction mixture filtered over Hyflo, AcOEt was added and the organic layer was washed with brine, dried over Na$_2$SO$_4$, filtered and concentrated under vacuum. The residue was dissolved in dioxane (6 mL) and added to a glass vial containing 5-bromo-2-methoxy-3-methylpyridine (1.76 g, 8.73 mmol), X-Phos (0.96 g, 2.01 mmol), Pd$_2$(dba)$_3$ (0.615 g, 0.672 mmol), Cs$_2$CO$_3$ (4.38 g, 13.44 mmol). The vial was capped and the reaction mixture was stirred at 120°

C. for 2 h. The reaction was cooled down to rt, the reaction mixture filtered over Hyflo, AcOEt was added and the organic layer was washed with brine, dried over $Na_2SO_4$, filtered and concentrated under vacuum. Purification by flash chromatography on silica gel ($CH_2Cl_2$ then TBME then TBME/MeOH 99/1 to 90/10) gave (S)-3-[6-(6-methoxy-5-methyl-pyridin-3-yl)-5,6,7,8-tetrahydro-pyrido[4,3-d]pyrimidin-4-yloxy]-pyrrolidine-1-carboxylic acid tert-butyl ester as a yellow foam (2.05 g, 69% yield). $^1$H NMR (400 MHz, DMSO-d6, 298K) δ ppm 1.35-1.44 (br.s., 9H) 2.07-2.23 (m, 2 H), 2.14 (s, 3 H), 2.87-2.93 (m, 2 H), 3.39-3.68 (m, 6 H), 3.81 (s, 3 H), 4.03-4.08 (m, 2 H), 5.56-5.63 (m, 1 H), 7.41-7.46 (m, 1 H), 7.67-7.73 (m, 1 H), 8.60 (s, 1 H). LCMS: $[M+H]^+$=342.2, $Rt^{(2)}$=0.94 min.

Crystallization of Example 1 by Heating and Cooling in Acetonitrile 1 part of Example 1 (eg. 100 mg) was mixed with 5 parts of acetonitrile (0.5 mL for each 100 mg of compound) with stirring. A solution was obtained by heating up to 40-60° C. The mixture was then allowed to slowly cooled down to RT. After further cooling overnight (5° C.), precipitation was observed. In case no precipitation is not observed, the volume of ethanol can be reduce using a nitrogen stream and repeating the overnight cooling step. The mixture was centrifuged to remove the ethanol. The solid was dried under vacuum at 25° C. and 70 mbar. A crystalline anhydrous form of Example 1 with a MP of 131° C. was obtained. This crystalline form was also observed under other methods and/or solvents, such as heating and cooling in ethanol, acetone, ethyl acetate, isopropanol, by slurry in heptane, or by antisolvent addition in THF or 3-methyl-1-butanol using heptane as antisolvent. These results show the reproducibility and scalability of the crystalline form as well as suggests that the same form can be prepared under different experimental conditions than the ones described above.

List of most significant peaks from X-ray Powder Diffraction Pattern of Example 1 anhydrous form (Method X2):

| 2-Theta in deg | Intensity in % |
| --- | --- |
| 7.5 | 56 |
| 10.9 | 12.5 |
| 11.7 | 25.1 |
| 14.3 | 23.8 |
| 15.1 | 100 |
| 15.8 | 40.9 |
| 16.7 | 22.1 |
| 17.7 | 65.1 |
| 18.9 | 28.9 |
| 20.5 | 24.7 |
| 21.8 | 26 |
| 22.5 | 28.3 |
| 23.3 | 31.3 |
| 24.2 | 76.1 |
| 24.6 | 51.8 |
| 25.0 | 41.3 |
| 25.6 | 20.4 |
| 26.2 | 20.8 |
| 27.0 | 14.2 |
| 28.0 | 17.5 |
| 29.1 | 16.1 |
| 32.8 | 14 |
| 34.6 | 11.4 |

Crystallization of Trihydrate Form of Example 1 by Slurry in Water

Slurry of Example 1 in water e.g., 1 part of Example 1 in 10 parts of water, at RT produced a trihydrate form of Example 1. The crystals were separated by centrifugation and dried at room environment.

List of most significant peaks from X-ray Powder Diffraction Pattern of Example 1 trihydrate form (Method X2):

| 2-Theta in deg | Intensity in % |
| --- | --- |
| 6.6 | 24.3 |
| 8.9 | 7.9 |
| 13.3 | 100 |
| 14.5 | 18.3 |
| 15.0 | 12.6 |
| 16.5 | 12.4 |
| 17.5 | 15.7 |
| 17.7 | 17.2 |
| 18.2 | 9.8 |
| 20.0 | 10.7 |
| 21.6 | 11.7 |
| 22.6 | 20.3 |
| 23.8 | 11.4 |
| 24.4 | 15.2 |
| 26.7 | 26.5 |
| 27.5 | 18.7 |
| 27.8 | 16.6 |
| 29.2 | 9.8 |
| 33.3 | 9 |
| 33.9 | 7.6 |
| 35.7 | 8.2 |
| 38.8 | 7 |

Preparation of Citrate Salt of Example 1

0.5 g of Example 1 (assay 91.8%) were dissolved in 5 mL of methylethylketone and 0.25 mL of water and heated at 60° C. 213 mg of citric acid were added at 50° C. and the mixture was allowed to cool down to RT within 30 min. Crystallization occurs at 45° C. The mixture was stirred for 16 h at RT. The crystals were collected by filtration. The filter cake was washed 3 times with 1 mL of methylethylketone and afterwards dried for 16 h at 50° C. and ca. 10 mbar vacuum. Elementary analysis of the citrate salt showed a 1:1 (monohydrate) form.

List of most significant peaks from X-ray Powder Diffraction Pattern of Example 1 citrate salt (Method X1):

| 2-Theta in deg | Intensity in % |
| --- | --- |
| 5.7 | 62 |
| 11.5 | 100 |
| 12.1 | 4 |
| 14.3 | 4 |
| 15.4 | 12 |
| 17.2 | 21 |
| 17.9 | 31 |
| 19.3 | 25 |
| 20.2 | 37 |
| 20.7 | 8 |
| 21.9 | 5 |
| 23.3 | 11 |
| 23.9 | 36 |
| 25.5 | 28 |
| 27.0 | 5 |
| 27.7 | 6 |

-continued

| 2-Theta in deg | Intensity in % |
|---|---|
| 29.8 | 8 |
| 30.3 | 7 |

Preparation of Fumarate Salt of Example 1

0.5 g Example 1 (assay 91.8%) were dissolved in 15 mL of acetonitrile and 0.2 mL of water and heated at 76° C. 129 mg of fumaric acid were added at 60° C. The solution was allowed to cool down to RT within 30 min. The salt precipitated and the suspension was stirred for 16 h at RT. The crystals were collected by filtration. The filter cake was washed 3 times with 1 mL of acetonitrile and afterwards dried for 16 h at 50° C. and ca. 10 mbar vacuum. Elementary analysis of the fumarate salt showed a 1:1 (monohydrate) form.

List of most significant peaks from X-ray Powder Diffraction Pattern of Example 1 fumarate salt (Method X1):

| 2-Theta in deg | Intensity in % |
|---|---|
| 6.0 | 100 |
| 6.5 | 12 |
| 9.8 | 8 |
| 12.3 | 10 |
| 13.1 | 14 |
| 15.6 | 22 |
| 17.7 | 16 |
| 19.1 | 21 |
| 19.7 | 27 |
| 23.9 | 40 |
| 24.7 | 6 |
| 24.9 | 10 |
| 25.2 | 5 |
| 26.4 | 11 |
| 27.0 | 4 |

Preparation of Napadisylate Salt of Example 1

0.5 g Example 1 (assay 91.8%) were dissolved in 5 mL of ethanol absolute and 0.25 mL of water at 60° C. 250 mg of naphthalendisulfonic acid were added at 50° C. and the mixture was allowed to cool down to RT within 30 min. Crystallization occurs at 40° C. The mixture was stirred for 16 h at RT. The crystals were collected by filtration. The filter cake was washed 3 times with 1 mL of ethanol and afterwards dried for 16 h at 50° C. and ca. 10 mbar vacuum. Elementary analysis of the napadisylate salt showed a 2:1 (monohydrate) form.

List of most significant peaks from X-ray Powder Diffraction Pattern of Example 1 napadisylate salt (Method X1):

| 2-Theta in deg | Intensity in % |
|---|---|
| 4.3 | 100 |
| 8.5 | 3 |
| 9.4 | 6 |
| 12.2 | 12 |
| 12.9 | 12 |
| 13.5 | 37 |
| 15.0 | 26 |
| 15.6 | 12 |
| 16.0 | 11 |
| 17.7 | 28 |
| 18.9 | 23 |
| 19.3 | 11 |
| 20.0 | 11 |
| 20.8 | 3 |
| 21.2 | 5 |
| 22.0 | 9 |
| 23.0 | 41 |
| 24.5 | 39 |
| 26.5 | 20 |

Examples 2-9 were prepared using procedures analogous to those used in Example 1 (method ib) using appropriate starting materials.

| | | Rt[(1)] (min.) | MS: [M + H]+ |
|---|---|---|---|
| Example 2 | 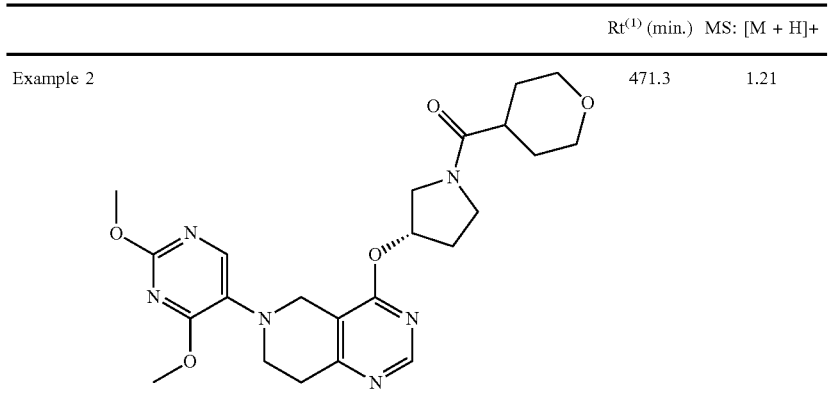 | 471.3 | 1.21 |

Name: {(S)-3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method C
Prepared using process step 3 of method 1b from intermediate 8 and tetrahydro-pyran-4-carbonyl chloride
$^1$H NMR (400 MHz, methanol-d4, 298K) δ ppm 1.50-1.86 (m, 4H) 2.20-2.45 (m, 2H) 2.70-2.87 (m, 1H) 2.96-2.99 (m, 2H) 3.35-4.14 (m, 18H) 5.69-5.85 (m, 1H) 7.96 (m, 1H) 8.58 (m, 1H)

|  | Rt(1) (min.) | MS: [M + H]+ |
|---|---|---|
| Example 3 | 1.42 | 465.2 |

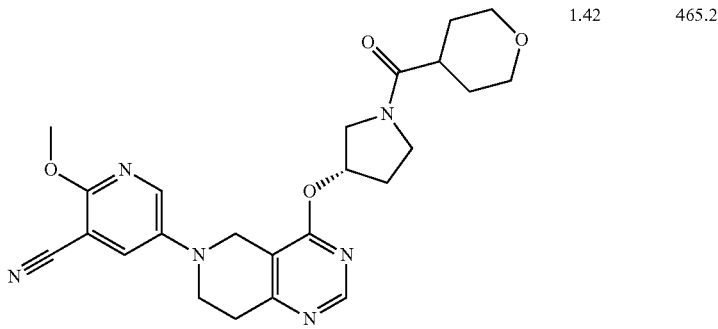

Name: 2-Methoxy-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile
Purification method: Reverse phase method A
Prepared using process steps 2-3 of method 1b from intermediate 11 and tetrahydro-pyran-4-carbonyl chloride
$^1$H NMR (400 MHz, DMSO-d6, 298K) δ ppm 1.50-1.64 (m, 4H) 2.10-2.31 (m, 2H) 2.62-2.77 (m, 1H) 2.87-2.95 (m, 2H) 3.29-3.96 (m, 13H) 4.08-4.21 (m, 2H) 5.58-5.73 (m, 1H) 8.06-8.09 (m, 1H) 8.23-8.27 (m, 1H) 8.60-8.64 (m, 1H)

|  | Rt(1) (min.) | MS: [M + H]+ |
|---|---|---|
| Example 4 | 1.27 | 414.2 |

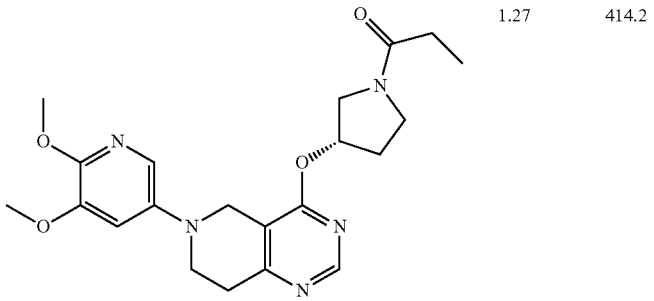

Name: 1-{(S)-3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one
Purification method: Reverse phase method A
Prepared using process steps 2-3 of method 1b from intermediate 10 and propionyl chloride
$^1$H NMR (400 MHz, CDCl$_3$-d, 298K) δ ppm 1.10-1.20 (m, 3H) 2.19-2.49 (m, 4H) 3.02-3.08 (m, 2H) 3.45-3.52 (m, 2H) 3.56-3.68 (m, 2H) 3.72-3.90 (m, 2H) 3.91 (s, 3H) 3.99 (s, 3H) 4.07-4.12 (m, 2H) 5.75-5.78 (m, 1H) 6.89-7.01 (m, 1H) 7.44-7.46 (m, 1H) 8.60-8.62 (m, 1H)

|  | Rt(1) (min.) | MS: [M + H]+ |
|---|---|---|
| Example 5 | 1.25 | 470.2 |

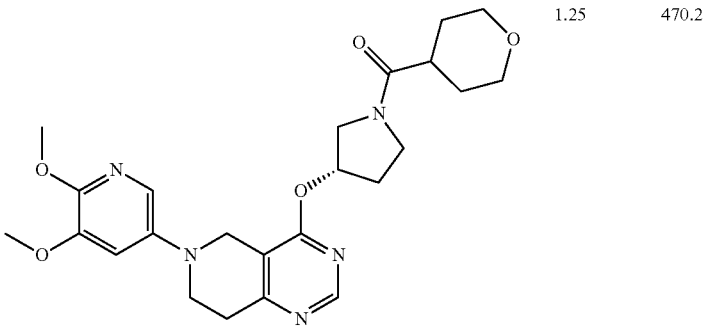

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method A
Prepared using process steps 2-3 of method 1b from intermediate 10 and tetrahydro-pyran-4-carbonyl chloride ¹H NMR (400 MHz, CDCl₃-d, 298K) δ ppm 1.56-1.68 (m, 2H) 1.88-2.00 (m, 2H) 2.20-2.38 (m, 2H) 2.53-2.70 (m, 1H) 3.05-3.10 (m, 2H) 3.39-3.54 (m, 4H) 3.59-3.82 (m, 4H) 3.91 (s, 3H) 3.99 (s, 3H) 4.01-4.10 (m, 4H) 5.62-5.78 (m, 1H) 6.89-6.90 (m, 1H) 7.40-7.43 (m, 1H) 8.60-8.65 (m, 1H)

| | Rt⁽¹⁾ (min.) | MS: [M + H]+ |
|---|---|---|

Example 6 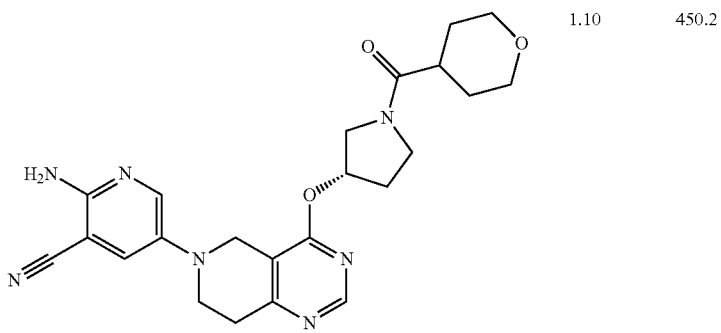 1.10 450.2

Name: 2-Amino-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile Prepared using process step 3 of method 1b from intermediate 9 and tetrahydro-pyran-4-carbonyl chloride Purification method: 1-Normal phase chromatography CH₂Cl₂/MeOH as solvent 2-Reverse phase method A ¹H NMR (400 MHz, CDCl₃-d, 298K) δ ppm 1.45-1.75 (m, 2H) 1.86-2.02 (m, 2H) 2.20-2.40 (m, 2H) 2.50-2.75 (m, 1H) 3.02-3.09 (m, 2H) 3.38-4.20 (m, 12H) 4.96 (s, 1H) 5.70-5.78 (m, 1H) 7.39 (m, 1H) 8.13-8.14 (m, 1H) 8.62-8.64 (m, 1H)

| | Rt⁽¹⁾ (min.) | MS: [M + H]+ |
|---|---|---|

Example 7 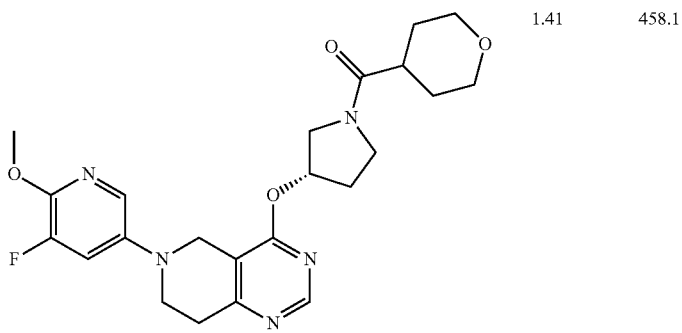 1.41 458.1

Name: {(S)-3-[6-(5-Fluoro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone Purification method: Biotage 11g KP-NH cartridge eluting with Heptane/EtOAc 100/0 to 0/100

Prepared using process steps 2-3 of method 1b from intermediate 12 and tetrahydro-pyran-4-carbonyl chloride ¹H NMR (400 MHz, CDCl₃, 298K) δ ppm 1.56-1.74 (m, 2H) 1.87-2.02 (m, 2H) 2.19-2.42 (m, 2H) 2.51-2.74 (m, 1H) 3.01-3.09 (m, 2H) 3.39-4.20 (m, 15H) 5.70-5.79 (m, 1H) 7.13-7.20 (m, 1H) 7.63-7.69 (m, 1H) 8.59-8.66 (m, 1H)

| | Rt(1) (min.) | MS: [M + H]+ |
|---|---|---|
| Example 8 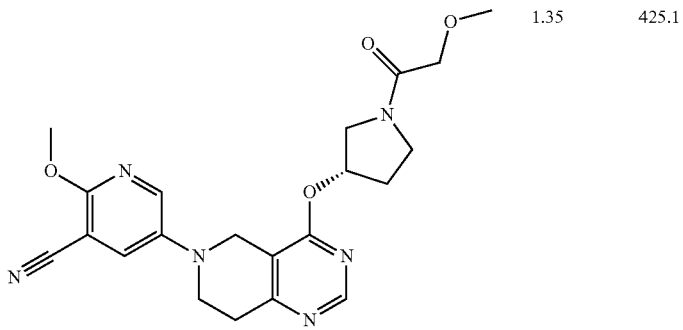 | 1.35 | 425.1 |

Name: 2-Methoxy-5-{4-[(S)-1-(2-methoxy-acetyl)-pyrrolidin-3-yloxy]-7,8-dihydro-5H-pyrido[4,3-d]pyrimidin-6-yl}-nicotinonitrile
Purification method: Reverse phase method A
Prepared using process steps 2-3 of method 1b from intermediate 11 and methoxy acetyl chloride
1H NMR (400 MHz, DMSO-d6, 298K) δ ppm 2.11-2.32 (m, 2H) 2.88-2.95 (m, 2H) 3.26-3.32 (m, 3H) 3.46-3.84 (m, 6H) 3.91-3.95 (m, 3H) 3.98-4.08 (m, 2H) 4.13-4.19 (m, 2H) 5.59-5.71 (m, 1H) 8.07-8.10 (m, 1H) 8.25-8.28 (m, 1H) 8.61-8.62 (m, 1H)

| | Rt(8) (min.) | MS: [M + H]+ |
|---|---|---|
| Example 9 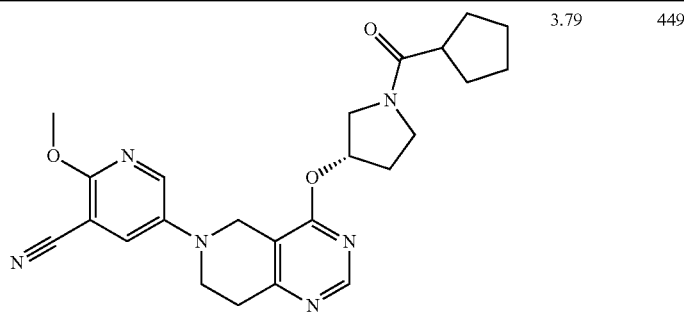 | 3.79 | 449.1 |

Name: 5-[4-((S)-1-Cyclopentanecarbonyl-pyrrolidin-3-yloxy)-7,8-dihydro-5H-pyrido[4,3-d]pyrimidin-6-yl]-2-methoxy-nicotinonitrile
Purification method: Reverse phase method A
Prepared using process steps 2-3 of method 1b from intermediate 11 and cyclopentanecarbonyl chloride

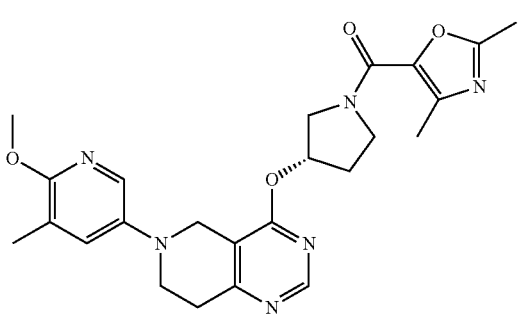 [SMILES: COc1ncc(N2CCc3ncnc(O[C@H]4CCN(C(=O)c5oc(C)nc5C)C4)c3C2)cc1C]

Example 10

(2,4-Dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone Step 1

A mixture of 2,4-dimethyl-oxazole-5-carboxylic acid (36.4 mg, 0.258 mmol), HTBU (98 mg, 0.258 mmol), DIPEA (86 μl, 0.49 mmol) in DMF (5 mL) was stirred at rt for 20 min. then a solution of 6-(6-methoxy-5-methyl-pyridin-3-yl)-4-((S)-pyrrolidin-3-yloxy)-5,6,7,8-tetrahydro-pyrido[4,3-d]pyrimidine (prepared in example 1, method 1b, step 2) (80 mg, 0.23 mmol) and DIPEA (86 μl, 0.49 mmol) in DMF (0.4 mL) was added. The reaction mixture was stirred 30 min at rt. The reaction mixture was directly purified by preparative reverse phase Gilson HPLC and subsequent neutralization of the combined fractions over PL-HCO3 MP gave (2,4-dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone (91 mg, 84% yield) as a white lyophilized powder.
1H-NMR (400 MHz, methanol-d4, 298K) δ ppm 2.17 (s, 3H) 2.27-2.52 (m, 8H) 2.95-3.03 (m, 2H) 3.44-3.55 (m, 2H) 3.70-4.26 (m, 9H) 5.76-5.92 (m, 1H) 7.40 (br. s., 1H) 7.64 (br. s., 1H) 8.55-8.62 (m, 1H), LCMS: [M+H]+=465.2, Rt(1)=1.51 min.

Examples 11-49 and 51-53 were prepared using procedures analogous to those used in Example 10, step 1 using appropriate starting materials.

|  | | Rt(1) (min.) | MS: [M + H]+ |
|---|---|---|---|
| Example 11 | 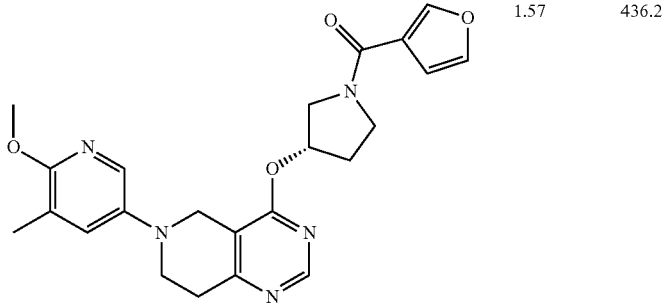 | 1.57 | 436.2 |

Name: Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using furan-3-carboxylic acid
$^1$H NMR (400 MHz, methanol-d4, 298K) δ ppm 2.17 (s, 3H) 2.30-2.45 (m, 2H) 2.93-3.05 (m, 2H) 3.45-3.54 (m, 2H) 3.72-4.21 (m, 9H) 5.79-5.86 (m, 1H) 6.78-6.82 (m, 1H) 7.37-7.44 (m, 1H) 7.56-7.61 (m, 1H) 7.61-7.69 (m, 1H) 8.01-8.12 (m, 1H) 8.54-8.62 (m, 1H)

|  | | Rt(1) (min.) | MS: [M + H]+ |
|---|---|---|---|
| Example 12 | 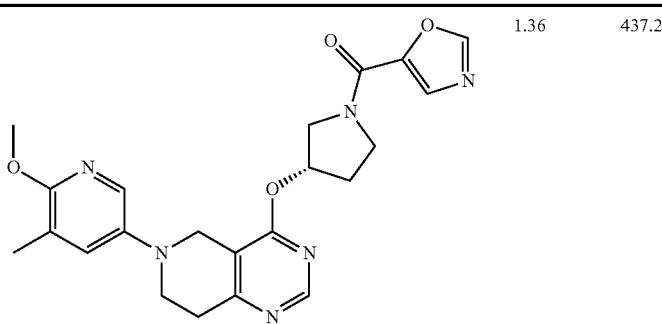 | 1.36 | 437.2 |

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using oxazole-5-carboxylic acid
$^1$H NMR (400 MHz, methanol-d4, 298K) δ ppm 2.17 (s, 3H) 2.30-2.39 (m, 1H) 2.41-2.50 (m, 1H) 2.95-3.03 (m, 2H) 3.45-3.52 (m, 2H) 3.76-4.32 (m, 9H) 5.79-5.94 (m, 1H) 7.40 (br. s., 1H) 7.62-7.66 (m, 1H) 7.75-7.82 (m, 1H) 8.34-8.40 (m, 1H) 8.56-8.61 (m, 1H)

|  | | Rt(1) (min.) | MS: [M + H]+ |
|---|---|---|---|
| Example 13 | 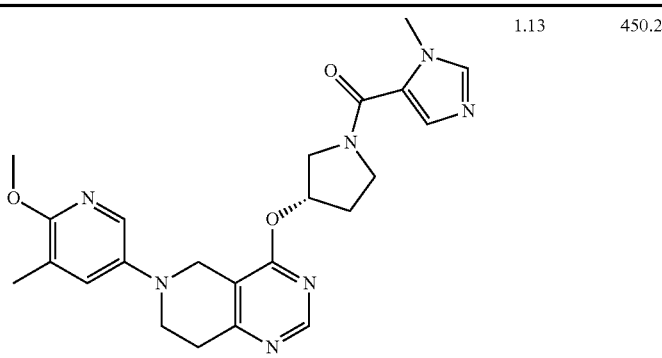 | 1.13 | 450.2 |

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone
Purification method: Reverse phase method A
Prepared using 3-methyl-3H-imidazole-4-carboxylic acid -continued ¹H NMR (400 MHz, methanol-d4, 298K) δ ppm 2.17 (s, 3H) 2.30-2.45 (m, 2H) 2.93-3.05 (m, 2H) 3.43-3.55 (m, 2H) 3.74-4.24 (m, 12H) 5.82 (br. s., 1H) 7.35-7.56 (m, 2H) 7.66 (m, 1H) 7.76 (br. s., 1H) 8.55-8.60 (m, 1H)

| | | Rt⁽¹⁾ (min.) | MS [M + H]+ |
|---|---|---|---|
| Example 14 | 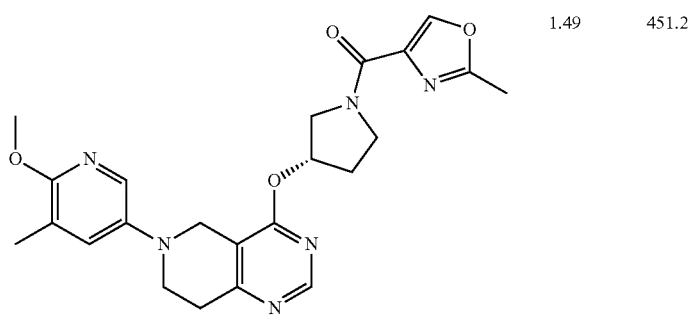 | 1.49 | 451.2 |

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone
Purification method: Reverse phase method A
Prepared using 2-methyl-oxazole-4-carboxylic acid
¹H NMR (400 MHz, methanol-d4, 298K) δ ppm 2.17 (s, 3H) 2.27-2.43 (m, 2H) 2.43-2.50 (m, 3H) 2.95-3.02 (m, 2H) 3.45-3.53 (m, 2H) 3.72-4.33 (m, 9H) 5.78-5.89 (m, 1H) 7.37-7.43 (m, 1H) 7.61-7.67 (m, 1H) 8.25-8.31 (m, 1H) 8.57-8.60 (m, 1H)

| | | Rt⁽¹⁾ (min.) | MS: [M + H]+ |
|---|---|---|---|
| Example 15 | 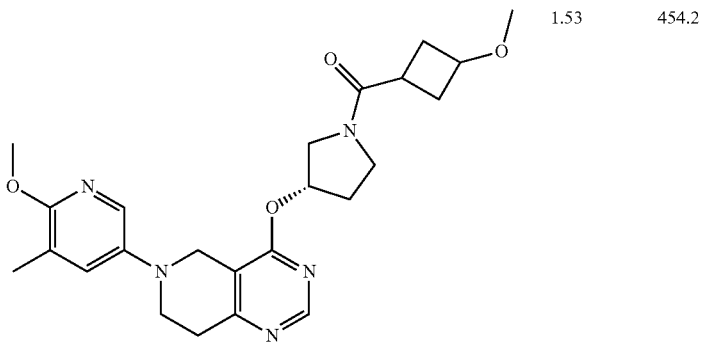 | 1.53 | 454.2 |

Name: (3-Methoxy-cyclobutyl)-{(S)-3-[6-(6-methoxy-5-methyl-pyridin-3-yl)-5,6,7,8-tetrahydro-pyrido[4,3-d]pyrimidin-4-yloxy]pyrrolidin-1-yl}-methanone
Purification method: Reverse phase method A
Prepared using 3-methoxy-cyclobutanecarboxylic acid
¹H NMR (400 MHz, methanol-d4, 298K) δ ppm 1.99-2.55 (m, 9H) 2.78-2.95 (m, 1H), 2.95-3.02 (m, 2H) 3.20-3.23 (m, 3H) 3.47-3.52 (m, 2H) 3.52-4.10 (m, 10H) 5.73-5.81 (m, 1H) 7.38-7.42 (m, 1) 7.63-7.67 (m, 1H) 8.57 (s, 1H)

| Example 16 | 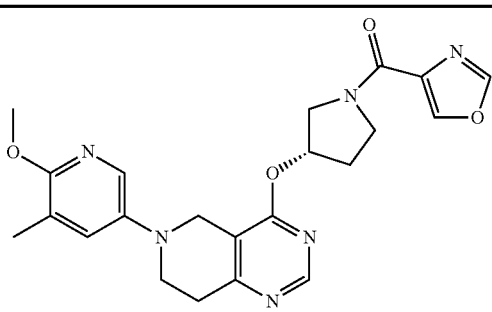 | Rt⁽¹⁾ (min.) 1.41 | MS: [M + H]+ 437.2 |
|---|---|---|---|

Name: ({(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone
Purification method: Reverse phase method A
Prepared using oxazole-4-carboxylic acid
¹H NMR (400 MHz, methanol-d4, 298K) δ ppm 2.17 (s, 3H) 2.29-2.37 (m, 1H) 2.37-2.44 (m, 1H) 2.94-
3.03 (m, 2H) 3.45-3.53 (m, 2H) 3.75-4.38 (m, 9H) 5.79-5.89 (m, 1H) 7.38-7.42 (m, 1H) 7.62-7.66 (m, 1H) 8.19-8.26 (m, 1H) 8.44-8.48 (m, 1H) 8.56-8.61 (m, 1H)

| Example 17 | 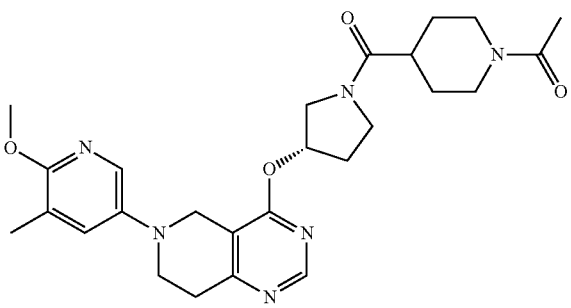 [SMILES: COc1ncc(N2CCc3ncnc(O[C@H]4CCN(C(=O)C5CCN(C(C)=O)CC5)C4)c3C2)cc1C] | Rt⁽¹⁾ (min.) 1.35 | MS: [M + H]+ 495.2 |
|---|---|---|---|

Name: 1-(4-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone
Purification method: Reverse phase method A
Prepared using 1-acetyl-piperidine-4-carboxylic acid
¹H NMR ((400 MHz, methanol-d4, 298K) δ ppm 1.49-1.89 (m, 4H) 2.06-2.13 (m,3 H) 2.18 (s, 3H) 2.23-2.43 (m, 2H) 2.61-2.93 (m, 2H) 2.95-3.04 (m, 2H) 3.15-3.25 (m, 1H) 3.42-3.53 (m, 2H) 3.55-4.12 (m, 10H) 4.46-4.59 (m, 1H) 5.74-5.86 (m, 1H) 7.38-7.45 (m, 1H) 7.62-7.67 (m, 1H) 8.56-8.61 (m, 1H)

| Example 18 | 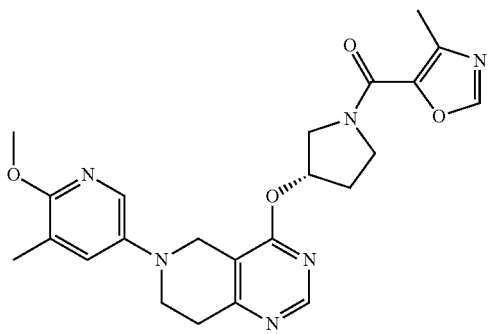 [SMILES: COc1ncc(N2CCc3ncnc(O[C@H]4CCN(C(=O)c5ocnc5C)C4)c3C2)cc1C] | Rt⁽¹⁾ (min.) 1.35 | MS: [M + H]+ 451.2 |
|---|---|---|---|

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone
Purification method: Reverse phase method A
Prepared using 4-methyl-oxazole-5-carboxylic acid
¹H NMR (400 MHz, methanol-d4, 298K) δ ppm 2.17 (s, 3H) 2.29-2.47 (m, 5H) 2.95-3.3.03 (m, 2H) 3.45-3.52 (m, 2H) 3.73-4.30 (m, 9H) 5.79-5.90 (m, 1H) 7.41 (m, 1H) 7.65 (br. s., 1H) 8.19-8.24 (m, 1H) 8.55-8.61 (m, 1H)

| Example 19 | 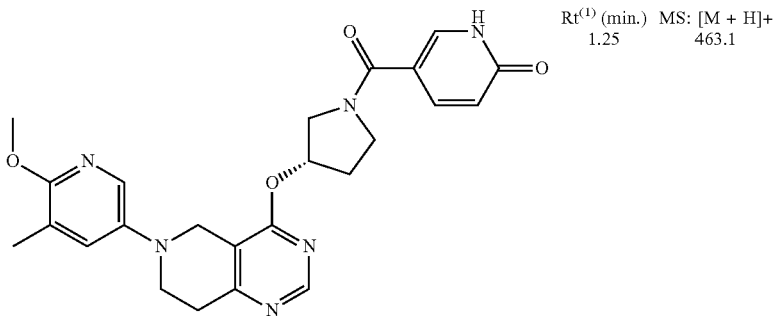 | Rt(1) (min.) 1.25 | MS: [M + H]+ 463.1 |

Name: 5-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one
Purification method: Reverse phase method A
Prepared using 6-oxo-1,6-dihydro-pyridine-3-carboxylic acid
$^1$H NMR (400 MHz, methanol-d4, 298K) δ ppm 2.19 (s, 3H) 2.30-2.40 (m, 2H) 2.95-3.05 (m, 2H) 3.45-3.55 (m, 2H) 3.74-4.22 (m, 9H) 5.73-5.85 (m, 1H) 6.50-6.56 (m, 1H) 7.39-7.45 (m, 1H) 7.60-7.70 (m, 1H) 7.78-7.90 (m, 2H) 8.50-8.60 (m, 1H)

| Example 20 | 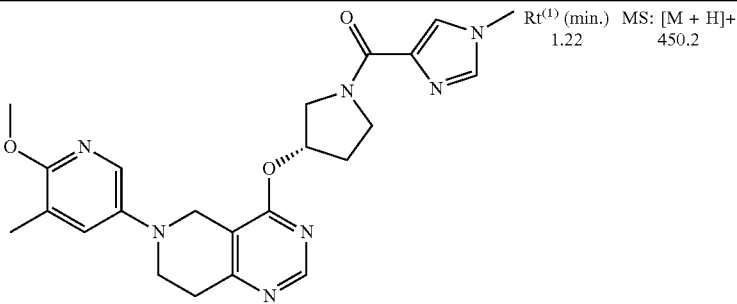 | Rt(1) (min.) 1.22 | MS: [M + H]+ 450.2 |

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone
Purification method: Reverse phase method A
Prepared using 1-methyl-1H-imidazole-4-carboxylic acid
$^1$H NMR (400 MHz, methanol-d4, 298K) δ ppm 2.17 (s, 3H) 2.28-2.41 (m, 2H) 2.94-3.02 (m, 2H) 3.45-3.52 (m, 2H) 3.73-4.35 (m, 12H) 5.80-5.85 (m, 1H) 7.38-7.43 (m, 1H) 7.60-7.69 (m, 3H) 8.55-8.61 (m, 1H)

| Example 21 | 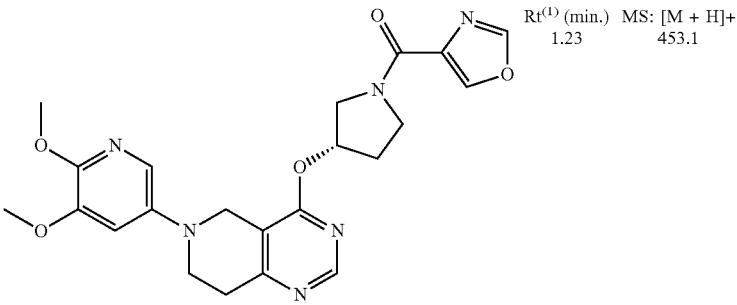 | Rt(1) (min.) 1.23 | MS: [M + H]+ 453.1 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone
Purification method: Normal phase chromatography with EtOAc/MeOH as solvent
Prepared using intermediate 10 and method 1b of process step 2 of example 1 followed by process step 1 of
example 10 using oxazole-4-carboxylic acid
$^1$H NMR (400 MHz, DMSO-d6, 298K) δ 2.10-2.37 (m, 2 H) 2.81-2.99 (m, 2 H) 3.46-4.27 (m, 14 H) 5.58-5.77 (m, 1 H) 7.08-7.20 (m, 1 H) 7.30-7.42 (m, 1 H) 8.43-8.54 (m, 1 H) 8.55-8.69 (m, 2 H)

| Example 22 | 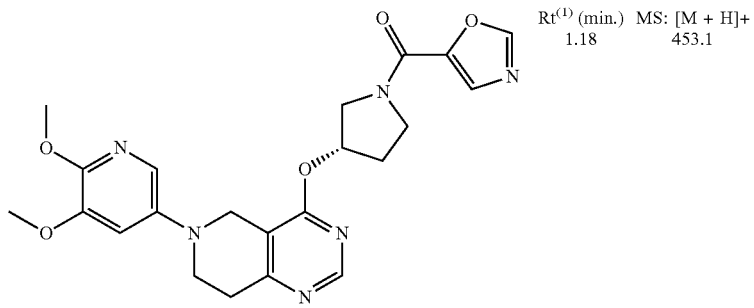 | Rt(1) (min.) 1.18 | MS: [M + H]+ 453.1 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using intermediate 10 and process step 2, method 1b of example 1 followed by process step 1 of example 10 using oxazole-5-carboxylic acid
1H NMR (400 MHz, DMSO-d6, 373K) δ ppm 2.22-2.42 (m, 2 H) 2.80-3.00 (m, 2 H) 3.50-4.30 (m, 14 H) 5.63-5.83 (m, 1 H) 7.06-7.09 (m, 1 H) 7.38-7.40 (m, 1 H) 7.69 (s, 1 H) 8.40 (s, 1 H) 8.57 (s, 1 H)

| Example 23 | 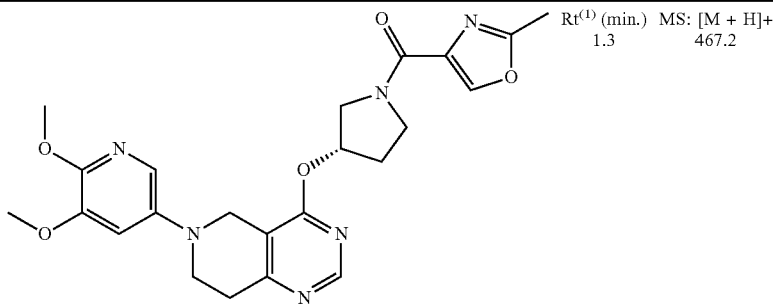 | Rt(1) (min.) 1.3 | MS: [M + H]+ 467.2 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone
Purification method: Reverse phase method A
Prepared using intermediate 10 and process step 2, method 1b of example 1 followed by process step 1 of example 10 using 2-methyl-oxazole-4-carboxylic acid
1H NMR (400 MHz, DMSO-d6, 298K) δ ppm 2.11-2.36 (m, 2 H) 2.40-2.44 (m, 3 H) 2.81-2.97 (m, 2 H) 3.40-4.28 (m, 14 H) 5.62-5.78 (m, 1 H) 7.11-7.21 (m, 1 H) 7.29-7.41 (m, 1 H) 8.42-8.52 (m, 1 H) 8.59-8.67 (m, 1 H)

| Example 24 | 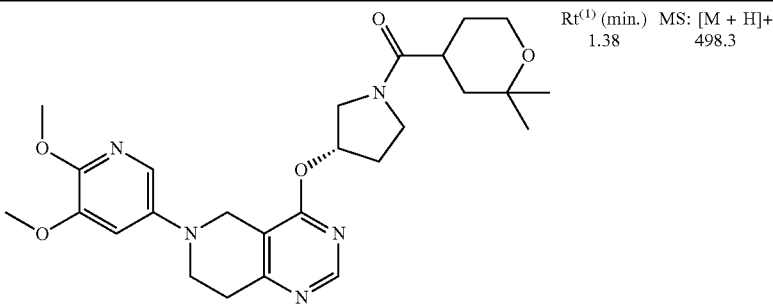 | Rt(1) (min.) 1.38 | MS: [M + H]+ 498.3 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone
Purification method: Reverse phase method A
Prepared using intermediate 10 and process step 2, method 1b of example 1 followed by process step 1 of example 10 using 2,2-dimethyl-tetrahydro-pyran-4-carboxylic acid
1H NMR (400 MHz, DMSO-d6, 298K) δ ppm 0.97-1.24 (m, 6 H) 1.28-1.58 (m, 4 H) 2.08-2.34 (m, 2 H) 2.72-2.97 (m, 3 H) 3.43-4.12 (m, 16 H) 5.55-5.76 (m, 1 H) 7.14-7.20 (m, 1 H) 7.31-7.37 (m, 1 H) 8.59-8.64 (m, 1 H)

| Example 25 | 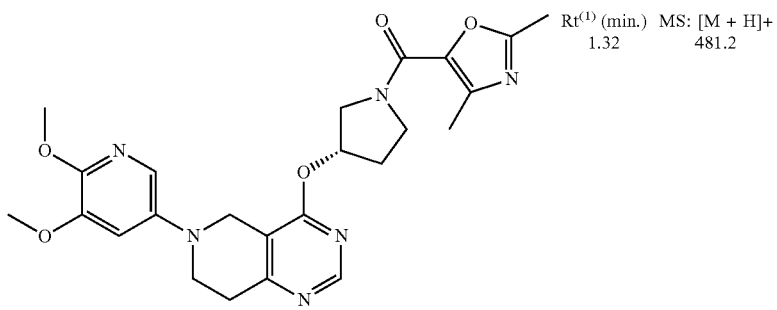 | Rt(1) (min.) 1.32 | MS: [M + H]+ 481.2 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone
Purification method: Reverse phase method A
Prepared using intermediate 10 and process step 2, method 1b of example 1 followed by process step 1 of example 10 using 2,2-dimethyl-tetrahydro-pyran-4-carboxylic acid
$^1$H NMR (400 MHz, DMSO-d6, 298K) δ ppm 2.11-2.48 (m, 8 H) 2.83-2.98 (m, 2 H) 3.43-4.18 (m, 14 H) 5.56-
5.89 (m, 1 H) 7.12-7.00 (m, 1 H) 7.32-7.40 (m, 1 H) 8.57-8.67 (m, 1 H)

| Example 26 | 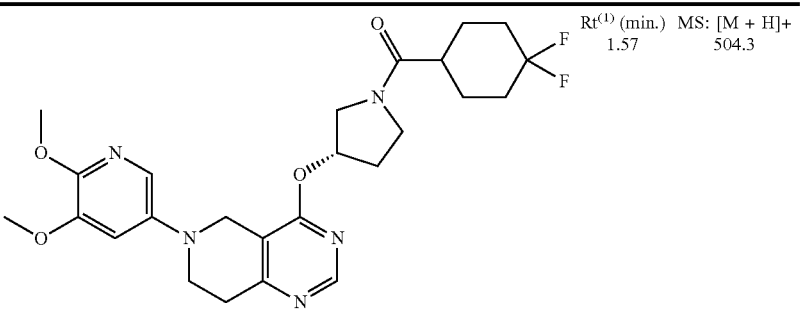 | Rt(1) (min.) 1.57 | MS: [M + H]+ 504.3 |

Name: (4,4-Difluoro-cyclohexyl)-{(S)-3-[6-(5,6-dimethoxy-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intemediate 10 and process step 2, method 1b of example 1 followed by process step 1 of example
10 using 4,4-difluoro-cyclohexanecarboxylic acid
$^1$H NMR (400 MHz, DMSO-d6, 298K) δ ppm 1.49-2.35 (m, 10 H) 2.61-2.67 (m, 1 H) 2.84-2.99 (m, 2 H) 3.42-3.83
(m, 12 H) 4.00-4.19 (m, 2 H) 5.57-5.78 (m, 1 H) 7.11-7.25 (m, 1 H) 7.29-7.43 (m, 1 H) 8.52-8.68 (m, 1 H)

| Example 27 | 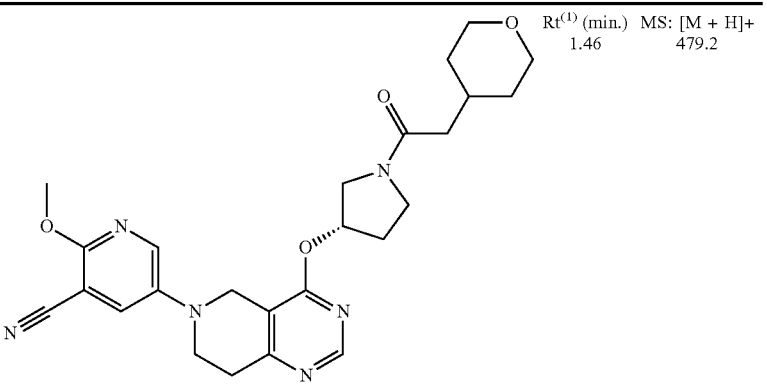 | Rt(1) (min.) 1.46 | MS: [M + H]+ 479.2 |

Name: 2-Methoxy-5-{4-[(S)-1-(2-tetrahydro-pyran-4-yl-acetyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using (tetrahydro-pyran-4-yl)-acetic acid -continued $^1$H NMR (400 MHz, DMSO-d6, 298K) δ ppm 1.11-1.28 (m, 2H) 1.49-1.64 (m, 2H) 1.87-1.99 (m, 1H) 2.07-2.29 (m, 4H) 2.86-2.95 (m, 2H) 3.19-3.30 (m, 2H) 3.42-3.88 (m, 8H) 3.90-3.96 (m, 3H) 4.09-4.19 (m, 2H) 5.57-5.70 (m, 1H) 8.07-8.11 (m, 1H) 8.22-8.28 (m, 1H) 8.58-8.65 (m, 1H)

| Example 28 | 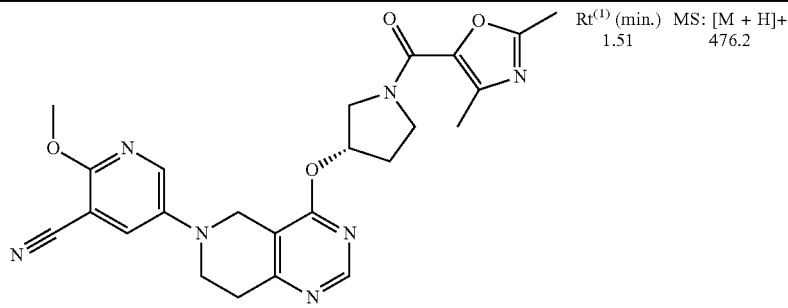 | Rt$^{(1)}$ (min.) 1.51 | MS: [M + H]+ 476.2 |
|---|---|---|---|

Name: 5-{4-[(S)-1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile
Purification method: Reverse phase method A
Prepared using intermediate 11 and process step 2, method 1b of example 1 followed by process step 1 of example 10 using 2,4-dimethyl-oxazole-5-carboxylic acid
$^1$H NMR (400 MHz, DMSO-d6, 298K) δ ppm 2.16-2.46 (m, 5H) 2.30 (s, 3H) 2.85-2.96 (m, 2H) 3.50-4.20 (m, 8H) 3.92 (s, 3H) 5.64-5.80 (m, 1H) 8.04-8.12 (m, 1H) 8.22-8.30 (m, 1H) 8.62 (s, 1H)

| Example 29 | 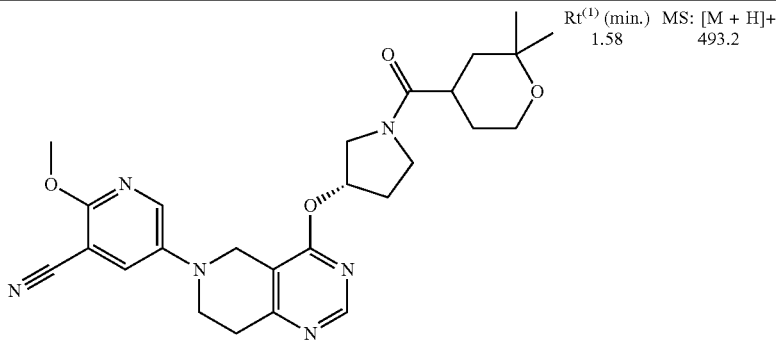 | Rt$^{(1)}$ (min.) 1.58 | MS: [M + H]+ 493.2 |
|---|---|---|---|

Name: 5-{4-[(S)-1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile
Purification method: Reverse phase method A
Prepared using intermediate 11 and process step 2, method 1b of example 1 followed by process step 1 of example 10 using 2,2-dimethyl-tetrahydro-pyran-4-carboxylic acid
$^1$H NMR (400 MHz, DMSO-d6, 298K) δ ppm 1.00-1.24 (m, 6H) 1.28-1.73 (m, 4H) 2.10-2.34 (m, 2H) 2.62-2.97 (m, 3H) 3.43-3.84 (m, 8H) 3.94 (s, 3H) 4.09-4.20 (m, 2H) 5.58-5.75 (m, 1H) 8.05-8.11 (m, 1H) 8.20-8.29 (m, 1H) 8.59-8.65 (m, 1H)

| Example 30 | 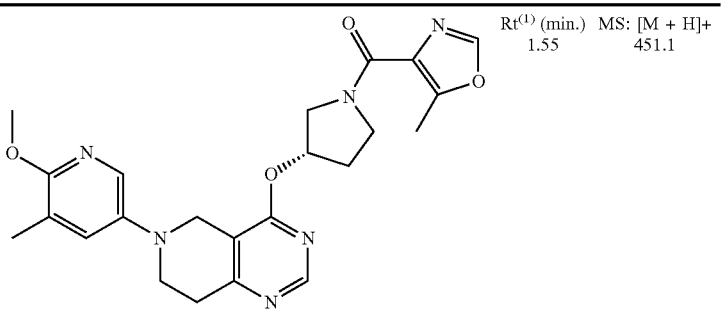 | Rt$^{(1)}$ (min.) 1.55 | MS: [M + H]+ 451.1 |
|---|---|---|---|

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone Purification method: Reverse phase method A
Prepared using 5-methyl-oxazole-4-carboxylic acid
$^1$H NMR (400 MHz, DMSO-d6, 298K) δ ppm 2.10-2.32 (m, 2H) 2.13 (s, 3H) 2.52-2.54 (m, 3H) 2.85-2.93 (m, 2H) 3.42-3.50 (m, 2H) 3.61-4.22 (m, 6H) 3.81 (s, 3H) 5.64-5.72 (m, 1H) 7.41-7.45 (m, 1H) 7.67-7.71 (m, 1H) 8.27-8.33 (m, 1H) 8.59-8.64 (m, 1H)

| Example 31 | 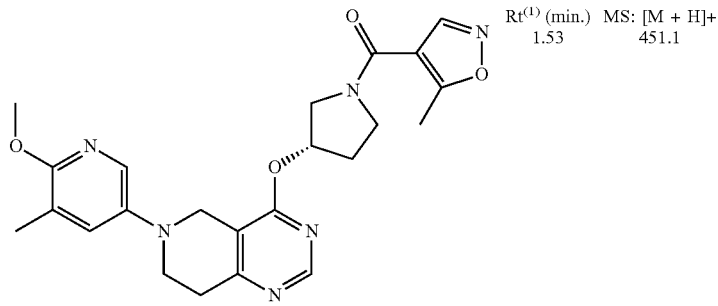 | Rt$^{(1)}$ (min.) 1.53 | MS: [M + H]+ 451.1 |
|---|---|---|---|

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone
Purification method: Reverse phase method A
Prepared using 5-methyl-isoxazole-4-carboxylic acid
$^1$H NMR (400 MHz, DMSO-d6, 298K) δ ppm 2.10-2.31(m, 2H) 2.14 (s, 3H) 2.54-2.59 (m, 3H) 2.83-2.97 (m, 2H) 3.41-3.53 (m, 2H) 3.59-4.15 (m, 6H) 3.81 (s, 3H) 5.65-5.73 (m, 1H) 7.40-7.48 (m, 1H) 7.67-7.74 (m, 1H) 8.56-8.66 (m, 1H) 8.83-8.95 (m, 1H)

| Example 32 | 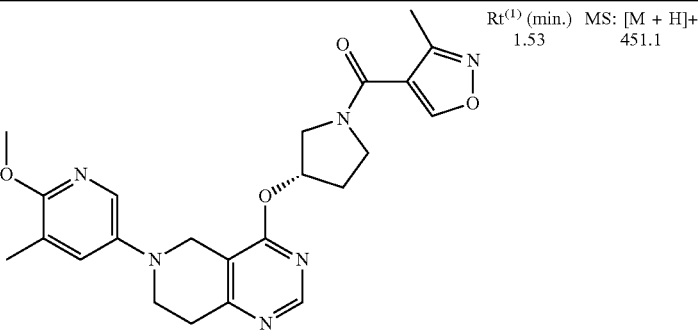 | Rt$^{(1)}$ (min.) 1.53 | MS: [M + H]+ 451.1 |
|---|---|---|---|

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone
Purification method: Reverse phase method A
Prepared using 3-methyl-isoxazole-4-carboxylic acid
$^1$H NMR (400 MHz, DMSO-d6, 298K) δ ppm 2.08-2.37 (m, 8H) 2.82-2.95 (m, 2H) 3.40-3.53 (m, 2H) 3.55-4.16 (m, 9H) 5.65-5.75 (m, 1H) 7.41-7.48 (m, 1H) 7.68-7.73 (m, 1H) 8.57-8.65 (m, 1H) 9.28-9.40 (m, 1H)

| Example 33 | 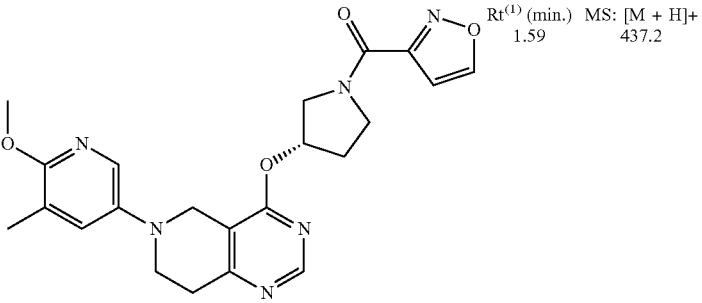 | Rt$^{(1)}$ (min.) 1.59 | MS: [M + H]+ 437.2 |
|---|---|---|---|

Name: Isoxazol-3-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone -continued Purification method: Reverse phase method A
Prepared using isoxazole-3-carboxylic acid
$^1$H NMR (400 MHz, DMSO-d6, 298K) δ ppm 2.13 (m, 3H) 2.21-2.31 (m, 2H) 2.86-2.94 (m, 2H) 3.43-3.50 (m, 2H) 3.66-4.15 (m, 9H) 5.67-5.73 (m, 1H) 6.84-6.91 (m, 1H) 7.42-7.46 (m, 1H) 7.67-7.74 (m, 1H) 8.57-8.64 (m, 1H) 9.05-9.13 (m, 1H)

| Example 34 | 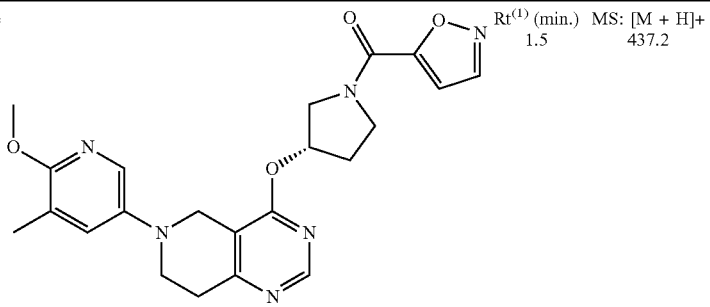 | Rt$^{(1)}$ (min.) 1.5 | MS: [M + H]+ 437.2 |
|---|---|---|---|

Name: Isoxazol-5-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using isoxazole-5-carboxylic acid
$^1$H NMR (400 MHz, DMSO-d6, 298K) δ ppm 2.08-2.16 (m, 3H) 2.19-2.36 (m, 2H) 2.85-2.95 (m, 2H) 3.42-3.49 (m, 2H) 3.66-4.23 (m, 9H) 5.66-5.78 (m, 1H) 7.06-7.13 (m, 1H) 7.41-7.46 (m, 1H) 7.68-7.74 (m, 1H) 8.59-8.64 (m, 1H) 8.73-8.79 (m, 1H)

| Example 35 | 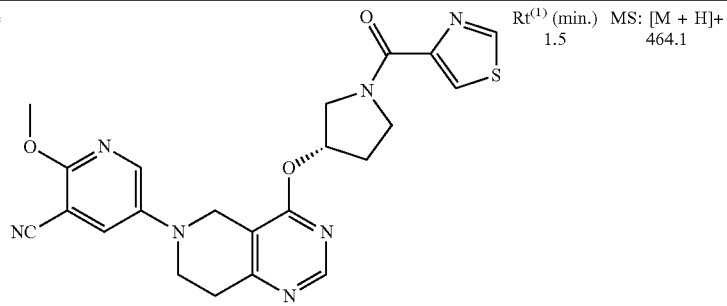 | Rt$^{(1)}$ (min.) 1.5 | MS: [M + H]+ 464.1 |
|---|---|---|---|

Name: 2-Methoxy-5-{4-[(S)-1-(thiazole-4-carbonyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using thiazole-4-carboxylic acid
$^1$H NMR (400 MHz, CDCl$_3$-d, 298K) δ ppm 2.30-2.37 (m, 2H) 3.07-3.12 (m, 2H) 3.46-3.53 (m, 2H) 3.81-4.43 (m, 9H) 5.80-5.85 (m, 1H) 7.55-7.59 (m, 1H) 8.09-8.13 (m, 1H) 8.18-8.23 (m, 1H) 8.63-8.69 (m, 1H) 8.75-8.85 (m, 1H)

| Example 36 | 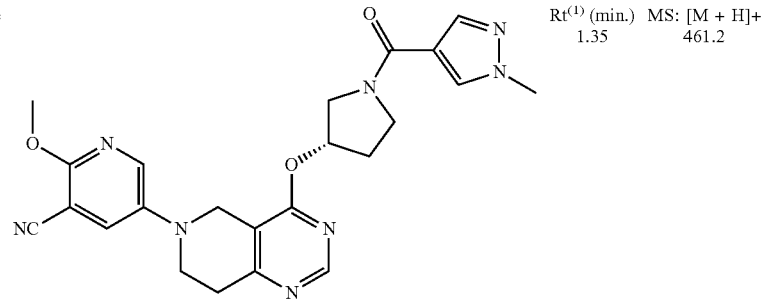 | Rt$^{(1)}$ (min.) 1.35 | MS: [M + H]+ 461.2 |
|---|---|---|---|

Name: 2-Methoxy-5-{4-[(S)-1-(1-methyl-1H-pyrazole-4-carbonyl)-pyrrolidin-3-yloxy]-7,8-dihydro-5H-pyrido[4,3-d]pyrimidin-6-yl}-nicotinonitrile Purification method: Reverse phase method A Prepared using intermediate 11 and process step 2, method 1b of example 1 followed by process step 1 of example 10 using 1-methyl-1H-imidazole-4-carboxylic acid ¹H NMR (400 MHz, CDCl₃-d, 298K) δ ppm 2.24-2.47 (m, 2H) 3.03-3.17 (m, 2H) 3.45-3.58 (m, 2H) 3.87-4.20 (m, 12H) 5.75-5.85 (m, 1H) 7.54-7.60 (m, 1H) 7.73-7.90 (m, 2H) 8.09-8.14 (m, 1H) 8.61-8.68 (m, 1H)

| Example 37 | 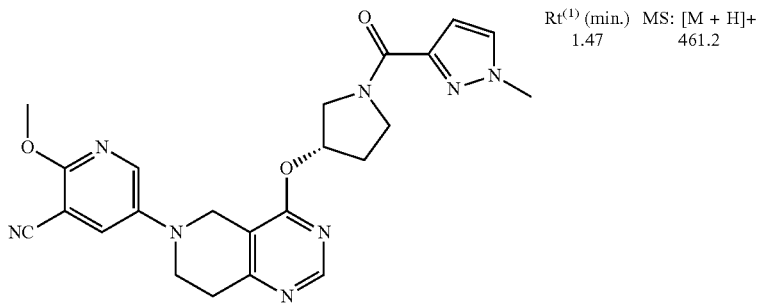 | Rt⁽¹⁾ (min.) 1.47 | MS: [M + H]+ 461.2 |
|---|---|---|---|

Name: 2-Methoxy-5-{4-[(S)-1-(1-methyl-1H-pyrazole-3-carbonyl)-pyrrolidin-3-yloxy]-7,8-dihydro-5H-pyrido[4,3-d]pyrimidin-6-yl}-nicotinonitrile Purification method: Reverse phase method A Prepared using intermediate 11 and process step 2, method 1b of example 1 followed by process step 1 of example 10 using 1-methyl-1H-pyrazole-3-carboxylic acid ¹H NMR (400 MHz, CDCl₃-d, 298K) δ ppm 2.24-2.41 (m, 2H) 3.07-3.14 (m, 2H) 3.44-3.58 (m, 2H) 3.74-4.44 (m, 12H) 5.77-5.86 (m, 1H) 6.78-6.84 (m, 1H) 7.33-7.39 (m, 1H) 7.54-7.59 (m, 1H) 8.08-8.14 (m, 1H) 8.63-8.70 (m, 1H)

| Example 38 | 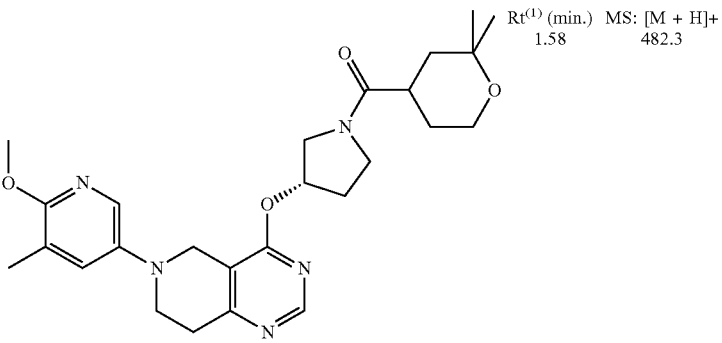 | Rt⁽¹⁾ (min.) 1.58 | MS: [M + H]+ 482.3 |
|---|---|---|---|

Name: (2,2-Dimethyl-tetrahydro-pyran-4yl)-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone Purification method: Reverse phase method A Prepared using 2,2-dimethyl-tetrahydro-pyran-4-carboxylic acid ¹H NMR (400 MHz, DMSO-d6, 298K) δ ppm 1.02-1.21 (m, 6H) 1.27-1.71 (m, 4H) 2.08-2.32 (m, 5H) 2.67-2.94 (m, 3H) 3.41-4.08 (m, 13H) 5.60-5.73 (m, 1H) 7.41-7.46 (m, 1H) 7.65-7.72 (m, 1H) 8.58-8.65 (m, 1H)

| Example 39 | 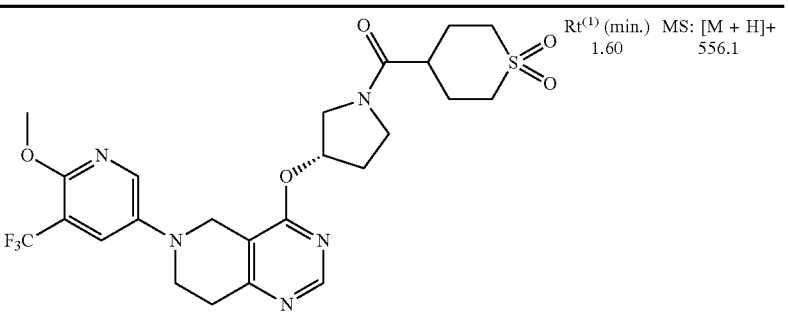 | Rt(1) (min.) 1.60 | MS: [M + H]+ 556.1 |

Name: (1,1-Dioxo-hexahydro-1lambda*6*-thiopyran-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1,1-dioxo-hexahydro-1lambda*6*-thiopyran-4-carboxylic acid
$^1$H NMR (400 MHz, DMSO-d6, 298K) δ ppm 1.90-2.37 (m, 6 H) 2.72-3.27 (m, 7 H) 3.43-3.81 (m, 6 H) 3.89-3.97 (m, 3 H) 4.13-4.20 (m, 2 H) 5.61-5.75 (m, 1 H) 7.80-7.86 (m, 1 H) 8.15-8.22 (m, 1 H) 8.60-8.65 (m, 1 H)

| Example 40 | 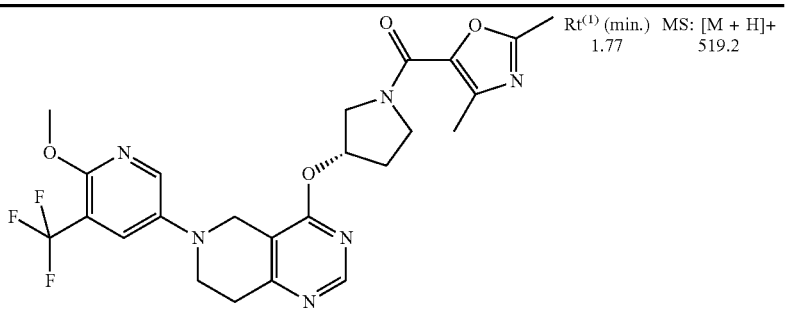 | Rt(1) (min.) 1.77 | MS: [M + H]+ 519.2 |

Name: (2,4-Dimethyl-oxazol-5-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 2,4-dimethyl-oxazole-5-carboxylic acid
$^1$H NMR (400 MHz, DMSO-d6, 298K) δ ppm 2.13-2.45 (m, 8H) 2.89-2.96 (m, 2H) 3.54-4.21 (m, 11H) 5.64-5.79 (m, 1H) 7.81-7.85 (m, 1H) 8.218-8.22 (m., 1H) 8.61-8.65 (m, 1H)

| Example 41 | 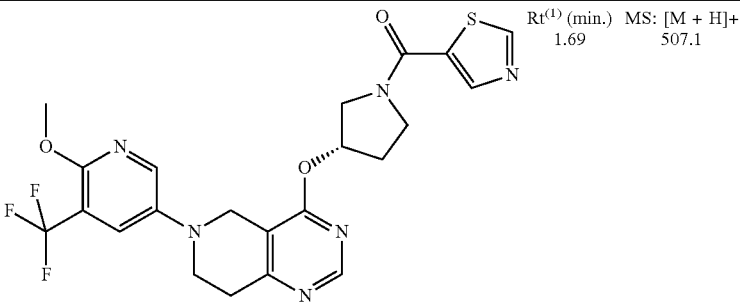 | Rt(1) (min.) 1.69 | MS: [M + H]+ 507.1 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-5-yl-methanone
Purification method: Reverse phase method A
Prepared using intermediate 13 and process step 2, method 1b of example 1 followed by process step 1 of example 10 using thiazole-5-carboxylic acid
$^1$H NMR (400 MHz, DMSO-d6, 298K) δ ppm 2.15-2.42 (m, 2H) 2.88-2.97 (m, 2H) 3.53-3.61 (m, 2H) 3.67-4.11 (m, 7 H) 4.15-4.24 (m, 2H) 5.67-5.79 (m, 1H) 7.81-7.88 (m, 1H) 8.18-8.23 (m, 1H) 8.35-8.45 (m, 1H) 8.60-8.66 (m, 1H) 9.22-9.29 (m, 1H)

| Example 42 | 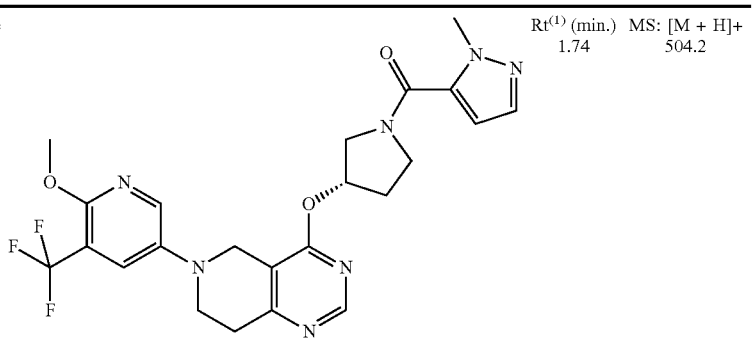 | Rt(1) (min.) 1.74 | MS: [M + H]+ 504.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(2-methyl-2H-pyrazol-3-yl)-methanone
Purification method: Reverse phase method A
Prepared using intermediate 13 and process step 2, method 1b of example 1 followed by process step 1 of example 10 using 2-methyl-2H-pyrazole-3-carboxylic acid
$^1$H NMR (400 MHz, DMSO-d6, 298K) δ ppm 2.15-2.35 (m, 2H) 2.88-2.97 (m, 2H) 3.51-4.13 (m, 12 H) 4.13-4.25 (m, 2H) 5.63-5.74 (m, 1H) 6.63-6.74 (m, 1H) 7.43-7.52 (m, 1H) 7.81-7.89 (m, 1H) 8.17-8.25 (m, 1H) 8.57-8.67 (m, 1H)

| Example 43 | 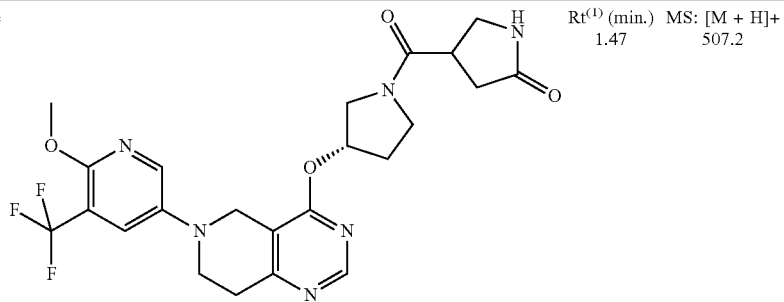 | Rt(1) (min.) 1.47 | MS: [M + H]+ 507.2 |

Name: 4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-pyrrolidin-2-one
Purification method: Reverse phase method A
Prepared using intermediate 13 and process step 2, method 1b of example 1 followed by process step 1 of example 10 using 5-oxo-pyrrolidine-3-carboxylic acid
$^1$H NMR (400 MHz, DMSO-d6, 298K) δ ppm 2.10-2.43 (m, 4H) 2.89-2.96 (m, 2H) 3.35-3.79 (m, 9H) 3.90-3.94 (m, 3H) 4.15-4.20 (m, 2H) 5.60-5.73 (m, 1H) 7.53-7.62 (m, 1H) 7.81-7.87 (m, 1H) 8.17-8.22 (m, 1H) 8.60-8.64 (m, 1H)

| Example 44 | 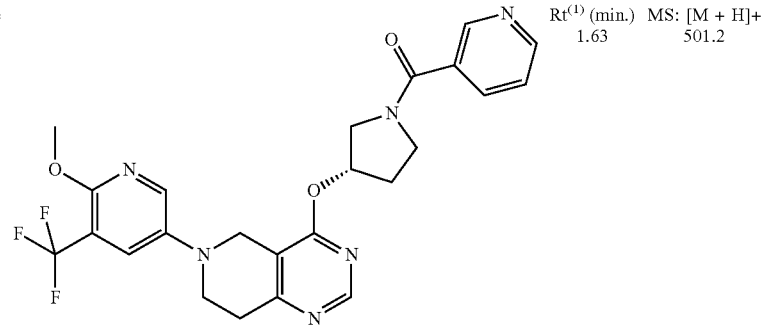 | Rt(1) (min.) 1.63 | MS: [M + H]+ 501.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyridin-3-yl-methanone
Purification method: Reverse phase method A
Prepared using intermediate 13 and process step 2, method 1b of example 1 followed by process step 1 of example 10 using nicotinic acid
$^1$H NMR (400 MHz, DMSO-d6, 298K) δ ppm 2.11-2.37 (m, 2H) 2.87-2.99 (m, 2H) 3.51-4.13 (m, 9H) 4.13-4.29 (m, 2H) 5.60-5.75 (m, 1H) 7.43-7.53 (m, 1H) 7.81-8.04 (m, 2H) 8.17-8.28 (m, 1H) 8.53-8.82 (m, 3H)

| Example 45 | 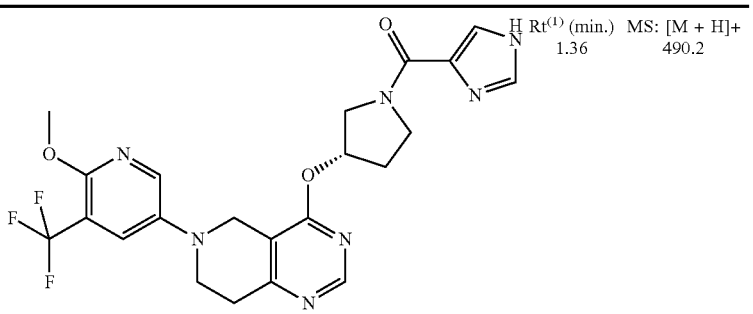 | Rt[(1)] (min.) 1.36 | MS: [M + H]+ 490.2 |

Name: (1H-Imidazol-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1H-imidazole-4-carboxylic acid
$^1$H NMR (400 MHz, DMSO-d6, 298K) δ ppm 2.12-2.35 (m, 2H) 2.87-2.95 (m, 2H) 3.60-4.31 (m, 11H) 5.63-5.76 (m, 1H) 7.57-7.65 (m, 1H) 7.70-7.78 (m, 1H) 7.80-7.85 (m, 1H) 8.16-8.21 (m, 1H) 8.61-8.65 (m, 1H)

| Example 46 | 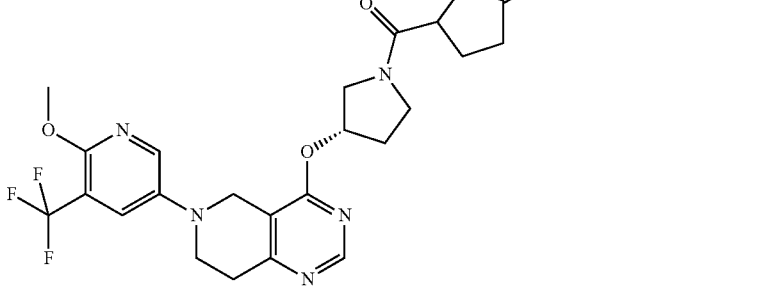 | Rt[(1)] (min.) 1.47 | MS: [M + H]+ 507.2 |

Name: 5-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-pyrrolidin-2-one
Purification method: Reverse phase method A
Prepared using intermediate 13 and process step 2, method 1b of example 1 followed by process step 1 of example 10 using 5-oxo-pyrrolidine-2-carboxylic acid
$^1$H NMR (400 MHz, DMSO-d6, 298K) δ ppm 1.78-2.40 (m, 6H) 2.89-2.97 (m, 2H) 3.43-3.86 (m, 6H) 3.90-3.94 (m, 3H) 4.15-4.20 (m, 2H) 4.30-4.45 (m, 1H) 5.60-5.75 (m, 1H) 7.70-7.89 (m, 2H) 8.16-8.22 (m, 1H) 8.61-8.63 (m, 1H)

| Example 47 | 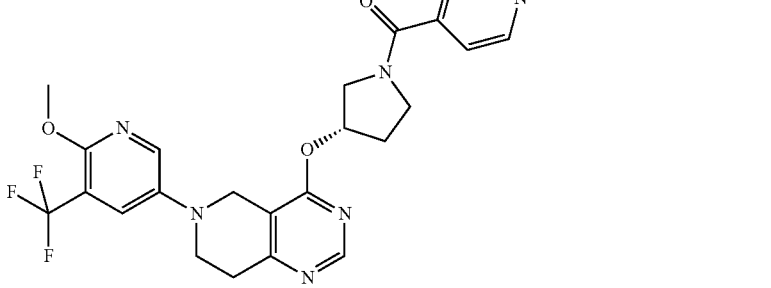 | Rt[(1)] (min.) 1.61 | MS: [M + H]+ 501.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyridin-4-yl-methanone
Purification method: Reverse phase method A
Prepared using intermediate 13 and process step 2, method 1b of example 1 followed by process step 1 of example 10 using isonicotinic acid
$^1$H NMR (400 MHz, DMSO-d6, 298K) δ ppm 2.12-2.36 (m, 2H) 2.86-2.99 (m, 2H) 3.46-3.81 (m, 5H) 3.84-4.13 (m, 4H) 4.14-4.28 (m, 2H) 5.59-5.74 (m, 1H) 7.44-7.56 (m, 2H) 7.82-7.91 (m, 1H) 8.18-8.27 (m, 1H) 8.52-8.72 (m, 3H)

| Example 48 | 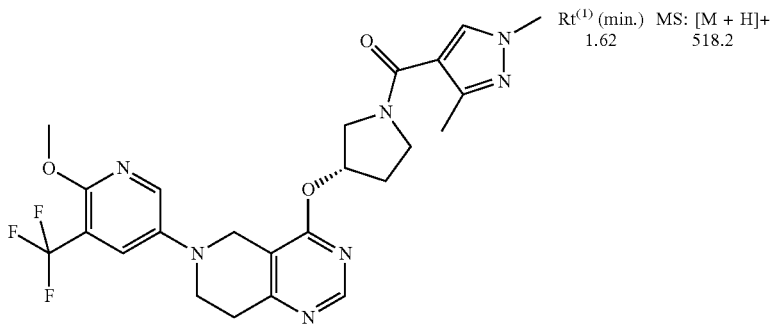 | Rt⁽¹⁾ (min.) 1.62 | MS: [M + H]+ 518.2 |

Name: (1,3-Dimethyl-1H-pyrazol-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1,3,-dimethyl-1H-pyrazole-4-carboxylic acid
¹H NMR (400 MHz, DMSO-d6, 298K) δ ppm 2.13-2.35 (m, 5H) 2.89-2.97 (m, 2H) 3.53-4.06 (m, 12H) 4.14-4.22 (m, 2H) 5.64-5.72 (m, 1H) 7.80-7.88 (m, 1H) 7.99-8.11 (m, 1H) 8.16-8.22 (m, 1H) 8.58-8.66 (m, 1H)

| Example 49 | 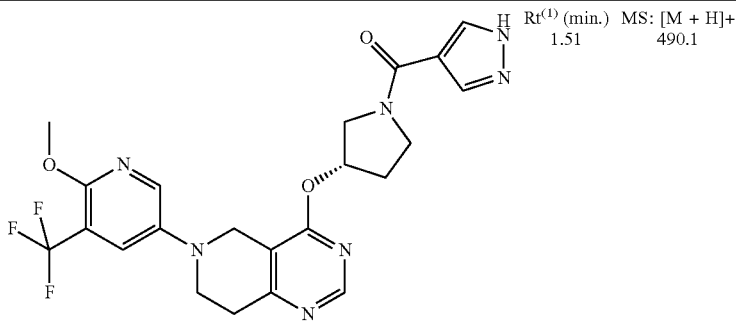 | Rt⁽¹⁾ (min.) 1.51 | MS: [M + H]+ 490.1 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1H-pyrazol-4-yl)-methanone
Purification method: Reverse phase method A
Prepared using intermediate 13 and process step 2, method 1b of example 1 followed by process step 1 of example 10 using 1H-pyrazole-4-carboxylic acid
¹H NMR (400 MHz, DMSO-d6, 298K) δ ppm 2.12-2.39 (m, 2H) 2.87-2.97 (m, 2H) 3.43-4.11 (m, 9H) 4.12-4.22 (m, 2H) 5.63-5.79 (m, 1H) 7.78-7.94 (m, 2H) 8.10-8.25 (m, 3H) 8.59-8.68 (m, 1H)

| Example 51 | 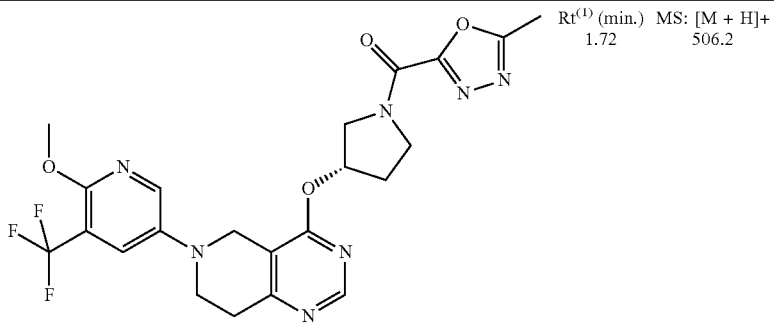 | Rt⁽¹⁾ (min.) 1.72 | MS: [M + H]+ 506.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(5-methyl-[1,3,4]oxadiazol-2-yl)-methanone
Purification method: Reverse phase method A
Prepared using intermediate 13 and process step 2, method 1b of example 1 followed by process step 1 of example 10 using 5-methyl-[1,3,4]oxadiazole-2-carboxylic acid

| Example 52 | 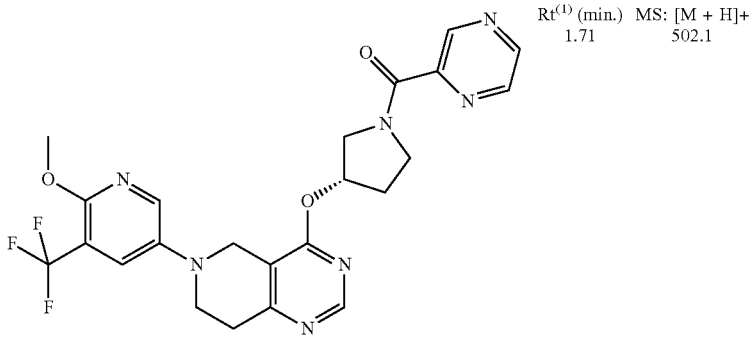 | Rt(1) (min.) 1.71 | MS: [M + H]+ 502.1 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyrazin-2-yl-methanone
Purification method: Reverse phase method A
Prepared using intermediate 13 and process step 2, method 1b of example 1 followed by process step 1 of example 10 using pyrazine-2-carboxylic acid
$^1$H NMR (400 MHz, DMSO-d6, 298K) δ ppm 2.15-2.36 (m, 2H) 2.87-2.97 (m, 2H) 3.52-3.64 (m, 2H) 3.66-4.11 (m, 7H) 4.12-4.24 (m, 2H) 5.67-5.75 (m, 1H) 7.81-7.87 (m, 1H) 8.17-8.25 (m, 1H) 8.56-8.80 (m, 3H) 8.97-9.02 (m, 1H)

| Example 53 | 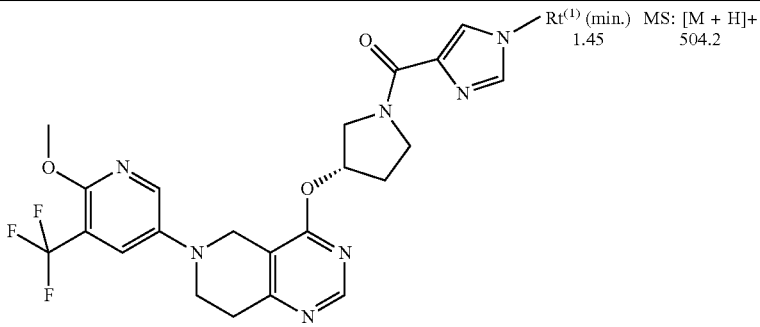 | Rt(1) (min.) 1.45 | MS: [M + H]+ 504.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone
Purification method: Reverse phase method A
Prepared using intermediate 13 and process step 2, method 1b of example 1 followed by process step 1 of example 10 using 1-methyl-1H-imidazole-4-carboxylic acid
$^1$H NMR (400 MHz, DMSO-d6, 298K) δ ppm 2.07-2.36 (m, 2 H) 2.82-3.05 (m, 2 H) 3.20-4.43 (m, 14 H) 5.60-5.74 (m, 1 H) 7.59-7.72 (m, 2 H) 7.78-7.87 (m, 1 H) 8.14-8.21 (m, 1 H) 8.59-8.66 (m, 1 H)

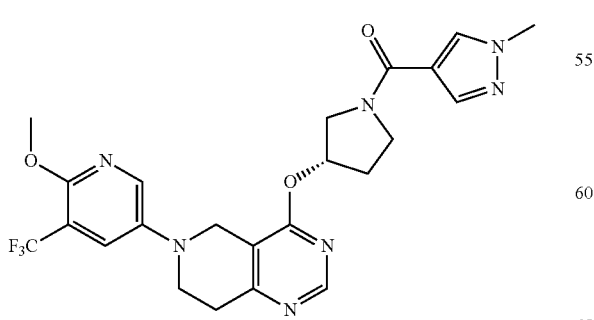

Example 54

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone To a mixture of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (44 mg, 0.11 mmol), 1-methyl-1H-pyrazole-4-carboxylic acid (15 mg, 0.12 mmol), benztriazol-1-ol (19 mg, 0.12 mmol) in CH$_2$Cl$_2$ (1.0 mL) was added EDC (34 mg, 0.18 mmol) and the resulting mixture was stirred at rt for 18 h. Partitioned between CH$_2$Cl$_2$ (10 mL) and sat. NaHCO$_3$(aq) (2.0 mL) and the organic layer separated by filtering through a phase separation tube. Concentrated in vacuo and purified by flash chromatography through Biotage® amino silica gel eluting with cyclohexane/EtOAc, 100/0 to 0/100 to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone as a white lyophilized powder (44 mg, 75% yield). 1H NMR (400 MHz, CDCl$_3$-d, 298K) δ ppm 2.26-2.45 (m, 2H) 3.04-3.10 (m, 2H) 3.49-3.57 (m, 2H) 3.89-4.00 (m, 7H) 4.01 (s, 3H) 4.10-4.18 (m, 2H) 5.78-5.83 (m, 1H) 7.60-7.62 (m, 1H) 7.76-7.89 (m, 2H) 8.04-8.07 (m, 1H) 8.61-8.66 (m, 1H) MS: [M+H]$^+$=504.2, Rt$^{(3)}$=1.59 min.

Example 55 was prepared using procedures analogous to those used in example 54 using appropriate starting materials.

stirred at ~3° C. for 30 min. The reaction mixture was concentrated under vacuum. Purification by preparative reverse phase Gilson HPLC and subsequent neutralization of the combined fractions over PL-HCO$_3$ MP gave {(S)-3-[6-(5-chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone (38 mg, 41% yield) as a white lyophilized powder. $^1$H NMR (400 MHz, CDCl$_3$-d, 298 K) δ ppm 1.56-1.68 (m, 2H) 1.86-2.04 (m, 2H) 2.20-2.40 (m, 2H) 2.50-2.72 (m, 1H) 3.05-3.13 (m, 2H) 3.38-4.16 (m, 16H) 5.70-5.78 (m, 1H) 7.42-7.45 (m, 1H) 7.78-7.81 (m, 1H) 8.61-8.66 (m, 1H). LCMS: [M+H]$^+$=474.2, Rt$^{(2)}$=1.52 min.

| Example | Structure | Rt$^{(1)}$ (min.) | MS: [M + H]+ |
|---|---|---|---|
| 55 | 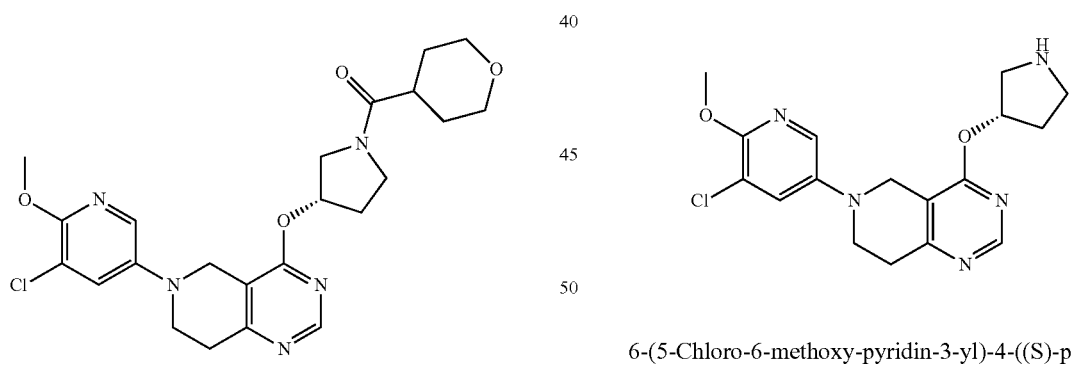 | 1.77 | 507.2 |

Name: {(S)-3-{6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone
Purification method: Flash chromatography on Biotage amino silica gel eluting with cyclohexane/EtOAc 100/0 to 0/100
Prepared using thiazole-4-carboxylic acid
$^1$H NMR (400 MHz, CDCl$_3$-d, 298K) δ ppm 2.29-2.40 (m, 2H) 3.05-3.12 (m, 2H) 3.49-3.56 (m, 2H) 3.80-4.45 (m, 9H) 5.80-5.86 (m, 1H) 7.60-7.62 (m, 1H) 8.04-8.18 (m, 1H) 8.21-8.25 (m, 1H) 8.64-8.68 (m, 1H) 8.79-8.84 (m, 1H)

Example 56

{(S)-3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone To a 6-(5-chloro-6-methoxy-pyridin-3-yl)-4-((S)-pyrrolidin-3-yloxy)-5,6,7,8-tetrahydro-pyrido[4,3-d]pyrimidine (97 mg, 0.196 mmol) in CH$_2$Cl$_2$ (5 mL) was added the acid chloride tetrahydro-2H-pyran-4-carbonyl chloride (36.7 mg, 0.235 mmol) and triethylamine (0.035 mL, 0.254 mmol) at temperature between 0-10° C. The reaction mixture was 6-(5-Chloro-6-methoxy-pyridin-3-yl)-4-((S)-pyrrolidin-3-yloxy)-5,6,7,8-tetrahydro-pyrido[4,3-d]pyrimidine (S)-3-[6-(5-Chloro-6-methoxy-pyridin-3-yl)-5,6,7,8-tetrahydro-pyrido[4,3-d]pyrimidin-4-yloxy]-pyrrolidine-1-carboxylic acid tert-butyl ester (766.2 mg, 1.66 mmol) was dissolved in a TFA/CH$_2$Cl$_2$ (½) solution and stirred at rt for 1 h. The reaction mixture was concentrated under vacuum, the residue was diluted with CH$_2$Cl$_2$, the organic layer washed with NaOH 1N then brine, dried over Na$_2$SO$_4$, filtered and evaporated to give 6-(5-chloro-6-methoxy-pyridin-3-yl)-4-((S)-pyrrolidin-3-yloxy)-5,6,7,8-tetrahydro-pyrido[4,3-d]pyrimidine. LCMS: [M+H]$^+$=362.1, Rt$^{(3)}$=1.28 min.

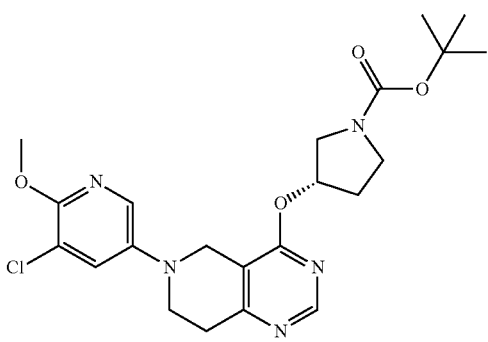 [SMILES: COc1ncc(N2CCc3ncnc(O[C@H]4CCN(C(=O)OC(C)(C)C)C4)c3C2)cc1Cl]

(S)-3-[6-(5-Chloro-6-methoxy-pyridin-3-yl)-5,6,7,8-tetrahydro-pyrido[4,3-d]pyrimidin-4-yloxy]-pyrrolidine-1-carboxylic acid tert-butyl ester X-Phos (0.073 g, 0.154 mmol), Pd$_2$(dba)$_3$ (0.100 g, 0.110 mmol), NaOtBu (0.395 g, 4.11 mmol) and 5-bromo-3-chloro-2-methoxy-pyridine (0.732 g, 3.29 mmol) were combined and flushed under a stream of argon for 10 min. To this mixture, a solution of (S)-3-(5,6,7,8-tetrahydro-pyrido[4,3-d]pyrimidin-4-yloxy)-pyrrolidine-1-carboxylic acid tert-butyl ester (Intermediate 7) (2.15 g, 6.72 mmol) in THF (6 mL) was added at rt and the reaction mixture was stirred at 90° C. for 3 h. The reaction was cooled down to rt, EtOAc was added, the mixture filtered through a celite pad and concentrated under vacuum. Purification by flash chromatography on silica gel (CH$_2$Cl$_2$/MeOH 99/1 to 95/5) gave (S)-3-[6-(5-chloro-6-methoxy-pyridin-3-yl)-5,6,7,8-tetrahydro-pyrido[4,3-d]pyrimidin-4-yloxy]-pyrrolidine-1-carboxylic acid tert-butyl ester as yellow foam (0.766 g, 60% yield). LCMS: [M+H]$^+$=462.1, Rt$^{(3)}$=1.84 min

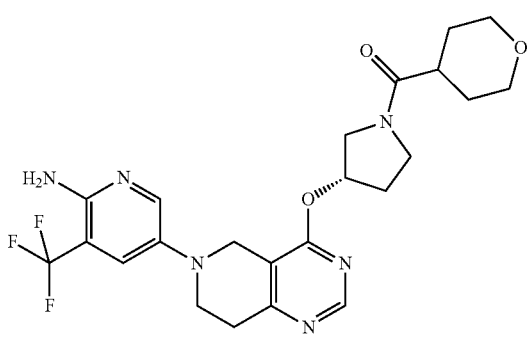 [SMILES: Nc1ncc(N2CCc3ncnc(O[C@H]4CCN(C(=O)C5CCOCC5)C4)c3C2)cc1C(F)(F)F]

Example 57

{(S)-3-[6-(6-Amino-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone To a solution of (S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1 (120 mg, 0.18 mmol) in CH$_2$Cl$_2$ (2.0 mL), was added TFA (2.0 mL) and the mixture stood at rt for 1 h. Concentrated in vacuo and eluted through an Isolute® SCX-2 cartridge, eluting with methanol, then with 2M ammonia in methanol. Basic fractions were concentrated in vacuo to give 5-[4-((S)-pyrrolidin-3-yloxy)-7,8-dihydro-5H-pyrido[4,3-d]pyrimidin-6-yl]-3-(trifluoromethyl)pyridin-2-yl)amine (61 mg, 90% yield). 5-[4-((S)-pyrrolidin-3-yloxy)-7,8-dihydro-5H-pyrido[4,3-d]pyrimidin-6-yl]-3-(trifluoromethyl)pyridin-2-yl)amine (30 mg, 0.079 mmol) was dissolved in CH$_2$Cl$_2$ (2.0 mL) and was added simultaneously portionwise with sat. NaHCO$_3$(aq) (2.0 mL) to a vigorously stirring solution of tetrahydro-2H-pyran-4-carbonyl chloride (15 mg, 0.10 mmol) in CH$_2$Cl$_2$ (2.0 mL) at rt. The resulting biphasic mixture was stirred at rt for 1 h. Diluted with CH$_2$Cl$_2$ (10 mL) and the organic layer was separated by filtering through a phase separation tube and concentrated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give {(S)-3-[6-(6-amino-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone as a pale yellow powder (19 mg, 50% yield) $^1$H NMR (400 MHz, CDCl$_3$, 298K) δ ppm 1.56-1.72 (m, 2H) 1.87-2.03 (m, 2H) 2.23-2.74 (m, 3H) 3.04-3.14 (m, 2H) 3.48-4.13 (m, 12H) 5.15-5.43 (m, 2H, Ar—NH2) 5.73-5.79 (m, 1H) 7.55-7.64 (m, 1H) 7.93-8.02 (m, 1H) 8.61-8.67 (m, 1H) LCMS: [M+H]+=397.1, Rt$^{(3)}$=1.32 min.

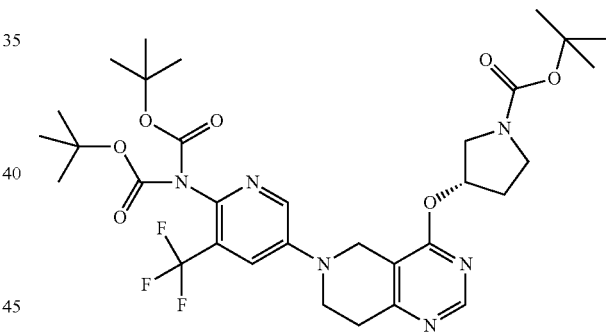

(S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1-carboxylate To a glass vial was added (S)-3-(5,6,7,8-Tetrahydro-pyrido[4,3-d]pyrimidin-4-yloxy)-pyrrolidine-1-carboxylic acid tert-butyl ester (Intermediate 7) (100 mg, 0.312 mmol), imidodicarbonic acid, 2-[5-bromo-3-(trifluoromethyl)-2-pyridinyl]-,1,3-bis(1,1-dimethylethyl)ester (138 mg, 0.312 mmol), cesium carbonate (203 mg, 0.62 mmol), tris(dibenzylideneacetone)dipalladium(0) (29 mg, 0.03 mmol), X-Phos (51 mg, 0.11 mmol) and anhydrous dioxane (2 mL). The vial was flushed with a stream of argon for 15 sec and capped. The mixture was heated with stirring for 1 h at 110° C. and then stirred at room temperature for 18 h. Allowed to cool and partitioned between CH$_2$Cl$_2$ (10 mL) and water (2 mL) and filtered the biphasic mixture through a celite pad. The organic layer was separated by filtering through phase separation tube and concentrated in vacuo. Purification by reverse phase Gilson HPLC (Method A) to give (S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1-carboxylate trifluoroacetate (as a yellow gum (120 mg, 48% yield). LCMS: [M+]+=681.5, Rt$^{(4)}$=1.49 min.

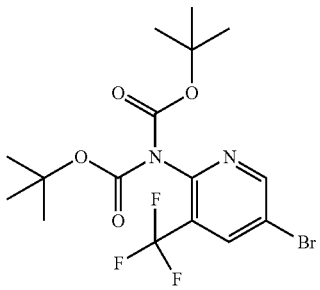 [SMILES: CC(C)(C)OC(=O)N(C(=O)OC(C)(C)C)c1ncc(Br)cc1C(F)(F)F]

Imidodicarbonic acid, 2-[5-bromo-3-(trifluoromethyl)-2-pyridinyl]-,1,3-bis(1,1-dimethylethyl)ester To 5-bromo-3-(trifluoromethyl)pyridin-2-amine (1.72 g, 7.14 mmol), triethylamine (0.995 mL, 7.14 mmol) and 4-dimethylaminoyridine (20 mg, 0.164 mmol) in CH$_2$Cl$_2$ (50 mL) was added di-tert-butyl-dicarbonate (3.89 g, 17.84 mmol) and the resulting mixture stirred at room temperature for 18 h. Evaporated to dryness in vacuo and triturated in heptane (25 mL) for 72 h. The resulting precipitate was filtered and washed with heptane (10 mL) to give Imidodicarbonic acid, 2-[5-bromo-3-(trifluoromethyl)-2-pyridinyl]-,1,3-bis(1,1-dimethylethyl)ester as a beige solid (2.23 g, 71% yield). $^1$H NMR (400 Mhz, CDCl$_3$, 298K) 1.35 (s, 18H) 8.15 (d, 1H) 8.76 (d, 1H) LCMS: [M+H]+=441/443.1, Rt$^{(4)}$=1.46 min.

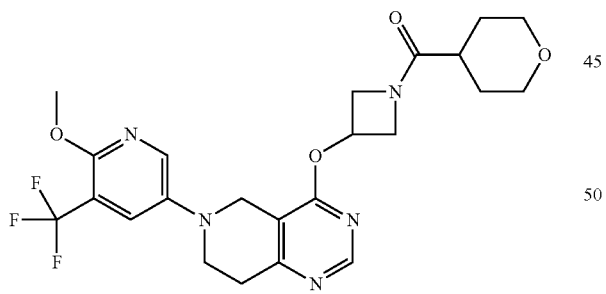

Example 58

{3-[6-(6-Methoxy-5-trifluoromethyl-pyridin-3-yl)-5,6,7,8-tetrahydro-pyrido[4,3-d]pyrimidin-4-yloxy]-azetidin-1-yl}-(tetrahydro-pyran-4-yl)-methanone 3-[6-(6-Methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester (186 mg, 0.312 mmol) in CH$_2$Cl$_2$ (2.0 mL) was added TFA (1.0 mL) and the mixture stirred at room temperature for 1 h. Evaporated in vacuo to give 4-(azetidin-3-yloxy)-(6-(6-methoxy-5-trifluoromethyl-pyridin-3-yl)-5,6,7,8-tetrahydro-pyrido[4,3-d]pyrimidine ditrifluoroacetate as a brown gum (110 mg). To a vigorously stirring solution of tetrahydro-2H-pyran-4-carbonyl chloride (19 mg, 0.128 mmol) in CH$_2$Cl$_2$ was added simultaneously portionwise sat. NaHCO$_3$(aq) (2.0 mL) and a solution of 4-(azetidin-3-yloxy)-(6-(6-methoxy-5-trifluoromethyl-pyridin-3-yl)-5,6,7,8-tetrahydro-pyrido[4,3-d]pyrimidine ditrifluoroacetate (60 mg, 0.099 mmol) in CH$_2$Cl$_2$ (2.0 mL) at rt. The resulting biphasic mixture was stirred vigorously at rt for 1 h. Diluted with CH$_2$Cl$_2$ (10 mL), the organic layer separated, dried (MgSO$_4$), concentrated in vacuo and purified by reverse phase Gilson HPLC (Method A) and subsequent neutralization of the combined fractions by eluting through an Isolute® SCX-2 cartridge, eluting with methanol, then with 2M ammonia in methanol. Basic fractions were concentrated in vacuo to give {3-[6-(6-methoxy-5-trifluoromethyl-pyridin-3-yl)-5,6,7,8-tetrahydro-pyrido[4,3-d]pyrimidin-4-yloxy]-azetidin-1-yl}-(tetrahydro-pyran-4-yl)-methanone as a yellow solid (3.0 mg, 5% yield 2$^{nd}$ step)$^1$H NMR (400 MHz, DMSO-d6, 298K) δ ppm 1.42-1.67 (m, 4H) 2.90-2.98 (m, 2H) 3.55-3.62 (m, 2H) 3.78-4.32 (m, 13H) 4.61-4.69 (m, 1H) 5.42-5.49 (m, 1H) 7.86-7.90 (m, 1H) 8.22-8.26 (m, 1H) 8.58-8.62 (s, 1H) LCMS: [M+H]+=494.6, Rt$^{(7)}$=0.98 min.

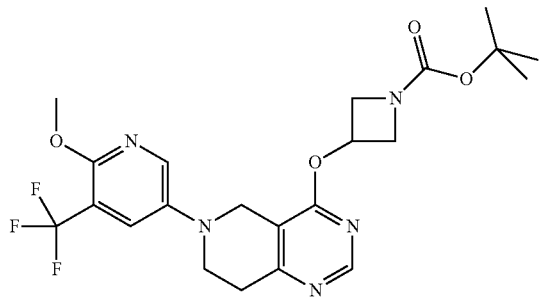 [SMILES: COc1ncc(N2CCc3ncnc(OC4CN(C(=O)OC(C)(C)C)C4)c3C2)cc1C(F)(F)F]

3-[6-(6-Methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester To a glass vial was added 3-(5,6,7,8-tetrahydro-pyrido[4,3-d]pyrimidin-4-yloxy)-azetidine-1-carboxylic acid tert-butyl ester (110 mg, 0.359 mmol), 5-Bromo-2-methoxy-3-(trifluoromethyl)pyridine (92 mg, 0.359 mmol), cesium carbonate (234 mg, 0.718 mmol), tris(dibenzylideneacetone)dipalladium(0) (33 mg, 0.036 mmol), X-Phos (58 mg, 0.122 mmol) and anhydrous dioxane (2.0 mL). The vial was flushed with a stream of argon for 15 sec and capped. The mixture was heated with stirring for 1.5 h at 110° C. and then stirred at room temperature for 18 h. Diluted with CH$_2$Cl$_2$ (50 mL), filtered through a celite pad and concentrated in vacuo. Purified by reverse phase Gilson HPLC (Method A) to give the 3-[6-(6-methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester trifluoroacetate as a brown gum (186 mg, 87% yield) LCMS: [M+H]+=482.3, Rt$^{(7)}$=1.56 min.

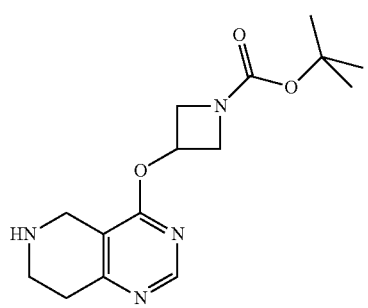 [SMILES: CC(C)(C)OC(=O)N1CC(Oc2ncnc3c2CNCC3)C1]

3-(5,6,7,8-Tetrahydro-pyrido[4,3-d]pyrimidin-4-yloxy)-azetidine-1-carboxylic acid tert-butyl ester To a solution of 3-(6-benzyl-5,6,7,8-tetrahydro-pyrido[4,3-d]pyrimidin-4-yloxy)-azetidine-1-carboxylic acid tert-butyl ester (425 mg, 1.07 mmol) in MeOH (20 mL) was added 20% palladium hydroxide on carbon (90 mg) then ammonium formate (473 mg, 7.51 mmol) and the mixture heated at reflux for 1 h. The reaction mixture was allowed to cool and filtered through a celite pad, washing with MeOH (20 mL) then $CH_2Cl_2$ (20 mL). The filtrate was evaporated in vacuo and purified by flash chromatography on silica gel with $CH_2Cl_2$/MeOH/0.88 $NH_4OH$, 100/0/0 to 90/10/1 to give 3-(5,6,7,8-tetrahydro-pyrido[4,3-d]pyrimidin-4-yloxy)-azetidine-1-carboxylic acid tert-butyl ester as a yellow gum (220 mg, 67% yield) LCMS: [M+H]+=307.3, $Rt^{(4)}$=0.81 min.

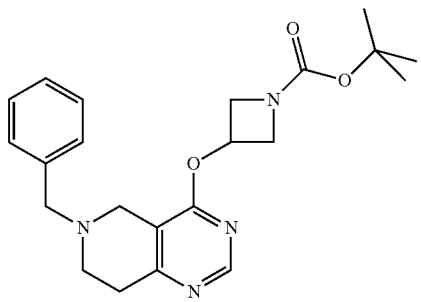 [SMILES: CC(C)(C)OC(=O)N1CC(Oc2ncnc3c2CN(Cc2ccccc2)CC3)C1]

3-(6-Benzyl-5,6,7,8-tetrahydro-pyrido[4,3-d]pyrimidin-4-yloxy)-azetidine-1-carboxylic acid tert-butyl ester 3-Hydroxy-azetidine-1-carboxylic acid tert-butyl ester (217 mg, 1.25 mmol) was dissolved under argon in THF (10 mL) and NaH (58 mg, 1.44 mmol) was added. The resulting suspension was stirred at rt under argon for 15 min following by the addition of a solution of 6-benzyl-4-chloro-5,6,7,8-tetrahydro-pyrido[4,3d]pyrimidine (250 mg, 0.963 mmol). The reaction mixture was stirred at rt for 18 h, quenched with water (20 mL) and diluted with $CH_2Cl_2$. The organic layer was filtered through a phase separation tube and concentrated in vacuo. Purification by flash chromatography on silica gel with heptane/$CH_2Cl_2$, 50/50 to 0/100 then EtOAc to give 3-(6-benzyl-5,6,7,8-tetrahydro-pyrido[4,3-d]pyrimidin-4-yloxy)-azetidine-1-carboxylic acid tert-butyl ester as a yellow gum (425 mg, 111% yield) LCMS: [M+H]+=397.4, $Rt^{(4)}$=0.98 min.

Example 59 was prepared according the general procedure described in scheme 2.

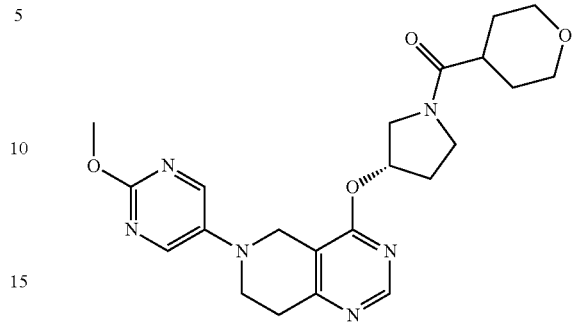

Example 59

{(S)-3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone Step 4

A mixture of 5-bromo-2-methoxy-pyrimidine (0.218 mmol), X-Phos (28.4 mg, 0.060 mmol), $Pd_2(dba)_3$ (18.2 mg, 0.020 mmol) and $Cs_2CO_3$ (129 mg, 0.397 mmol) was flushed with argon before the addition of a solution of (tetrahydro-pyran-4-yl)-[(S)-3-(5,6,7,8-tetrahydro-pyrido[4,3-d]pyrimidin-4-yloxy)-pyrrolidin-1-yl]-methanone in dioxane (2 mL). The reaction mixture was heated at 120° C. for 1 h in a sealed vial, cooled down to rt and filtered over Hyflo, The recovered organic phase was washed with $NaHCO_3$ and brine, dried over $Na_2SO_4$, filtered and concentrated. Purification by preparative reverse phase Gilson HPLC and neutralization of the combined fractions by passing through a SCX-2 cartridge (The cartridge was washed with acetonitrile, $CH_2Cl_2$ and MeOH, then a solution of $NH_3$ in MeOH 3.5 N was used to released the expected product) gave {(S)-3-[6-(2-methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone (18.7 mg, 21% yield) $^1$H NMR (400 MHz, $CDCl_3$-d, 298K) δ ppm 1.62-1.70 (m, 2H) 1.87-2.01 (m, 2H) 2.20-2.41 (m, 2H) 2.49-2.71 (m, 1H) 3.07-3.19 (m, 2H) 3.37-4.19 (m, 16H) 5.76 (m, 1H) 8.32 (s, 2H) 8.65-8.67 (m, 1H). LCMS: [M+H]+=441.2, $Rt^{(1)}$=1.12 min.

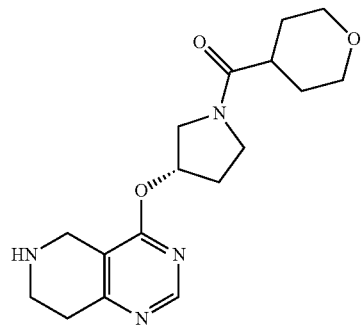 [SMILES: O=C(C1CCOCC1)N1CC[C@H](Oc2ncnc3c2CNCC3)C1]

(Tetrahydro-pyran-4-yl)-[(S)-3-(5,6,7,8-tetrahydro-pyrido[4,3-d]pyrimidin-4-yloxy)-pyrrolidin-1-yl]-methanone Step 3

A solution of [(S)-3-(6-benzyl-5,6,7,8-tetrahydro-pyrido[4,3-d]pyrimidin-4-yloxy)-pyrrolidin-1-yl]-(tetrahydro-pyran-4-yl)-methanone (10.9 g, 25.8 mmol) was dissolved in methanol (300 mL) and Pd(OH)$_2$ on Carbon (2 g, 14.24 mmol) and ammonium formate (3.35 g, 51.6 mmol) were added. The reaction mixture was refluxed for 2 h. The reaction was cooled down to rt, the reaction mixture was filtered and evaporated under high vacuum for 2 h to yield (tetrahydro-pyran-4-yl)-[(S)-3-(5,6,7,8-tetrahydro-pyrido[4,3-d]pyrimidin-4-yloxy)-pyrrolidin-1-yl]-methanone (8.45 g, 95% yield) as a light yellow foam. $^1$H NMR (400 MHz, DMSO-d6, 298K) δ ppm 1.44-1.67 (m, 4H) 2.08-2.32 (m, 2H) 2.55-2.83 (m, 3H) 2.96 (t, 2H) 3.22-3.96 (m, 11H) 5.53-5.68 (m, 1H) 8.49-8.59 (m, 1H). LCMS: [M+H]+=333.5, Rt$^{(6)}$=1.24 min.

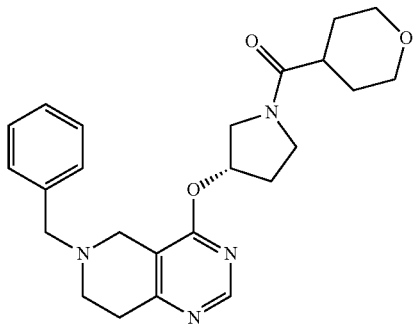 [SMILES: O=C(C1CCOCC1)N1CC[C@H](Oc2ncnc3c2CN(Cc2ccccc2)CC3)C1]

[(S)-3-(6-Benzyl-5,6,7,8-tetrahydro-pyrido[4,3-d]pyrimidin-4-yloxy)-pyrrolidin-1-yl]-(tetrahydro-pyran-4-yl)-methanone Step 2

To a solution of 6-benzyl-4-((S)-pyrrolidin-3-yloxy)-5,6,7,8-tetrahydro-pyrido[4,3-d]pyrimidine (420 mg, 1.35 mmol) in 4 mL of CH$_2$Cl$_2$ was added tetrahydro-pyran-4-carbonyl chloride (0.210 mL, 1.637 mmol) and Et$_3$N (0.380 mL, 2.73 mmol). The reaction mixture was stirred at room temperature for 30 min then was quenched with H$_2$O, extracted with CH$_2$Cl$_2$, filtered and evaporated under vacuum. Purification by flash-chromatography on silica gel (CH$_2$Cl$_2$/MeOH 95/5) gave [(S)-3-(6-benzyl-5,6,7,8-tetrahydro-pyrido[4,3-d]pyrimidin-4-yloxy)-pyrrolidin-1-yl]-(tetrahydro-pyran-4-yl)-methanone (420 mg, 73% yield) as a yellow foam. $^1$H NMR (400 MHz, DMSO-d6, 298K) δ ppm 1.37-1.64 (m, 4H) 1.95-2.29 (m, 2H) 2.56-2.83 (m, 4H) 3.28-3.91 (m, 13H) 5.54-5.68 (m, 1H) 7.24-7.36 (m, 5H) 8.54-8.59 (m, 1H). LCMS: [M+H]+=423.6, Rt$^{(7)}$=0.68.

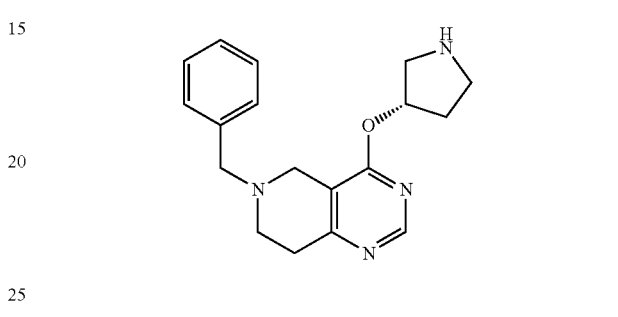

6-Benzyl-4-((S)-pyrrolidin-3-yloxy)-5,6,7,8-tetrahydro-pyrido[4,3-d]pyrimidine

Step 1

To a solution of (S)-3-(6-benzyl-5,6,7,8-tetrahydro-pyrido[4,3-d]pyrimidin-4-yloxy)-pyrrolidine-1-carboxylic acid tert-butyl ester (560 mg, 1.364 mmol) in 2 mL of CH$_2$Cl$_2$ was added TFA (1.576 mL, 20.46 mmol). The reaction mixture was stirred at rt for 1 h, concentrated and then eluted through an Isolute SCX-2 cartridge (10 g) to remove excess TFA with (i) MeOH (ii) NH$_3$/MeOH and the basic fraction evaporated in vacuum to give 6-benzyl-4-((S)-pyrrolidin-3-yloxy)-5,6,7,8-tetrahydro-pyrido[4,3-d]pyrimidine (420 mg, quantitative yield) as a yellow gum. LCMS: [M+H]+=311.2, Rt$^{(3)}$=0.11.

Examples 60-62 were prepared using procedures analogous to those used in Example 59 using appropriate starting materials.

| Example | | Rt$^{(1)}$ (min.) | MS: [M + H]+ |
|---|---|---|---|
| 60 | 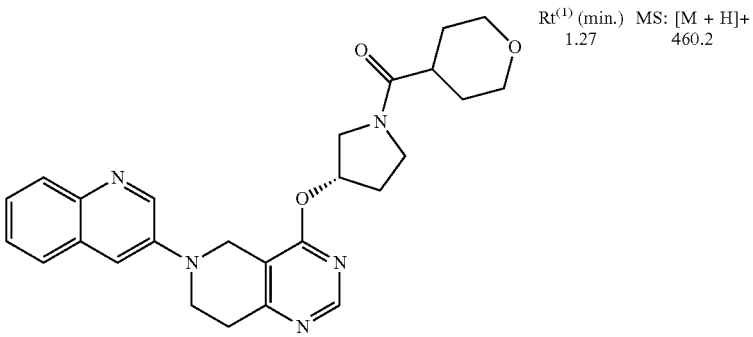 | 1.27 | 460.2 |

Name: [(S)-3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone
Purification method: Reverse phase method A
Prepared using 3-bromo-quinoline
$^1$H NMR (400 MHz, CDCl$_3$-d, 298K) δ ppm 1.60-1.72 (m, 3H) 1.89-2.04 (m, 2H) 2.24-2.46 (m, 2H) 2.53-2.73 (m ,1H) 3.08-3.21 (m, 2H) 3.39-3.52 (m, 2H) 3.67-4.11 (m, 8H) 4.20-4.40 (m, 2H) 5.73-5.83 (m, 1H) 7.47-7.62 (m, 3H) 7.73-7.80 (m, 1H) 8.02-8.14 (m, 1H) 8.62-8.68 (m, 1H) 8.86-8.91 (m, 1H).

Example 61

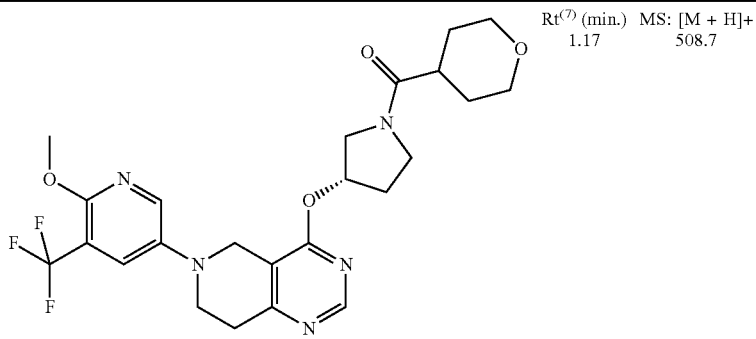

Rt⁽⁷⁾ (min.) 1.17   MS: [M + H]+ 508.7

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method A
Prepared using intermediate 1
$^1$H NMR (400 MHz, DMSO-d6, 298K) δ ppm 1.50-1.66 (m, 4H) 2.07-2.46 (m, 2H) 2.60-2.80 (m, 1H) 2.88-2.97 (m, 2H) 3.30-3.95 (m, 13H) 4.08-4.23 (m, 2H) 5.59-5.74 (m, 1H) 7.79-7.85 (m, 1H) 8.16-8.23 (m, 1H) 8.60-8.65 (m, 1H)

Example 62

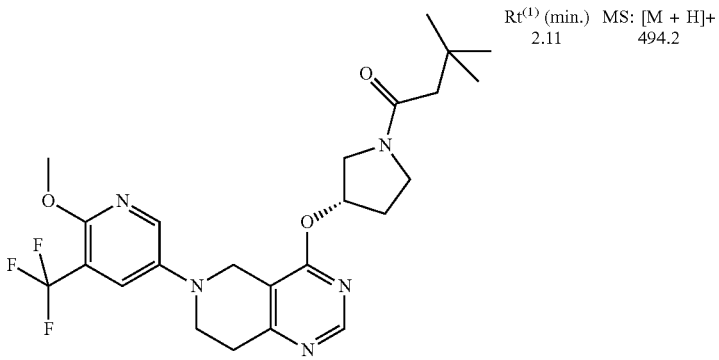

Rt⁽¹⁾ (min.) 2.11   MS: [M + H]+ 494.2

Name: 1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-3,3-dimethyl-butan-1-one
Purification method: Reverse phse method A
Prepared using step 2 of example 59 and 3,3-dimethyl-butyryl chloride followed by steps 3-4 of example 59 using intermediate 1
$^1$H NMR (400 MHz, CDCl$_3$, 298K) δ ppm 1.00-1.12 (m, 9H) 2.13-2.35 (m, 4H) 3.08-3.15 (m, 2H) 3.45-3.93 (m, 6H) 4.02 (s, 3H) 4.03-4.15 (m, 2H) 5.72-5.79 (m, 1H) 7.57-7.62 (m, 1H) 8.03-8.07 (m, 1H) 8.64-8.69 (m, 1H)

Example 63 was prepared according the general procedure described in scheme 2.

Example 63

1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one Step 3

1-[(S)-3-(5,6,7,8-tetrahydro-pyrido[4,3-d]pyrimidin-4-yloxy)-pyrrolidin-1-yl]-propan-1-one (47.8 mg, 0.173 mmol), X-Phos (28 mg, 0.059 mmol) and Pd$_2$(dba)$_3$.CHCl$_3$ (17.90 mg, 0.017 mmol) were combined and flushed with argon during several min before addition of degassed dioxane. 5-Bromo-2-methoxy-3-trifluoromethyl-pyridine (intermediate 1) (54.5 mg, 0.213 mmol) and Cs$_2$CO$_3$ (113 mg, 0.346 mmol) were then added to the reaction mixture and the resulting mixture flushed with argon and heated at 150° C. for 30 min. in a sealed tube. The reaction mixture was cooled to rt, filtered over Hyflo and evaporated. Purification by preparative reverse phase Gilson HPLC and subsequent neutralization of the combined fractions over PL-HCO$_3$ MP gave 1-{(S)-3-[6-(6-methoxy-5-trifluoromethyl-pyridin-3-yl)-5,6,7,8-tetrahydro-pyrido[4,3-d]pyrimidin-4-yloxy]-

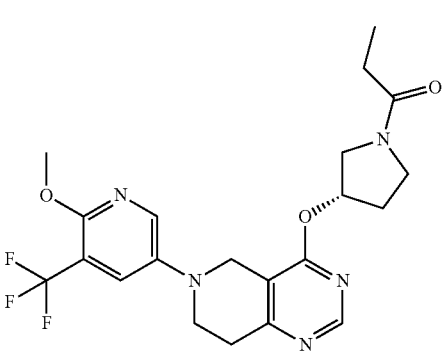 [SMILES: CCC(=O)N1CC[C@H](Oc2ncnc3c2CN(c2cnc(OC)c(C(F)(F)F)c2)CC3)C1]

pyrrolidin-1-yl}-propan-1-one (26 mg, 33% yield) $^1$H NMR (400 MHz, DMSO-d6, 298K) δ ppm 0.94-1.00 (m, 3H) 2.05-2.17 (m, 4H) 2.95-3.0 (m, 2H) 3.45-3.97 (m, 9H) 4.07-4.11 (m, 2H) 5.58-5.72 (m, 1H) 7.81-7.86 (m, 1H) 8.18-8.23 (m, 1H) 8.62 (s, 1H). MS: [M+H]+=452.2, Rt$^{(1)}$=1.74 min.

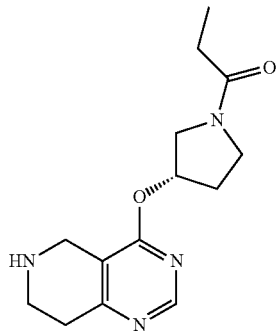 [SMILES: CCC(=O)N1CC[C@H](Oc2ncnc3c2CNCC3)C1]

1-[(S)-3-(5,6,7,8-Tetrahydro-pyrido[4,3-d]pyrimidin-4-yloxy)-pyrrolidin-1-yl]-propan-1-one Step 2

Pd(OH)$_2$ (150 mg, 1.070 mmol) was put into a round flask and flushed under argon for 5 minutes. A solution of 1-[(S)-3-(6-benzyl-5,6,7,8-tetrahydro-pyrido[4,3-d]pyrimidin-4-yloxy)-pyrrolidin-1-yl]-propan-1-one (560 mg, 1.528 mmol) in 22 mL of MeOH was added followed by ammonium formate (482 mg, 7.64 mmol). The reaction mixture was stirred under reflux (70° C.) for 2 h. The mixture was filtered over a pad of celite and dried under high vacuum to give 1-[(S)-3-(5,6,7,8-tetrahydro-pyrido[4,3-d]pyrimidin-4-yloxy)-pyrrolidin-1-yl]-propan-1-one. No further purification (m=420 mg, quantitative yield). MS: [M+H]+=277.5 Rt$^{(6)}$=0.71 min.

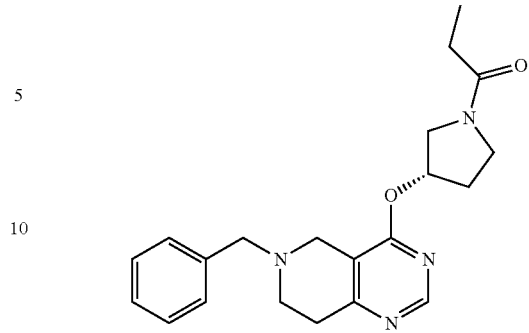

1-[(S)-3-(6-Benzyl-5,6,7,8-tetrahydro-pyrido[4,3-d]pyrimidin-4-yloxy)-pyrrolidin-1-yl]-propan-1-one Step 1

To a solution of 1-((S)-3-hydroxy-pyrrolidin-1-yl)-propan-1-one (intermediate 2) (358 mg, 2.503 mmol) in 5 mL of THF was added NaH (108 mg, 2.70 mmol) under Ar. The mixture was stirred at rt for 15 min, then 6-benzyl-4-chloro-5,6,7,8-tetrahydro-pyrido[4,3-d]pyrimidine (500 mg, 1.925 mmol) and 5 mL of THF were added and stirred at rt for 5 h. The reaction was quenched with H$_2$O and extracted with ethylacetate, the org. layer was washed with brine, dried over MgSO$_4$, filtered and evaporated to dryness. The residue was purified by flash-chromatography using Isco Companion system (12 g of SiO$_2$) CH$_2$Cl$_2$/MeOH (95/5). The collected fractions were combined, evaporated and dried over high vacuum to give 1-[(S)-3-(6-benzyl-5,6,7,8-tetrahydro-pyrido[4,3-d]pyrimidin-4-yloxy)-pyrrolidin-1-yl]-propan-1-one. (m=560 mg, yield 78%) MS: [M+H]+=367.6, Rt$^{(7)}$=0.64 min.

Example 64 was prepared using procedures analogous to those used in Example 63 using appropriate starting materials.

| Example | | Rt$^{(1)}$ (min.) | MS: [M + H]+ |
|---|---|---|---|
| 64 | 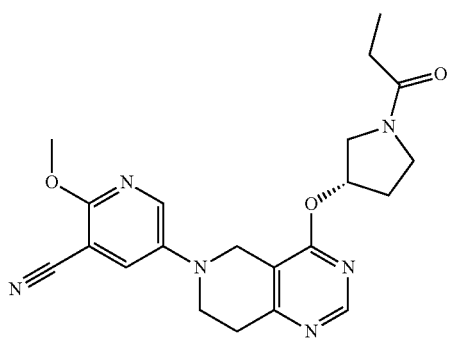 [SMILES: CCC(=O)N1CC[C@H](Oc2ncnc3c2CN(c2cnc(OC)c(C#N)c2)CC3)C1] | 1.46 | 409.2 |

Name: 2-Methoxy-5-[4-((S)-1-propionyl-pyrrolidin-3-yloxy)-7,8-dihydro-5H-pyrido[4,3-d]pyrimidin-6-yl]-nicotinonitrile Purification method: Reverse phse method A Prepared using step 3 of example 59 and 5-bromo-2-methoxynicotinonitrile $^1$H NMR (400 MHz, DMSO-d6, 298K) δ ppm 0.95-1.02 (m, 3H) 2.10-2.35 (m, 5H) 2.89-2.98 (m, 2H) 3.40-3.90 (m, 5H) 3.93 (s, 3H) 4.16 (s, 2H) 5.58-5.71 (m, 1H) 8.08-8.10 (m, 1H) 8.24-8.28 (m, 1H) 8.61 (m, 1H).

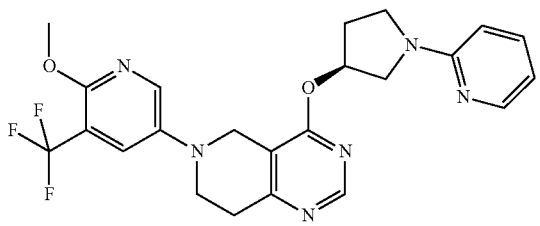 [SMILES: COc1ncc(N2CCc3ncnc(O[C@H]4CCN(c5ccccn5)C4)c3C2)cc1C(F)(F)F]

Examples 65

6-(6-Methoxy-5-trifluoromethyl-pyridin-3-yl)-4-((S)-1-pyridin-2-yl-pyrrolidin-3-yloxy)-5,6,7,8-tetrahydro-pyrido[4,3-d]pyrimidine To a glass vial was added 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (prepared using step 1 of example 91 from intermediate 13) (75 mg, 0.16 mmol), 2-bromopyridine (1 mL, 10.25 mmol) and N,N-diisopropylethylamine (0.14 mL, 0.80 mmol). The vial was capped and the mixture heated in the microwave at 160° C. for 20 min. Purification by reverse phase Gilson HPLC (Method A) and subsequent neutralization of the combined fractions over PL-HCO$_3$ MP to give 6-(6-methoxy-5-trifluoromethyl-pyridin-3-yl)-4-((S)-1-pyridin-2-yl-pyrrolidin-3-yloxy)-5,6,7,8-tetrahydro-pyrido[4,3-d]pyrimidine as a light brown solid (19 mg, 25% yield) $^1$H NMR (400 MHz, DMSO-d6, 298K) δ ppm 2.24-2.44 (m, 2 H) 2.92 (t, 2 H) 3.47-3.69 (m, 5 H) 3.77-3.85 (m, 1H) 3.88-3.93 (m, 3 H) 4.12-17 (m, 2 H) 5.73-5.81 (m, 1 H) 6.40-6.52 (d, 1 H) 6.56-6.58 (m, 1 H) 7.43-7.54 (m, 1 H) 7.77-7.84 (m, 1 H) 8.02-8.09 (m, 1 H) 8.13-8.20 (m, 1 H) 8.61-8.66 (m, 1 H) LCMS: [M+H]+=473.0, Rt$^{(4)}$=0.85 min.

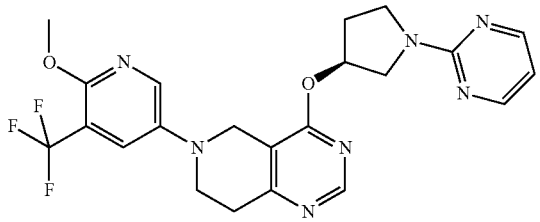 [SMILES: COc1ncc(N2CCc3ncnc(O[C@H]4CCN(c5ncccn5)C4)c3C2)cc1C(F)(F)F]

Examples 66

6-(6-Methoxy-5-trifluoromethyl-pyridin-3-yl)-4-((S)-1-pyrimidin-2-yl-pyrrolidin-3-yloxy)-5,6,7,8-tetrahydro-pyrido[4,3-d]pyrimidine To a glass vial was added 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (prepared using step 1 of example 91 from intermediate 13) (75 mg, 0.16 mmol), 2-bromopyrimidine (55 mg, 0.342 mmol) and N,N-diisopropylethylamine (0.15 mL, 0.85 mmol). The vial was capped and the mixture heated in the microwave at 160° C. for 20 min. Purification by reverse phase Gilson HPLC (Method A) and subsequent neutralization of the combined fractions over PL-HCO$_3$ MP to give 6-(6-methoxy-5-trifluoromethyl-pyridin-3-yl)-4-((S)-1-pyrimidin-2-yl-pyrrolidin-3-yloxy)-5,6,7,8-tetrahydro-pyrido[4,3-d]pyrimidine as a brown solid (17 mg, 21% yield) $^1$H NMR (400 MHz, DMSO-d6, 298K) δ ppm 2.23-2.43 (m, 2 H) 2.85-2.99 (t, 2 H) 3.22-3.94 (m, 9 H) 4.08-4.27 (m, 2 H) 5.70-5.80 (m, 1 H) 6.56-6.66 (t, 1 H) 7.76-7.87 (m, 1 H) 8.12-8.27 (m, 1 H) 8.28-8.42 (m, 2 H) 8.59-8.68 (m, 1 H) LCMS: [M+H]+=474.2, Rt$^{(1)}$=1.91 min.

Example 67 was prepared according the general procedure described in scheme 4

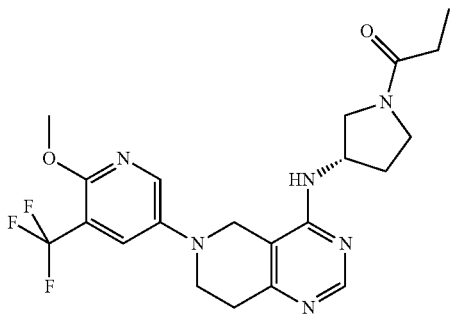 [SMILES: CCC(=O)N1CC[C@H](Nc2ncnc3c2CN(c2cnc(OC)c(C(F)(F)F)c2)CC3)C1]

Example 67

1-{(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-propan-1-one To a solution of (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (13.4 g, 27.1 mmol) in CH$_2$Cl$_2$ (100 mL), was added TFA (41.8 mL) and the mixture stirred at rt for 1 h. Concentrated in vacuo and partitioned between 2M NaOH (aq) (300 mL) and CH$_2$Cl$_2$ (200 mL). The organic phase was separated and the aqueous phase extracted with CH$_2$Cl$_2$ (2×200 mL). The organic phases were combined, dried (MgSO$_4$) and evaporated in vacuo to give a brown foam. The foam was dissolved in CH$_2$Cl$_2$ (50 mL) and was added simultaneously portionwise with sat.NaHCO$_3$(aq) (50 mL) to a vigorously stirring solution of propionyl chloride (2.63 g, 28.5 mmol) in CH$_2$Cl$_2$ (50 mL) at rt. The resulting biphasic mixture was stirred at rt for 1 h. Further propionyl chloride (0.566 g, 6.12 mmol) was added and continued stirring vigorously for 20 min. The organic layer was separated and the aqueous layer extracted with CH$_2$Cl$_2$ (100 mL). The organic layers were combined, dried (MgSO$_4$) and concentrated in vacuo to give a brown gum. The gum was stirred in EtOAc (100 mL) and the resulting solid filtered (9.4 g). The mother liquors were concentrated in vacuo and purified by column chromatography through a Biotage® amino silica gel eluting with EtOAc/MeOH, 100/0 to 90/10 to give a yellow foam which was then stirred in EtOAc (20 mL) and the resulting solid filtered (870 mg). Both batches of solids were combined and stirred in refluxing EtOAc (50 mL) for 1 h. Filtered to give 1-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-propan-1-one as a colourless solid (9.42 g, 76% yield). $^1$H NMR (400 MHz, DMSO-d6, 298K) δ ppm 0.95-1.05 (m, 3H) 1.87-2.32 (m, 4H) 2.77-2.86 (m, 2H) 3.25-3.88 (m, 6H) 3.93 (s, 3H) 3.98 (s, 2H) 4.55-4.80 (m, 1H) 6.70-6.80 (m, 1H, N—H) 7.86-

7.92 (m, 1H) 8.27-8.33 (m, 1H) 8.33-8.37 (m, 1H) LCMS: [M+H]+=451.0, Rt[(6)]=1.49 min.

Alternative Synthesis for Example 67

A solution of (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (29.04 g, 58.73 mmol) in 2-Me-THF (100 mL) was dropwise added into aqueous HCl solution (150 mL, 31%) over 15 min. The reaction mixture was partitioned between water (300 mL) and isopropyl acetate (100 mL) and the upper organic phase was discarded. The aqueous phase was partitioned between 25% NaOH (aq) (200 g) and 2-Me-THF (200 mL), and the organic phase was collected and dried. Triethylamine (16.32 mL, 117.48 mmol) was added into the organic phase followed by dropwise addition of propionyl chloride (6.0 g, 64.6 mmol) at 0° C. The resulting mixture was stirred at 0° C. for 1 h. The reaction mixture was washed with water (110 mL) and the resulting organic phase was concentrated in vacuo to give a brown gum. The residue was recrystallized with isopropanol and methyl tert-butyl ether to give 1-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-propan-1-one as a colourless solid (17.2 g, 65% yield).

Crystallization of Example 67 by Heating in Acetonitrile/Water 2.0 g of Example 67 (4.440 mol) were dissolved in 10 mL of acetonitrile and 0.5 mL of water at 75° C. The solution was allowed to cool down to rt within 30 min resulting in a suspension. The mixture was stirred for 16 h at rt. The crystals were collected by filtration. The filter cake was washed 2 times with 1 mL of acetonitrile and afterwards dried for 16 h at 24° C. and ca. 10 mbar vacuum. Elementary analysis of the material showed a waterless form.

List of most significant peaks from X-ray Powder Diffraction Pattern of Example 67 anhydrous form Method X1):

| 2-Theta in deg | Intensity in % |
| --- | --- |
| 7.9 | 31 |
| 9.6 | 88 |
| 11.5 | 29 |
| 13.4 | 8 |
| 15.2 | 7 |
| 15.9 | 100 |
| 16.8 | 57 |
| 17.6 | 9 |
| 18.7 | 20 |
| 20.0 | 8 |
| 20.6 | 40 |
| 22.0 | 32 |
| 22.4 | 53 |
| 22.7 | 26 |
| 23.4 | 17 |
| 23.9 | 23 |
| 24.5 | 41 |
| 25.1 | 20 |
| 25.8 | 13 |
| 26.7 | 31 |

Preparation of Phosphate Salt of Example 67

2.0 g of Example 67 (4.440 mol) were dissolved in 10 mL of acetonitrile and 0.5 mL of water at 75° C. 512 mg of ortho-phosphoric acid 85% (4.440 mol) were added at 70° C. Crystallization occurs quickly at 70° C. The suspension was allowed to cool down to rt within 30 min. The suspension was diluted with 10 ml acetonitrile and stirred for 16 h at rt. The crystals were collected by filtration. The filter cake was washed 3 times with 1 mL of acetonitrile and afterwards dried for 16 h at 24° C. and ca. 10 mbar vacuum. Elementary analysis of the phosphate salt showed a 1:1 (waterless) form List of most significant peaks from X-ray Powder Diffraction Pattern of Example 67 phosphate salt (Method X1):

| 2-Theta in deg | Intensity in % |
| --- | --- |
| 5.2 | 51 |
| 9.8 | 56 |
| 10.3 | 19 |
| 11.6 | 100 |
| 14.9 | 14 |
| 15.5 | 48 |
| 15.9 | 11 |
| 16.6 | 65 |
| 19.5 | 54 |
| 20.7 | 62 |
| 21.5 | 10 |
| 22.1 | 21 |
| 23.3 | 57 |
| 25.8 | 18 |
| 26.4 | 29 |
| 27.2 | 20 |
| 28.2 | 13 |

Preparation of Hydrochloride Salt of Example 67

2.0 g of Example 67 (4.440 mol) were dissolved in 20 mL of acetonitrile and 1.0 mL of water at 70° C. 459 mg of hydrochloric acid 37% (4.440 mol) were added at 70° C. Crystallization occurs quickly at 70° C. The suspension was allowed to cool down to rt within 30 min and stirred for 16 h at rt. The crystals were collected by filtration. The filter cake was washed 3 times with 1 mL of acetonitrile and afterwards dried for 16 h at 24° C. and ca. 10 mbar vacuum. Elementary analysis of the HCl salt showed a 1:1 (waterless) form List of most significant peaks from X-ray Powder Diffraction Pattern of Example 67 hydrochloride salt (Method X1):

| 2-Theta in deg | Intensity in % |
| --- | --- |
| 5.6 | 100 |
| 11.0 | 18 |
| 11.3 | 42 |
| 11.8 | 12 |
| 14.7 | 33 |
| 17.1 | 13 |
| 18.7 | 19 |
| 19.4 | 29 |
| 22.0 | 23 |
| 22.6 | 28 |
| 23.1 | 50 |
| 23.7 | 28 |
| 24.9 | 29 |
| 25.5 | 15 |

Preparation of Hippurate Salt of Example 67

0.4 g of Example 67 (0.888 mmol) were dissolved in 8 mL of acetonitrile and 0.2 mL of water at 70° C. 167 mg of hippuric acid (0.888 mmol) were added at 70° C. The solution was allowed to cool down to rt within 30 min.

Crystallization occurs at 40° C. The suspension was stirred for 16 h at rt. The crystals were collected by filtration. The filter cake was washed 3 times with 1 mL of acetonitrile and afterwards dried for 16 h at 50° C. and ca. 10 mbar vacuum List of most significant peaks from X-ray Powder Diffraction Pattern of Example 67 hippurate salt (Method X1):

| 2-Theta in deg | Intensity in % |
|---|---|
| 5.2 | 76 |
| 7.5 | 100 |
| 10.3 | 60 |
| 10.9 | 63 |
| 11.8 | 9 |

-continued

| 2-Theta in deg | Intensity in % |
|---|---|
| 13.1 | 16 |
| 16.1 | 44 |
| 16.7 | 26 |
| 17.7 | 49 |
| 18.4 | 38 |
| 21.2 | 49 |
| 23.2 | 74 |
| 24.2 | 67 |
| 26.2 | 28 |

Examples 68-69 were prepared using procedures analogous to those used in example 67 using appropriate starting materials.

| Example 68 | | Rt$^{(1)}$ (min.) | MS: [M + H]+ |
|---|---|---|---|
| | | 1.26 | 507.2 |

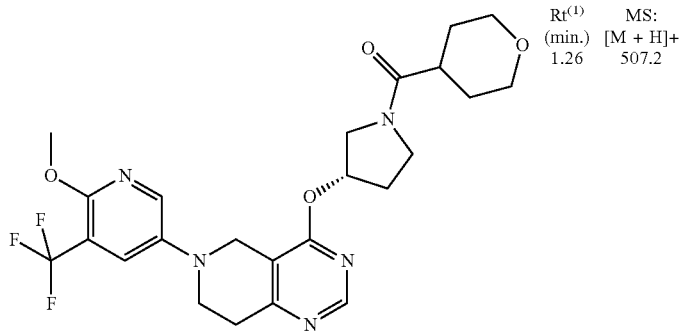

Name: {(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-(tetrahydro-pyran-4-yl)-methanone Purification method: Reverse phase HPLC Method A Prepared using tetrahydro-pyran-4-carbonyl chloride $^1$H NMR (400 MHz, DMSO-d6, 298K) δ ppm 1.48-1.67 (m, 4H) 1.88-2.35 (m, 2H) 2.59-2.87 (m, 3H) 3.26-4.03 (m, 15H) 4.56-4.83 (m, 1H) 6.82-6.92 (m, 1H, N—H) 7.86-7.90 (m, 1H) 8.26-8.32 (m, 1H) 8.37-8.42 (m, 1H)

| Example 69 | | Rt$^{(1)}$ (min.) | MS: [M + H]+ |
|---|---|---|---|
| | | 1.06 | 464.2 |

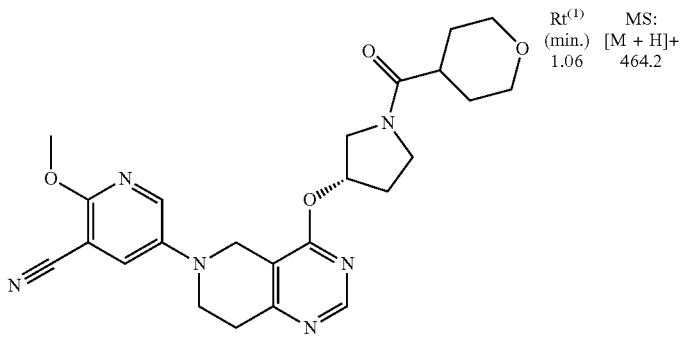

Name: 2-Methoxy-5-{4-[(S)-1-(tetrahydro-pyran-4-carbonyl)-pyrrolidin-3-ylamino]-7,8-dihydro-5H-pyrido[4,3-d]pyrimidin-6-yl}-nicotinonitrile Purification method: Reverse phase HPLC Method A Prepared using intermediate 25 and tetrahydro-pyran-4-carbonyl chloride $^1$H NMR (400 MHz, MeOH-d4, 298K) δ ppm 1.59-1.86 (m, 4H) 2.07-2.47 (m, 2H) 2.75-2.98 (m, 3H) 3.44-4.13 (m, 15H) 4.64-5.24 (m, 1H, signal masked by water peak) 7.94-7.99 (m, 1H) 8.20-8.26 (m, 1H) 8.33-8.39 (m, 1H)

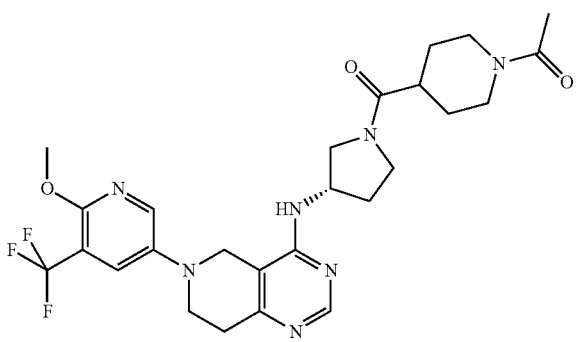 [SMILES: COc1ncc(N2CCc3ncnc(N[C@H]4CCN(C(=O)C5CCN(C(C)=O)CC5)C4)c3C2)cc1C(F)(F)F]

Example 70

1-(4-{(S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carbonyl}-piperidin-1-yl)-ethanone (S)-3-[6-(6-Methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (160 mg, 0.32 mmol) was dissolved in CH₂Cl₂ (2.0 mL) and TFA (1.0 mL) added. The resulting mixture was stirred at room temperature for 1 h then evaporated in vacuo to give [6-(6-methoxy-5-trifluoromethyl-pyridin-3-yl)-5,6,7,8-tetrahydro-pyrido[4,3-d]pyrimidin-4-yl]-(S)-pyrrolidin-3-yl-amine ditrifluoroacetate as a brown gum (160 mg), which was used without further purification. To [6-(6-methoxy-5-trifluoromethyl-pyridin-3-yl)-5,6,7,8-tetrahydro-pyrido[4,3-d]pyrimidin-4-yl]-(S)-pyrrolidin-3-yl-amine ditrifluoroacetate (40 mg, 0.06 mmol) was added 1-acetylpiperidine-4-carboxylic acid (12 mg, 0.07 mmol)), N,N-diisopropylethylamine (0.05 mL, 0.26 mmol), CH₂Cl₂ (3.0 mL) and then HBTU (29 mg, 0.08 mmol). The mixture was allowed to stir at room temperature for 18 h and then partitioned between CH₂Cl₂ (10 mL) and water (5 mL). The organic phase was filtered through a phase separation tube and evaporated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give 1-(4-{(S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carbonyl}-piperidin-1-yl)-ethanone as a pale yellow solid (19 mg, 50% yield for 2$^{nd}$ step)¹H NMR (400 MHz, DMSO-d6, 298K) δ ppm 1.20-1.70 (m, 4H) 1.79-2.35 (m, 5H) 2.53-2.85 (m, 4H) 3.04-3.14 (m, 1H) 3.35-4.79 (m, 14H) 6.80-6.87 (m, 1H, N—H) 7.87-7.91 (m, 1H) 8.26-8.31 (m, 1H) 8.35-8.41 (m, 1H) LCMS: [M+H]+=548.2, Rt$^{(1)}$=1.22 min.

Examples 71-80 were prepared using procedures analogous to those used in example 70 using appropriate starting materials

| Example 71 | 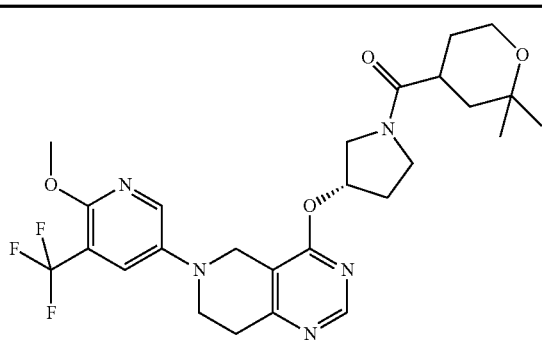 | Rt$^{(1)}$ (min.) 1.40 | MS: [M + H]+ 535.3 |
|---|---|---|---|
| Name: (2,2-Dimethyl-tetrahydro-pyran-4-yl)-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-methanone Purification method: Reverse phase HPLC Method A Prepared using 2,2-dimethyl-tetrahydro-pyran-4-carboxylic acid ¹H NMR (400 MHz, DMSO-d6, 298K) δ ppm 1.05-1.20 (m, 6H) 1.30-1.58 (m, 4H) 1.86-2.35 (m, 2H) 2.70-2.90 (m, 3H) 3.34-4.03 (m, 13H) 4.55-4.80 (m, 1H) 6.67-6.76 (m, 1H, N—H) 7.86-7.89 (m, 1H) 8.26-8.31 (m, 1H) 8.32-8.37 (m, 1H) | | | |

| Example 72 | 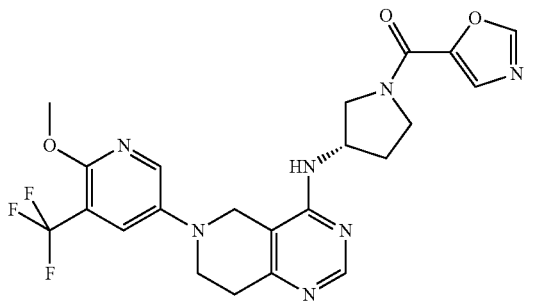 [SMILES: COc1ncc(N2CCc3ncnc(N[C@H]4CCN(C(=O)c5cnco5)C4)c3C2)cc1C(F)(F)F] | Rt$^{(1)}$ (min.) 1.22 | MS: [M + H]+ 490.1 |
|---|---|---|---|
| Name: {(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-oxazol-5-yl-methanone | | | |

Purification method: Reverse phase HPLC Method A
Prepared using oxazole-5-carboxylic acid
¹H NMR (400 MHz, DMSO-d6, 298K) δ ppm 1.89-2.39 (m, 2H) 2.78-2.86 (m, 2H) 3.50-4.20 (m, 11H) 4.65-4.84 (m, 1H) 6.75-6.83 (m, 1H, N—H) 7.75-7.83 (m, 1H) 7.86-7.92 (m, 1H) 8.26-8.32 (m, 1H) 8.35-8.38 (m, 1H) 8.55-8.60 (m, 1H)

| Example 73 | 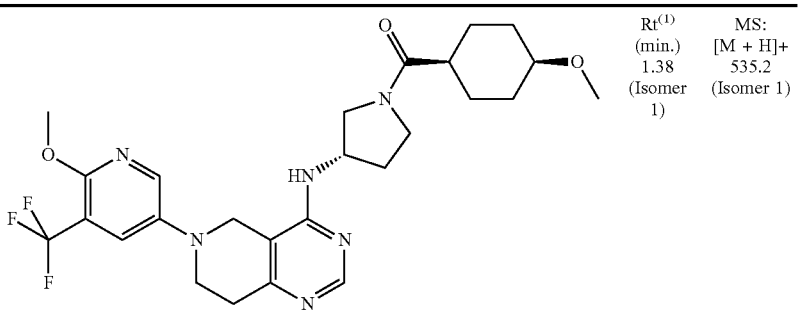 | Rt⁽¹⁾ (min.) 1.38 (Isomer 1) | MS: [M + H]+ 535.2 (Isomer 1) |
|---|---|---|---|
| Example 74 | 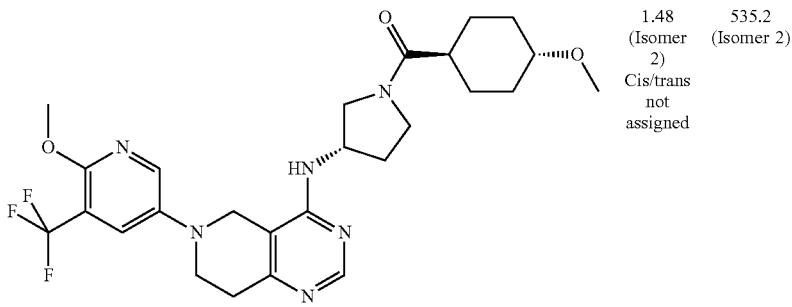 | 1.48 (Isomer 2) Cis/trans not assigned | 535.2 (Isomer 2) |

Name: ((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)((1R,4R)-4-methoxycyclohexyl)methanone
((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)((1R,4S)-4-methoxycyclohexyl)methanone
Purification method: Reverse phase HPLC Method A
Prepared using 4-methoxy-cyclohexanecarboxylic acid (mixture of cis/trans)
¹H NMR (Isomer 1 cis/trans not assigned) (400 MHz, DMSO-d6, 298K) δ ppm 1.04-1.47 (m, 4H) 1.64-2.45 (m, 7H) 2.77-2.86 (m, 2H) 3.00-3.77 (m, 10H) 3.87-4.03 (m, 5H) 4.53-4.80 (m, 1H) 6.67-6.78 (m, 1H, N—H) 7.85-7.91 (m, 1H) 8.26-8.32 (m, 1H) 8.33-8.38 (m, 1H)
¹H NMR (Isomer 2 cis/trans not assigned) (400 MHz, DMSO-d6, 298K) δ ppm 1.32-1.48 (m, 4H) 1.55-2.50 (m, 7H) 2.78-2.84 (m, 2H) 3.01-3.77 (m, 10H) 3.87-4.03 (m, 5H) 4.53-4.80 (m, 1H) 6.67-6.78 (m, 1H, N—H) 7.85-7.91 (m, 1H) 8.26-8.32 (m, 1H) 8.33-8.38 (m, 1H)

| Example 75 | 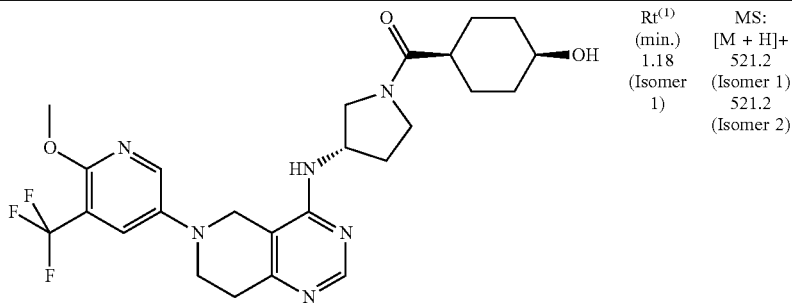 | Rt⁽¹⁾ (min.) 1.18 (Isomer 1) | MS: [M + H]+ 521.2 (Isomer 1) 521.2 (Isomer 2) |
|---|---|---|---|

| Example 76 | 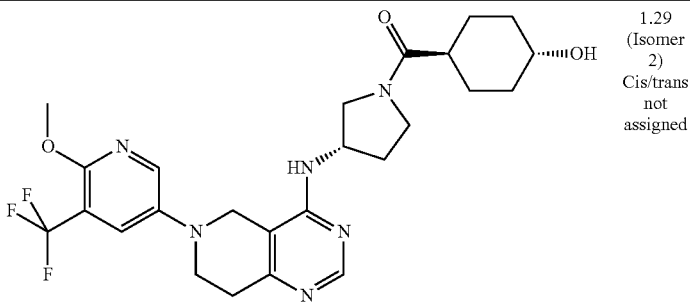 | 1.29 (Isomer 2) Cis/trans not assigned |

Name: ((1S,4R)-4-hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone
((1R,4S)-4-hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone
Purification method: Reverse phase HPLC Method A
Prepared using 4-hydroxy-cyclohexanecarboxylic acid (mixture of cis/trans)
$^1$H NMR (Isomer 1 cis/trans not assigned) (400 MHz, DMSO-d6, 298K) δ ppm 1.06-1.44 (m, 4H) 1.57-2.86 (m, 9H) 3.01-3.76 (m, 7H) 3.88-4.03 (m, 5H) 4.50-4.78 (m, 2H) 6.68-6.78 (m, 1H, N—H) 7.86-7.91 (m, 1H) 8.26-8.32 (m, 1H) 8.33-8.39 (m, 1H)
1H NMR (Isomer 1 cis/trans not assigned) (400 MHz, DMSO-d6, 298K) δ ppm 1.28-1.52 (m, 4H) 1.59-2.85 (m, 9H) 3.03-3.83 (m, 8H) 3.88-4.03 (m, 5H) 4.55-4.79 (m, 1H) 6.68-6.77 (m, 1H, N—H) 7.85-7.91 (m, 1H) 8.26-8.32 (m, 1H) 8.33-8.39 (m, 1H)

| Example 77 | 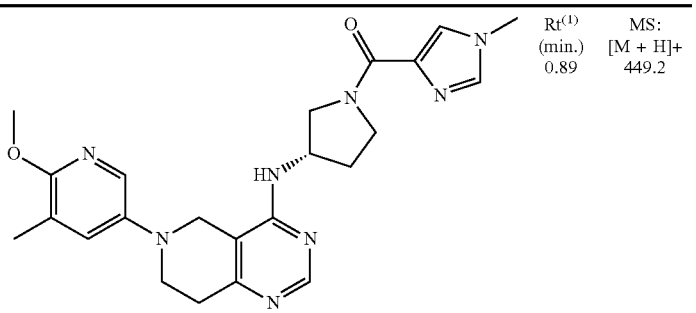 | Rt$^{(1)}$ (min.) 0.89 | MS: [M + H]+ 449.2 |

Name: -{(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-(1-methyl-1H-imidazol-4-yl)-methanone
Purification method: Reverse phase HPLC Method A
Prepared using intermediate 20 and 1-methyl-1H-imidazole-4-carboxylic acid
$^1$H NMR (400 MHz, MeOH-d4, 298K) δ ppm 2.07-2.44 (m, 5H) 2.86-2.95 (m, 2H) 3.44-4.43 (m, 14H) 4.77-4.87 (m, 1H) 7.44-7.48 (m, 1H) 7.60-7.70 (m, 2H) 7.72-7.79 m, 1H) 8.32-8.41 (m, 1H)

| Example 78 | 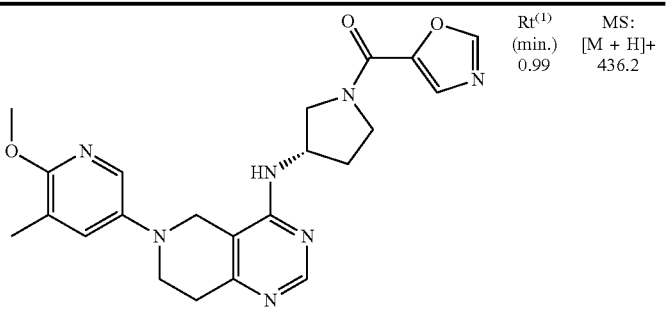 | Rt$^{(1)}$ (min.) 0.99 | MS: [M + H]+ 436.2 |

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-oxazol-5-yl-methanone
Purification method: Reverse phase HPLC Method A
Prepared using intermediate 20 and oxazole-5-carboxylic acid
$^1$H NMR (400 MHz, DMSO-d6, 298K) δ ppm 1.95-2.35 (m, 5H) 2.74-2.83 (m, 2H) 3.35-4.20 (m, 11H) 4.62-4.83 (m, 1H) 6.73-6.81 (m, 1H) 7.44-7.49 (m, 1H) 7.75-7.85 (m, 2H) 8.33-8.38 (m, 1H) 8.54-8.59 (m, 1H)

| Example 79 | 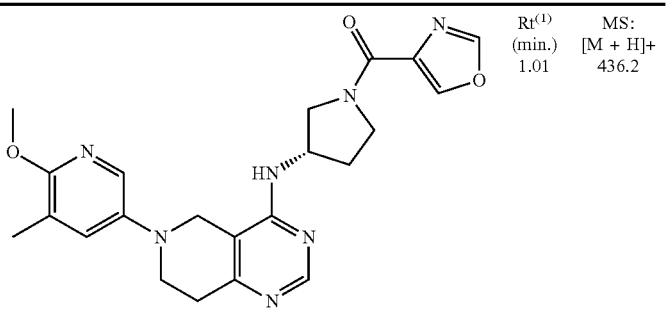 | Rt(1) (min.) 1.01 | MS: [M + H]+ 436.2 |

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-oxazol-4-yl-methanone
Purification method: Reverse phase HPLC Method A
Prepared using intermediate 20 and oxazole-4-carboxylic acid
$^1$H NMR (400 MHz, DMSO-d6, 298K) δ ppm 1.93-2.35 (m, 5H) 2.75-2.82 (m, 2H) 3.38-4.27 (m, 11H) 4.61-4.78 (m, 1H) 6.74-6.80 (m, 1H) 7.45-7.49 (m, 1H) 7.78-7.84 (m, 1H) 8.32-8.37 (m, 1H) 8.47-8.53 (m, 1H) 8.61-8.66 (m, 1H)

| Example 80 | 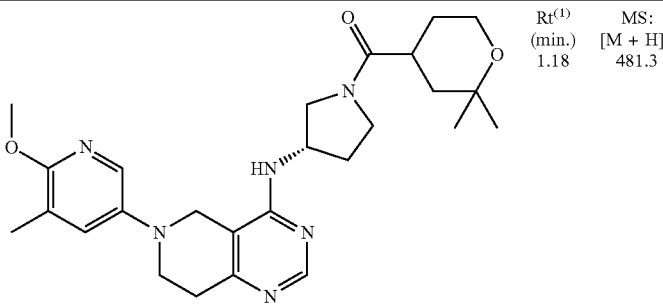 | Rt(1) (min.) 1.18 | MS: [M + H]+ 481.3 |

Name: (2,2-Dimethyl-tetrahydro-pyran-4-yl)-{(S)-3-[6-(6-methoxy-5-methyl-pyridin-3-yl)-5,6,7,8-tetrahydro-pyrido[4,3-d]pyrimidin-4-ylamino]-pyrrolidin-1-yl}-methanone
Purification method: Reverse phase HPLC Method A
Prepared using intermediate 20 and 2,2-dimethyl-tetrahydro-pyran-4-carboxylic acid
$^1$H NMR (400 MHz, DMSO-d6, 298K) δ ppm 1.05-1.22 (m, 6H) 1.30-1.58 (m, 4H) 1.90-2.29 (m, 5H) 2.75-2.85 (m, 3H) 3.35-3.77 (m, 7H) 3.82 (s, 3H) 3.87-3.97 (m, 3H) 4.54-4.79 (m, 1H) 6.66-6.75 (m, 1H) 7.47 (d, 1H) 7.81 (d, 1H) 8.35 (d, 1H)

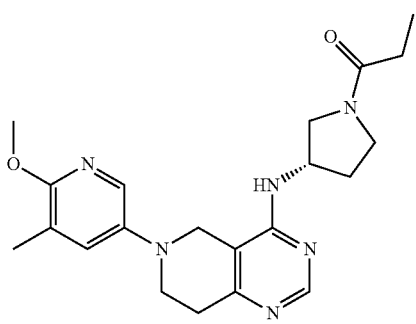 [SMILES: CCC(=O)N1CC[C@H](Nc2ncnc3c2CN(c2cnc(OC)c(C)c2)CC3)C1]

Example 81

1-{(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-propan-1-one To a solution of (S)-3-[6-(6-methoxy-5-methyl-pyridin-3-yl)-5,6,7,8-tetrahydro-pyrido[4,3-d]pyrimidin-4-ylamino]-pyrrolidine-1-carboxylic acid tert-butyl ester trifluoroacetate (intermediate 20) (60 mg, 0.11 mmol) in CH$_2$Cl$_2$ (2.0 mL), was added TFA (2.0 mL) and the mixture stirred at rt for 1 h. Concentrated in vacuo to give [6-(6-methoxy-5-methylpyridin-3-yl)-5,6,7,8-tetrahydropyrido[4,3-d]pyrimidin-4-yl)]-(S)-pyrrolidin-3-yl)amine ditrifluoroacetate (60 mg). [6-(6-Methoxy-5-methyl-pyridin-3-yl)-5,6,7,8-tetrahydro-pyrido[4,3-d]pyrimidin-4-yl]-(S)-pyrrolidin-3-yl)amine ditrifluoroacetate (30 mg, 0.053 mmol) was dissolved in CH$_2$Cl$_2$ (2.0 mL) and was added simultaneously portionwise with sat.NaHCO$_3$(aq) (2.0 mL) to a vigorously stirring solution of propionyl chloride (7 mg, 0.07 mmol) in CH$_2$Cl$_2$ (2.0 mL) at rt. The resulting biphasic mixture was stirred at rt for 45 min. Diluted with CH$_2$Cl$_2$ (10 mL) and sat.NaHCO$_3$(aq) (2.0 mL). The organic layer was separated by filtering through phase separation tube and concentrated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo gave 1-{(S)-3-[6-(6-methoxy-5-methyl-pyridin-3-yl)-5,6,7,8-tetrahydro-pyrido[4,3-d]pyrimidin-4-ylamino]-pyrrolidin-1-yl}-propan-1-one as a colourless powder (7 mg, 21% yield) $^1$H NMR (400 MHz, MeOH-d4, 298K) δ ppm 1.20-1.28 (m, 3H) 2.04-2.44 (m, 7H) 2.88-2.94 (m, 2H) 3.48-4.04 (m, 11H) 4.73-4.88 (m, 1H) 7.44-7.48 (m, 1H) 7.73-7.77 (m, 1H) 8.34-8.38 (m, 1H) LCMS: [M+H]+=397.1, Rt(3)=1.32 min.

Examples 82-83 were prepared using procedures analogous to those used in Example 81 using appropriate starting materials.

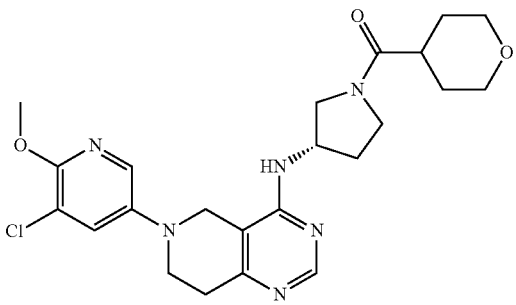 [SMILES: COc1ncc(N2CCc3ncnc(N[C@H]4CCN(C(=O)C5CCOCC5)C4)c3C2)cc1Cl]

| Example 82 | | Rt[(1)] (min.) 1.13 | MS: [M + H]+ 473.2 |
|---|---|---|---|

Name: {(S)-3-[6-(5-Chloro-6-methoxy-pyridin-3-yl)-5,6,7,8-tetrahydro-pyrido[4,3-d]pyrimidin-4-ylamino]-pyrrolidin-1-yl}-(tetrahydro-pyran-4-yl)-methanone
Purification method: Reverse phase HPLC Method A
Prepared using intermediate 21 and tetrahydro-pyran-4-carbonyl chloride
$^1$H NMR (400 MHz, MeOH-d4, 298K) δ ppm 1.58-1.87 (m, 4H) 2.04-2.45 (m, 2H) 2.73-2.96 (m, 3H) 3.39-4.14 (m, 15H) 4.71-4.90 (m, 1H) 7.67-7.74 (m, 1H) 7.88-7.93 (m, 1H) 8.34-8.39 (m, 1H)

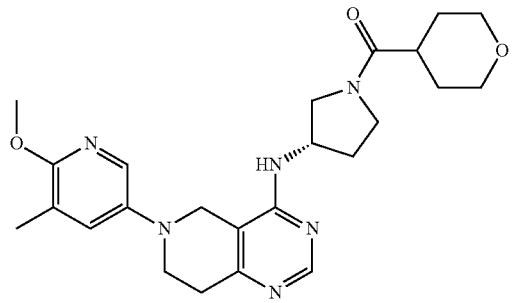 [SMILES: COc1ncc(N2CCc3ncnc(N[C@H]4CCN(C(=O)C5CCOCC5)C4)c3C2)cc1C]

| Example 83 | | Rt[(7)] (min.) 0.86 | MS: [M + H]+ 453.6 |
|---|---|---|---|

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-(tetrahydro-pyran-4-yl)-methanone
Purification method: Reverse phase HPLC Method A then Method C
Prepared using intermediate 20 and tetrahydro-pyran-4-carbonyl chloride
$^1$H NMR (400 MHz, MeOD-d6, 298K) δ ppm 1.57-1.88 (m, 4H) 2.04-2.45 (m, 5H) 2.73-2.96 (m, 3H) 3.37-4.12 (m, 15H) 4.73-4.88 (m, 1H) 7.45-7.48 (m, 1H) 7.73-7.77 (m, 1H) 8.36-8.39 (m, 1H)

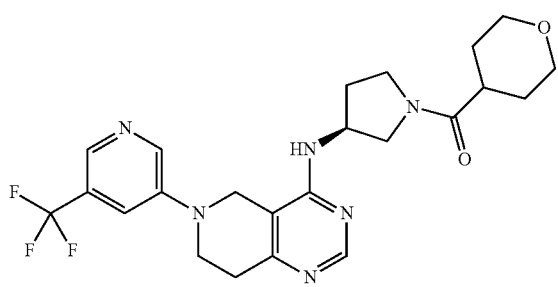 [SMILES: O=C(C1CCOCC1)N1CC[C@H](Nc2ncnc3c2CN(c2cncc(C(F)(F)F)c2)CC3)C1]

Example 84

(Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone To 6-(5-(trifluoromethyl-pyridin-3-yl)-5,6,7,8-tetrahydropyrido[4,3-d]pyrimidin-4-ol (intermediate 19) (59 mg) in acetonitrile (1.0 ml) was added BOP (114 mg, 0.258 mmol) and DBU (0.060 ml, 0.398 mmol). The resulting solution was stood at RT for 1 min then added [(S)-3-Amino-pyrrolidin-1-yl-(tetrahydro-pyran-4-yl)-methanone (intermediate 5) (79 mg, 0.398 mmol) in acetonitrile (1.0 ml) and heated the mixture at 85° C. for 25 h. The reaction mixture was evaporated in vacuo and purified by reverse phase Gilson HPLC and subsequent neutralization of the combined fractions by eluting through an Isolute® SCX-2 cartridge, eluting with methanol, then with 2M ammonia in methanol. Basic fractions were concentrated in vacuo gave crude title compound which was further purified by flash chromatography on silica gel with EtOAc/MeOH 100/0 to 80/20 to give (Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone (19 mg, 6% yield) as a colourless solid. $^1$H NMR (400 MHz, DMSO-d6, 298K) δ ppm 1.47-1.69 (m, 4H) 1.83-2.37 (m, 2H) 2.58-2.89 (m, 3H) 3.23-4.20 (m, 12H) 4.56-4.82 (m, 1H) 6.75-6.89 (m, 1H, N—H) 7.68-7.79 (m, 1H) 8.28-8.42 (m, 2H) 8.74-8.83 (m, 1H). LCMS: [M+H]+=477.6, Rt[(7)]=0.84 min.

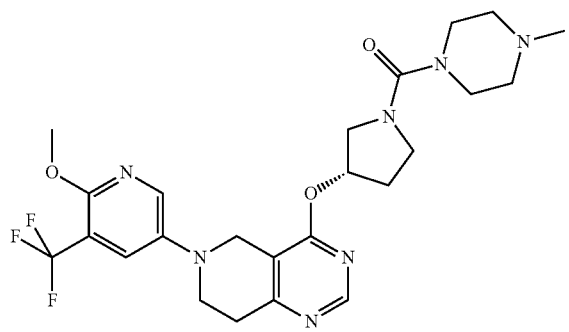 [SMILES: COc1ncc(N2CCc3ncnc(O[C@H]4CCN(C(=O)N5CCN(C)CC5)C4)c3C2)cc1C(F)(F)F]

Example 85

{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(4-methyl-piperazin-1-yl)-methanone To a solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (23.0 mg, 0.058 mmol) and triethylamine (0.016 mL, 0.116 mmol) in $CH_2Cl_2$ (2 mL) was added 4-methylpiperazine-1-carbonyl chloride hydrochloride (11.6 mg, 0.058 mmol) and the mixture stirred at rt for 18 h. Diluted with $CH_2Cl_2$ (10 mL) and washed with sat. $NaHCO_3$ (aq) (2 mL). The organic layer was filtered through a phase separation tube and evaporated in vacuo. Purification was performed by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(4-methyl-piperazin-1-yl)-methanone (25 mg, 58% yield) as a yellow powder. $^1$H NMR (400 MHz, $CDCl_3$, 298K) δ ppm 2.17-2.27 (m, 2H) 2.55 (s, 3H) 2.65-2.78 (m, 4H) 3.07 (t, 2H) 3.45-3.73 (m, 9H) 3.86-3.95 (m, 1H) 4.02 (s, 3H) 4.13 (s, 2H) 5.66-5.73 (m, 1H) 7.62 (d, 1H) 8.06 (d, 1H) 8.64 (s, 1H) LCMS: [M+H]+=522.3, Rt$^{(1)}$=1.21 min.

Example 86 was prepared using procedures analogous to those used in Example 85 using appropriate starting materials.

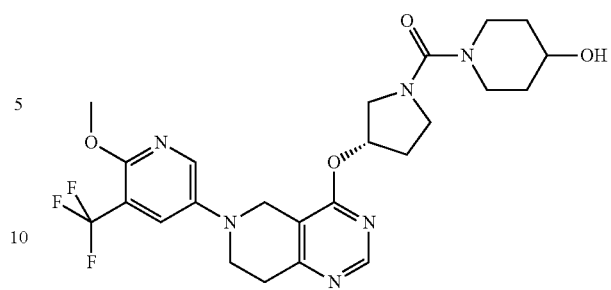

Example 87

(4-Hydroxy-piperidin-1-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone To $CH_2Cl_2$ (5 mL) in a round bottomed flask was added phosgene (20% solution in toluene, 0.20 mL, 0.379 mmol) and the resulting solution cooled to 5° C. under argon. A solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (50.0 mg, 0.126 mmol) and triethylamine (0.053 mL, 0.380 mmol) in $CH_2Cl_2$ (1.0 mL) was added and the mixture allowed to warm to room temperature with stirring under argon over 1 h. Evaporated to dryness by bubbling a stream of argon into the mixture to give a brown gum. Dissolved in $CH_2Cl_2$ (3 mL) to give (S)-3-[6-(6-methoxy-5-trifluoromethyl-pyridin-3-yl)-5,6,7,8-tetrahydro-pyrido[4,3-d]pyrimidin-4-yloxy]-pyrrolidine-1-carbonyl chloride as a solution in $CH_2Cl_2$. LCMS: 458.4 [M+1]+, Rt$^{(7)}$=1.38 min. This solution was used without further purification. 1.5 mL of this solution was added to a solution of piperidin-4-ol (6.4 mg, 0.063 mmol) and triethylamine (0.053 mL, 0.380 mmol) in $CH_2Cl_2$ and the mixture stirred at room temperature under argon for 1 h. N,N-dimethylformamide (0.5 mL) was added and stirring continued for 2 h. Diluted with $CH_2Cl_2$ (2 mL) and washed with sat. $NaHCO_3$(aq) (2 mL). The organic layer was filtered through a phase separation tube and evaporated in vacuo. Purification by reverse phase Gilson HPLC

| Example 86 | 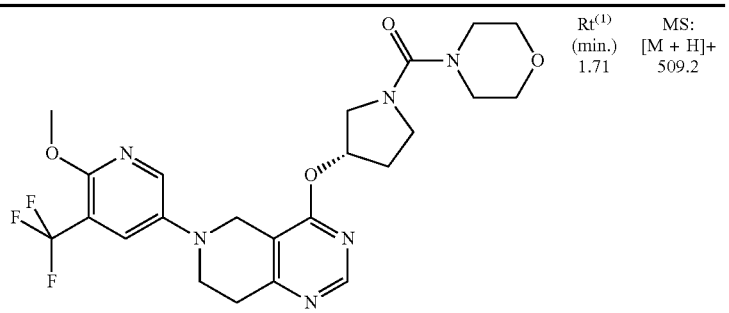 | Rt$^{(1)}$ (min.) | MS: [M + H]+ |
|---|---|---|---|
| | | 1.71 | 509.2 |

Name: -{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-morpholin-4-yl-methanone
Purification method: Reverse phase HPLC Method A
Prepared using morpholine 4-carbonyl chloride
$^1$H NMR (400 MHz, MeOH-d4, 298K) δ ppm 2.21-2.31 (m, 2H) 3.03 (t, 2H) 3.23-3.42 (m, 4H) 3.48-3.81 (m, 9H) 3.82-3.88 (m, 1H) 3.99 (s, 3H) 4.17 (s, 2H) 5.72-5.77 (m, 1H) 7.79 (d, 1H) 8.13 (d, 1H) 8.59 (s, 1H)

(Method A) and subsequent neutralization of the combined fractions by elution through an Isolute® SCX-2 cartridge, eluting with methanol, then with 2M ammonia in methanol. Basic fractions were concentrated in vacuo to give (4-hydroxy-piperidin-1-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone as a pale yellow powder (22 mg, 64% yield). $^1$H NMR (400 MHz, MeOH-d4, 298K) δ ppm 1.35-1.57 (m, 2H) 1.80-.1.94 (m, 2H) 2.20-2.31 (m, 2H) 2.94-3.09 (m, 4H) 3.45-3.87 (m, 10H) 3.98 (s, 3H) 4.17 (s, 2H) 5.70-5.76 (m, 1H) 7.78 (d, 1H) 8.13 (d, 1H) 8.58 (s, 1H) LCMS: [M+H]+=523.2, Rt$^{(1)}$=1.58 min.

Example 88 was prepared using procedures analogous to those used in Example 87 using appropriate starting materials.

Partitioned between CH$_2$Cl$_2$ (10 mL) and sat. NaHCO$_3$(aq) (2 mL) and the organic layer was filtered through a phase separation tube and evaporated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give 1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperazin-1-yl)-ethanone as a pale yellow powder (9 mg, 25% yield). $^1$H NMR (400 MHz, MeOH-d4, 298K) δ ppm 2.14 (s, 3H) 2.24-2.33 (m, 2H) 3.04 (t, 2H) 3.25-3.91 (m, 13H) 3.99 (s, 3H) 4.18 (s, 2H) 5.74-5.78 (m, 1H) 7.79 (d, 1H) 8.14 (d, 1H) 8.60 (s, 1H) LCMS: [M+H]+=550.2, Rt$^{(1)}$=1.58 min.

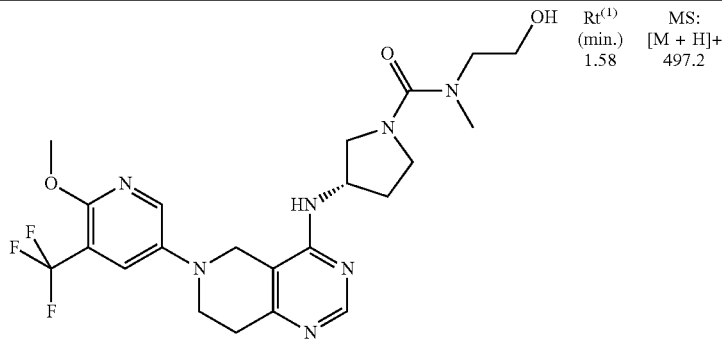

| Example 88 | Rt$^{(1)}$ (min.) | MS: [M + H]+ |
|---|---|---|
|  | 1.58 | 497.2 |

Name: (S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid (2-hydroxy-ethyl)-methyl-amide
Purification method: Reverse phase HPLC Method A
Prepared using 2-methylamino-ethanol
$^1$H NMR (400 MHz, MeOH-d4, 298K) δ ppm 2.20-2.32 (m, 2H) 2.97 (s, 3H) 2.98-3.06 (t, 2H) 3.27-3.38 (m, 1H) 3.40-3.80 (m, 8H) 3.82-3.89 (m, 1H) 3.98 (s, 3H) 4.18 (s, 2H) 5.71-5.76 (m, 1H) 7.78 (d, 1H) 8.14 (d, 1H) 8.58 (s, 1H)

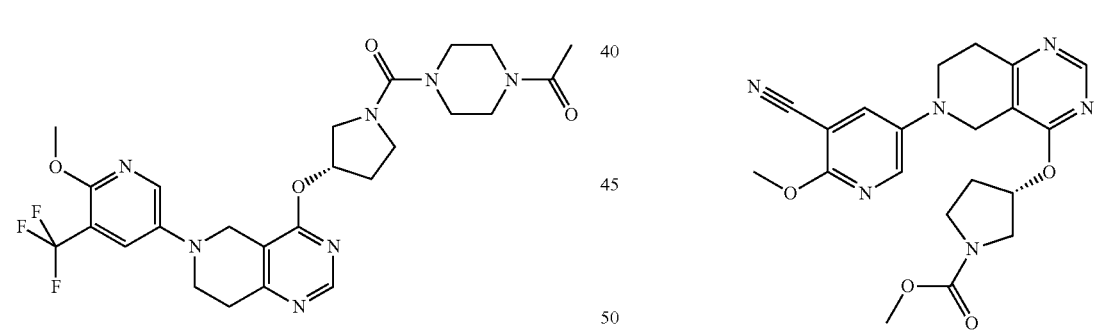

Example 89

1-(4-{(S)-3-[6-(6-methoxy-5-trifluoromethyl-pyridin-3-yl)-5,6,7,8-tetrahydro-pyrido[4,3-d]pyrimidin-4-yloxy]-pyrrolidine-1-carbonyl}-piperazin-1-yl)-ethanone To a solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (25 mg, 0.063 mmol) and triethylamine (0.013 mL, 0.095 mmol) in CH$_2$Cl$_2$ (2 mL) was added 3-(4-acetyl-piperazine-1-carbonyl)-1-methyl-3H-imidazol-3-ium iodide (Intermediate 6) (15 mg, 0.063 mmol) and the mixture stirred at room temperature under argon for 18 h.

Example 90

(S)-3-[6-(5-cyano-6-methoxy-pyridin-3-yl)-5,6,7,8-tetrahydro-pyrido[4,3-d]pyrimidin-4-yloxy]-pyrrolidine-1-carboxylic acid methyl ester To a solution of 2-methoxy-5-[4-((S)-pyrrolidin-3-yloxy)-7,8-dihydro-5H-pyrido[4,3-d]pyrimidin-6-yl]-nicotinonitrile (prepared using intermediate 11 and method 1 b, process step 2, example 1) (25.0 mg, 0.071 mmol) and triethylamine (0.04 mL, 0.29 mmol) in CH$_2$Cl$_2$ (2 mL) was added methyl carbonochloridate (0.006 mL, 0.078 mmol) and the mixture stirred at room temperature for 18 h. Diluted with CH$_2$Cl$_2$ (2 mL) and washed with sat. NaHCO$_3$(aq) (1 mL). The organic layer was filtered through a phase separation tube and evaporated in vacuo. Purification was performed by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo gave (S)-3-[6-(5-cyano-6-methoxy-pyridin-3-yl)-5,6,7,8-tetrahydro-pyrido[4,3-d]pyrimidin-4-yloxy]-pyrrolidine-1-carboxylic acid methyl ester (10 mg, 35% yield) as a yellow powder. $^1$H NMR (400 MHz, DMSO-d6, 298K) δ ppm 2.09-2.31 (m, 2H) 2.91 (t, 2H) 3.45-3.75 (m, 9H) 3.93 (s, 3H) 4.17 (s, 2H) 5.58-5.65 (m, 1H) 8.09 (d, 1H) 8.27 (d, 1H) 8.61 (s, 1H) LCMS: [M+H]+=411.1, Rt$^{(1)}$=1.58 min.

allowed to stir at room temperature for 30 min. Purified by reverse phase Gilson HPLC (Method A) and subsequent neutralization of the combined fractions over PL-HCO$_3$ MP to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-oxazol-4-yl-methanone as a yellow solid (38 mg, 36% yield) $^1$H NMR (400 MHz, DMSO-d6, 298K) δ ppm 2.11-2.39 (m, 2 H) 2.80-3.01 (m, 2 H) 3.22-4.29 (m, 11 H) 5.59-5.80 (m, 1 H) 7.72-7.94 (m, 1 H) 8.10-8.29 (m, 1 H) 8.41-8.55 (m, 1 H) 8.57-8.77 (m, 2 H) LCMS: [M+H]+=491.1, Rt$^{(1)}$=1.69 min.

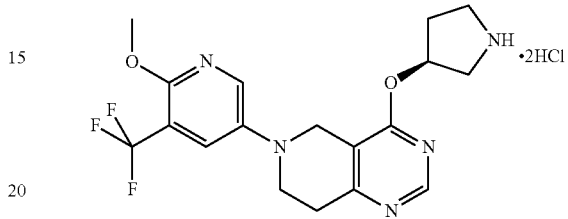

6-(6-Methoxy-5-trifluoromethyl-pyridin-3-yl)-4-((S)-pyrrolidin-3-yloxy)-5,6,7,8-tetrahydro-pyrido[4,3-d]pyrimidine dihydrochloride

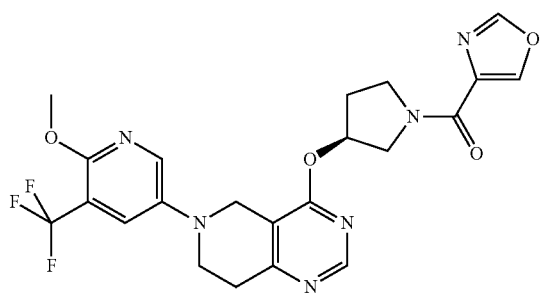 [SMILES: COc1ncc(N2CCc3ncnc(O[C@H]4CCN(C(=O)c5cocn5)C4)c3C2)cc1C(F)(F)F]

Example 91

{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-oxazol-4-yl-methanone Step 2

To the oxazole-4-carboxylic acid (27 mg, 0.24 mmol)) and HBTU (89 mg, 0.24 mmol) in DMF (1 mL) was added N,N-diisopropylethylamine (0.08 mL, 0.45 mmol). The mixture was stirred for 20 min and then 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (100 mg, 0.214 mmol) and additional N,N-diisopropylethylamine (0.08 mL, 0.45 mmol) were added. The mixture was Step 1

(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester (1.0 g, 1.69 mmol) in CH$_2$Cl$_2$ (5 mL) was added 2M anhydrous HCl in diethyl ether (25.3 mL, 50.5 mmol) and the mixture stirred at rt for 3 h. The resulting precipitate was filtered and washed with diethyl ether to give 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride as a yellow solid (1.01 g, 128% yield). [M+H]+=396.0, Rt$^{(4)}$=0.71 min. The free base can be generated by partitioning the dihydrochloride salt between dichloromethane and 1N sodium hydroxide solution(aq), separating the organic phase and evaporating in vacuo. [M+H]+=396.0, Rt$^{(4)}$=0.71 min.

Example 92 was prepared using procedures analogous to those used in Example 91 using appropriate starting materials.

| Example | | Rt$^{(1)}$ (min.) | MS: [M + H]+ |
|---|---|---|---|
| 92 | 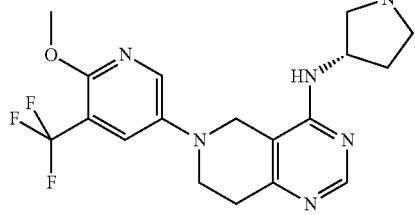 | 1.58 | 549.2 |

Name: 1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone
Purification method: Reverse phase method A
Prepared using 1-acetyl-piperidine-4-carboxylic acid
$^1$H NMR (400 MHz, DMSO-d6, 298K) δ ppm 1.21-1.77 (m, 4 H) 1.92-2.02 (m, 3 H) 2.08-2.36 (m, 2 H) 2.42-2.80 (m, 2 H) 2.88-2.98 (m, 2H) 3.00-3.18 (m, 1 H) 3.39-4.24 (m, 13 H) 5.60-5.74 (m, 1 H) 7.80-7.87 (m, 1 H) 8.15-8.22 (m, 1 H) 8.59-8.65 (m, 1 H)

| Example 93 | 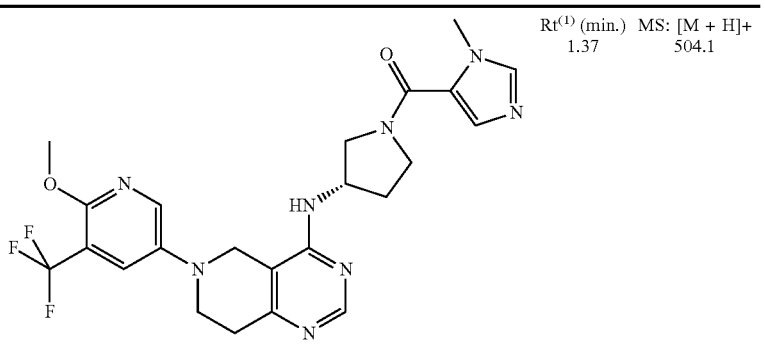 | Rt(1) (min.) 1.37 | MS: [M + H]+ 504.1 |
|---|---|---|---|

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone
Purification method: Reverse phase method A
Prepared using 3-methyl-3H-imidazole-4-carboxylic acid
$^{1}$H NMR (400 MHz, DMSO-d6, 298K) δ ppm 2.14-2.38 (m, 2 H) 2.78-3.08 (m, 2 H) 3.44-4.04 (m, 12 H) 4.08-4.27 (m, 2 H) 5.66-5.73 (m, 1 H) 7.32-7.57 (m, 1 H) 7.70-7.97 (m, 2 H) 8.13-8.28 (m, 1 H) 8.56-8.69 (m, 1 H)

| Example 94 | 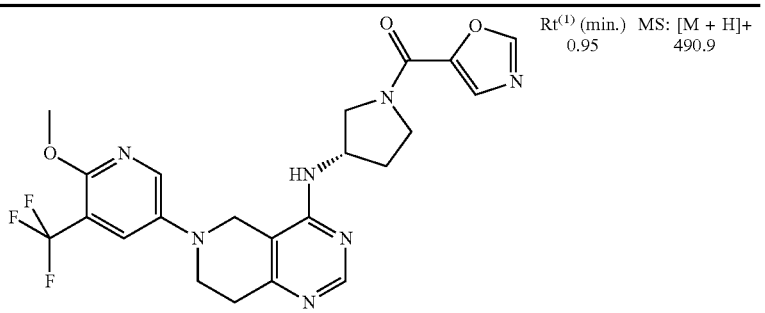 | Rt(1) (min.) 0.95 | MS: [M + H]+ 490.9 |
|---|---|---|---|

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using oxazole-5-carboxylic acid
$^{1}$H NMR (400 MHz, DMSO-d6, 298K) δ ppm 2.28-2.43 (m, 2 H) 2.86-3.00 (m, 2 H) 3.39-4.27 (m, 11 H) 5.60-5.85 (m, 1 H) 7.72-7.91 (m, 2 H) 8.15-8.30 (m, 1 H) 8.53-8.68 (m, 2 H)

Example 95 was prepared using procedures analogous to those used in Example 1, method 1a using appropriate starting materials according to scheme 8.

| Example 95 | Structure 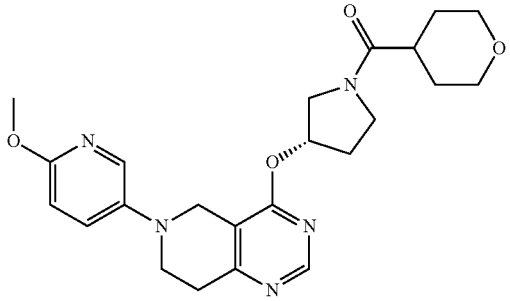 | Rt(3) (min.) 1.39( | MS: [M + H]+ 440.1 |
|---|---|---|---|

Name: {(S)-3-[6-(6-Methoxy-pyridin-3-yl)-5,6,7,8-tetrahydro-pyrido[4,3-d]pyrimidin-4-yloxy)pyrrolidin-1-yl}-(tetrahydro-pyran-4-yl)-methanone
Purification method: Flash-chromatography on silica gel with CH$_2$Cl$_2$/MeOH
Prepared using 1-benzyl-1-methyl-4-oxo-piperidinium iodide (Ref: Tortolani, R.; Org. Lett., Vol. 1, No 8, 1999) and 2-methoxypyridine
$^{1}$H NMR (400 MHz, DMSO-d6, 298K) δ ppm 1.48-1.65 (m, 4H) 2.05-2.30 (m, 2H) 2.59-2.78

(m, 1H) 2.85-2.93 (m, 2H) 3.25-4.11 (m, 15H) 5.59-5.73 (m, 1H) 6.73-6.79 (m, 1H) 7.53-7.59 (m, 1H) 7.86-7.89 (m, 1H) 8.58-8.64 (m, 1H).

The pharmaceutical composition or combination of the present invention can be in unit dosage of about 1-2000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The PI3K inhibitor, wherein said inhibitor has an inhibitory action on the PI3K isoform delta, can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

coupling between 6-Bromo-4-chloro-quinazoline and 3-(ethoxycarbonyl)phenyl-boronic acid or 3-(ethoxycarbonyl)phenyl-boronate is performed under customary Suzuki conditions using palladium catalyst such as preferably Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Saponification of the carboxylic ester was performed under customary saponification conditions, using among the possible aqueous bases lithium hydroxyide is preferred and organic solvent such a preferably dioxane. The reaction may preferably be carried out at room temperature. d) Condenation of a carboxylic acid with amines of the formula R'"NHR" preferably takes place under customary condensation conditions. The reaction can be carried on by dissolving the carboxylic acid and the amine of formula R'"NHR" in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriaz- Scheme 2'

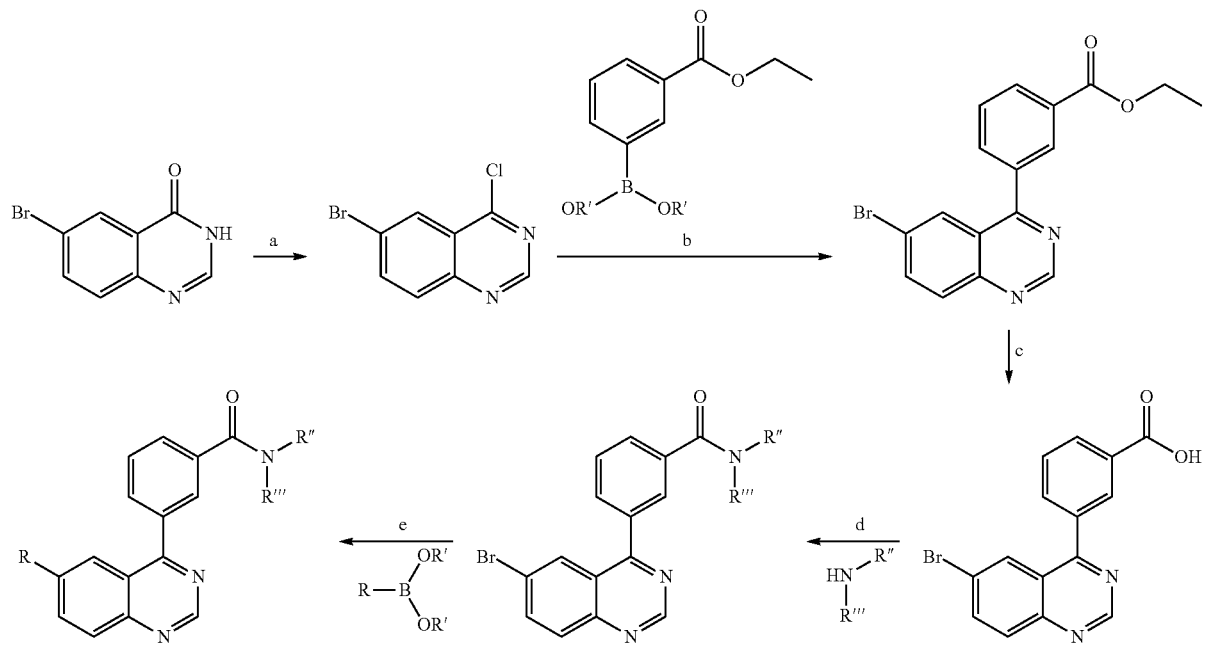

a) Chloronation of 6-Bromo-3H-quinazolin-4-one is performed under customary phosphorus oxychoride condition by heating at reflux or 130° C. in diluted (such as in CH2Cl2) or neat phosphorus oxychoride. b) Suzuki crossole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon. e) Suzuki cross-coupling between aryl bromide and boronic acid or boronic acid derivatives such as boronate of formula R—B(OR')$_2$ is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon.

The final compounds described herein were according the general procedure described in scheme 2'.

Example 1'

5-{4-[3-(4-Acetyl-piperazine-1-carbonyl)-phenyl]-quinazolin-6-yl}-2-methoxy-nicotinonitrile

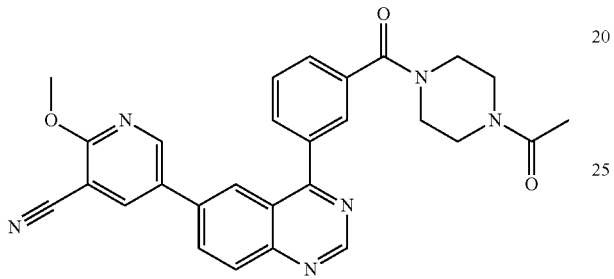

To a mixture of 1-{4-[3-(6-Bromo-quinazolin-4-yl)-benzoyl]-piperazin-1-yl}-ethanone (100 mg, 0.228 mmol), 2-Methoxy-5-(4,4,5,5-tetramethyl-[1,3,2]dioxaborolan-2-yl)-nicotinonitrile (89 mg, 0.273 mmol) and Pd(PPh$_3$)$_4$ (13.14 mg, 0.011 mmol) was added 3 mL of DME. The reaction mixture was flushed with argon and a 1M aqueous solution of Na$_2$CO$_3$ (0.455 mL, 0.455 mmol) was added and the vial was capped. The reaction mixture was heated to 140° C. for 10 min using a microwave oven then cooled down to rt, diluted with EtOAc, filtered through a Celite pad and portioned between H$_2$O/EtOAc. The organic layer was washed with brine, dried over MgSO$_4$, filtered and evaporated. Purification by preparative reverse phase Gilson HPLC and subsequent neutralization of the combined fractions over PL-HCO$_3$ MP gave the title compound (47 mg, 41% yield) as a white powder. $^1$H-NMR (400 MHz, DMSO-d$_6$, 298 K): δ ppm 1.98 (br.s., 3 H) 3.37-3.70 (m, 8 H) 4.07 (s, 3 H) 7.71 (dt, 1 H) 7.75 (t, 1 H) 7.91 (br.s., 1 H) 8.04 (dt, 1 H) 8.25 (d, 1 H) 8.35 (br.s., 1 H) 8.43 (dd, 1 H) 8.80 (br.s., 1 H) 8.92 (br.s., 1 H) 9.41 (s, 1 H). MS: 493.2 [M+1]$^+$, Rt$^{(1')}$=1.14 min.

1-{4-[3-(6-Bromo-quinazolin-4-yl)-benzoyl]-piperazin-1-yl}-ethanone

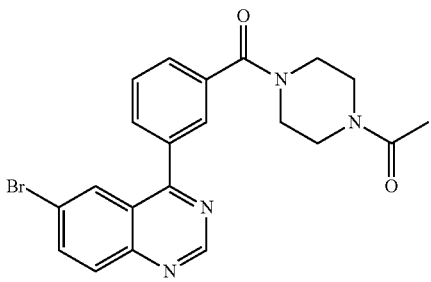

To a solution of 3-(6-Bromo-quinazolin-4-yl)-benzoic acid (2 g, 6.08 mmol) in 60 mL of CH$_2$Cl$_2$ was added HBTU (2.53 g, 6.68 mmol) and DIPEA (2.122 mL, 12.15 mmol). The reaction mixture was stirred at rt for 10 min, 1-Piperazin-1-yl-ethanone (0.935 g, 7.29 mmol) was added at rt and the reaction mixture was stirred at rt for a further 2 h. The reaction was quenched with a saturated aqueous solution of NaHCO$_3$, extracted with CH$_2$Cl$_2$. The organic layer was washed with brine, dried over MgSO$_4$, filtered and evaporated under vacuum. Purification by flash chromatography on silica gel (CH$_2$Cl$_2$/MeOH, 95/5) gave the title compound (3.03 mg, 91% purity (HPLC), quantitative yield). $^1$H-NMR (400 MHz, DMSO-d$_6$, 298 K): δ ppm 2.03 (br.s., 3 H) 3.52 (br.s., 8 H) 7.69-7.76 (m, 2 H) 7.84 (s, 1 H) 7.91 (d, 1 H) 8.09 (d, 1 H) 8.19-8.22 (m, 2 H) 9.43 (s, 1 H). MS: 439.6-441.8 [M+1]$^+$, Rt$^{(2')}$=1.02 min.

3-(6-Bromo-quinazolin-4-yl)-benzoic acid

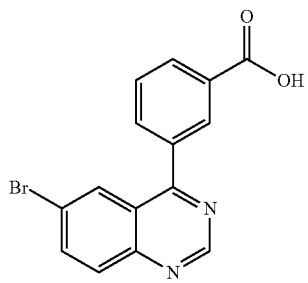

To a solution of 3-(6-Bromo-quinazolin-4-yl)-benzoic acid ethyl ester (1.41 g, 4.11 mmol) in dioxane (45 mL) was added at rt a 1M aqueous solution of LiOH.H$_2$O (8.22 ml, 8.22 mmol) and the reaction mixture was stirred 3 h at rt. The reaction was quenched with a 1M aqueous solution of HCl (5 mL), the formed precipitate was filtered and dried under vacuum to gave the title compound (880 mg, 65% yield) as a light yellow solid. The filtrate was extracted with EtOAc, the organic layer was washed with brine, dried over MgSO$_4$, filtered and evaporated to give the title compound (555 mg, 35% yield) as a light yellow solid. The two isolated solids were combined to gave the title compound as a light yellow solid (880+550 mg=1.43 g, quantitative yield). MS: 331.0 [M+1]$^+$, Rt$^{(1')}$=1.14 min.

3-(6-Bromo-quinazolin-4-yl)-benzoic acid ethyl ester

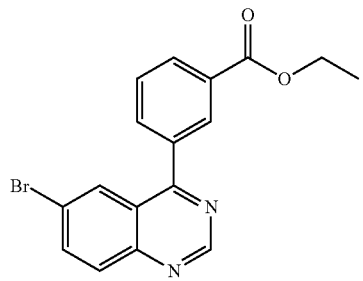 [SMILES: CCOC(=O)c1cccc(-c2ncnc3ccc(Br)cc23)c1]

To a mixture of 6-Bromo-4-chloro-quinazoline (2 g, 8.21 mmol), 3-(ethoxycarbonyl)phenyl-boronic acid (1.673 g, 8.62 mmol), Pd(PPh₃)₂Cl₂ (0.288 g, 0.411 mmol) and K₃PO₄ (2.62 g, 12.32 mmol) was added 16 mL of acetonitrile. The reaction mixture was flushed with argon, 2 mL of water was added, the tube was capped, heated to 100° C. for 15 min using a microwave oven and then cooled down to rt. The formed yellow solid was filtered, washed with ether and dried under vacuum to gave the title compound (1.54 g) as a yellow solid. The filtrate was diluted with EtOAc, the organic layer washed with brine, dried over MgSO₄, filtered and evaporated. The obtained residue was triturated in MeOH to afford the title compound as a yellow solid (580 mg). The two solids were combined to gave 2.12 g of the title compound as a yellow solid. ¹H-NMR (400 MHz, MeOD, 298 K): δ ppm 1.42 (t, 3 H) 4.43 (q, 2 H) 7.77 (t, 1 H) 7.97-8.07 (m, 2 H) 8.16 (dd, 1 H) 8.22 (d, 1 H) 8.29 (d, 1 H) 8.41 (s, 1 H) 9.34 (s, 1 H). MS: 357.0-359.0 [M+1]⁺, Rt$^{(1')}$=1.52 min.

6-Bromo-4-chloro-quinazoline

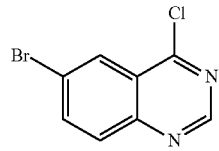

6-Bromo-3H-quinazolin-4-one (20 g, 89 mmol) was suspended in 140 mL of POCl₃ and stirred 3 h at 140° C. The reaction mixture was concentrated under vacuum, the residue was dissolved in 500 mL of dry CH₂Cl₂ and neutralized with 200 g of solid NaHCO₃. The mixture was filtered and the filtrate evaporated under vacuum to gave the title compound (21 g, 95% yield) as a beige solid. ¹H-NMR (400 MHz, CDCl3, 298 K): δ ppm 7.98 (d, 1 H) 8.09 (d, 1 H) 8.5 (s, 1 H) 9.1 (s, 1 H). MS: 243.0-244.9 [M+1]⁺, Rt$^{(1')}$=1.24 min.

Example 2'

{3-[7-(2-Methoxy-pyrimidin-5-yl)-naphthalen-1-yl]-phenyl}-(4-methyl-piperazin-1-yl)-methanone

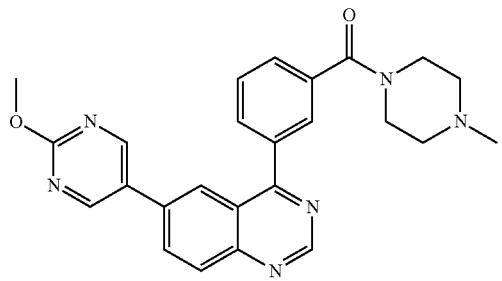 [SMILES: COc1ncc(-c2ccc3ncnc(-c4cccc(C(=O)N5CCN(C)CC5)c4)c3c2)cn1]

To a mixture of [3-(6-Bromo-quinazolin-4-yl)-phenyl]-(4-methyl-piperazin-1-yl)-methanone (50 mg, 0.122 mmol), 2-Methoxy-pyrimidine-5-boronic acid (22 mg, 0.146 mmol) and Pd(PPh₃)₄ (7 mg, 0.006 mmol) was added 2 mL of DME. The reaction mixture was flushed with argon and a 1M aqueous solution of Na₂CO₃ (0.243 mL, 0.243 mmol) was added and the vial was capped. The reaction mixture was heated to 140° C. for 10 min using a microwave oven then cooled down to rt, diluted with CH₂Cl₂, filtered through a Celite pad and portioned between H₂O/CH₂Cl₂. The organic layer was washed with brine, dried over MgSO₄, filtered and evaporated. Purification by preparative reverse phase Gilson HPLC and subsequent neutralization of the combined fractions over PL-HCO₃ MP gave the title compound (38 mg, 71% yield). ¹H-NMR (400 MHz, DMSO-d₆, 298 K): δ ppm 2.15 (s, 3 H) 2.20-2.38 (m, 4 H) 3.37-3.70 (m, 4 H) 3.99 (s, 3 H) 7.65 (d, 1 H) 7.73 (t, 1 H) 7.86 (s, 1 H) 8.02 (d, 1 H) 8.24 (d, 1 H) 8.33 (s, 1 H) 8.43 (d, 1 H) 9.05 (s, 2 H) 9.41 (s, 1 H) MS: 441.1 [M+1]⁺, Rt$^{(2')}$=0.75 min.

[3-(6-Bromo-quinazolin-4-yl)-phenyl]-(4-methyl-piperazin-1-yl)-methanone

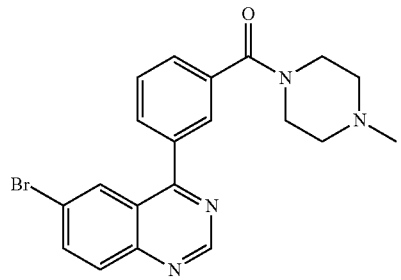 [SMILES: CN1CCN(C(=O)c2cccc(-c3ncnc4ccc(Br)cc34)c2)CC1]

To a mixture of 3-(6-Bromo-quinazolin-4-yl)-benzoic acid (2 g, 6.16 mmol) and HBTU (2.57 g, 6.78 mmol) was added DMF (15 mL) and DIPEA (2.26 mL, 12.95 mmol). The reaction mixture was stirred at rt for 10 min, 1-Methyl-piperazine (1.23 g, 12.33 mmol) was added at rt, followed by DIPEA (2.26 mL, 12.95 mmol) and the reaction mixture was stirred at rt for a further 5 min. The reaction was quenched with a saturated aqueous solution of NaHCO₃, extracted with AcOEt. The organic layer was washed with NaHCO₃, brine, dried over Na₂SO₄, filtered and evaporated under vacuum. Purification by flash chromatography on silica gel (CH₂Cl₂/MeOH, 99/1 to 90/10) gave the title compound (2.26 g, 90% purity (HPLC), 80% yield). ¹H-NMR (400 MHz, MeOD-d₄, 298 K): δ ppm 2.21 (s, 3 H) 2.25-2.44 (m, 4 H) 3.37-3.70 (m, 4 H) 7.62-7.81 (m, 3 H) 7.86-7.96 (m, 1 H) 8.08 (d, 1 H) 8.17-8.24 (m, 2 H) 9.41 (s, 1 H). MS: 411.4 [M+1]⁺, Rt$^{(3')}$=1.38 min.

Examples 3' to 29', were prepared or can be prepared using procedures analogous to those used in example 1', using appropriate starting materials.

Examples 20', 21' and 22' were not neutralized after purification and were obtained as TFA salt.

| Example | Structure/Name | Rt (min.) | MS(ES): [M + H]+ | 1H-NMR |
|---|---|---|---|---|
| 3' | 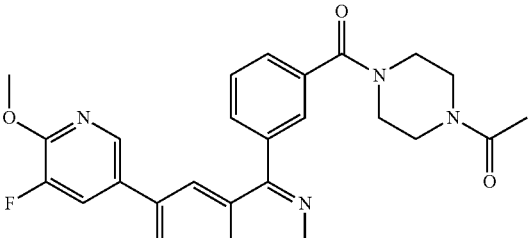<br>1-(4-{3-[6-(5-Fluoro-6-methoxy-pyridin-3-yl)-quinazolin-4-yl]-benzoyl}-piperazin-1-yl)-ethanone | 1.14 (1') | 486.2 | 1H-NMR (400 MHz, DMSO-d6, 298K): δ ppm 1.91-2.06 (br.s., 3 H) 3.38-3.73 (m, 8 H) 4.01 (s, 3 H) 7.69 (dt, 1 H) 7.75 (t, 1 H) 7.91 (br.s., 1 H) 8.02 (dt, 1 H) 8.22 (d, 2 H) 8.29 (d, 1 H) 8.42 (dd, 1 H) 8.45 (d, 1 H) 9.40 (s, 1 H) |
| 4' | 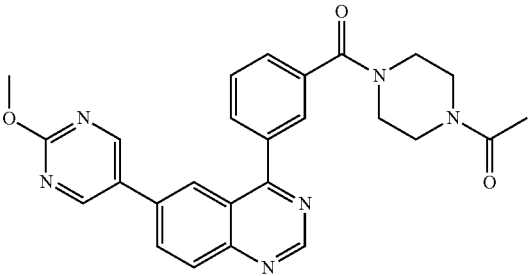 [SMILES: COc1ncc(-c2ccc3ncnc(-c4cccc(C(=O)N5CCN(C(C)=O)CC5)c4)c3c2)cn1]<br>1-(4-{3-[6-(2-Methoxy-pyrimidin-5-yl)-quinazolin-4-yl]-benzoyl}-piperazin-1-yl)-ethanone | 1.34 (3') | 469.5 | 1H-NMR (400 MHz, DMSO-d6, 298K): δ ppm 2.15 (s, 3H) 3.36-3.89 (m, 8 H) 4.09 (s, 3 H) 7.61-7.75 (m, 2 H) 7.90 (dd, 1 H) 7.92 (s, 1 H) 8.13 (dd, 1 H) 8.19 (d, 1 H) 8.29 (d, 1 H) 8.79 (s, 2 H) 9.44 (s, 1 H) |
| 5' | 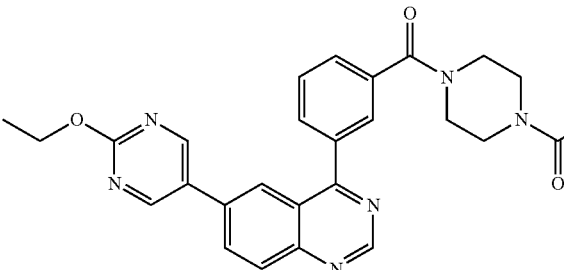<br>1-(4-{3-[6-(2-Ethoxy-pyrimidin-5-yl)-quinazolin-4-yl]-benzoyl}-piperazin-1-yl)-ethanone | 0.96 (2') | 483.6 | 1H-NMR (400 MHz, DMSO-d6, 298K): δ ppm 1.37 (t, 3 H) 2.00 (br.s., 3 H) 3.35-3.76 (m, 8 H) 4.42 (q, 2 H) 7.69 (dt, 1 H) 7.74 (t, 1 H) 7.91 (br.s., 1 H) 8.02 (dt, 1 H) 8.23 (d, 1 H) 8.32 (d, 1 H) 8.43 (dd, 1 H) 9.04 (s, 2 H) 9.40 (s, 1 H) |
| 6' | 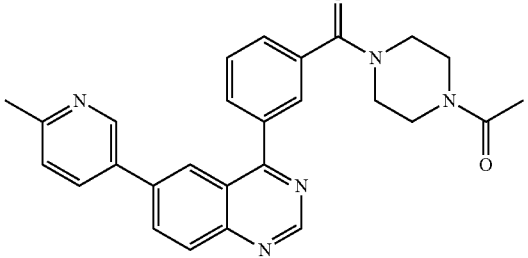<br>1-(4-{3-[6-(6-Methyl-pyridin-3-yl)-quinazolin-4-yl]-benzoyl}-piperazin-1-yl)-ethanone | 0.61 (1') | 481.4 | 1H-NMR (400 MHz, DMSO-d6, 298K): δ ppm 2.00 (br.s., 3 H) 2.66 (br.s., 3 H) 3.29-3.73 (m, 8 H) 7.67-7.79 (m, 3 H) 7.92 (br.s., 1 H) 8.03 (d, 1 H) 8.28 (d, 1 H) 8.38 (d, 1 H) 8.47 (dd, 1 H) 8.51 (br.s., 1 H) 9.08 (br.s., 1 H) 9.44 (s, 1 H) |

| Example | Structure/Name | Rt (min.) | MS(ES): [M + H]⁺ | 1H-NMR |
|---|---|---|---|---|
| 7' | 1-[4-(3-{6-[4-Methoxy-3-(pyrrolidine-1-sulfonyl)-phenyl]-quinazolin-4-yl}-benzoyl)-piperazin-1-yl]-ethanone | 1.72 (3') | 600.3 | ¹H-NMR (400 MHz, DMSO-d₆, 298K): δ ppm 1.83-1.91 (m, 4 H) 2.13 (br.s, 3 H) 3.36-3.45 (m, 4 H) 3.47-3.93 (m, 8 H) 4.01 (s, 3 H) 7.15 (d, 1 H) 7.66 (dt, 1 H) 7.70 (t, 1 H) 7.77 (dd, 1 H) 7.90 (br.s., 1 H) 7.93 (dt, 1 H) 8.11-8.30 (m, 4 H) 9.40 (s, 1 H) |
| 8' | 1-(4-{3-[6-(2-Amino-pyrimidin-5-yl)-quinazolin-4-yl]-benzoyl}-piperazin-1-yl)-ethanone | 0.71 (2') | 454.5 | ¹H-NMR (400 MHz, DMSO-d₆, 298K): δ ppm 2.00 (br.s., 3 H) 3.39-3.73 (m, 8 H) 6.94 (br.s., 2 H) 7.68 (d, 1 H) 7.74 (t, 1 H) 7.90 (br.s., 1 H) 8.01 (d, 1 H) 8.21 (d, 2 H) 8.37 (dd, 1 H) 8.70 (s, 2 H) 9.36 (s, 1 H) |
| 9' | 1-(4-{3-[6-(4-Methoxy-3-trifluoromethyl-phenyl)-quinazolin-4-yl]-benzoyl}-piperazin-1-yl)-ethanone | 2.05 (4') | 544 | ¹H-NMR (400 MHz, DMSO-d₆, 298K): δ ppm 1.80-2.10 (m, 3 H); 3.30-3.80 (m, 8H), 3.96 (s, 3H), 7.42 (d, 1H), 7.70 (dd, 1 H), 7.75 (dd, 1 H), 7.92 (s, 1H), 7.97 (d, 1H), 8.02 (d, 1H), 8.06 (d, 1H), 8.21 (d, 1H), 8.25 (d, 1H), 8.44 (dd, 1 H), 9.39 (s, 1H) |
| 10' | 5-{4-[3-(4-Acetyl-piperazine-1-carbonyl)-phenyl]-quinazolin-6-yl}-2-amino-3-trifluoromethyl-benzonitrile | 1.16 (2') | 545.7 | ¹H-NMR (400 MHz, DMSO-d₆, 298K): δ ppm 1.97 (br.s., 3 H) 3.36-3.76 (m, 8 H) 6.55 (br.s., 2 H) 7.6-7.78 (m, 2 H) 7.91 (br.s., 1 H) 7.99-8.07 (m, 2 H) 8.16 (d, 1 H) 8.24 (d, 1 H) 8.29 (br.s., 1 H) 8.41 (dd, 1 H) 9.37 (s, 1 H) |

| Example | Structure/Name | Rt (min.) | MS(ES): [M + H]+ | 1H-NMR |
|---|---|---|---|---|
| 11' | {3-[6-(2-Dimethylamino-pyrimidin-5-yl)-quinazolin-4-yl]-phenyl}-(4-methyl-piperazin-1-yl)-methanone | 0.81 (1) | 454.4 | 1H-NMR (400 MHz, DMSO-d6, 298K): δ ppm 2.16 (s, 3 H) 2.20-2.45 (m, 4 H) 3.18 (s, 6 H) 3.38-3.70 (m, 4 H) 7.65 (d, 1 H) 7.73 (t, 1 H) 7.84 (s, 1 H) 8.00 (d, 1 H) 8.16-8.20 (m, 2 H) 8.37 (d, 1 H) 8.78 (s, 2 H) 9.35 (s, 1 H) |
| 12' | 1-(4-{3-[6-(6-Methoxy-pyridin-3-yl)-quinazolin-4-yl]-benzoyl}-piperazin-1-yl)-ethanone | 2.82 (5) | 468.2 | 1H-NMR (400 MHz, MeOD-d4, 298K): δ ppm 2.13 (m, 3 H) 3.49-3.90 (m, 8 H) 3.97 (s, 3 H) 6.92 (d, 1 H) 7.75 (dt., 1 H) 7.78 (m, 1 H) 7.93 (s, 1 H) 7.98-8.04 (m, 2 H) 8.19 (d, 1 H) 8.23 (d, 1 H) 8.32 (dd, 1 H) 8.46 (d, 1 H) 9.31 (s, 1 H) |
| 13' | {3-[6-(6-Difluoromethoxy-pyridin-3-yl)-quinazolin-4-yl]-phenyl}-(4-methyl-piperazin-1-yl)-methanone | 1.00 (2) | 476.1 | 1H-NMR (400 MHz, DMSO-d6, 298K): δ ppm 2.15 (s, 3 H) 2.19-2.39 (m, 4 H) 3.39-3.68 (m, 4 H) 7.25 (d, 1 H) 7.65 (dt, 1 H) 7.73 (t, 1 H) 7.78 (t, 1 H) 7.84 (br.s., 1 H) 8.01 (dt, 1 H) 8.24 (d, 1 H) 8.30 (d, 1 H) 8.34 (dd, 1 H) 8.42 (dd, 1 H) 8.69 (d, 1 H) 9.41 (s, 1 H) |
| 14' | {3-[6-(6-Methoxy-5-trifluoromethyl-pyridin-3-yl)-quinazolin-4-yl]-phenyl}-(4-methyl-piperazin-1-yl)-methanone | 1.03 (1) | 508.3 | 1H-NMR (400 MHz, DMSO-d6, 298K): δ ppm 2.13 (s, 3 H) 2.15-2.41 (m, 4 H) 3.38-3.71 (m, 4 H) 4.05 (s, 3 H) 7.65 (dt, 1 H) 7.74 (t, 1 H) 7.85 (t, 1 H) 8.03 (dt, 1 H) 8.23 (d, 1 H) 8.33 (d, 1 H) 8.45-8.47 (dd, 2 H) 8.86 (d, 1 H) 9.41 (s, 1 H) |

| Example | Structure/Name | Rt (min.) | MS(ES): [M + H]+ | 1H-NMR |
|---|---|---|---|---|
| 15' | (4-Methyl-piperazin-1-yl)-{3-[6-(6-pyrrolidin-1-yl-pyridin-3-yl)-quinazolin-4-yl]-phenyl}-methanone | 0.52 (1) | 479.3 | 1H-NMR (400 MHz, DMSO-d6, 298K): δ ppm 1.97 (m, 4 H) 2.20-2.65 (m, 7 H) 3.38-3.85 (m, 8 H) 6.56 (d, 1 H) 7.65 (d, 1 H) 7.74 (t, 1 H) 7.85 (s, 1 H) 7.89 (dd, 1 H) 7.99 (dt, 1 H) 8.14-8.16 (m, 2 H) 8.35 (dd, 1 H) 8.50 (d, 1 H) 9.33 (s, 1 H) |
| 16' | {3-[6-(6-Ethoxy-pyridin-3-yl)-quinazolin-4-yl]-phenyl}-(4-methyl-piperazin-1-yl)-methanone | 0.92 (1) | 454.3 | 1H-NMR (400 MHz, DMSO-d6, 298K): δ ppm 1.35 (t, 4 H) 2.21 (br.s., 3 H) 2.25-2.49 (m, 4 H) 3.40-3.75 (m, 4 H) 4.36 (q, 3 H) 6.93 (d, 1 H) 7.65 (dt, 1 H) 7.74 (t, 1 H) 7.84 (s, 1 H) 8.00 (dt, 1 H) 8.10 (dd, 1 H) 8.20-8.24 (m, 2 H) 8.39 (dd, 1 H) 8.57 (d, 1 H) 9.38 (s, 1 H) |
| 17' | {3-[6-(6-Dimethylamino-pyridin-3-yl)-quinazolin-4-yl]-phenyl}-(4-methyl-piperazin-1-yl)-methanone | 0.55 (2) | 453.2 | 1H-NMR (400 MHz, DMSO-d6, 298K): δ ppm 2.16-2.44 (m, 7 H) 3.09 (s, 6 H) 3.40-3.70 (m, 4 H) 6.76 (d, 1 H) 7.66 (d, 1 H) 7.74 (t, 1 H) 7.84 (br.s., 1 H) 7.91 (dd, 1 H) 7.99 (d, 1 H) 8.15-8.17 (m, 2 H) 8.36 (dd, 1 H) 8.52 (d, 1 H) 9.34 (s, 1 H) |
| 18' | (4-Methyl-piperazin-1-yl)-{3-[6-(6-piperazin-1-yl-pyridin-3-yl)-quinazolin-4-yl]-phenyl}-methanone | 0.61 (1) | 494.3 | 1H-NMR (400 MHz, DMSO-d6, 298K): δ ppm 2.15 (s, 3 H) 2.18-2.42 (m, 4 H) 2.83 (t, 4 H) 3.40-3.72 (m, 8 H) 6.93 (d, 1 H) 7.65 (d, 1 H) 7.73 (t, 1 H) 7.82 (s, 1 H) 7.95 (dd, 1 H) 7.98 (dt, 1 H) 8.15-8.17 (m, 2 H) 8.37 (dd, 1 H) 8.53 (d, 1 H) 9.34 (s, 1 H) |

| Example | Structure/Name | Rt (min.) | MS(ES): [M + H]+ | 1H-NMR |
|---|---|---|---|---|
| 19' | 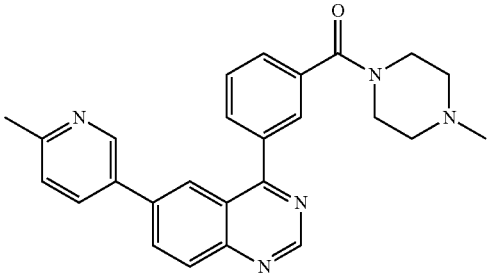<br>(4-Methyl-piperazin-1-yl)-{3-[6-(6-methyl-pyridin-3-yl)-quinazolin-4-yl]-phenyl}-methanone | 0.7 (3') | 242.2 | 1H-NMR (400 MHz, DMSO-d6, 298K): δ ppm 2.17 (br.s., 3 H) 2.20-2.38 (m, 4 H) 2.53 (s, 3 H) 3.35-3.70 (m, 4 H) 7.39 (d, 1 H) 7.59 (d, 1 H) 7.73 (t, 1 H) 7.84 (s, 1 H) 8.00 (d, 1 H) 8.07 (d, 1 H) 8.23 (d, 1 H) 8.27 (s, 1 H) 8.40 (d, 1 H) 8.84 (s, 1 H) 9.40 (s, 1 H) |
| 20' | 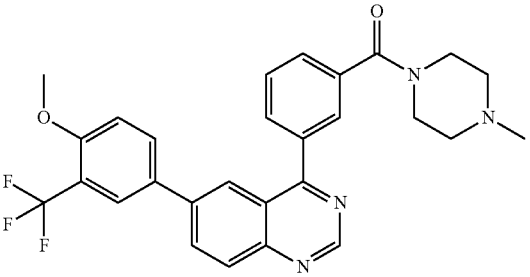<br>{3-[6-(4-Methoxy-3-trifluoromethyl-phenyl)-quinazolin-4-yl]-phenyl}-(4-methyl-piperazin-1-yl)-methanone | 1.85 (3') | 507.1 | 1H-NMR (400 MHz, DMSO-d6, 298K): δ ppm 2.08-2.43 (m, 7 H) 3.42 (br.s., 2 H) 3.62 (br.s., 2 H) 3.95 (s, 3 H) 7.41 (d, 1 H) 7.60-7.67 (m, 1 H) 7.73 (t, 1 H) 7.83 (s, 1 H) 7.94 (d, 1 H) 7.97-8.07 (m, 2 H) 8.16-8.25 (m, 2 H) 8.41 (dd, 1 H) 9.38 (s, 1 H) |
| 21' | 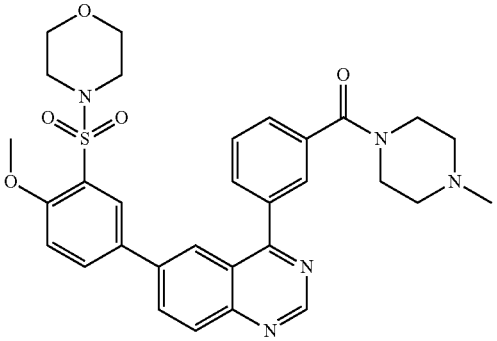 [SMILES: COc1ccc(-c2ccc3ncnc(-c4cccc(C(=O)N5CCN(C)CC5)c4)c3c2)cc1S(=O)(=O)N1CCOCC1]<br>(3-{6-[4-Methoxy-3-(morpholine-4-sulfonyl)-phenyl]-quinazolin-4-yl}-phenyl)-(4-methyl-piperazin-1-yl)-methanone | 1.49 (1') | 588.4 | 1H-NMR (400 MHz, DMSO-d6, 298K): δ ppm 2.73 (d., 3 H) 3.02-3.18 (br.s., 6 H) 3.45-3.65 (m, 10 H) 3.99 (s, 3 H) 7.42 (d, 1 H) 7.75 (m, 2 H) 7.95 (s, 1 H) 8.05 (m, 3 H) 8.23 (m, 2 H) 8.40 (m, 1 H) 9.40 (s, 1 H) 11.00 (br.s., 1H) |
| 22' | 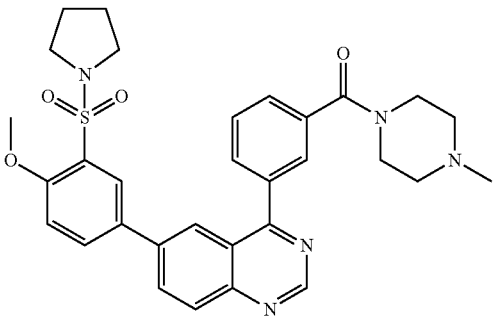 [SMILES: COc1ccc(-c2ccc3ncnc(-c4cccc(C(=O)N5CCN(C)CC5)c4)c3c2)cc1S(=O)(=O)N1CCCC1]<br>(3-{6-[4-Methoxy-3-(pyrrolidine-1-sulfonyl)-phenyl]-quinazolin-4-yl}-phenyl)-(4-methyl-piperazin-1-yl)-methanone | 1.54 (1') | 472.3 | 1H-NMR (400 MHz, DMSO-d6, 298K): δ ppm 1.75 (m, 4 H) 2.73 (d, 3 H) 3.02-3.18 (br.s., 2 H) 3.25 (m, 4 H) 3.55-3.70 (br.s., 6 H) 3.99 (s, 3 H) 7.42 (d, 1 H) 7.75 (m, 2 H) 7.95 (s, 1 H) 8.05 (m, 3 H) 8.23 (m, 2 H) 8.40 (m, 1 H) 9.40 (s, 1 H) 10.95 (br.s., 1H) |

| Example | Structure/Name | Rt (min.) | MS(ES): [M + H]+ | 1H-NMR |
|---|---|---|---|---|
| 23' | N,N-Diethyl-2-methoxy-5-{4-[3-(4-methyl-piperazine-1-carbonyl)-phenyl]-quinazolin-6-yl}-benzenesulfonamide | 1.59 (1') | 574.3 | 1H-NMR (400 MHz, DMSO-d6, 298K): δ ppm 1.05 (t, 6 H) 2.75 (d, 3 H) 3.02-3.18 (br.s., 2 H) 3.30 (q, 4 H) 3.45-3.60 (br.s., 6 H) 3.95 (s, 3 H) 7.42 (d, 1 H) 7.75 (m, 2 H) 7.95 (s, 1 H) 8.05 (m, 3 H) 8.23 (m, 2 H) 8.40 (m., 1 H) 9.40 (s, 1 H) 11.35 (br.s., 1H) |
| 24' | {3-[6-(5-Methanesulfonyl-pyridin-3-yl)-quinazolin-4-yl]-phenyl}-(4-methyl-piperazin-1-yl)-methanone | 1.07 (3') | 488.2 | 1H-NMR (400 MHz, DMSO-d6, 298K): δ ppm 2.17-2.47 (m, 7 H) 3.42 (s, 3 H) 3.45-3.81 (m, 4 H) 7.67 (d, 1 H) 7.74 (t, 1 H) 7.89 (s, 1 H) 8.05 (d, 1 H) 8.30 (d, 1 H) 8.44 (s, 1 H) 8.54 (d, 1 H) 8.67 (s, 1 H) 9.12 (s, 1 H) 9.33 (s, 1 H) 9.45 (s, 1 H) |
| 25' | {3-[6-(6-Amino-pyridin-3-yl)-quinazolin-4-yl]-phenyl}-(4-methyl-piperazin-1-yl)-methanone | 0.43 (1') | 425.3 | 1H-NMR (400 MHz, DMSO-d6, 298K): δ ppm 2.11 (s, 3 H) 2.13-2.34 (m, 4 H) 3.33-3.65 (m, 4 H) 6.22 (s, 2 H) 6.50 (d, 1 H) 7.59 (d, 1 H) 7.65-7.78 (m, 3 H) 7.92 (d, 1 H) 8.05-8.11 (m, 2 H) 8-25-8.30 (m, 2 H) 9.28 (s, 1 H) |
| 26' | {3-[6-(2-Methoxy-pyrimidin-5-yl)-quinazolin-4-yl]-phenyl}-(3,3,4-trimethyl-piperazin-1-yl)-methanone | 0.78 (2') | 469.2 | 1H-NMR (400 MHz, DMSO-d6, 298K): δ ppm 0.82 (br.s., 3 H) 0.98 (br.s., 3 H) 2.10 (s, 3 H) 2.35 (br.s., 1 H) 2.49 (br.s., 1 H) 3.17 (br.s., 1 H) 3.35-3.65 (m, 3 H) 3.99 (s, 3 H) 7.65 (br.s., 1 H) 7.73 (t, 1 H) 7.85 (br.s., 1 H) 8.01 d, 1 H) 8.24 (d, 1 H) 8.32 (br.s., 1 H) 8.43 (dd, 1 H) 9.04 (s, 2 H) 9.41 (s, 1 H) |

-continued

| Example | Structure/Name | Rt (min.) | MS(ES): [M + H]+ | 1H-NMR |
|---|---|---|---|---|
| 27' | 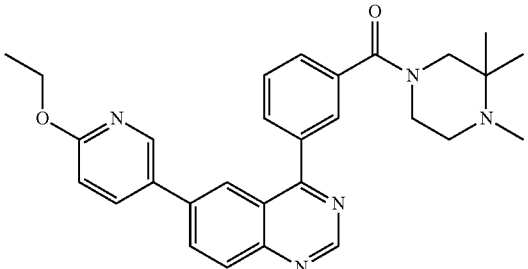 {3-[6-(6-Ethoxy-pyrimidin-3-yl)-quinazolin-4-yl]-phenyl}-(3,3,4-trimethyl-piperazin-1-yl)-methanone | 0.98 (2') | 482.2 | 1H-NMR (400 MHz, DMSO-d6, 298K): δ ppm 0.82 (br.s., 3 H) 0.98 (br.s., 3 H) 1.34 (t, 3 H) 2.09 (s, 3 H) 2.34 (br.s., 2 H) 3.18 (br.s., 1 H) 3.41-3.65 (m, 3 H) 4.36 (q, 2 H) 6.92 (d, 1 H) 7.64 (br.s., 1 H) 7.73 (t, 1 H) 7.83 (br.s., 1 H) 7.99 (d, 1 H) 8.09 (dd, 1 H) 8.19-8.22 (m, 2 H) 8.38 (dd, 1 H) 8.56 (d, 1 H) 9.38 (s, 1 H) |
| 28' | 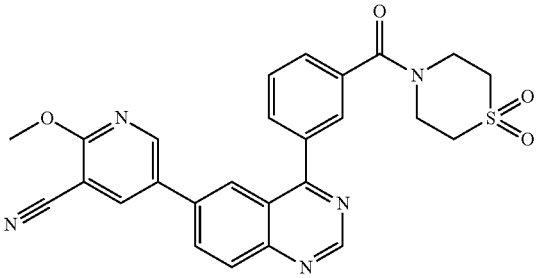 [SMILES: COc1ncc(-c2ccc3ncnc(-c4cccc(C(=O)N5CCS(=O)(=O)CC5)c4)c3c2)cc1C#N] 5-{4-[3-(1,1-Dioxo-1lambda*6*-thiomorpholine-4-carbonyl)-phenyl]-quinazolin-6-yl}-2-methoxy-nicotinonitrile | 1.12 (2') | 500.5 | 1H-NMR (400 MHz, DMSO-d6, 298K): δ ppm 3.12-3.29 (br.s., 4 H) 3.73-4.05 (br.s., 4 H) 4.07 (s, 3 H) 7.75 (d, 2 H) 8.02-8.06 (m, 2 H) 8.24 (d, 1 H) 8.35 (d, 1 H) 8.44 (dd, 1 H) 8.78 (d, 1 H) 8.91 (d, 1 H) 9.41 (s, 1 H) |
| 29' | 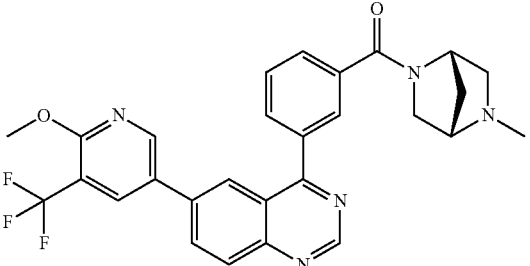 2-Methoxy-5-{4-[3-((1S,4S)-5-methyl-2,5-diaza-bicyclo[2.2.1]heptane-2-carbonyl)-phenyl]-quinazolin-6-yl}-nicotinonitrile | 1.06 (1') | 520.3 | 1H-NMR (400 MHz, DMSO-d6, 298K): δ ppm 1.67 (m, 1 H) 1.78 (dd, 1 H) 2.22-2.26 (d, 3 H) 2.45-2.82 (m, 2 H) 3.24-3.48 (m, 3 H) 4.05 (s, 3 H) 4.30-4.61 (d, 1 H) 7.71-7.81 (m, 2 H) 7.90-8.00 (d, 1 H) 8.04 (m, 1 H) 8.23 (d, 1 H) 8.32 (dd, 1 H) 8.445 (d, 1 H) 8.47 (m, 1 H) 8.86 (dd, 1 H) 9.41 (s, 1 H) |
| 30' | 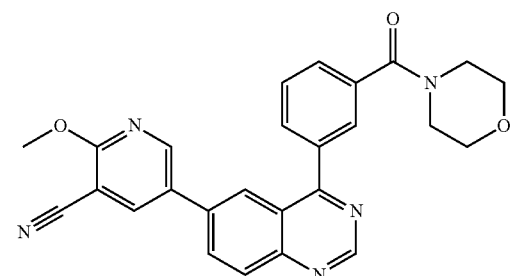 2-Methoxy-5-{4-[3-(morpholine-4-carbonyl)-phenyl]-quinazolin-6-yl}-nicotinonitrile | 1.14 (2') | 452.5 | 1H-NMR (400 MHz, DMSO-d6, 298K): δ ppm 3.40-3.73 (m, 8 H) 4.07 (s, 3 H) 7.68 (dt, 1 H) 7.74 (t, 1 H) 7.89 (br.s., 1 H) 8.02 (dt, 1 H) 8.23 (d, 1 H) 8.34 (d, 1 H) 8.44 (dd, 1 H) 8.79 (d, 1 H) 8.91 (d, 1 H) 9.41 (s, 1 H) |

-continued

| Example | Structure/Name | Rt (min.) | MS(ES): [M + H]+ | 1H-NMR |
|---|---|---|---|---|
| 31' | 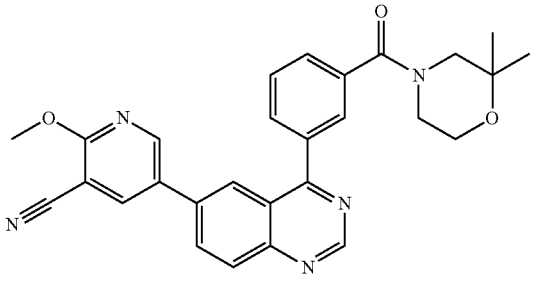<br>5-{4-[3-(2,2-Dimethyl-morpholine-4-carbonyl)-phenyl]-quinazolin-6-yl}-2-methoxy-nicotinonitrile | 1.21 (2') | 480.6 | 1H-NMR (400 MHz, DMSO-d6, 298K): δ ppm 1.06 (br.s., 3 H) 1.18 (br.s., 3 H) 3.37-3.73 (m, 6 H) 3.91 (s, 3 H) 6.95 (d, 1 H) 7.67 (br.s., 1 H) 7.74 (t, 1 H) 7.87 (br.s., 1 H) 8.00 (d, 1 H) 8.12 (dd, 1 H) 8.21 (d, 1 H) 8.24 (d, 1 H) 8.39 (dd, 1 H) 8.59 (d, 1 H) 9.39 (s, 1 H) |
| 32' | 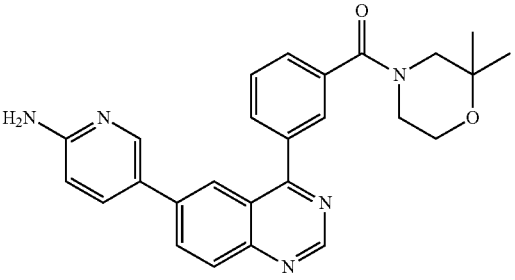<br>{3-[6-(6-Amino-pyridin-3-yl)-quinazolin-4-yl]-phenyl}-(2,2-dimethyl-morpholin-4-yl)-methanone | 0.82 (1') | 440.4 | 1H-NMR (400 MHz, DMSO-d6, 298K): δ ppm 1.05-1.23 (m, 6 H) 3.40-3.72 (m, 6 H) 6.24 (s, 2 H) 6.55 (d, J = 8.56 Hz, 1 H) 7.67 (br.s., 1 H) 7.71-7.75 (m, 1 H) 7.75-7.81 (m, 1 H) 7.86 (br.s., 1 H) 7.98 (d, J = 7.34 Hz, 1 H) 8.10-8.16 (m, 2 H) 8.30-8.37 (m, 2 H) 9.33 (s, 1 H) |
| 33' | 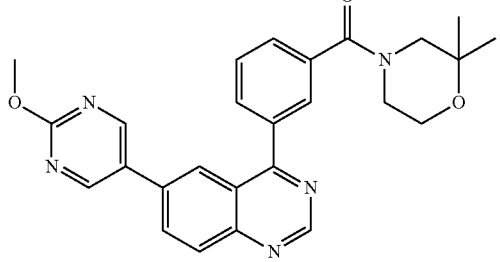<br>(2,2-Dimethyl-morpholin-4-yl)-{3-[6-(2-methoxy-pyrimidin-5-yl)-quinazolin-4-yl]-phenyl}-methanone | 1.09 (1') | 456.3 | 1H-NMR (400 MHz, DMSO-d6, 298K): δ ppm 1.00-1.23 (m, 6 H) 3.35-3.72 (m, 6 H) 3.99 (s, 3 H) 7.68 (br. s., 1 H) 7.74 (t, J = 7.58 Hz, 1 H) 7.89 (br.s., 1 H) 8.02 (d, J = 7.34 Hz, 1 H) 8.24 (d, J = 8.80 Hz, 1 H) 8.33 (d, J = 1.71 Hz, 1 H) 8.44 (dd, J = 8.68, 1.83 Hz, 1 H) 9.05 (s, 2 H) 9.41 (s, 1 H) |

(1') LC method 1',
(2') LC method 2',
(3') LC method 3',
(4') LC method 4',
(5') LC method 5'

Example 34'

2-Methoxy-5-{4-[3-((R)-3-methyl-piperazine-1-carbonyl)-phenyl]-quinazolin-6-yl}-nicotinonitrile

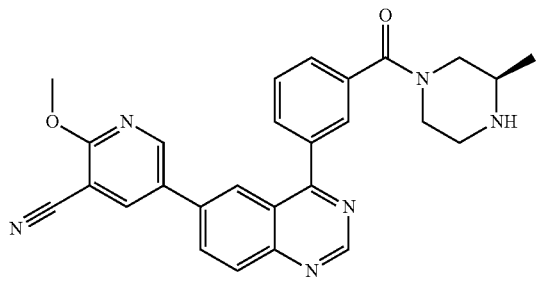 [SMILES: COc1ncc(-c2ccc3ncnc(-c4cccc(C(=O)N5CCN[C@H](C)C5)c4)c3c2)cc1C#N]

To a mixture (R)-4-[3-(6-bromo-quinazolin-4-yl)-benzoyl]-2-methyl-piperazine-1-carboxylic acid tert-butyl ester (100 mg, 0.196 mmol), 2-methoxy-5-(4,4,5,5-tetramethyl-[1,3,2]dioxaborolan-2-yl)-nicotinonitrile (76 mg, 0.235 mmol, 80% purity) and Pd(PPh$_3$)$_4$ (11.30 mg, 0.009 mmol) was added 3 mL of DME. The reaction mixture was flushed with argon and a 1M aqueous solution of Na$_2$CO$_3$ (0.391 mL, 0.391 mmol) was added and the vial capped. The reaction mixture was heated to 140° C. for 10 min using a microwave oven then cooled down to room temperature, diluted with EtOAc, filtered through a Celite pad and portioned between H$_2$O/EtOAc. The organic layer was washed with brine, dried over MgSO$_4$, filtered and evaporated. The residue was dissolved in 2 ml of CH$_2$Cl$_2$ and TFA (0.301 mL, 3.91 mmol) was added. The reaction mixture was stirred at room temperature for 2 h. After this period of time, the mixture was concentrated and purified by preparative reverse phase Gilson HPLC and subsequent neutralization of the combined fractions over PL-HCO$_3$ MP gave the title compound (36 mg, 39% yield) as a white powder. $^1$H-NMR (400 MHz, DMSO-d$_6$, 298 K): δ ppm 0.74-1.05 (br.s., 3 H), 2.35-3.10 (m, 5 H) 3.47-3.65 (m, 1 H) 4.06 (s, 3 H) 4.33 (br.s., 1 H) 7.64 (dt, 1 H) 7.73 (t, 1 H) 7.84 (t, 1 H) 8.00 (dt, 1 H) 8.23 (d, 1 H) 8.33 (d, 1 H) 8.43 (dd, 1 H) 8.78 (br.s., 1 H) 8.90 (d, 1 H) 9.40 (s, 1 H). MS: 464.6 [M+1]$^+$, Rt$^{(1')}$=0.98 min.

(R)-4-[3-(6-bromo-quinazolin-4-yl)-benzoyl]-2-methyl-piperazine-1-carboxylic acid tert-butyl ester

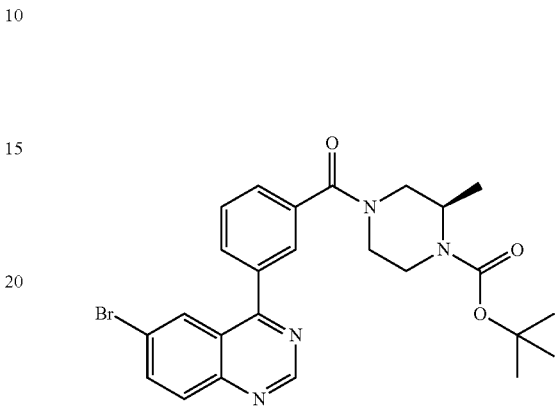

To a solution of 3-(6-bromo-quinazolin-4-yl)-benzoic acid (0.5 g, 1.519 mmol) in 15 mL of CH$_2$Cl$_2$ was added HBTU (0.634 g, 1.671 mmol) and DIPEA (0.796 mL, 4.56 mmol). The reaction mixture was stirred at room temperature for 30 minutes, (R)-2-methyl-piperazine-1-carboxylic acid tert-butyl ester (0.365 g, 1.823 mmol) was added and the reaction mixture was stirred at ambient temperature for a further 2 h. The reaction was quenched with H$_2$O and extracted with CH$_2$Cl$_2$. The organic layer was washed with brine, dried over MgSO$_4$, filtered and evaporated under vacuum. Purification by flash chromatography on silica gel (CH$_2$Cl$_2$/MeOH, 95/5) gave the title compound (1 g, 89% purity, quantitative yield). MS: 511.2-513.1 [M+1]$^+$, Rt$^{(1')}$=1.51 min.

Examples 35' was prepared using procedures analogous to those used in example 34', using appropriate starting materials.

| Example | Structure/Name | Rt (min.) | MS(ES): [M + H]$^+$ | 1H-NMR |
|---|---|---|---|---|
| 35' | 2-Methoxy-5-{4-[3-(piperazine-1-caronyl)-phenyl]-quinazolin-6-yl}-nicotinonitrile | 0.98 $^{(2')}$ | 451.6 | $^1$H-NMR (400 MHz, DMSO-d$_6$, 298K): δ ppm 2.57-2.78 (m, 4 H) 3.35-3.62 (m, 4 H) 4.07 (s, 3 H) 7.65 (d, 1 H) 7.73 (t, 1 H) 7.85 (br.s., 1 H) 8.00 (d, 1 H) 8.23 (d, 1 H) 8.34 (d, 1 H) 8.43 (dd, 1 H) 8.79 (d, 1 H) 8.91 (d, 1 H) 9.41 (s, 1 H) |

$^{(2')}$ LC methode 2'

Example 36'

1-(4-{3-[6-(6-Methoxy-pyridin-3-yl)-quinazolin-4-yl]-benzoyl}-2,2-dimethyl-piperazin-1-yl)-ethanone

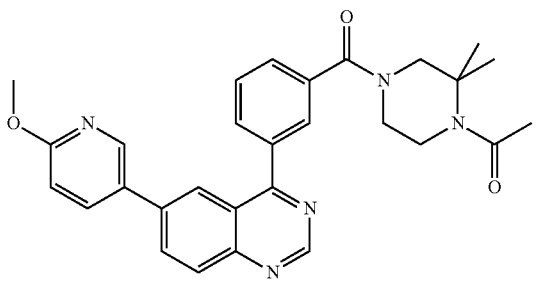 [SMILES: COc1ccc(-c2ccc3ncnc(-c4cccc(C(=O)N5CCN(C(C)=O)C(C)(C)C5)c4)c3c2)cn1]

To (3,3-dimethyl-piperazin-1-yl)-{3-[6-(6-methoxy-pyridin-3-yl)-quinazolin-4-yl]-phenyl}methanone (117.7 mg, 0.213 mmol) was added 4 mL of THF. Triethylamine (0.188 mL, 0.851 mmol) followed by acetyl chloride (0.023 mL, 0.319 mmol) were added. The reaction mixture was stirred for 5 min at room temperature. To the reaction mixture, addition of EtOAc. The organic layer was washed with NaHCO₃ sat. and brine, dried over Na₂SO₄, filtered and evaporated under vacuum. Purification by preparative reverse phase Gilson HPLC and subsequent neutralization of the combined fractions over PL-HCO3 MP gave the title compound (82.7 mg, 78% yield) as a white powder. $^1$H-NMR (400 MHz, DMSO-$d_6$, 298 K): δ ppm 1.16-1.53 (m, 6 H) 1.86-2.05 (m, 3 H) 3.46-3.75 (m, 6H) 3.90 (s, 3 H) 6.88-7.00 (m, 1 H) 7.60-7.80 (m, 2 H) 7.82-8.05 (m, 2 H) 8.11 (dd, 1 H) 8.18-8.27 (m, 2 H) 8.38 (d, 1 H) 8.58 (d, 1 H) 9.38 (s, 1 H). MS: 496.5 [M+1]⁺, Rt$^{(3')}$=1.70 min.

(3,3-Dimethyl-piperazin-1-yl)-{3-[6-(6-methoxy-pyridin-3-yl)-quinazolin-4-yl]-phenyl}-methanone

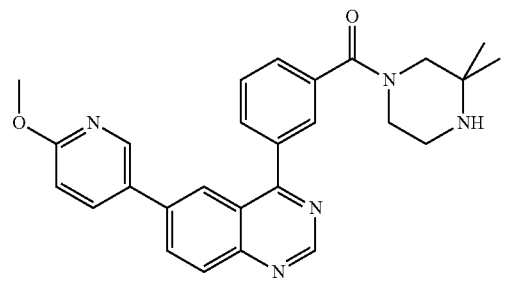 [SMILES: COc1ccc(-c2ccc3ncnc(-c4cccc(C(=O)N5CCNC(C)(C)C5)c4)c3c2)cn1]

To a mixture of [3-(6-bromo-quinazolin-4-yl)-phenyl]-(3,3-dimethyl-piperazin-1-yl)-methanone (111.9 mg, 0.263 mmol), 6-methoxypyridin-3-ylboronic acid (42.4 mg, 0.263 mmol) and Pd(PPh₃)₄ (30.4 mg, 0.026 mmol) was added 2.5 mL of acetonitrile. The reaction mixture was flushed with argon and a 1M aqueous solution of Na₂CO₃ (0.789 mL, 0.789 mmol) was added and the vial capped. The reaction mixture was heated to 130° C. for 20 min using a microwave oven then cooled down to rt, diluted with EtOAc, filtered through a Celite pad and portioned between aqueous NaHCO₃ sat./EtOAc. The organic layer was washed with brine, dried over Na₂SO₄, filtered and evaporated to give the crude compound (117.7 mg, 81% yield). MS: 454.5 [M+1]⁺, Rt$^{(3')}$=1.40 min.

[3-(6-Bromo-quinazolin-4-yl)-phenyl]-(3,3-dimethyl-piperazin-1-yl)-methanone

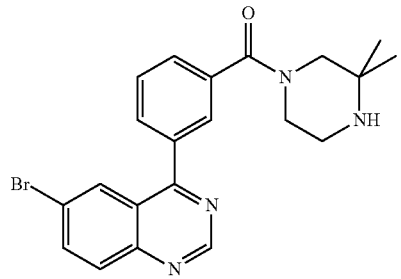 [SMILES: CC1(C)CN(C(=O)c2cccc(-c3ncnc4ccc(Br)cc34)c2)CCN1]

To a solution of 3-(6-bromo-quinazolin-4-yl)-benzoic acid (428.1 mg, 1.301 mmol) in 8 mL of DMF was added HBTU (543 mg, 1.431 mmol) and DIPEA (0.477 mL, 2.73 mmol). The reaction mixture was stirred at rt for 20 min, 2,2-dimethyl-piperazine (163 mg, 1.431 mmol) and DIPEA (0.477 mL, 2.73 mmol) were added at rt and the reaction mixture was stirred at rt overnight. The reaction was quenched with a saturated aqueous solution of NaHCO₃, extracted with EtOAc. The organic layer was washed with brine, dried over Na₂SO₄, filtered and evaporated under vacuum. Purification by flash chromatography on silica gel (CH₂Cl₂/MeOH, 99/1 to 90/10) gave the title compound (234.9 mg, >99% purity, 42.5% yield). MS: 427.1 [M+1]⁺, Rt$^{(7')}$=1.17 min.

Examples 37' was prepared using procedures analogous to those used in example 36', using appropriate starting materials.

| Example | Structure/Name | Rt (min.) | MS(ES): [M + H]+ | 1H-NMR |
|---|---|---|---|---|
| 37' | 5-{4-[3-(4-Acetyl-3,3-dimethyl-piperazine-1-carbonyl)-phenyl]-quinazolin-6-yl}-2-methoxy-nicotinonitrile | 1.782 (3') | 521.6 | 1H-NMR (400 MHz, DMSO-$d_6$, 298K): δ ppm 1.14-1.53 (m, 6 H) 1.81-2.05 (m, 3 H) 3.43-3.81 (m, 6 H) 4.06 (s, 3 H) 7.60-7.79 (m, 2 H) 7.81-7.96 (m, 1 H) 8.03 (d, 1 H) 8.23 (d, 1 H) 8.28-8.34 (m, 1 H) 8.41 (d, 1 H) 8.77 (d, 1 H) 8.88 (d, 1 H) 9.40 (s, 1 H) |

(3') LC methode 3'

Example 38'

(2,5-Diaza-bicyclo[2.2.1]hept-2-yl)-{3-[6-(6-methoxy-pyridin-3-yl)-quinazolin-4-yl]-phenyl}-methanone

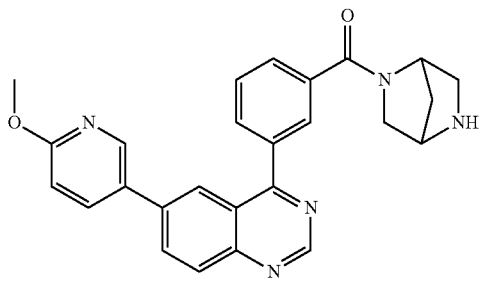 [SMILES: COc1ccc(-c2ccc3ncnc(-c4cccc(C(=O)N5CC6CC5CN6)c4)c3c2)cn1]

To a mixture of [3-(7-bromo-naphthalen-1-yl)-phenyl]-(2,5-diaza-bicyclo[2.2.1]hept-2-yl)-methanone (56.8 mg, 0.139 mmol), 6-methoxypyridin-3-ylboronic acid (23.35 mg, 0.153 mmol) and Pd(PPh$_3$)$_4$ (16.04 mg, 0.014 mmol) was added 1.5 mL of acetonitrile. The reaction mixture was flushed with argon and a 1M aqueous solution of Na$_2$CO$_3$ (0.416 mL, 0.416 mmol) was added and the vial capped. The reaction mixture was heated to 130° C. for 20 min using a microwave oven then cooled down to rt. After filtration, the mixture was directly purified by preparative reverse phase Gilson HPLC and subsequent neutralization of the combined fractions over PL-HCO$_3$ MP gave the title compound (26.7 mg, 44% yield) as a white powder. 1H-NMR (400 MHz, DMSO-$d_6$, 298 K): δ ppm 1.50-1.85 (m, 2 H) 2.73-3.05 (m, 2 H) 3.35-3.75 (m, 3 H) 3.91 (s, 3 H) 4.35-4.70 (d, 1 H) 6.95 (d, 1 H) 7.69-7.78 (m, 2 H) 7.91-8.01 (m, 2 H) 8.10 (t, 1 H) 8.19-8.24 (m, 2 H) 8.39 (d, 1 H) 8.59 (d, 1 H) 9.38 (s, 1 H). MS: 438.2 [M+1]+, Rt$^{(3')}$=1.35 min.

[3-(7-Bromo-naphthalen-1-yl)-phenyl]-(2,5-diaza-bicyclo[2.2.1]hept-2-yl)-methanone

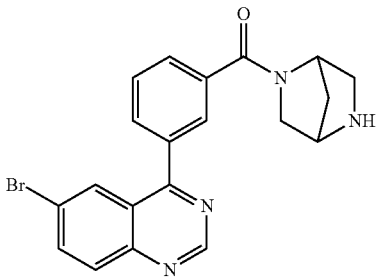 [SMILES: O=C(c1cccc(-c2ncnc3ccc(Br)cc23)c1)N1CC2CC1CN2]

To tert-butyl-5-(3-(6-bromoquinazolin-4-yl)benzoyl)-2,5-diazabicyclo[2.2.1]heptane-2-carboxylate (400.4 mg, 0.786 mmol) diluted in 10 mL of CH$_2$Cl$_2$, TFA (4 mL, 51.9 mmol) was added. The reaction mixture was stirred for 30 min at room temperature. The volatiles were evaporated and EtOAc was added. The organic layer was washed with an aqueous solution of NaHCO$_3$ and brine, dried over Na$_2$SO$_4$, filtered and evaporated to give the crude compound (158 mg, >99% purity, 49.1% yield). MS: 409.0-410.9 [M+1]+, Rt$^{(3')}$=1.22 min.

223 tert-butyl 5-(3-(6-bromoquinazolin-4-yl)benzoyl)-2,5-diazabicyclo[2.2.1]heptane-2-carboxylate

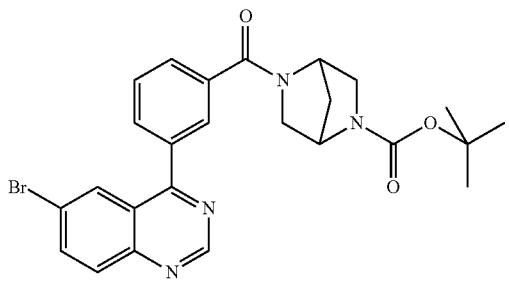 [SMILES: CC(C)(C)OC(=O)N1CC2CC1CN2C(=O)c1cccc(-c2ncnc3ccc(Br)cc23)c1]

To a solution of 3-(6-bromo-quinazolin-4-yl)-benzoic acid (310 mg, 0.942 mmol) in 8 mL of DMF was added HBTU (429 mg, 1.130 mmol) and DIPEA (0.3455 mL, 1.98 mmol). The reaction mixture was stirred at rt for 20 min. Tert-butyl 2,5-diazabicyclo[2.2.1]heptane-2-carboxylate (373 mg, 1.884 mmol) and DIPEA (0.3455 mL, 1.98 mmol) were added at rt and the reaction mixture was stirred for 10 min at rt. The reaction was quenched with a saturated aqueous solution of $NaHCO_3$, extracted with EtOAc. The organic layer was washed with brine, dried over $Na_2SO_4$, filtered and evaporated under vacuum. Purification by flash chromatography on silica gel (Heptane/EtOAc, 80/20 to 0/100) gave the title compound (400.4 mg, >99% purity, 83% yield). MS: 511.3 [M+]+, $Rt^{(3')}$=2.19 min.

Examples 39' was prepared using procedures analogous to those used for example 38', using appropriate starting materials.

224

Example 40'

{3-[6-(5-Methyl-6-methylamino-pyridin-3-yl)-quinazolin-4-yl]-phenyl}-(4-methyl-piperazin-1-yl)-methanone

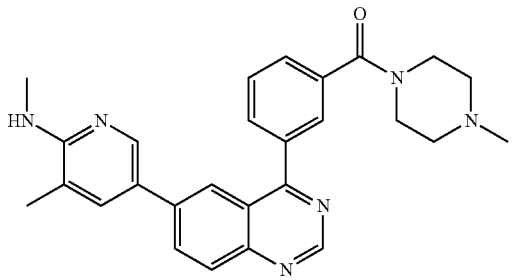 [SMILES: CNc1ncc(-c2ccc3ncnc(-c4cccc(C(=O)N5CCN(C)CC5)c4)c3c2)cc1C]

To a mixture of [3-(6-bromo-quinazolin-4-yl)-phenyl]-(4-methyl-piperazin-1-yl)-methanone (100 mg, 0.243 mmol), methyl-[3-methyl-5-(4,4,5,5-tetramethyl-[1,3,2]dioxaborolan-2yl)-pyridin-2-yl]-carbamic acid tert-butylester (102 mg, 0.292 mmol) and Pd(PPh$_3$)$_4$ (14.05 mg, 0.012 mmol) was added 3 mL of DME. The reaction mixture was flushed with argon and a 1M aqueous solution of $Na_2CO_3$ (0.486 mL, 0.486 mmol) was added and the vial capped. The reaction mixture was heated to 140° C. for 10 min using a microwave oven then cooled down to rt, diluted with EtOAc, filtered through a Celite pad and portioned between $H_2O$/EtOAc. The organic layer was washed with brine, dried over MgSO$_4$, filtered and evaporated. The residue was dissolved in 3 ml of $CH_2Cl_2$ and TFA (0.562 mL, 7.29 mmol) was added. The reaction mixture was stirred at ambient temperature for 16 h. The reaction mixture was then concentrated and purified by preparative reverse phase Gilson HPLC and subsequent neutralization of the combined fractions over PL-HCO$_3$ MP gave the title compound (70 mg, 64% yield) as a white powder. $^1$H-NMR (400 MHz, DMSO-d$_6$, 298 K): δ ppm 2.12 (s, 3 H) 2.15 (s, 3 H) 2.17-2.40 (m, 4 H) 2.90 (d, 3 H) 3.39-3.70 (m, 4 H) 6.28 (q, 1 H) 7.65 (br.s., 2 H) 7.74 (t, 1 H) 7.82 (s, 1 H) 7.98 (d, 1 H) 8.13 (d, 2 H) 8.33 (d, 2 H) 9.32 (s, 1 H). MS: 453.3 [M+1]+, $Rt^{(8')}$=1.25 min.

| Example | Structure/Name | Rt (min.) | MS(ES): [M + H]+ | 1H-NMR |
|---|---|---|---|---|
| 39' | (1S,4S)-2,5-Diaza-bicyclo[2.2.1]hept-2-yl-{3-[6-(4-methoxy-3-trifluoromethyl-phenyl)-quinazolin-4-yl]-phenyl}-methanone | 1.82 $^{(3')}$ | 505.2 | $^1$H-NMR (400 MHz, DMSO-d$_6$, 298K): δ ppm 1.41-1.62 (m, 1 H) 1.66-1.80 (m, 1 H) 2.65-2.87 (m, 1 H) 2.88-2.98 (m, 1 H) 3.19-3.27 (m, 1 H) 3.43-3.67 (m, 2 H) 3.95 (s, 3 H) 4.25-4.69 (m, 1 H) 7.40 (dd, 1 H) 7.61-7.80 (m, 2 H) 7.87-8.06 (m, 4 H) 8.15-8.27 (m, 2 H) 8.41 (dd, 1 H) 9.37 (d, 1 H) |

$^{(3')}$ LC methode 3'

Examples 41' was prepared using procedures analogous to those used for example 40', using appropriate starting materials.
| Example | Structure/Name | Rt (min.) | MS(ES): [M + H]+ | 1H-NMR |
|---------|---------------|-----------|------------------|--------|
| 41' | 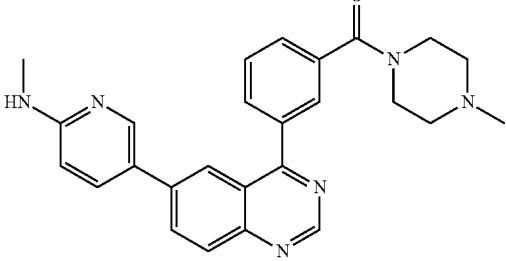 {3-[6-(6-Methylamino-pyridin-3-yl)-quinazolin-4-yl]-phenyl}-(4-methyl-piperazin-1-yl)-methanone | 1.21 (8') | 439.3 | 1H-NMR (400 MHz, DMSO-d6, 298K): δ ppm 2.16 (s, 3 H) 2.25 (br.s., 2 H) 2.36 (br.s., 2 H) 2.82 (d, 3 H) 3.43 (br.s., 2 H) 3.64 (br.s., 2 H) 6.56 (d, 1 H) 6.82 (q, 1 H) 7.65 (dt, 1 H) 7.73 (t, 1 H) 7.80 (dd, 1 H) 7.82 br.s., 1 H) 7.97 (dt, 1 H) 8.12 (d, 1 H) 8.14 (d, 1 H) 8.33 (dd, 1 H) 8.42 (d, 1 H) 9.32 (s, 1 H) |
(8') LC methode 8'
Scheme 3'
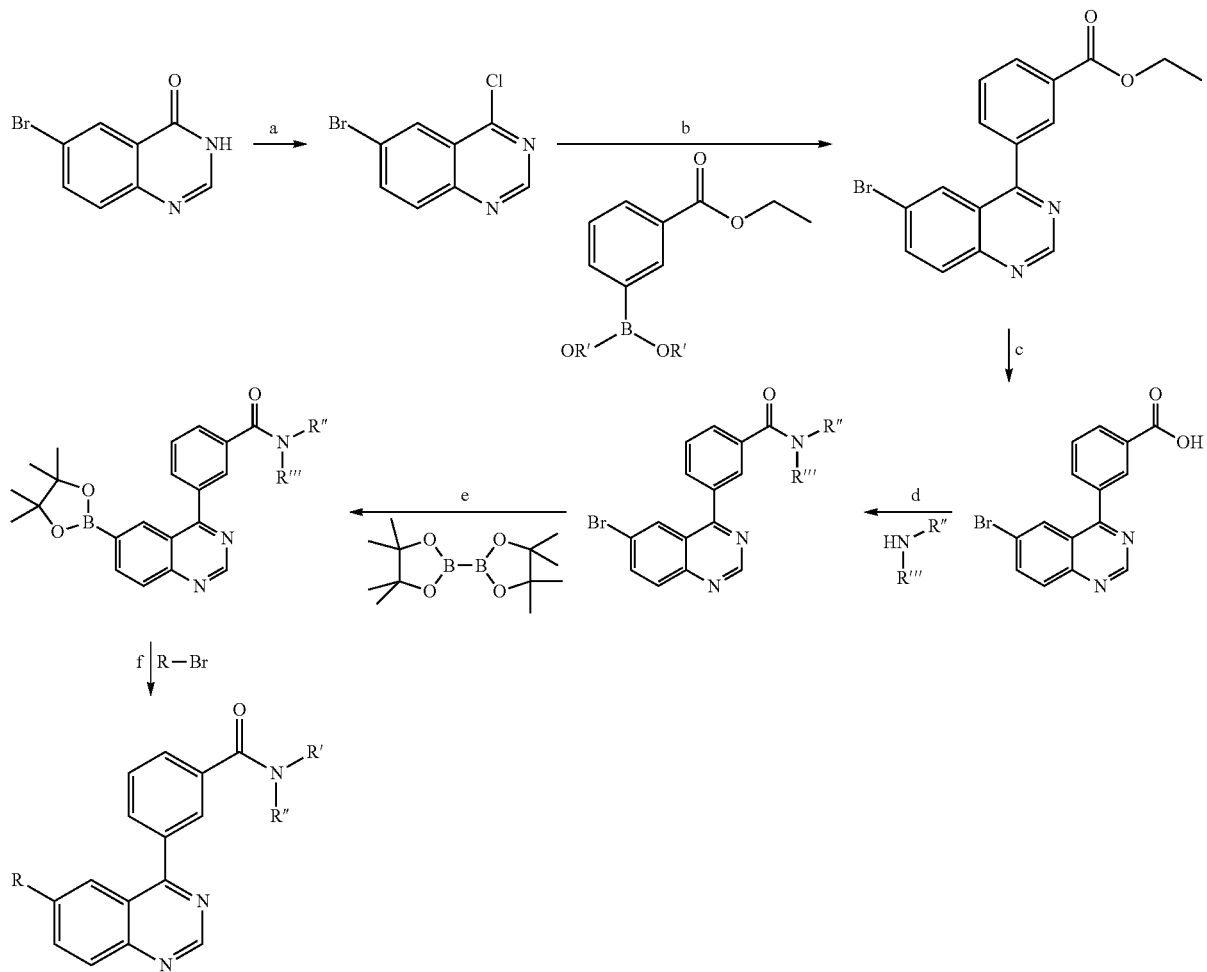

a) Chloronation of 6-Bromo-3H-quinazolin-4-one is performed under customary phosphorus oxychoride condition by heating at reflux or 130° C. in diluted (such as in CH2Cl2) or neat phosphorus oxychoride. b) Suzuki cross-coupling between 6-Bromo-4-chloro-quinazoline and 3-(ethoxycarbonyl)phenyl-boronic acid or 3-(ethoxycarbonyl)phenyl-boronate is performed under customary Suzuki conditions using palladium catalyst such as preferably Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Saponification of the carboxylic ester was performed under customary saponification conditions, using among the possible aqueous bases lithium hydroxyide is preferred and organic solvent such a preferably dioxane. The reaction may preferably be carried out at room temperature. d) Condenation of a carboxylic acid with amines of the formula R'''NHR'' preferably takes place under customary condensation conditions. The reaction can be carried on by dissolving the carboxylic acid and the amine of formula R'''NHR'' in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethyl-amine (DIPEA) or N-methylmorpholine and a suitable coupling agent that forms a reactive derivative of the carboxylic acid in situ, for example and preferably (2-(1H-Benzotriaz-ole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon. e) Formation of the boronate ester was performed using palladium catalyst such as preferably 1,1-Bis(diphenylphosphino)ferrocene]dichloropalladium (PdCl2(dppf)-CH$_2$Cl$_2$), aqueous base such as preferably potassium acetate organic solvent such as preferably dioxane and Bis-(pinacolato)-diboron. The reaction is preferably stirred at approximately 80° C. for several hours. f) Suzuki cross-coupling between aryl bromide (R-Br) and boronate is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon.

The final compounds described herein were according the general procedure described in scheme 3'.

Example 42'

{3-[6-(6-Ethoxy-5-trifluoromethyl-pyridin-3-yl)-quinazolin-4-yl]-phenyl}-(4-methyl-piperazin-1-yl)-methanone

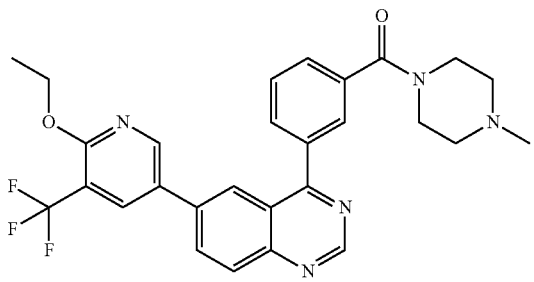 [SMILES: CCOc1ncc(-c2ccc3ncnc(-c4cccc(C(=O)N5CCN(C)CC5)c4)c3c2)cc1C(F)(F)F]

To a mixture of (4-methyl-piperazin-1-yl)-{3-[6-(4,4,5,5-tetramethyl-[1,3,2]dioxaborolan-2-yl)-quinazolin-4-yl]-phenyl}-methanone (100 mg, 0.218 mmol), 5-bromo-2-ethoxy-3-(trifluoromethyl)pyridine (70.7 mg, 0.262 mmol) and Pd(PPh$_3$)$_4$ (12.61 mg, 0.011 mmol) was added 2 mL of DME. The reaction mixture was flushed with argon and a 1M aqueous solution of Na$_2$CO$_3$ (0.436 mL, 0.436 mmol) was added and the vial capped. The reaction mixture was heated to 140° C. for 10 min using a microwave oven then cooled down to rt, diluted with EtOAc, filtered through a Celite pad and portioned between H$_2$O/EtOAc. The organic layer was washed with brine, dried over MgSO$_4$, filtered and evaporated. Purification by preparative reverse phase Gilson HPLC and subsequent neutralization of the combined fractions over PL-HCO$_3$ MP gave the title compound (70 mg, 61% yield) as a white powder. $^1$H-NMR (400 MHz, DMSO-d$_6$, 298 K): δ ppm 1.37 (t, 3 H) 2.13 (s, 3 H) 2.17 (br.s., 2 H) 2.34 (br.s., 2 H) 3.43 (br.s., 2 H) 3.62 (br.s., 2 H) 4.53 (q, 2 H) 7.65 (dt, 1 H) 7.74 (t, 1 H) 7.85 (t, 1 H) 8.02 (dt, 1 H) 8.23 (d, 1 H) 8.32 (d, 1 H) 8.44-8.47 (m, 2 H) 8.84 (d, 1 H) 9.41 (s, 1 H). MS$^{(2)}$: 522.6 [M+1]$^+$, Rt$^{(2')}$=1.16 min.

(4-Methyl-piperazin-1-yl)-{3-[6-(4,4,5,5-tetramethyl-[1,3,2]dioxaborolan-2-yl)-quinazolin-4-yl]-phenyl}-methanone

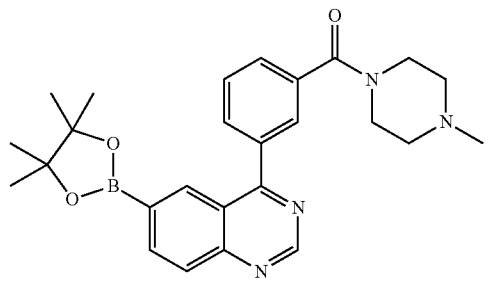

Bis-(pinacolato)-diboron (463 mg, 1.824 mmol), PdCl$_2$(dppf)-CH$_2$Cl$_2$ adduct (99 mg, 0.122 mmol) and KOAc (477 mg, 4.86 mmol) were placed into a a vial and degassed with stream of argon for 2 min. In a separate vial, [3-(6-Bromo-quinazolin-4-yl)-phenyl]-(4-methyl-piperazin-1-yl)-methanone (500 mg, 1.216 mmol) was dissolved in 10 mL of anhydrous dioxane. The dioxane solution of [3-(6-bromoquinazolin-4-yl)-phenyl]-(4-methyl-piperazin-1-yl)-methanone was added to the "catalyst" vial and then heated at 80° C. for 2 h. After cooling to rt, 30 ml ethylacetate was added and the mixture was filtered trough a Celite pad. The dark filtrate was concentrated and then diluted in 30 ml heptane. A dark precipitate was formed and the mixture was filtered and the filtrate concentrated and then dried over high vacuum to give the title compound as a brown solid (710 mg, 50% purity, 55% yield). $^1$H-NMR (400 MHz, CDCl3, 298 K): δ ppm 1.37 (s, 12 H) 2.35 (s, 3 H) 2.45 (br.s., 2 H) 2.53 (br.s., 2 H) 3.62 (br.s., 2 H) 3.85 (br.s., 2 H) 7.69 (d, 2 H) 7.84 (br.s., 1 H) 7.87 (m, 1 H) 8.12 (d, 1 H) 8.32 (dd, 1 H) 8.52 (br.s., 1 H) 9.41 (s, 1 H). MS: 459.3 [M+1]$^+$, Rt$^{(1')}$=1.0 min.

Examples 43' to 48', were prepared using procedures analogous to those used for example 42', using appropriate starting materials.

| Example | Structure | Rt (min.) | MS(ES): [M + H]$^+$ | 1H-NMR |
|---|---|---|---|---|
| 43' | {3-[6-(3-Methanesulfonyl-4-methyl-phenyl)-quinazolin-4-yl]-phenyl}-(4-methyl-piperazin-1-yl)-methanone | 0.89 $^{(2')}$ | 501.5 | $^1$H-NMR (400 MHz, DMSO-d$_6$, 298K): δ ppm 2.13 (s, 3 H) 2.18 (m, 2 H) 2.32 (m, 2 H) 2.70 (s, 3 H) 3.29 (s, 3 H) 3.42 (m, 2 H) 3.60 (m, 2 H) 7.62 (d, 1 H) 7.66 (dt, 1 H) 7.73 (t, 1 H) 7.83 (br.s., 1 H) 7.97-8.04 (m, 2 H) 8.18 (d, 1 H) 8.22-8.29 (m, 2 H) 8.42 (dd, 1 H) 9.41 (s, 1 H) |
| 44' | 2-Methoxy-5-{4-[3-(4-methyl-piperazine-1-carbonyl)-phenyl]-quinazolin-6-yl}-nicotinonitrile | 0.94 $^{(2')}$ | 465.1 | $^1$H-NMR (400 MHz, DMSO-d$_6$, 298K): δ ppm 2.15 (s, 3 H) 2.22 (br.s., 2 H) 2.35 (br.s., 2 H) 3.46 (br.s., 2 H) 3.62 (br.s., 2 H) 4.07 (s, 3 H) 7.65 (dt, 1 H) 7.74 (t, 1 H) 7.83 (br.s., 1 H) 8.01 (dt, 1 H) 8.23 (d, 1 H) 8.34 (d, 1 H) 8.43 (dd, 1 H) 8.79 (d, 1 H) 8.90 (d, 1 H) 9.41 (s, 1 H) |
| 45' | 2-Methoxy-5-{4-[3-(4-methyl-piperazine-1-carbonyl)-phenyl]-quinazolin-6-yl}-benzonitrile | 0.88 $^{(1')}$ | 464.3 | $^1$H-NMR (400 MHz, DMSO-d$_6$, 298K): δ ppm 2.14 (s, 3 H) 2.19 (br.s., 2 H) 2.34 (br.s., 2 H) 3.44 (br.s., 2 H) 3.62 (br.s., 2 H) 3.98 (s, 3 H) 7.39 (d, 1 H) 7.65 (d, 1 H) 7.74 (t, 1 H) 7.82 (br.s., 1 H) 8.01 (d, 1 H) 8.08 (dd, 1 H) 8.20 (d, 1 H) 8.23 (d, 1 H) 8.26 (d, 1 H) 8.40 (dd, 1 H) 9.39 (s, 1 H) |

| Example | Structure | Rt (min.) | MS(ES): [M + H]+ | 1H-NMR |
|---|---|---|---|---|
| 46' | 4-{4-[3-(4-Methyl-piperazine-1-carbonyl)-phenyl]-quinazolin-6-yl}-2-trifluoromethyl-benzenesulfonamide | 1.49 [1'] | 556.2 | 1H-NMR (400 MHz, DMSO-d6, 298K): δ ppm 2.09-2.41 (m, 7 H) 3.35-3.70 (m, 4 H) 7.68 (d, 1 H) 7.75 (t, 1 H) 7.85 (m, 2 H) 8.03 (d, 1 H) 8.21-8.30 (m, 4 H) 8.40 (s, 1 H) 8.50 (d, 1 H) 9.41 (s, 1 H) |
| 47' | N-(3-{4-[3-(4-Methyl-piperazine-1-carbonyl)-phenyl]-quinazolin-6-yl}-5-trifluoromethyl-phenyl)-methanesulfonamide | 1.01 [1'] | 570.3 | 1H-NMR (400 MHz, DMSO-d6, 298K): δ ppm 2.12 (m, 5 H) 2.32 (m, 2 H) 3.13 (s, 3 H) 3.35-3.68 (m, 4 H) 7.56 (s, 1 H) 7.66 (d, 1 H) 7.72-7.76 (m, 2 H) 7.83 (s, 3 H) 8.01 (d, 1 H) 8.26 (d, 2 H) 8.40 (d, 1 H) 9.43 (s, 1 H) |
| 48' | N-(4-{4-[3-(4-Methyl-piperazine-1-carbonyl)-phenyl]-quinazolin-6-yl}-2-trifluoromethyl-phenyl)-methanesulfonamide | 0.92 [1'] | 570.3 | 1H-NMR (400 MHz, DMSO-d6, 298K): δ ppm 2.12 (s, 3 H) 2.13 (br.s., 2 H) 2.35 (br.s., 2 H) 3.13 (s, 3 H) 3.39 (br.s., 2 H) 3.61 (br.s., 2 H) 7.56 (br.s., 1 H) 7.66 (dt, 1 H) 7.73 (d, 1 H) 7.76 (br.s., 1 H) 7.83 (d, 2 H) 8.01 (dt, 1 H) 8.26 (d, 1 H) 8.27 (s, 1 H) 8.40 (dd, 1 H) 9.43 (s, 1 H) |

[1'] LC method 1',
[2'] LC methode 2'

Example 49'

2-Methoxy-N,N-dimethyl-5-{4-[3-(4-methyl-piperazine-1-carbonyl)-phenyl]-quinazolin-6-yl}-benzamide

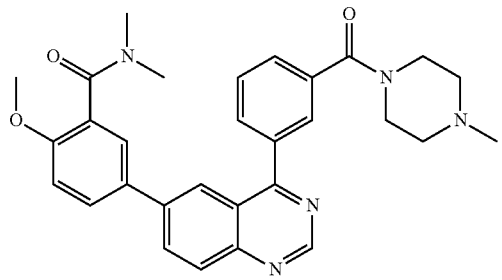 [SMILES: COc1ccc(-c2ccc3ncnc(-c4cccc(C(=O)N5CCN(C)CC5)c4)c3c2)cc1C(=O)N(C)C]

To a solution of 2-methoxy-5-{4-[3-(4-methyl-piperazine-1-carbonyl)-phenyl]-quinazolin-6-yl}-benzoic acid (50 mg, 0.084 mmol) in 2 mL of $CH_2Cl_2$ were added HBTU (38.1 mg, 0.101 mmol) and DIPEA (0.044 mL, 0.251 mmol). The reaction mixture was stirred at rt for 10 min, a solution of dimethyl amine in THF (2M) (0.210 mL, 0.419 mmol) was added at rt and the reaction mixture was stirred at rt for a further 30 min. The reaction was quenched with $H_2O$, extracted with $CH_2Cl_2$. The organic layer was washed with brine, dried over $MgSO_4$, filtered and evaporated under vacuum. Purification by reverse phase Gilson HPLC and subsequent neutralization of the combined fractions over PL-HCO$_3$ MP gave the title compound (25 mg, 58% yield) as a white powder. $^1$H-NMR (400 MHz, DMSO-d$_6$, 298 K): δ ppm 2.15 (s, 3 H) 2.22 (br.s., 2 H) 2.36 (br.s., 2 H) 2.79 (s, 3 H), 2.99 (s, 3 H) 3.41 (br.s., 2 H) 3.62 (br.s., 2 H) 3.86 (s, 3 H) 7.22 (d, 1 H) 7.56 (d, 1 H) 7.65 (dt, 1 H) 7.73 (t, 1 H) 7.79 (dd, 1 H) 7.82 (t, 1 H) 7.98 (dt, 1 H) 8.17 (d, 1 H) 8.19 (s, 1 H) 8.38 (dd, 1 H) 9.37 (s, 1 H). MS: 510.6 [M+1]$^+$, Rt$^{(2')}$=0.85 min.

2-Methoxy-5-{4-[3-(4-methyl-piperazine-1-carbonyl)-phenyl]-quinazolin-6-yl}-benzoic acid

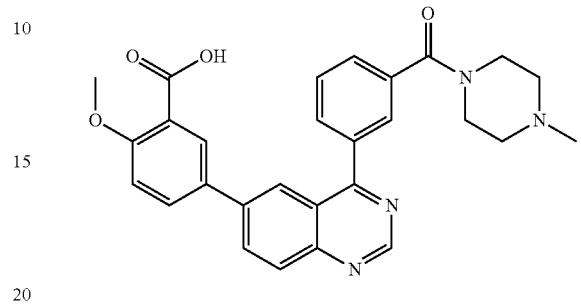

To a mixture of (4-methyl-piperazin-1-yl)-{3-[6-(4,4,5,5-tetramethyl-[1,3,2]dioxaborolan-2-yl)-quinazolin-4-yl]-phenyl}-methanone (300 mg, 0.655 mmol), 5-bromo-2-methoxy-benzoic acid (181 mg, 0.785 mmol) and Pd(PPh$_3$)$_4$ (37.8 mg, 0.033 mmol) was added 4 mL of DME. The reaction mixture was flushed with argon and a 1M aqueous solution of Na$_2$CO$_3$ (1.309 mL, 1.309 mmol) was added and the vial capped. The reaction mixture was heated to 140° C. for 10 min using a microwave oven then cooled down to rt, diluted with EtOAc, filtered through a Celite pad and concentrated. Purification by preparative reverse phase Gilson HPLC and the combined fractions gave the title compound (60 mg, 15% yield) as a white powder. $^1$H-NMR (400 MHz, DMSO-d$_6$, 298 K): δ ppm 2.79 (s, 3 H) 3.03-3.82 (m, 8 H) 3.89 (s, 3 H) 7.28 (d, 1 H) 7.72 (dt, 1 H) 7.77 (t, 1 H) 7.92 (dd, 2 H) 7.98 (d, 1 H) 8.05 (dt, 1 H) 8.20-8.22 (m, 2 H) 8.41 (dd, 1 H) 9.39 (s, 1 H). MS: 483.4 [M+1]$^+$, Rt$^{(1')}$=0.75 min.

Scheme 4'

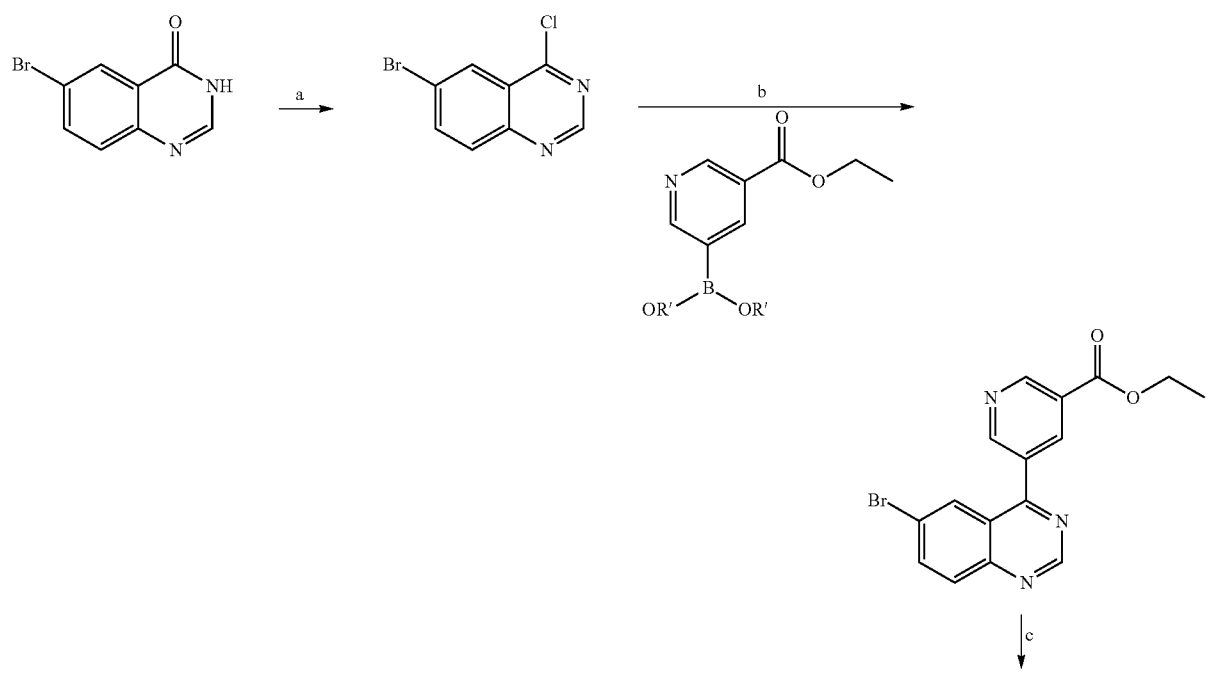

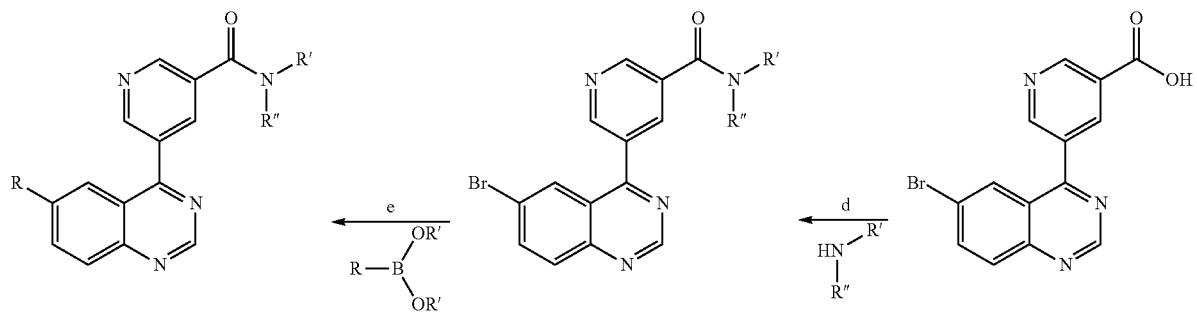

-continued a) Chloronation of 6-Bromo-3H-quinazolin-4-one is performed under customary phosphorus oxychloride condition by heating at reflux or 130° C. in diluted (such as in CH$_2$Cl$_2$) or neat phosphorus oxychloride. b) Suzuki cross-coupling between 6-Bromo-4-chloro-quinazoline and 3-(ethoxycarbonyl)pyridyl-boronic acid or 3-(ethoxycarbonyl)pyridyl-boronate is performed under customary Suzuki conditions using palladium catalyst such as preferably Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Saponification of the carboxylic ester was performed under customary saponification conditions, using among the possible aqueous bases lithium hydroxyide is preferred and organic solvent such a preferably dioxane. The reaction may preferably be carried out at room temperature. d) Condenation of a carboxylic acid with amines of the formula R'''NHR'' preferably takes place under customary condensation conditions. The reaction can be carried on by dissolving the carboxylic acid and the amine of formula R'''NHR'' in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriazole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon. e) Suzuki cross-coupling between aryl bromide and boronic acid or boronic acid derivatives such as boronate of formula R(OR')$_2$ is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon.

The final compounds described herein were according the general procedure described in scheme 4'.

Example 50'

1-(4-{5-[6-(5-Trifluoromethyl-pyridin-3-yl)-quinazolin-4-yl]-pyridine-3-carbonyl}-piperazin-1-yl)-ethanone

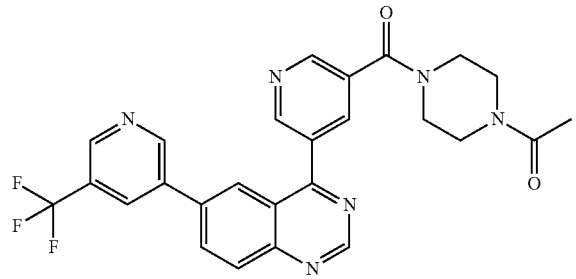 [SMILES: CC(=O)N1CCN(C(=O)c2cncc(-c3ncnc4ccc(-c5cncc(C(F)(F)F)c5)cc34)c2)CC1]

To a mixture of 1-{4-[5-(6-bromo-quinazolin-4-yl)-pyridine-3-carbonyl]-piperazin-1-yl}-ethanone (100 mg, 0.204 mmol, 90% purity (UPLC)), boronic acid 3-(4,4,5,5-tetramethyl-[1,3,2]dioxaborolan-2-yl)-5-trifluoromethyl-pyridine (80 mg, 0.204 mmol, 70% purity) and Pd(PPh$_3$)$_4$ (11.81 mg, 0.010 mmol) was added 2 mL of DME. The reaction mixture was flushed with argon and a 1M aqueous solution of Na$_2$CO$_3$ (0.409 mL, 0.409 mmol) was added and the vial capped. The reaction mixture was heated to 120° C. for 10 min using a microwave oven then cooled down to rt, diluted with EtOAc, filtered through a Celite pad and portioned between H$_2$O/EtOAc. The organic layer was washed with brine, dried over MgSO$_4$, filtered and evaporated. Purification by preparative reverse phase Gilson HPLC and subsequent neutralization of the combined fractions over PL-HCO$_3$ MP gave the title compound (55 mg, 53% yield) as a white powder. $^1$H-NMR (400 MHz, DMSO-d$_6$, 298 K): δ ppm 1.96-2.1 (br.s., 3 H) 3.41-3.70 (m, 8 H) 8.31 (d, 1 H) 8.40 (s, 1 H) 8.50 (s, 1 H) 8.56 (d, 1 H) 8.69 (br.s., 1 H) 8.90 (s, 1 H) 9.04 (s, 1 H) 9.20 (s., 1 H) 9.35 (br.s., 1 H) 9.49 (s, 1 H). MS: 507.6 [M+1]$^+$, Rt$^{(2')}$=0.93 min.

1-{4-[5-(6-Bromo-quinazolin-4-yl)-pyridine-3-carbonyl]-piperazin-1-yl}-ethanone

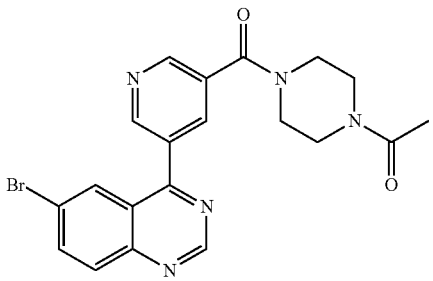 [SMILES: CC(=O)N1CCN(C(=O)c2cncc(-c3ncnc4ccc(Br)cc34)c2)CC1]

To a solution of 5-(6-bromo-quinazolin-4-yl)-nicotinic acid (1 g, 3.03 mmol) in 10 mL of CH$_2$Cl$_2$ was added HBTU (1.38 g, 3.63 mmol) and DIPEA (1.06 mL, 6.06 mmol). The reaction mixture was stirred at rt for 10 min, 1-Piperazin-1-yl-ethanone (0.466 g, 3.63 mmol) was added at rt and the reaction mixture was stirred at rt for a further 3 h. The reaction was quenched with a saturated aqueous solution of NaHCO$_3$, extracted with CH$_2$Cl$_2$. The organic layer was washed with brine, dried over MgSO$_4$, filtered and evaporated under vacuum. Purification by flash chromatography on silica gel (CH$_2$Cl$_2$/MeOH, 95/5) gave the title compound (1.13 g, 90% purity, 76% yield). $^1$H-NMR (400 MHz, DMSO-d$_6$, 298 K): δ ppm 2.04 (br.s., 3 H) 3.41-3.70 (m, 8 H) 8.12 (d, 1 H) 8.24 (br.s., 2 H) 8.31 (br.s., 1 H) 8.89 (s, 1 H) 9.07 (s, 1 H) 9.47 (s, 1 H). MS: 440.4-442.4 [M+1]$^+$, Rt$^{(9')}$=1.48 min.

5-(6-Bromo-quinazolin-4-yl)-nicotinic acid

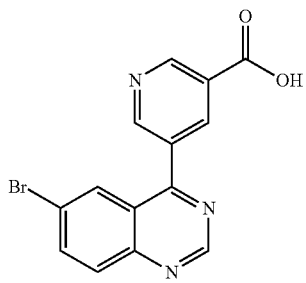

To a solution of 5-(6-bromo-quinazolin-4-yl)-nicotinic acid ethyl ester (1.34 g, 3.74 mmol) in dioxane (45 mL) was added at rt a 1M aqueous solution of LiOH.H$_2$O (7.48 ml, 7.48 mmol) and the reaction mixture was stirred 1.5 h at rt. The reaction was quenched with a 1M aqueous solution of HCl (5 mL), the formed precipitate was filtered and dried under vacuum to gave the title compound as a light yellow solid. The filtrate was extracted with EtOAc, the organic layer was washed with brine, dried over MgSO$_4$, filtered and evaporated to give the title compound as a light yellow solid. The two isolated solids were combined to gave the title compound as a light yellow solid (1.1 g, 81% yield). MS: 330.5-332.5 [M+1]$^+$, Rt$^{(2')}$=0.97 min.

5-(6-Bromo-quinazolin-4-yl)-nicotinic acid ethyl ester

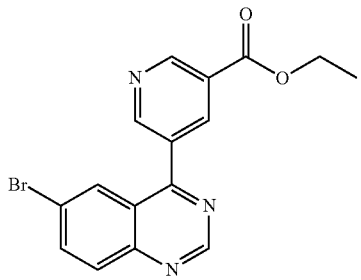 [SMILES: CCOC(=O)c1cncc(-c2ncnc3ccc(Br)cc23)c1]

To a mixture of 6-bromo-4-chloro-quinazoline (6 g, 23.41 mmol), boronic acid 5-(4,4,5,5-tetramethyl-[1,3,2]dioxaborolan-2-yl)-nicotinic acid ethyl ester (6.81 g, 24.58 mmol), Pd(PPh$_3$)$_2$Cl$_2$ (0.822 g, 1.17 mmol) and K$_3$PO$_4$ (7.45 g, 35.1 mmol) was added 96 mL of acetonitril. The reaction mixture was flushed with argon and 12 ml water was added and the vial capped. The reaction mixture was heated to 100° C. for 12 min using a microwave oven and then cooled down to rt. The mixture was quenched with water, extracted with dichloromethane. The organic layer was washed with brine, dried over MgSO$_4$, filtered through a Celite pad and evaporated. The obtained residue was triturated in MeOH to afford the title compound as a light orange solid (5.3 g, 95% purity, 60% yield). $^1$H-NMR (400 MHz, DMSO-d$_6$, 298 K): δ ppm 1.38 (t, 3 H) 4.41 (q, 2 H) 8.1 (d, 1 H) 8.25 (d, 2 H) 8.65 (s, 1 H) 9.22 (s, 1 H) 9.32 (s, 1 H) 9.48 (s, 1 H). MS: 358.1-360.1 [M+1]$^+$, Rt$^{(1')}$=1.28 min.

Examples 51' to 74', were prepared using procedures analogous to those used for example 50', using appropriate starting materials.

| Example | Structure/Name | Rt (min.) | MS(ES): [M + H]$^+$ | 1H-NMR |
|---|---|---|---|---|
| 51' | 1-(4-{5-[6-(5-Fluoro-6-methoxy-pyridin-3-yl)-quinazolin-4-yl]-pyridine-3-carbonyl}-piperazin-1-yl)-ethanone | 0.95 $^{(1')}$ | 487.3 | $^1$H-NMR (400 MHz, DMSO-d$_6$, 298K): δ ppm 1.85-2.03 (br.s., 3 H) 3.33-3.72 (m, 8 H) 3.96 (s, 3 H) 8.16-8.23 (m, 2 H) 8.27 (s, 1 H) 8.31 (s, 1 H) 8.41 (d, 1 H) 8.44 (s, 1 H) 8.84 (s, 1 H) 9.10 (s, 1 H) 9.39 (s, 1 H) |

| Example | Structure/Name | Rt (min.) | MS(ES): [M + H]+ | 1H-NMR |
|---|---|---|---|---|
| 52' | 1-(4-{5-[6-(6-Methoxy-pyridin-3-yl)-quinazolin-4-yl]-pyridine-3-carbonyl}-piperazin-1-yl)-ethanone | 0.86 (1) | 469.3 | 1H-NMR (400 MHz, DMSO-d6, 298K): δ ppm 1.89-2.08 (br.s., 3 H) 3.37-3.75 (m, 8 H) 3.92 (s, 3 H) 6.97 (d, 1 H) 8.15-8.20 (d, 1 H) 8.23 (d, 1 H) 8.26 (d, 1 H) 8.37 (t, 1 H) 8.44 (dd, 1 H) 8.64 (d, 1 H) 8.88 (d, 1 H) 9.15 (d, 1 H) 9.43 (s, 1 H) |
| 53' | 5-{4-[5-(4-Acetyl-piperazine-1-carbonyl)-pyridin-3-yl]-quinazolin-6-yl}-2-methoxy-nicotinonitrile | 0.93 (1) | 494.3 | 1H-NMR (400 MHz, DMSO-d6, 298K): δ ppm 1.82-2.02 (br.s., 3 H) 3.31-3.70 (m, 8 H) 4.03 (s, 3 H) 8.16-8.25 (m, 1 H) 8.32 (m, 2 H) 8.44 (m, 1 H) 8.80 (br.s., 1 H) 8.85 (d, 1 H) 8.92 (br.s., 1 H) 9.12 (d, 1 H) 9.41 (s, 1 H) |
| 54' | 1-(4-{5-[6-(6-Methoxy-5-trifluoromethyl-pyridin-3-yl)-quinazolin-4-yl]-pyridine-3-carbonyl}-piperazin-1-yl)-ethanone | 1.15 (1) | 537.3 | 1H-NMR (400 MHz, DMSO-d6, 298K): δ ppm 1.90-2.08 (br.s., 3 H) 3.36-3.74 (m, 8 H) 4.06 (s, 3 H) 8.26 (d, 1 H) 8.37-8.39 (m, 2 H) 8.49-8.52 (m, 2 H) 8.89 (d, 1 H) 8.91 (d, 1 H) 9.17 (d, 1 H) 9.45 (s, 1 H) |
| 55' | {5-[6-(5-Fluoro-6-methoxy-pyridin-3-yl)-quinazolin-4-yl]-pyridin-3-yl}-(4-methyl-piperazin-1-yl)-methanone | 0.84 (2) | 459.1 | 1H-NMR (400 MHz, DMSO-d6, 298K): δ ppm 2.16 (s, 3 H) 2.25 (br.s., 2 H) 2.37 (br.s., 2 H) 3.49 (br.s., 2 H) 3.65 (br.s., 2 H) 4.01 (s, 3 H) 8.21-8.26 (m, 2 H) 8.30-8.32 (m, 2 H) 8.44 (dd, 1 H) 8.47 (d, 1 H) 8.84 (d, 1 H) 9.13 (d, 1 H) 9.43 (s, 1 H) |

-continued

| Example | Structure/Name | Rt (min.) | MS(ES): [M + H]+ | 1H-NMR |
|---|---|---|---|---|
| 56' | 2-Methoxy-5-{4-[5-(4-methyl-piperazine-1-carbonyl)-pyridin-3-yl]-quinazolin-6-yl}-nicotinonitrile | 0.79 (1) | 466.3 | 1H-NMR (400 MHz, DMSO-d6, 298K): δ ppm 2.16 (s, 3 H) 2.25 (br.s., 2 H) 2.37 (br.s., 2 H) 3.49 (br.s., 2 H) 3.65 (br.s., 2 H) 4.07 (s, 3 H) 8.25 (d, 1 H) 8.30 (t, 1 H) 8.37 (d, 1 H) 8.47 (dd, 1 H) 8.83 (d, 1 H) 8.85 (d, 1 H) 8.95 (d, 1 H) 9.15 (d, 1 H) 9.45 (s, 1 H) |
| 57' | {5-[6-(6-Methoxy-pyridin-3-yl)-quinazolin-4-yl]-pyridin-3-yl}-(4-methyl-piperazin-1-yl)-methanone | 1.10 (1) | 441.4 | 1H-NMR (400 MHz, DMSO-d6, 298K): δ ppm 2.20 (br.s., 3 H) 2.26-2.48 (m, 4 H) 3.48 (br.s., 2 H) 3.66 (br.s., 2 H) 3.91 (s, 3 H) 6.96 (d, 1 H) 8.16 (dd, 1 H) 8.20-8.27 (m, 2 H) 8.31 (t, 1 H) 8.42 (dd, 1 H) 8.63 (d, 1 H) 8.84 (d, 1 H) 9.13 (d, 1 H) 9.42 (s, 1 H) |
| 58' | {5-[6-(4-Methoxy-3-trifluoromethyl-phenyl)-quinazolin-4-yl]-pyridin-3-yl}-(4-methyl-piperazin-1-yl)-methanone | 1.57 (1) | 508.4 | 1H-NMR (400 MHz, DMSO-d6, 298K): δ ppm 2.01-2.44 (m, 7 H) 3.45 (br.s., 2 H) 3.64 (br.s., 2 H) 3.95 (s, 3 H) 7.41 (d, 1 H) 7.99 (s, 1 H) 8.07 (dd, 1 H) 8.18-8.26 (m, 2 H) 8.30 (s, 1 H) 8.44 (dd, 1 H) 8.84 (d, 1 H) 9.15 (d, 1 H) 9.42 (s, 1 H) |
| 59' | {5-[6-(2-Methoxy-pyrimidin-5-yl)-quinazolin-4-yl]-pyridin-3-yl}-(4-methyl-piperazin-1-yl)-methanone | 0.56 (1) | 442.3 | 1H-NMR (400 MHz, DMSO-d6, 298K): δ ppm 2.17 (s, 3 H) 2.26 (br.s., 2 H) 2.38 (br.s., 2 H) 3.48 (br.s., 2 H) 3.66 (br.s., 2 H) 3.99 (s, 3 H) 8.27 (d, 1 H) 8.33 (t, 1 H) 8.36 (d, 1 H) 8.47 (dd, 1 H) 8.84 (d, 1 H) 9.09 (s, 2 H) 9.14 (d, 1 H) 9.45 (s, 1 H) |

-continued

| Example | Structure/Name | Rt (min.) | MS(ES): [M + H]+ | 1H-NMR |
|---|---|---|---|---|
| 60' | {5-[6-(2-Amino-pyrimidin-5-yl)-quinazolin-4-yl]-pyridin-3-yl}-(4-methyl-piperazin-1-yl)-methanone | 1.13 (1) | 427.3 | 1H-NMR (400 MHz, DMSO-d6, 298K): δ ppm 2.17 (s, 3 H) 2.27 (br.s., 2 H) 2.37 (br.s., 2 H) 3.48 (br.s., 2 H) 3.66 (br.s., 2 H) 6.97 (br.s., 2 H) 8.19 (d, 1 H) 8.22 (d, 1 H) 8.30 (t, 1 H) 8.40 (dd, 1 H) 8.72 (s, 2 H) 8.83 (d, 1 H) 9.13 (d, 1 H) 9.39 (s, 1 H) |
| 61' | (2,2-Dimethyl-morpholin-4-yl)-{5-[6-(6-methoxy-5-trifluoromethyl-pyridin-3-yl)-quinazolin-4-yl]pyridin-3-yl}-methanone | 1.28 (2) | 524.5 | 1H-NMR (400 MHz, DMSO-d6, 298K): δ ppm 1.04 (br.s., 3 H) 1.21 (br.s., 3 H) 3.37-3.75 (m, 6 H) 4.05 (s, 3 H) 8.24 (d, 1 H) 8.29-8.42 (m, 2 H) 8.43-8.54 (m, 2 H) 8.78-8.94 (m, 2 H) 9.16 (s, 1 H) 9.44 (s, 1 H) |
| 62' | 5-{4-[5-(2,2-Dimethyl-morpholine-4-carbonyl)-pyridin-3-yl]-quinazolin-6-yl}-2-methoxy-nicotinonitrile | 1.11 (2) | 481.6 | 1H-NMR (400 MHz, DMSO-d6, 298K): δ ppm 1.06 (br.s., 3 H) 1.21 (br.s., 3 H) 3.43-3.73 (m, 6 H) 4.07 (s, 3 H) 8.25 (d, 1 H) 8.30-8.36 (m, 2 H) 8.46 (br.s., 1 H) 8.82-8.90 (m, 2 H) 8.94 (d, 1 H) 9.15 (d, 1 H) 9.45 (s, 1 H) |
| 63' | (2,2-Dimethyl-morpholin-4-yl)-{5-[6-(5-fluoro-6-methoxy-pyridin-3-yl)-quinazolin-4-yl]-pyridin-3-yl}-methanone | 1.12 (2) | 474.5 | 1H-NMR (400 MHz, DMSO-d6, 298K): δ ppm 1.06 (br.s., 3 H) 1.21 (br.s., 3 H) 3.34-3.75 (m, 6 H) 4.01 (s, 3 H) 8.20-8.26 (m, 2 H) 8.30-8.40 (m, 2 H) 8.45 (d, 1 H) 8.47 (d, 1 H) 8.79-8.93 (m, 1 H) 9.14 (d, 1 H) 9.43 (s, 1 H) |

| Example | Structure/Name | Rt (min.) | MS(ES): [M + H]+ | 1H-NMR |
|---|---|---|---|---|
| 64' | (2,2-Dimethyl-morpholin-4-yl)-{5-[6-(5-methanesulfonyl-pyridin-3-yl)-quinazolin-4-yl]-pyridin-3-yl}-methanone | 0.94 (2') | 504.8 | 1H-NMR (400 MHz, DMSO-d6, 298K): δ ppm 1.04 (br.s., 3 H) 1.21 (br.s., 3 H) 3.42 (s, 3 H) 3.43-3.74 (m, 6 H) 8.32 (d, 1 H) 8.34-8.43 (m, 1 H) 8.48 (d, 1 H) 8.53-8.60 (m, 1 H) 8.70 (br.s., 1 H) 8.81-8.92 (m, 1 H) 9.12 (d, 1 H) 9.18 (d, 1 H) 9.35 (d, 1 H) 9.49 (s, 1 H) |
| 65' | {5-[6-(2-Amino-pyrimidin-5-yl)-quinazolin-4-yl]-pyridin-3-yl}-(2,2-dimethyl-morpholin-4-yl)-methanone | 0.82 (2') | 442.9 | 1H-NMR (400 MHz, DMSO-d6, 298K): δ ppm 1.08 (br.s., 3 H) 1.21 (br.s., 3 H) 3.43-3.76 (m, 6 H) 6.95 (br.s., 2 H) 8.19 (d, 1 H) 8.22 (d, 1 H) 8.28-8.44 (m, 2 H) 8.72 (s, 2 H) 8.79-8.91 (m, 1 H) 9.13 (d, 1 H) 9.39 (s, 1 H) |
| 66' | (2,2-Dimethyl-morpholin-4-yl)-{5-[6-(4-methoxy-3-trifluoromethyl-phenyl)-quinazolin-4-yl]-pyridin-3-yl}-methanone | 1.34 (2') | 523.7 | 1H-NMR (400 MHz, DMSO-d6, 298K): δ ppm 1.04 (br.s., 3 H) 1.20 (br.s., 3 H) 3.39-3.74 (m, 6 H) 3.96 (s, 3 H) 7.40 (d, 1 H) 7.99 (br.s., 1 H) 8.06 (d, 1 H) 8.20-8.26 (m, 2 H) 8.28-8.47 (m, 2 H) 8.80-8.92 (m, 1 H) 9.16 (d, 1 H) 9.43 (s, 1 H) |
| 67' | (2,2-Dimethyl-morpholin-4-yl)-{5-[6-(6-methoxy-pyridin-3-yl)-quinazolin-4-yl]-pyridin-3-yl}-methanone | 1.10 (2') | 456.8 | 1H-NMR (400 MHz, DMSO-d6, 298K): δ ppm 1.06 (br.s., 3 H) 1.21 (br.s., 3 H) 3.41-3.74 (m, 6 H) 3.91 (s, 3 H) 6.96 (d, 1 H) 8.16 (d, 1 H) 8.21-8.26 (m, 2 H) 8.30-8.38 (m, 1 H) 8.43 (d, 1 H) 8.63 (d, 1 H) 8.80-8.92 (m, 1 H) 9.14 (d, 1 H) 9.43 (s, 1 H) |

| Example | Structure/Name | Rt (min.) | MS(ES): [M + H]⁺ | 1H-NMR |
|---|---|---|---|---|
| 68' | {5-[6-(6-Methoxy-5-trifluoromethyl-pyridin-3-yl)-quinazolin-4-yl]-pyridin-3-yl}-morpholin-4-yl-methanone | 1.24 $^{(1')}$ | 496.2 | ¹H-NMR (400 MHz, DMSO-d₆, 298K): δ ppm 3.46-3.60 (m, 4 H) 3.60-3.73 (br.s., 4 H) 4.06 (s, 3 H) 8.25 (d, 1 H) 8.38-8.39 (m, 2 H) 8.49-8.53 (m, 2 H) 8.87 (d, 1 H) 8.91 (d, 1 H) 9.13 (d, 1 H) 9.45 (s, 1 H) |
| 69' | 2-Methoxy-5-{4-[5-(morpholine-4-carbonyl)-pyridin-3-yl]-quinazolin-6-yl}-nicotinonitrile | 1.00 $^{(1')}$ | 453.3 | ¹H-NMR (400 MHz, DMSO-d₆, 298K): δ ppm 3.46-3.75 (m, 8 H) 4.07 (s, 3 H) 8.25 (d, 1 H) 8.35 (t, 1 H) 8.37 (d, 1 H) 8.46-8.49 (dd, 1 H) 8.82 (d, 1 H) 8.86 (d, 1 H) 8.95 (d, 1 H) 9.15 (d, 1 H) 9.45 (s, 1 H) |
| 70' | {5-[6-(2-Methoxy-pyrimidin-5-yl)-quinazolin-4-yl]-pyridin-3-yl}-morpholin-4-yl-methanone | 1.45 $^{(3')}$ | 429.3 | ¹H-NMR (400 MHz, DMSO-d₆, 298K): δ ppm 3.37-3.90 (m, 8 H) 3.99 (s, 3 H) 8.26 (d, 1 H) 8.37 (m, 2 H) 8.48 (d, 1 H) 8.88 (s, 1 H) 9.09 (s, 2 H) 9.15 (s, 1 H) 9.45 (s, 1 H) |
| 71' | 5-{4-[5-(1,1-Dioxo-1lambda*6*-thiomorpholine-4-carbonyl)-pyridin-3-yl]-quinazolin-6-yl}-2-methoxy-nicotinonitrile | 1.02 $^{(2')}$ | 501.5 | ¹H-NMR (400 MHz, DMSO-d₆, 298K): δ ppm 3.24 (br.s., 4 H) 3.87 (br.s., 2 H) 4.05 (br.s., 2 H) 4.07 (s, 3 H) 8.26 (d, 1 H) 8.39 (d, 1 H) 8.45 (t, 1 H) 8.49 (dd, 1 H) 8.83 (d, 1 H) 8.94 (d, 1 H) 8.96 (d, 1 H) 9.17 (d, 1 H) 9.46 (s, 1 H) |

| Example | Structure/Name | Rt (min.) | MS(ES): [M + H]+ | 1H-NMR |
|---|---|---|---|---|
| 72' | 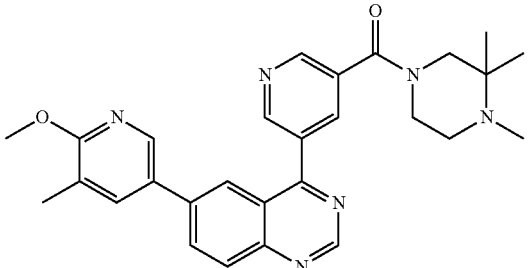<br>{5-[6-(6-Methoxy-5-methyl-pyridin-3-yl)-quinazolin-4-yl]-pyridin-3-yl}-(3,3,4-trimethyl-piperazin-1-yl)-methanone | 0.92 (1') | 483.3 | 1H-NMR (400 MHz, DMSO-d6, 298K): δ ppm 0.82 (br.s., 3 H) 0.99 (br.s., 3 H) 2.09 (m, 3 H) 2.22 (s, 3 H) 2.35 (br.s., 1 H) 2.50 (br.s., 1 H) 3.20 (br.s., 1 H) 3.39 (br.s., 1 H) 3.47 (br.s., 1 H) 3.67 (br.s., 1 H) 3.94 (s, 3 H) 8.01 (br.s., 1 H) 8.21-8.23 (d, 2 H) 8.29-8.31 (d, 1 H) 8.40 (d, 1 H) 8.43 (d, 1 H) 8.83 (d, 1 H) 9.13 (d, 1 H) 9.42 (s, 1 H) |
| 73' | 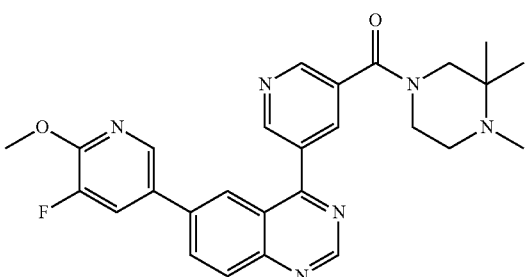<br>{5-[6-(5-Fluoro-6-methoxy-pyridin-3-yl)-quinazolin-4-yl]-pyridin-3-yl}-(3,3,4-trimethyl-piperazin-1-yl)-methanone | 0.88 (1') | 487.3 | 1H-NMR (400 MHz, DMSO-d6, 298K): δ ppm 0.82 (br.s., 3 H) 0.99 (br.s., 3 H) 2.10 (br.s., 3 H) 2.37 (br.s., 1 H) 2.50 (br.s., 1 H) 3.21 (br.s., 1 H) 3.40 (br.s., 1 H) 3.49 (br.s., 1 H) 3.67 (br.s., 1 H) 4.01 (s, 3 H) 8.22-8.26 (m, 2 H) 8.30 (br.s., 2 H) 8.44 (d, 1 H) 8.47 (d, 1 H) 8.83 (d, 1 H) 9.13 (br.s., 1 H) 9.43 (s, 1 H) |
| 74' | 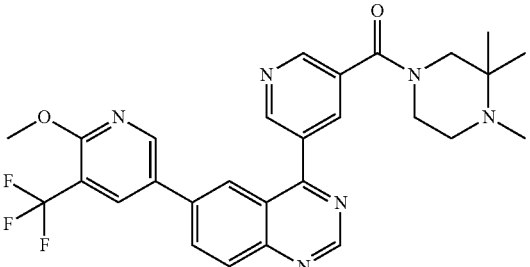<br>{5-[6-(6-Methoxy-5-trifluoromethyl-pyridin-3-yl)-quinazolin-4-yl]-pyridin-3-yl}-(3,3,4-trimethyl-piperazin-1-yl)-methanone | 1.02 (1') | 537.3 | 1H-NMR (400 MHz, DMSO-d6, 298K): δ ppm 0.81 (br.s., 3 H) 0.99 (br.s., 3 H) 2.08 (br.s., 3 H) 2.33 (br.s., 1 H) 2.50 (br.s., 1 H) 3.19 (br.s., 1 H) 3.39 (br.s., 1 H) 3.47 (br.s., 1 H) 3.66 (br.s., 1 H) 4.05 (s, 3 H) 8.25 (d, 1 H) 8.27-8.38 (m, 2 H) 8.44-8.53 (m, 2 H) 8.78-8.85 (d, 1 H) 8.89 (br.s., 1 H) 9.15 (d, 1 H) 9.45 (s, 1 H) |

(1') LC methode 1',
(2') LC methode 2',
(3') LC methode 3'

Example 75'

{5-[6-(5-Methyl-6-methylamino-pyridin-3-yl)-quinazolin-4-yl]-pyridin-3-yl}-(4-methyl-piperazin-1-yl)-methanone

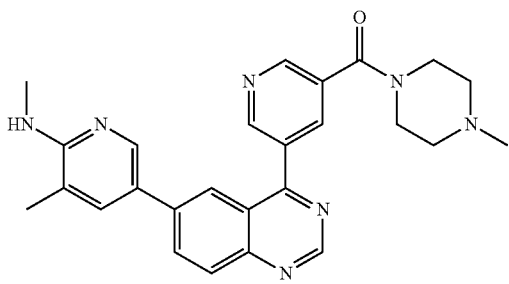

To a mixture of [5-(6-bromo-quinazolin-4-yl)-pyridin-3-yl]-(4-methyl-piperazin-1-yl)-methanone (100 mg, 0.243 mmol), tert-butyl methyl(3-methyl-5-(4,4,5,5-tetramethyl-1,3,2-dioxaborolan-2-yl)pyridin-2-yl) (107 mg, 0.291 mmol) and Pd(PPh3)4 (14.01 mg, 0.012 mmol) was added 2 mL of DME. The reaction mixture was flushed with argon and a 1M aqueous solution of $Na_2CO_3$ (0.485 mL, 0.485 mmol) was added and the vial capped. The reaction mixture was heated to 120° C. for 10 min using a microwave oven then cooled down to rt, diluted with EtOAc, filtered through a Celite pad and portioned between $H_2O$/EtOAc. The organic layer was washed with brine, dried over $MgSO_4$, filtered and evaporated. The residue was dissolved in 2 ml of $CH_2Cl_2$ and TFA (0.374 mL, 4.85 mmol) was added. The reaction mixture was stirred at room temperature for 3 h. After this period of time, the mixture was concentrated and purified by preparative reverse phase Gilson HPLC and subsequent neutralization of the combined fractions over PL-$HCO_3$ MP gave the title compound (32 mg, 29% yield) as a white powder. $^1$H-NMR (400 MHz, DMSO-$d_6$, 298 K): δ ppm 2.12 (s, 3 H) 2.16 (s, 3 H) 2.25 (br.s., 2 H) 2.37 (br.s., 2 H) 2.89 (d, 3 H) 3.49 (br.s., 2 H) 3.66 (br.s., 2 H) 6.29 (q, 1 H) 7.69 (d, 1 H) 8.12 (d, 1 H) 8.16 (d, 1 H) 8.30 (t, 1 H) 8.36-8.38 (m, 2 H) 8.84 (d, 1 H) 9.12 (d, 1 H) 9.36 (s, 1 H). MS: 454.2 [M+1]$^+$, $Rt^{(9')}$=1.21 min.

Scheme 5'

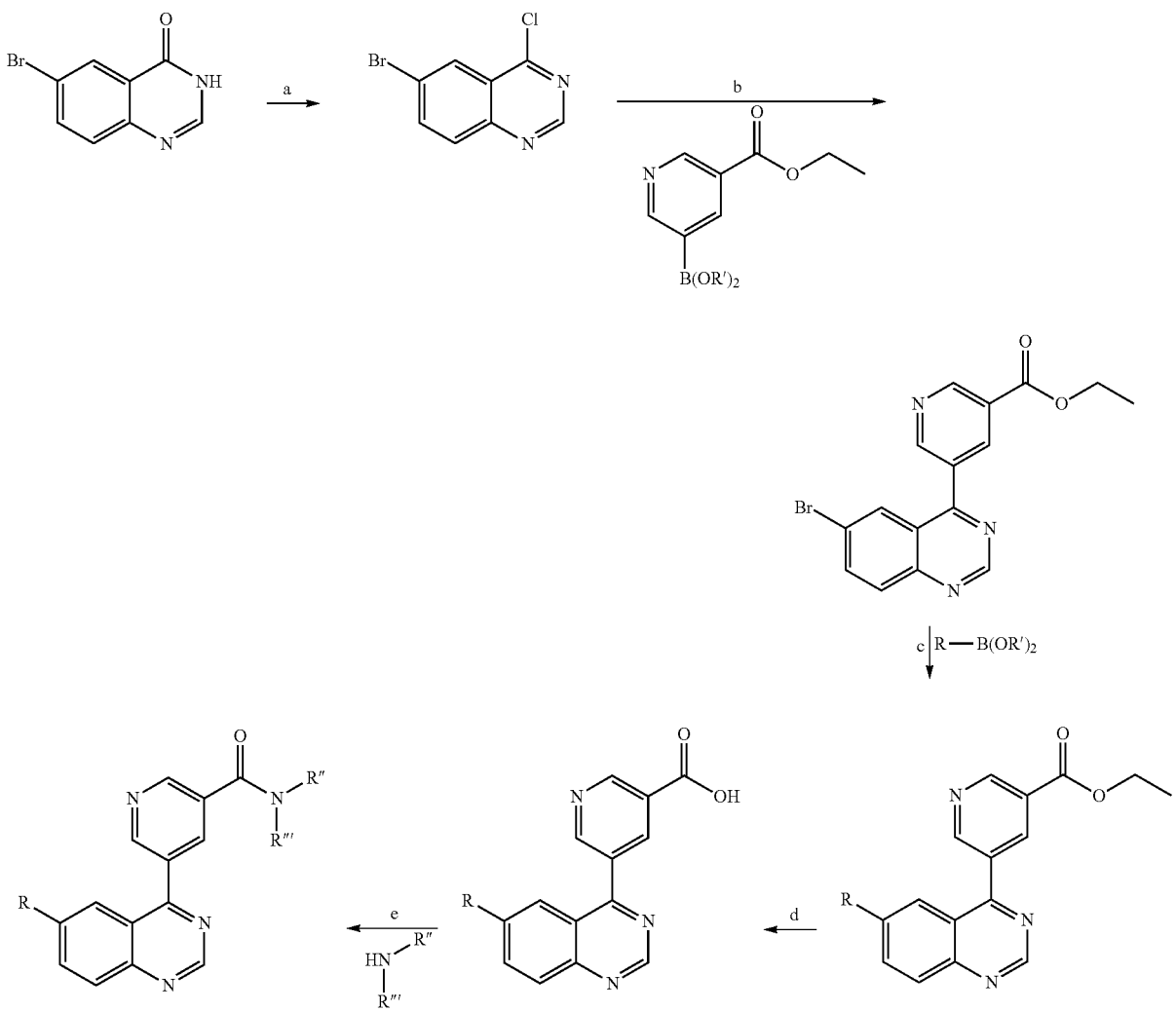

a) Chloronation of 6-Bromo-3H-quinazolin-4-one is performed under customary phosphorus oxychoride condition by heating at reflux or 130° C. in diluted (such as in CH2Cl2) or neat phosphorus oxychoride. b) Suzuki cross-coupling between 6-Bromo-4-chloro-quinazoline and 3-(ethoxycarbonyl)pyridyl-boronic acid or 3-(ethoxycarbonyl)pyridyl-boronate is performed under customary Suzuki conditions using palladium catalyst such as preferably Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Suzuki cross-coupling between aryl bromide and boronic acid or boronic acid derivatives such as boronate of formula R—B(OR')$_2$ is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon. d) Saponification of the carboxylic ester was performed under customary saponification conditions, using among the possible aqueous bases lithium hydroxyide is preferred and organic solvent such a preferably dioxane. The reaction may preferably be carried out at room temperature. e) Condenation of a carboxylic acid with amines of the formula R'''NHR'' preferably takes place under customary condensation conditions. The reaction can be carried on by dissolving the carboxylic acid and the amine of formula R'''NHR'' in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriazole-1-yl)-1,1,3,3-tetramethyluronium hexafluorophosphate (HBTU). The reaction mixture is preferably stirred at a temperature of from approximately –20 to 50° C., especially from –5° C. to 30° C., e.g at 0° C. to room temperature. The reaction my preferably be carried out under an inert gas, e.g. nitrogen or argon.

The final compounds described herein were according the general procedure described in scheme 5'.

Example 76'

{5-[6-(6-Methoxy-pyridin-3-yl)-quinazolin-4-yl]-pyridine-3-yl}-(4-methyl-[1,4]-diazepan-1-yl)-methanone

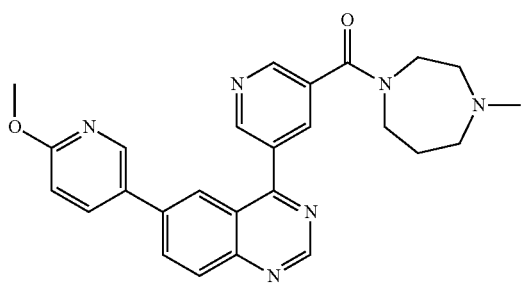 [SMILES: COc1ccc(-c2ccc3ncnc(-c4cncc(C(=O)N5CCCN(C)CC5)c4)c3c2)cn1]

To a solution of 5-[6-(6-methoxy-pyridin-3-yl)-quinazolin-4-yl]-nicotinic acid (100 mg, 0.279 mmol) in 2 mL of CH$_2$Cl$_2$ were added DIPEA (0.097 mL, 0.558 mmol) and propylphosphonic anhydride (solution on DMF, 50%) (0.244 mL, 0.419 mmol). The reaction mixture was stirred at rt for 30 min, 1-methyl-[1,4]-diazepane (65.7 mg, 0.557 mmol) was added and the reaction mixture was stirred at ambient temperature for a further 2 h. More 1-methyl-[1,4]-diazepane (49.27 mg, 0.418 mmol) and DIPEA (0.097 mL, 0.558 mmol) were added and the reaction mixture was stirred at ambient temperature for 16 h. The reaction was quenched with water and extracted with CH$_2$Cl$_2$. The organic layer was washed with brine, dried over MgSO$_4$, filtered and evaporated under vacuum. Purification by preparative reverse phase Gilson HPLC and subsequent neutralization of the combined fractions over PL-HCO$_3$ MP gave the title compound (54 mg, 43% yield) as a white powder. $^1$H-NMR (400 MHz, DMSO-d$_6$, 298 K): δ ppm 1.77 (m, 1 H) 1.86 (m, 1 H) 2.17-2.28 (d, 3 H) 2.44-2.56 (m, 3 H) 2.66 (m, 1 H) 3.50-3.59 (m, 2 H) 3.63-3.72 (m, 2 H) 3.92 (s, 3 H) 6.96 (d, 1 H) 8.14-8.18 (m, 1 H) 8.22-8.24 (dd, 2 H) 8.33 (dt, 1 H) 8.43 (dd, 1 H), 8.63 (t, 1 H) 8.84 (dd, 1 H) 9.12 (dd, 1 H) 9.42 (s, 1 H). MS: 455.2 [M+1]$^+$, Rt$^{(2')}$=0.79 min.

5-[6-(6-Methoxy-pyridin-3-yl)-quinazolin-4-yl]-nicotinic acid

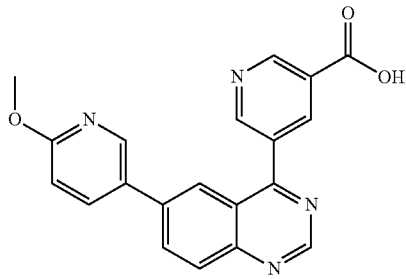 [SMILES: COc1ccc(-c2ccc3ncnc(-c4cncc(C(=O)O)c4)c3c2)cn1]

To a solution of 5-[6-(6-methoxy-pyridin-3-yl)-quinazolin-4-yl]-nicotinic acid ethyl ester (0.91 g, 2.19 mmol, 93% purity (HPLC)) in dioxane (30 mL) was added at rt a 1M aqueous solution of LiOH.H$_2$O (4.38 mL, 4.38 mmol) and the reaction mixture was stirred 3 hours at ambient temperature. The reaction was quenched with a 1M aqueous solution of HCl, the formed precipitate was filtered and dried under vacuum to gave the title compound (570 mg, 72% yield) as a light yellow solid. The filtrate was extracted with EtOAc, the organic layer was washed with brine, dried over MgSO$_4$, filtered and evaporated to give the title compound (205 mg, 27% yield) as a yellow solid. The two isolated solids were combined to gave the title compound (570+205 mg=775 mg, 99% yield). MS: 359.2 [M+1]$^+$, Rt$^{(1')}$=0.96 min.

5-[6-(6-Methoxy-pyridin-3-yl)-quinazolin-4-yl]-nicotinic acid ethyl ester

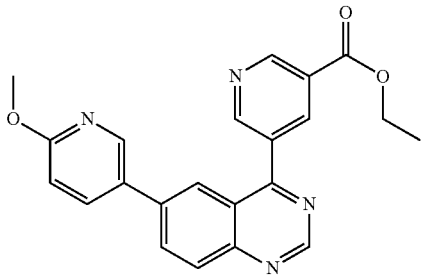 [SMILES: CCOC(=O)c1cncc(-c2ncnc3ccc(-c4ccc(OC)nc4)cc23)c1]

To a mixture of [5-(6-bromo-quinazolin-4-yl)-nicotinic acid ethyl ester (1 g, 2.79 mmol), 2-methoxy-5-pyridin boronic acid (0.448 g, 2.93 mmol) and Pd(PPh$_3$)$_4$ (0.161 mg, 0.140 mmol) was added 15 mL of DME. The reaction mixture was flushed with argon and a 1M aqueous solution of Na$_2$CO$_3$ (5.58 mL, 5.58 mmol) was added and the vial capped. The reaction mixture was heated to 120° C. for 20 min using a microwave oven then cooled down to rt, diluted with EtOAc, filtered through a Celite pad and portioned between H$_2$O/EtOAc. The organic layer was washed with brine, dried over MgSO$_4$, filtered and evaporated. The residue gave the title compound (910 mg, 93% purity, 78% yield). $^1$H-NMR (400 MHz, DMSO-d$_6$, 298 K): δ ppm 1.37 (t, 3 H) 3.91 (s, 3 H) 4.42 (q, 2 H) 6.96 (d, 1 H) 8.14 (dd, 1 H) 8.23-8.25 (m, 2 H) 8.43 (dd, 1 H) 8.62 (d, 1 H) 8.72 (t, 1 H) 9.31 (dd, 2 H) 9.43 (s, 1 H). MS: 387.1 [M+1]$^+$, Rt$^{(2')}$=1.24 min.

Examples 77' to 83', were prepared using procedures analogous to those used for example 76', using appropriate starting materials.

| Example | Structure/Name | Rt (min.) | MS (ES): [M + H]$^+$ | 1H-NMR |
|---|---|---|---|---|
| 77' | {5-[6-(6-Methoxy-pyridin-3-yl)-quinazolin-4-yl]-pyridin-3-yl}-((1S,4S)-5-methyl-2,4-diaza-bicyclo[2.2.1]hept-2-yl)-methanone | 0.78 $^{(2')}$ | 453.2 | $^1$H-NMR (400 MHz, DMSO-d$_6$, 298K): δ ppm 1.68-1.85 (m, 2 H) 2.25-2.27 (d, 3 H) 2.45-2.84 (m, 2 H) 3.28-3.56 (m, 3 H) 3.92 (s, 3 H) 4.35-4.64 (d, 1 H) 6.96 (d, 1 H) 8.14-8.19 (m, 1 H) 8.22-8.26 (m, 2 H) 8.33-8.47 (m, 2 H) 8.62-8.64 (dd, 1 H) 8.90-8.97 (dd, 1 H) 9.15 (m, 1 H) 9.42 (s, 1 H) |
| 78' | {5-[6-(6-Methoxy-pyridin-3-yl)-quinazolin-4-yl]-pyridin-3-yl}-(3,3,4-trimethyl-piperazin-1-yl)-methanone | 0.83 $^{(2')}$ | 469.2 | $^1$H-NMR (400 MHz, DMSO-d$_6$, 298K): δ ppm 0.84 (br. s., 3 H) 0.99 (br. s., 3 H) 2.10 (br. s., 3 H) 2.37 (br. s., 1 H) 2.50 (br. s., 1 H) 3.20 (br. s., 1 H) 3.40 (br. s., 1 H) 3.47 (br. s., 1 H) 3.68 (br. s., 1 H) 3.91 (s, 3 H) 6.92-6.99 (m, 1 H) 8.16 (dd, 1 H) 8.22-8.25 (m, 2 H) 8.29-8.32 (m, 1 H) 8.42 (dd, 1 H) 8.62 (d, 1 H) 8.78-8.87 (d, 1 H) 9.13 (d, 1 H) 9.42 (s, 1 H) |
| 79' | (3,3-Dimethyl-piperazin-1-yl)-{5-[6-(6-methoxy-pyridin-3-yl)-quinazolin-4-yl]-pyridin-3-yl}-methanone | 0.81 $^{(2')}$ | 455.2 | $^1$H-NMR (400 MHz, DMSO-d$_6$, 298K): δ ppm 0.91 (br. s., 3 H) 1.07 (br. s., 3 H) 2.69 (br. s., 1 H) 2.79 (br. s., 1 H) 3.18 (br. s., 1 H) 3.38 (m, 2 H) 3.55 (br. s., 1 H) 3.92 (s, 3 H) 6.95 (br. s., 1 H) 8.16 (dd, 1 H) 8.22-8.25 (m, 2 H) 8.26-8.34 (m, 1 H) 8.40-8.46 (m, 1 H) 8.64 (br. s., 1 H) 8.78-8.85 (m, 1 H) 9.12 (d, 1 H) 9.43 (s, 1 H) |

| Example | Structure/Name | Rt (min.) | MS (ES): [M + H]+ | 1H-NMR |
|---|---|---|---|---|
| 80' | (3,5-Dimethyl-piperazin-1-yl)-{5-[6-(4-methoxy-3-trifluoromethyl-phenyl)-quinazolin-4-yl]-pyridin-3-yl}-methanone | 0.99 (1') | 522.3 | 1H-NMR (400 MHz, DMSO-d6, 298K): δ ppm 0.82 (br. s., 3 H) 1.03 (br. s., 3 H) 2.34 (br. s., 1 H) 2.73 (br. s., 3 H) 3.52 (br. s., 1 H) 3.95 (s, 3 H) 4.41 (br. s., 1 H) 7.40 (d, 1 H) 7.98 (br. s., 1 H) 8.06 (d, 1 H) 8.21-8.23 (m, 2 H) 8.31 (t, 1 H) 8.43 (dd, 1 H) 8.84 (d, 1 H) 9.14 (d, 1 H) 9.43 (s, 1 H) |
| 81' | (3,3-Dimethyl-piperazin-1-yl)-{5-[6-(4-methoxy-3-trifluoromethyl-phenyl)-quinazolin-4-yl]-pyridin-3-yl}-methanone | 0.99 (1') | 522.3 | 1H-NMR (400 MHz, DMSO-d6, 298K): δ ppm 0.90 (br. s., 3 H) 1.08 (br. s., 3 H) 2.69 (br. s., 1 H) 2.80 (br. s., 1 H) 3.17 (br. s., 1 H) 3.39 (m, 2 H) 3.56 (br. s., 1 H) 3.96 (s, 3 H) 7.40 (d, 1 H) 7.98 (br. s., 1 H) 8.07 (d, 1 H) 8.22 (d, 2 H) 8.30 (d, 1 H) 8.43 (m, 1 H) 8.83 (d, 1 H) 9.14 (d, 1 H) 9.42 (s, 1 H) |
| 82' | {5-[6-(4-Methoxy-3-trifluoromethyl-phenyl)-quinazolin-4-yl]-pyridin-3-yl}-morpholin-4-yl-methanone | 1.19 (1') | 495.2 | 1H-NMR (400 MHz, DMSO-d6, 298K): δ ppm 3.43-3.73 (m, 8 H) 3.95 (s, 3 H) 7.41 (d, 1 H) 8.00 (br. s., 1 H) 8.07 (d, 1 H) 8.07 (d, 1 H) 8.21-8.25 (m, 2 H) 8.36 (t, 1 H) 8.44 (dd, 1 H) 8.87 (d, 1 H) 9.15 (d, 1 H) 9.42 (s, 1 H) |
| 83' | (6,6-Difluoro-[1,4]diazepan-1-yl)-{5-[6-(4-methoxy-3-trifluoromethyl-phenyl)-quinazolin-4-yl]-pyridin-3-yl}-methanone | 1.01 (1') | 544.2 | 1H-NMR (400 MHz, DMSO-d6, 298K): δ ppm 2.81 (br. s., 1 H) 2.95-3.23 (m, 3 H) 3.49 (br. s., 1 H) 3.72-3.96 (m, 5 H) 4.16 (m, 1 H) 7.41 (d, 1 H) 7.97 (m, 1 H) 8.06 (m, 1 H) 8.18-8.24 (m, 2 H) 8.40 (br. s., 1 H) 8.45 (m, 1 H) 8.88 (m, 1 H) 9.15 (br. s., 1 H) 9.43 (s, 1 H) |

(1') LC/MS methode 1', (2') LC methode 2'

Example 84'

{5-[6-(4-Methoxy-3-trifluoromethyl-phenyl)-quinazolin-4-yl]-pyridin-3-yl}-((S)-2-methyl-piperazin-1-yl)-methanone

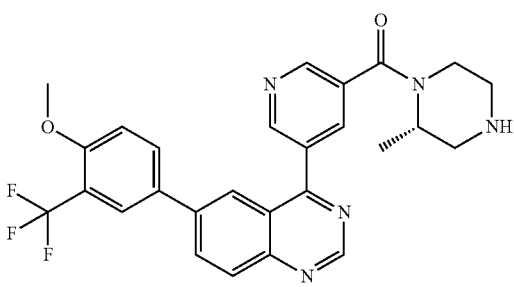 [SMILES: COc1ccc(-c2ccc3ncnc(-c4cncc(C(=O)N5CCNC[C@@H]5C)c4)c3c2)cc1C(F)(F)F]

To a solution of 5-[6-(4-methoxy-3-trifluoromethyl-phenyl)-quinazolin-4-yl)-nicotinic acid (70 mg, 0.165 mmol) in 3 mL of $CH_2Cl_2$ was added HBTU (68.7 mg, 0.181 mmol) and DIPEA (0.057 mL, 0.329 mmol). The reaction mixture was stirred at rt for 20 min, (S)-3-methyl-piperazine-1-carboxylic acid tert-butyl ester (49.4 mg, 0.247 mmol) and DIPEA (0.057 mL, 0.329 mmol) were added and the reaction mixture was stirred at ambient temperature for another 1 h. The reaction mixture was concentrated. The residue was dissolved in 2 ml of $CH_2Cl_2$ and TFA (0.120 mL, 1.646 mmol) was added. The reaction mixture was stirred at room temperature for 3 h. After this period of time, the mixture was concentrated and purified by preparative reverse phase Gilson HPLC and subsequent neutralization of the combined fractions over PL-HCO3 MP gave the title compound (60 mg, 68% yield) as a white powder. $^1$H-NMR (400 MHz, DMSO-$d_6$, 298 K): δ ppm 1.24 (br.s., 3 H) 2.53-2.89 (m, 7 H) 3.96 (s, 3 H) 7.41 (d, 1 H) 7.99 (d, 1 H) 8.07 (dd, 1 H) 8.21-8.23 (dd, 2 H) 8.30 (t, 1 H), 8.44 (dd, 1 H) 8.82 (d, 1 H) 9.13 (d, 1 H) 9.43 (s, 1 H). MS: 508.3 [M+1]$^+$, Rt$^{(1')}$=0.99 min.

Examples 85' was prepared using procedures analogous to those used for example 84', using appropriate starting materials.

| Example | Structure/Name | Rt (min.) | MS (ES): [M + H]$^+$ | 1H-NMR |
|---------|----------------|-----------|----------------------|--------|
| 85' | (1S,4S)-2,5-Diaza-bicyclo[2.2.1]hept-2-yl-{5-[6-(4-methoxy-3-trifluoromethyl-phenyl)-quinazolin-4-yl]-pyridin-3-yl}methanone | 0.97 $^{(1')}$ | 506.2 | $^1$H-NMR (400 MHz, DMSO-$d_6$, 298K): δ ppm 1.48-1.83 (m, 2 H) 2.62-3.07 (m, 2 H) 3.47-3.71 (m, 3 H) 3.96 (s, 3 H) 4.39-4.71 (d, 1 H) 7.39-7.44 (m, 1 H) 7.99 (d, 1 H) 8.8 (m, 1 H) 8.19-8.28 (m, 2 H) 8.33-8.43 (dt, 1 H) 8.45 (d,1 H) 8.93 (dd, 1 H) 9.16 (dd, 1 H) 9.43 (s, 1 H) |

$^{(1')}$ LC methode 1'

Scheme 6'

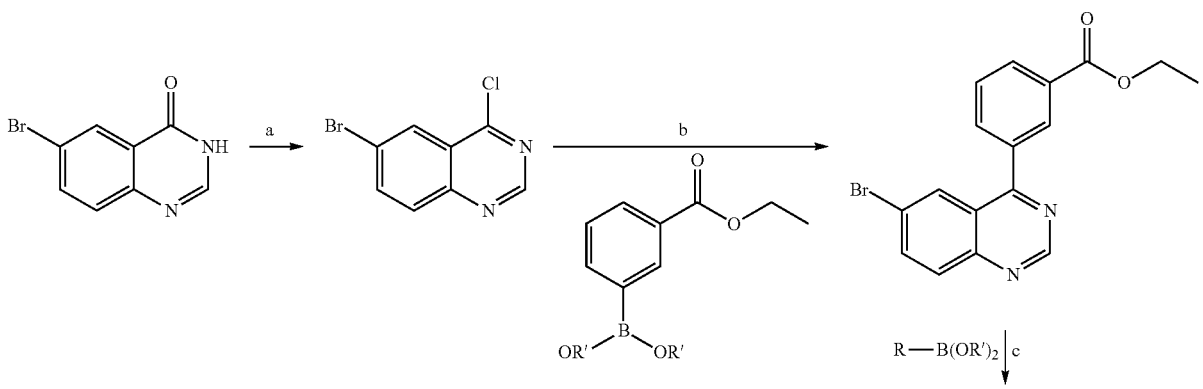

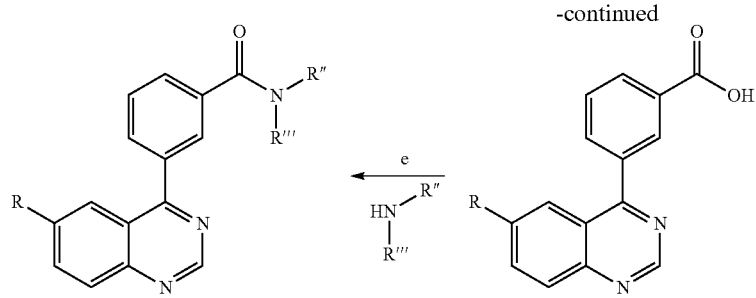 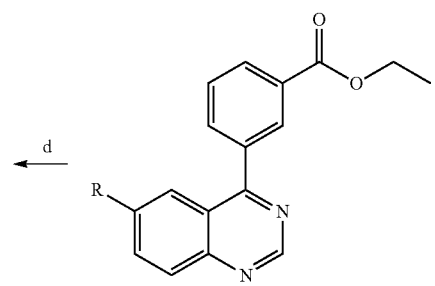

-continued a) Chloronation of 6-Bromo-3H-quinazolin-4-one is performed under customary phosphorus oxychoride condition by heating at reflux or 130° C. in diluted (such as in $CH_2Cl_2$) or neat phosphorus oxychoride. b) Suzuki cross-coupling between 6-Bromo-4-chloro-quinazoline and 3-(ethoxycarbonyl)phenyl-boronic acid or 3-(ethoxycarbonyl)phenyl-boronate is performed under customary Suzuki conditions using palladium catalyst such as preferably Dichlorodiphenylphosphine palladium ($PdCl_2(PPh_3)_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Suzuki cross-coupling between aryl bromide and boronic acid or boronic acid derivatives such as boronate of formula R—B(OR')$_2$ is performed under customary Suzuki conditions using palladium catalyst such as preferably palladium tetrakis(triphenylphosphine) palladium ($Pd(PPh_3)_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon. d) Saponification of the carboxylic ester was performed under customary saponification conditions, using among the possible aqueous bases lithium hydroxyide is preferred and organic solvent such a preferably dioxane. The reaction may preferably be carried out at room temperature. e) Condenation of a carboxylic acid with amines of the formula R'''NHR'' preferably takes place under customary condensation conditions. The reaction can be carried on by dissolving the carboxylic acid and the amine of formula R'''NHR'' in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriazole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon.

The final compounds described herein were according the general procedure described in scheme 6'.

Example 86'

(4-Ethyl-piperazin-1-yl)-{3-[6-(6-methoxy-pyridin-3-yl)-quinazolin-4-yl]-phenyl}-methanone

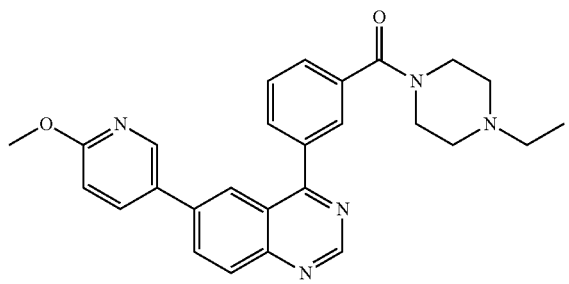 [SMILES: CCN1CCN(C(=O)c2cccc(-c3ncnc4ccc(-c5ccc(OC)nc5)cc34)c2)CC1]

To a stirred solution of 3-[6-(6-methoxy-pyridin-3-yl)-quinazolin-4-yl]-benzoic acid (100 mg, 0.280 mmol) in 2 mL of $CH_2Cl_2$, was added HBTU (127 mg, 0.336 mmol) and DIPEA (0.147 mL, 0.839 mmol). The reaction mixture was stirred at rt for 10 min, 1-ethyl-piperazine (38 mg, 0.336 mmol) was added and the resulting reaction mixture stirred for a further 30 min at rt. The reaction was quenched with $H_2O$, and extracted with $CH_2Cl_2$. The organic layer was washed with brine, dried over $MgSO_4$, filtered and evaporated under vacuum. Purification by preparative reverse phase Gilson HPLC and subsequent neutralization of the combined fractions over PL-$HCO_3$ MP gave the title compound (40 mg, 35% yield) as a white powder. $^1$H-NMR (400 MHz, DMSO-$d_6$, 298 K): δ ppm 0.97 (t, 3 H) 2.18-2.50 (m, 6 H) 3.37-3.71 (m, 4 H) 3.91 (s, 3H) 6.97 (d, 1 H) 7.66 (d, 1 H) 7.74 (dd, 1 H) 7.83 (s, 1 H) 7.99 (d, 1 H) 8.12 (d, 1 H) 8.23 (br.s, 2 H) 8.38 (d, 1 H) 8.60 (s, 1 H) 9.39 (s, 1H). MS: 454.2 [M+1]$^+$, Rt$^{(2')}$=0.89 min.

3-[6-(6-Methoxy-pyridin-3-yl)-quinazolin-4-yl]-benzoic acid

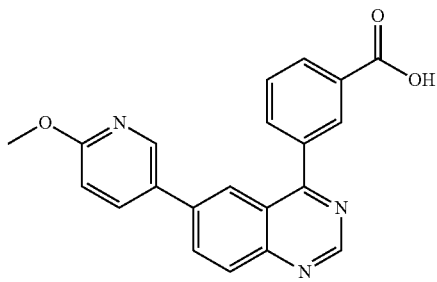 [SMILES: COc1ccc(-c2ccc3ncnc(-c4cccc(C(=O)O)c4)c3c2)cn1]

To a suspension of 3-[6-(6-methoxy-pyridin-3-yl)-quinazolin-4-yl]-benzoic acid ethyl ester (800 mg, 1.91 mmol) in dioxane (20 mL) was added at rt a 1M aqueous solution of LiOH.$H_2O$ (9.55 ml, 9.55 mmol) and the reaction mixture was stirred 4 h at rt. The reaction was quenched with a 1M aqueous solution of HCl (5 mL), the formed precipitate was filtered and dried under vacuum to gave the title compound (700 mg, 90% purity, 92% yield) as a light yellow solid. The compound was used in the next step without further purification. MS: 358.1 [M+1]$^+$, Rt$^{(2')}$=1.11 min.

3-[6-(6-Methoxy-pyridin-3-yl)-quinazolin-4-yl]-benzoic acid ethyl ester

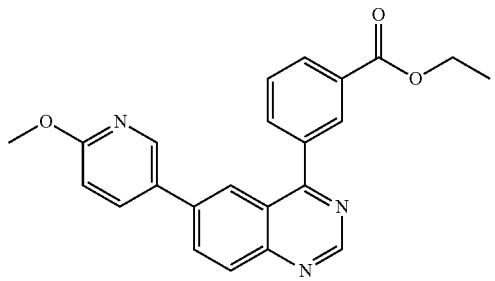 [SMILES: CCOC(=O)c1cccc(-c2ncnc3ccc(-c4ccc(OC)nc4)cc23)c1]

To a mixture of 3-(6-bromo-quinazolin-4-yl)-benzoic acid ethyl ester (845 mg, 2.176 mmol), 2-methoxy-5-pyridineboronic acid (399 mg, 2.61 mmol) and Pd(PPh$_3$)$_4$ (126 mg, 0.109 mmol) was added 20 mL of DME. The reaction mixture was flushed with argon and a 1M aqueous solution of Na$_2$CO$_3$ (4.35 mL, 4.35 mmol) was added and the vial capped. The reaction mixture was heated to 120° C. for 15 min using a microwave oven then cooled down to rt, diluted with CH$_2$Cl$_2$, filtered through a Celite pad and portioned between brine/CH$_2$Cl$_2$. The organic layer was washed with brine, dried over MgSO$_4$, filtered and evaporated. Purification by flash chromatography on silica gel (CH$_2$Cl$_2$/MeOH, 95/5) gave the title compound (800 mg, 92% purity, 88% yield). MS: 386.5 [M+1]$^+$, Rt$^{(2')}$=1.45 min.

Examples 87' to 96', were prepared using procedures analogous to those used for example 86', using appropriate starting materials.

| Example | Structure/Name | Rt (min.) | MS (ES): [M + H]$^+$ | 1H-NMR |
|---|---|---|---|---|
| 87' | {3-[6-(6-Methoxy-pyridin-3-yl)-quinazolin-4-yl]-phenyl}-[4-(2,2,2-trifluoro-ethyl)-piperazin-1-yl]-methanone | 1.36 $^{(1')}$ | 508.3 | $^1$H-NMR (400 MHz, DMSO-d$_6$, 298K): δ ppm 2.46 (br. s., 2 H) 2.68 (br. s., 2 H) 3.17 (q, 2 H) 3.45 (br. s., 2 H) 3.64 (br. s., 2 H) 3.64 (br. s., 2 H) 3.91 (s, 3 H) 6.96 (d, 1 H) 7.66 (dt, 1 H) 7.74 (t, 1 H) 7.85 (br. s., 1 H) 8.00 (dt, 1 H) 8.12 (dd, 1 H) 8.21 (d, 1 H) 8.24 (d, 1 H) 8.40 (dd, 1 H) 8.60 (d, 1 H) 9.39 (s, 1 H) |
| 88' | (3,3-Dimethyl-piperazin-1-yl)-{3-[6-(6-methoxy-pyridin-3-yl)-quinazolin-4-yl]-phenyl}-methanone | 0.95 $^{(2')}$ | 454.3 | $^1$H-NMR (400 MHz, DMSO-d$_6$, 298K): δ ppm 0.92 (br. s., 3 H) 1.08 (br. s., 3 H) 2.65-2.85 (m, 2 H) 3.17 (br. s., 1 H) 3.35-3.40 (m, 2 H) 3.57 (br. s., 1 H) 3.91 (s, 3 H) 6.96 (d, 1 H) 7.64 (br. s., 1 H) 7.73 (t, 1 H) 7.83 (br. s., 1 H) 7.98 (d, 1 H) 8.12 (dd, 1 H) 8.20-8.22 (m, 2 H) 8.39 (d, 1 H) 8.59 (d, 1 H) 9.38 (s, 1 H) |
| 89' | {3-[6-(6-Methoxy-pyridin-3-yl)-quinazolin-4-yl]-phenyl}-(3,3,4-trimethyl-piperazin-1-yl)-methanone | 0.95 $^{(2')}$ | 468.3 | $^1$H-NMR (400 MHz, DMSO-d$_6$, 298K): δ ppm 0.82 (br. s., 3 H) 0.97 (br. s., 3 H) 2.09 (br. s., 3 H) 2.33 (br. s., 1 H) 3.16 (br. s., 1 H) 3.35-3.50 (m, 3 H) 3.65 (br. s., 1 H) 3.91 (s, 3 H) 6.95 (d, 1 H) 7.64 (br. s., 1 H) 7.73 (t, 1 H) 7.83 (br. s., 1 H) 7.99 (d, 1 H) 8.11 (dd, 1 H) 8.19-8.23 (m, 2 H) 8.38 (dd, 1 H) 8.58 (d, 1 H) 9.38 (s, 1 H) |

| Example | Structure/Name | Rt (min.) | MS (ES): [M + H]+ | 1H-NMR |
|---|---|---|---|---|
| 90' | (3,5-Dimethyl-piperazin-1-yl)-{3-[6-(6-methoxy-pyridin-3-yl)-quinazolin-4-yl]-phenyl}-methanone | 0.94 (2') | 454.2 | 1H-NMR (400 MHz, DMSO-d6, 298K): δ ppm 0.83 (br. s., 3 H) 1.02 (br. s., 3 H) 2.29 (br. s., 1 H) 2.68 (br. s., 3 H) 3.51 (br. s. 1 H) 3.91 (s, 3 H) 4.40 (br. s., 1 H) 6.96 (d, 1 H) 7.64 (dt, 1 H) 7.72 (t, 1 H) 7.84 (br. s., 1 H) 7.98 (dt, 1 H) 8.11 (dd, 1 H) 8.20-8.23 (m, 2 H) 8.39 (d, 1 H) 8.59 (d, 1 H) 9.38 (s, 1 H) |
| 91' | {3-[6-(6-Methoxy-pyridin-3-yl)-quinazolin-4-yl]-phenyl}-((1S,4S)-5-methyl-2,5-diaza-bicyclo[2.2.1]hept-2-yl)-methanone | 0.92 (2') | 452.2 | 1H-NMR (400 MHz, DMSO-d6, 298K): δ ppm 1.69 (s, 1 H) 1.72-1.79 (dd, 1 H) 2.26 (d, 3 H) 2.50-2.83 (m, 2 H) 3.33-3.40 (m, 1 H) 3.41-3.52 (m, 2 H) 3.91 (s, 3 H) 4.28-4.61 (d, 1 H) 6.96 (d, 1 H) 7.70-7.82 (m, 2 H) 7.89-8.05 (m, 2 H) 8.09-8.16 (m, 1 H) 8.19-8.26 (m, 2 H) 8.37-8.42 (d, 1 H) 8.57-8.63 (m, 1 H) 9.39 (s, 1 H) |
| 92' | {3-[6-(6-Methoxy-pyridin-3-yl)-quinazolin-4-yl]-phenyl}-(4-methyl-[1,4]diazepan-1-yl)-methanone | 0.93 (2') | 454.2 | 1H-NMR (400 MHz, DMSO-d6, 298K): δ ppm 1.74 (m, 1 H) 1.85 (m, 1 H) 2.15-2.29 (br. s., 3 H) 2.40-2.66 (m, 4 H) 3.45-3.54 (m, 2 H) 3.61-3.69 (m, 2 H) 3.91 (s, 3 H) 3.91 (s, 3 H) 6.96 (d, 1 H) 7.65 (d, 1 H) 7.72 (t, 1 H) 7.83 (br. s., 1 H) 7.98 (m, 1 H) 8.12 (dt, 1 H) 8.21 (d, 2 H) 8.39 (dd, 1 H) 8.59 (br. s, 1 H) 9.38 (s, 1 H) |
| 93' | (1,1-Dioxo-1lambda*6*-thiomorpholin-4-yl)-{3-[6-(6-methoxy-pyridin-3-yl)-quinazolin-4-yl]-phenyl}-methanone | 1.02 (1') | 475.2 | 1H-NMR (400 MHz, DMSO-d6, 298K): δ ppm 3.07-3.38 (br. s., 4 H) 3.67-3.89 (br. s., 2 H) 3.91 (s, 3 H) 3.94-4.17 (br. s., 2 H) 6.97 (d, 1 H) 7.74 (d, 2 H) 8.02 (m, 2 H) 8.13 (dd, 1 H) 8.22 (d, 1 H) 8.24 (d, 1 H) 8.40 (dd, 1 H) 8.60 (d, 1 H) 9.39 (s, 1 H) |

-continued

| Example | Structure/Name | Rt (min.) | MS (ES): [M + H]+ | 1H-NMR |
|---|---|---|---|---|
| 94' | 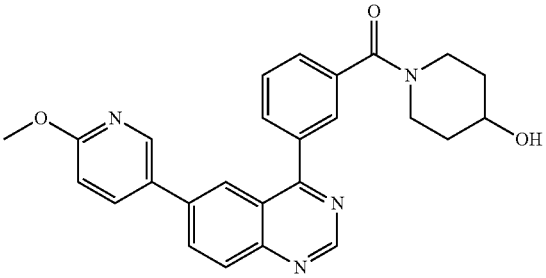<br>(4-Hydroxy-piperidin-1-yl)-{3-[6-(6-methoxy-pyridin-3-yl)-quinazolin-4-yl]-phenyl}-methanone | 0.97 [2'] | 441.5 | 1H-NMR (400 MHz, DMSO-d6, 298K): δ ppm 1.25-1.47 (m, 2 H) 1.62-1.86 (m, 2 H) 3.23 (m, 2 H) 3.54-3.68 (m, 1 H) 3.69-3.76 (m, 1 H) 3.92 (s, 3 H) 3.97-4.11 (m, 1 H) 4.78 (d, 1 H) 6.96 (d, 1 H) 7.64 (d, 1 H) 7.72 (t, 1 H) 7.85 (s, 1 H) 7.98 (dt, 1 H) 8.12 (dd, 1 H) 8.20-8.23 (m, 2 H) 8.40 (d, 1 H) 8.60 (s, 1 H) 9.38 (s, 1 H) |
| 95' | 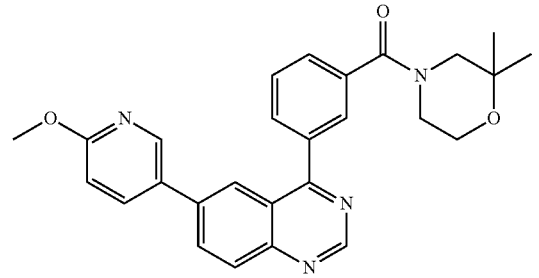<br>(2,2-Dimethyl-morpholin-4-yl)-{3-[6-(6-methoxy-pyridin-3-yl)-quinazolin-4-yl]-phenyl}-methanone | 1.22 [2'] | 455.7 | 1H-NMR (400 MHz, DMSO-d6, 298K): δ ppm 1.06 (br. s., 3 H) 1.18 (br. s., 3 H) 3.37-3.73 (m, 6 H) 3.91 (s, 3 H) 6.95 (d, 1 H) 7.67 (br. s., 1 H) 7.74 (t, 1 H) 7.87 (br. s., 1 H) 8.00 (d, 1 H) 8.12 (dd, 1 H) 8.21 (d, 1 H) 8.24 (d, 1 H) 8.39 (dd, 1 H) 8.59 (d, 1 H) 9.39 (s, 1 H) |
| 96' | 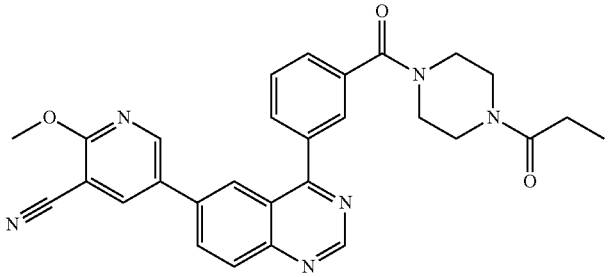<br>2-Methoxy-5-{4-[3-(4-propionyl-piperazine-1-carbonyl)-phenyl]-quinazolin-6-yl}-nicotinonitrile | 1.09 [2'] | 507.6 | 1H-NMR (400 MHz, DMSO-d6, 298K): δ ppm 0.98 (t, 3 H) 2.17-2.40 (m, 2 H) 3.35-3.72 (m, 8 H) 4.07 (s, 3 H) 7.70 (d, 1 H) 7.75 (t, 1 H) 7.90 (br. s., 1 H) 8.02 (d, 1 H) 8.23 (d, 1 H) 8.35 (d, 1 H) 8.43 (dd, 1 H) 8.80 (br. s., 1 H) 8.91 (br. s., 1 H) 9.41 (s, 1 H) |

[1] LC method 1, [2'] LC method 2

Example 97'

{3-[6-(6-Methoxy-pyridin-3-yl)-quinazolin-4-yl]-phenyl}-((R)-2-methyl-piperazin-1-yl)-methanone

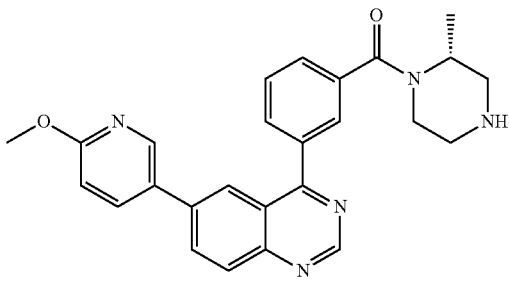 [SMILES: COc1ccc(-c2ccc3ncnc(-c4cccc(C(=O)N5CCNC[C@H]5C)c4)c3c2)cn1]

To a stirred solution of 3-[6-(6-methoxy-pyridin-3-yl)-quinazolin-4-yl]-benzoic acid (100 mg, 0.254 mmol) in 2 mL of DMF, was added HBTU (144 mg, 0.381 mmol) and DIPEA (0.177 mL, 1.016 mmol). The reaction mixture was stirred at rt for 30 min, (R)-3-methyl-piperazine-1-carboxylic acid tert-butyl ester (76 mg, 0.381 mmol) was added and the resulting reaction mixture stirred for a further 2 h at rt. The reaction was quenched with $H_2O$, and extracted with $CH_2Cl_2$. The organic layer was washed with brine, dried over $MgSO_4$, filtered and evaporated under vacuum. The residue was dissolved in 3 ml of $CH_2Cl_2$ and TFA (1 ml) was added. The reaction mixture was stirred at ambient temperature for 2 h. After this period of time, the mixture was concentrated and purified by preparative reverse phase Gilson HPLC and subsequent neutralization of the combined fractions over PL-HCO3 MP gave the title compound (29 mg, 26% yield) as a white powder. 1H-NMR (400 MHz, DMSO-d6, 298 K): δ ppm 1.23 (d, 3 H) 2.55-3.2 (m, 7 H) 3.91 (s, 3H) 6.95 (d, 1 H) 7.62 (d, 1 H) 7.72 (t, 1 H) 7.81 (s, 1 H) 7.98 (d, 1 H) 8.11 (d, 1 H) 8.22 (d, 2 H) 8.38 (d, 1 H) 8.59 (s, 1 H) 9.38 (s, 1H). MS: 440.1 [M+1]+, Rt[2']=0.89 min.

Example 98'

{3-[6-(6-Methoxy-pyridin-3-yl)-quinazolin-4-yl]-phenyl}-((S)-2-methyl-piperazin-1-yl)-methanone

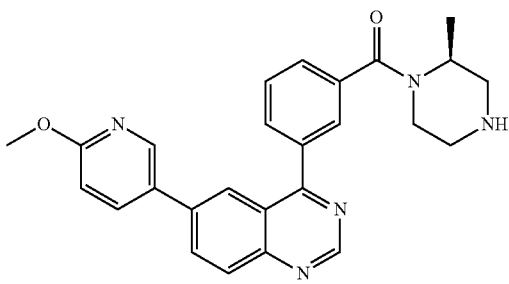 [SMILES: COc1ccc(-c2ccc3ncnc(-c4cccc(C(=O)N5CCNC[C@@H]5C)c4)c3c2)cn1]

To a stirred solution of 3-[6-(6-methoxy-pyridin-3-yl)-quinazolin-4-yl]-benzoic acid (110 mg, 0.308 mmol) in 2.5 mL of DMF, was added HBTU (175 mg, 0.462 mmol) and DIPEA (0.108 mL, 0.616 mmol). The reaction mixture was stirred at rt for 20 min, (S)-3-Methyl-piperazine-1-carboxylic acid tert-butyl ester (123 mg, 0.616 mmol) and DIPEA (0.108 mL, 0.616 mmol) were added and the resulting reaction mixture stirred for a further 2 h at rt. The reaction was quenched with H$_2$O, and extracted with CH$_2$Cl$_2$. The organic layer was washed with brine, dried over MgSO$_4$, filtered and evaporated under vacuum. Purification by flash chromatography on silica gel (Heptane/Ethylacetate, 1/1) gave the intermediate compound (170 mg, 91% purity (UPLC), 93% yield), MS: 540.3 [M+1]$^+$. This residue (170 mg, 0.287 mmol) was dissolved in 2 ml of CH$_2$Cl$_2$ and TFA (0.331 mL, 4.30 mmol) was added. The reaction mixture was stirred at ambient temperature for 2 h. After this period of time, the mixture was quenched with a solution of NaOH (1M) and extracted with CH$_2$Cl$_2$. The organic layer was washed with brine, dried over MgSO$_4$, filtered and evaporated under vacuum. Purification by preparative reverse phase Gilson HPLC and subsequent neutralization of the combined fractions over PL-HCO$_3$ MP gave the title compound (58 mg, 31% yield) as a white powder. $^1$H-NMR (400 MHz, DMSO-d$_6$, 298 K): δ ppm 1.23 (d, 3 H) 2.55-3.15 (m, 7 H) 3.91 (s, 3H) 6.95 (d, 1 H) 7.62 (d, 1 H) 7.72 (t, 1 H) 7.81 (s, 1 H) 7.98 (dt, 1 H) 8.12 (dd, 1 H) 8.21 (d, 1 H) 8.22 (s, 1 H) 8.38 (dd, 1 H) 8.59 (d, 1 H) 9.38 (s, 1H). MS: 440.3 [M+1]$^+$, Rt$^{(1')}$=0.85 min.

Example 99'

((S)-2,4-Dimethyl-piperazin-1-yl)-{3-[6-(6-methoxy-pyridin-3-yl)-quinazolin-4-yl]-phenyl}-methanone

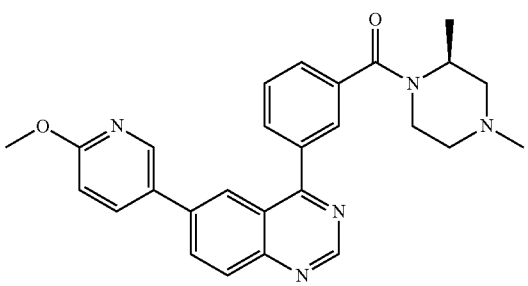

To a solution of {3-[6-(6-methoxy-pyridin-3-yl)-quinazolin-4-yl]-phenyl}-((S)-2-methyl-piperazin-1-yl)-methanone (50 mg, 0.091 mmol) in 1 mL of MeOH was added a 37% solution of formaldehyde (0.008 mL, 0.109 mmol). The reaction mixture was stirred at rt for 30 min, then NaBH$_3$CN (6.86 mg, 0.109 mmol) was added and the resulting reaction mixture stirred for a further 2 h at rt. The reaction was quenched with a solution of NaHCO$_3$ sat and extracted with ethylacetate. The organic layer was washed with brine, dried over MgSO$_4$, filtered and evaporated under vacuum. Purification by preparative reverse phase Gilson HPLC and subsequent neutralization of the combined fractions over PL-HCO$_3$ MP gave the title compound (20 mg, 48% yield) as a white powder. $^1$H-NMR (400 MHz, DMSO-d$_6$, 298 K): δ ppm 1.25 (d, 3 H) 1.82 (m, 1 H) 1.99 (m, 1 H) 2.11 (s, 3 H) 2.53-2.74 (m, 3 H) 3.12-3.27 (m, 2 H) 3.91 (s, 3H) 6.96 (d, 1 H) 7.63 (dt, 1 H) 7.74 (t, 1 H) 7.81 (br.s., 1 H) 7.99 (dt, 1 H) 8.11 (dd, 1 H) 8.21 (d, 1 H) 8.22 (s, 1 H) 8.39 (dd, 1 H) 8.59 (d, 1 H) 9.39 (s, 1H). MS: 454.3 [M+1]$^+$, Rt$^{(1')}$=0.85 min.

Scheme 7'

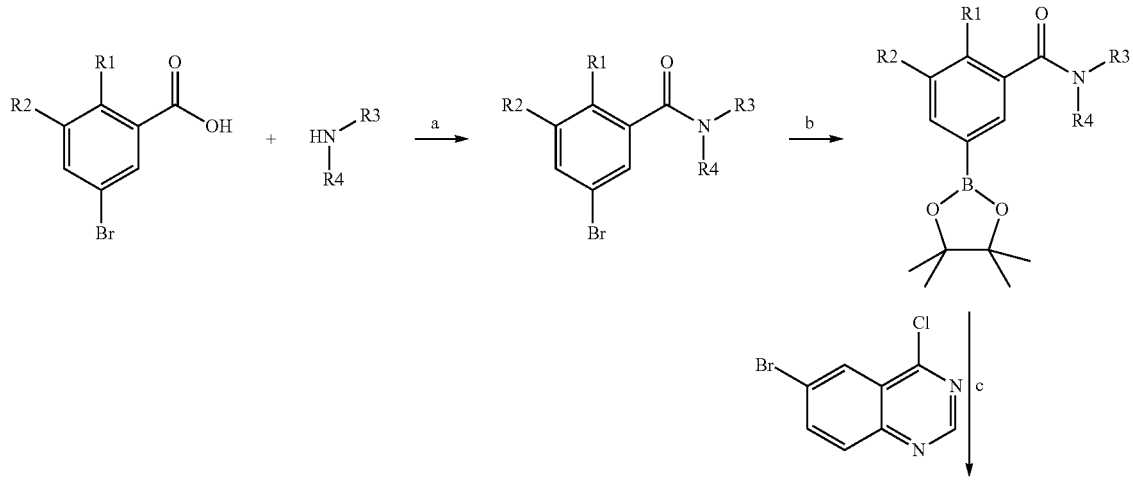

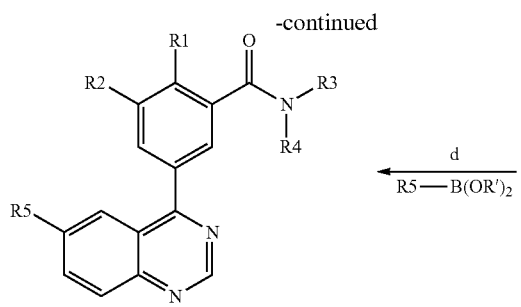
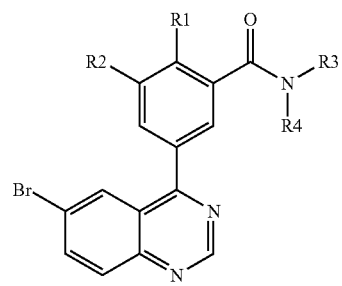

a) Condenation of a carboxylic acid with amines of the formula R3NHR4 preferably takes place under customary condensation conditions. The reaction can be carried on by dissolving the carboxylic acid and the amine of formula R3NHR4 in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriazole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 000° C. to room temperature. The reaction my preferably be carried out under an inert gas, e.g. nitrogen or argon. b) Formation of the boronate ester was performed using palladium catalyst such as preferably 1,1-Bis(diphenylphosphino)-ferrocene]-dichloropalladium (PdCl2(dppf)-CH$_2$Cl$_2$), aqueous base such as preferably potassium acetate organic solvent such as preferably dioxane and Bis-(pinacolato)-diboron. The reaction is preferably stirred at approximately 80° C. for several hours. c) Suzuki cross-coupling between 6-Bromo-4-chloro-quinazoline and the boronate is performed under customary Suzuki conditions using Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. d) Suzuki cross-coupling between aryl bromide and boronic acid or boronic acid derivatives such as boronate of formula R5-B(OR')$_2$ is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon The final compounds described herein were according the general procedure described in scheme 7'.

Example 100'

1-(4-{5-[6-(6-Methoxy-pyridin-3-yl)-quinazolin-4-yl]-2-methyl-benzoyl}-piperazin-1-yl)-ethanone

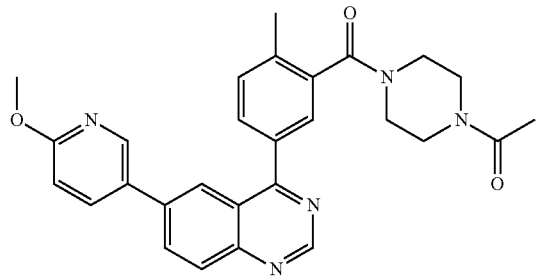 [SMILES: COc1ccc(-c2ccc3ncnc(-c4ccc(C)c(C(=O)N5CCN(C(C)=O)CC5)c4)c3c2)cn1]

A mixture of 1-{4-[5-(6-bromo-quinazolin-4-yl)-2-methyl-benzoyl]-piperazin-1-yl}-ethanone (150 mg, 0.331 mmol), 6-methoxypyridin-3-ylboronic acid (50.6 mg, 0.331 mmol), K$_3$PO$_4$ (105 mg, 0.496 mmol) and PdCl$_2$(PPh$_3$)$_2$ (11.61 mg, 0.017 mmol) was flushed with argon for few minutes. To the mixture was then added 4 ml of Acetonitrile followed by 0.4 ml of water. The vial was capped and the reaction mixture was heated to 120° C. for 10 min using a microwave oven. The mixture was then cooled down to rt, diluted with CH$_2$Cl$_2$ and filtered through a Celite pad. The organic layer was washed with sat. Bicarbonate solution, dried by passing through a phase separating cartridge and evaporated. Purification by preparative reverse phase Gilson HPLC and subsequent neutralization of the combined fractions over SCx-2 cartridge gave the title compound (100 mg, 60% yield) as a powder. 1H-NMR (400 MHz, DMSO-d6) δ ppm 1.90-2.10 (m, 3H) 2.37 (s, 3 H) 3.20-3.80 (br. m., 8 H) 3.91 (s, 3 H), 6.96 (dd, 1 H) 7.57 (dd, 1 H) 7.73 (d, 1 H) 7.87 (dd, 1 H), 8.12 (d, 1 H) 8.18 (s, 1 H) 8.20 (s, 1 H) 8.23 (br. s., 1 H) 8.38 (dd, 1 H) 8.60 (br. s., 1 H) 9.36 (s, 1 H). MS: 482.3 [M+1]$^+$, Rt$^{(1')}$=1.01 min.

1-{4-[5-(6-Bromo-quinazolin-4-yl)-2-methyl-benzoyl]-piperazin-1-yl}-ethanone

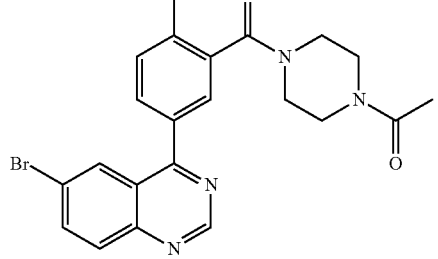

A mixture of 6-bromo-4-chloroquinazoline (1.8 g, 7.39 mmol) (commercial source), 1-{4-[2-methyl-5-(4,4,5,5-tetramethyl-[1,3,2]dioxaborolan-2-yl)-benzoyl]-piperazin-1-yl}-ethanone (4.23 g, 7.39 mmol, 65% purity (UPLC)), K₃PO₄ (2.354 g, 11.09 mmol) and PdCl₂(PPh₃)₂ (0.259 g, 0.370 mmol) was flushed with argon for few minutes. To the mixture was then added 15 ml of Acetonitrile followed by 1.5 ml of water. The vial was capped and the reaction mixture was heated to 120° C. for 10 min using a microwave oven. The mixture was then cooled down to rt, diluted with CH₂Cl₂ and filtered through a Celite pad. The organic layer was washed with sat. Bicarbonate solution, dried by passing through a phase separating cartridge and evaporated. Purification by Flash chromatography using Biotage Isolera system (amine functionalized silica KP-NH, eluting with Cyclohexane/EtOAc 0 to 100%) gave the title compound (1.65 g, 49% yield) as a yellow powder. MS: 453.2-455.1 [M+1]⁺, Rt$^{(1')}$=0.99 min.

Example 101'

1-(4-{3-[6-(6-Methoxy-pyridin-3-yl)-quinazolin-4-yl]-5-trifluoromethyl-benzoyl}-piperazin-1-yl)-ethanone

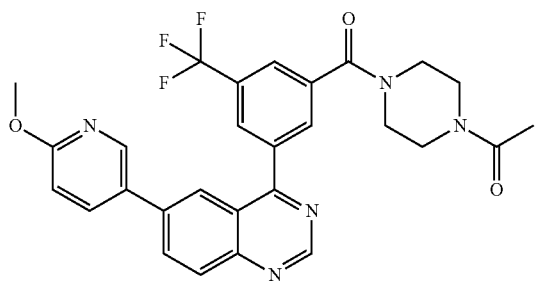 [SMILES: COc1ccc(-c2ccc3ncnc(-c4cc(C(=O)N5CCN(C(C)=O)CC5)cc(C(F)(F)F)c4)c3c2)cn1]

To a mixture of 1-{4-[3-(6-bromo-quinazolin-4-yl)-5-trifluoromethyl-benzoyl]-piperazin-1-yl}-ethanone (120 mg, 0.19 mmol, 80% purity (HPLC)), 2-methoxy-5-pyridine boronic acid (34.9 mg, 0.228 mmol) and Pd(PPh₃)₄ (10.98 mg, 0.009 mmol) was added 2 mL of Acetonitrile. The reaction mixture was flushed with argon and a 1M aqueous solution of Na₂CO₃ (0.380 mL, 0.380 mmol) was added and the vial capped. The reaction mixture was heated to 120° C. for 10 min using a microwave oven then cooled down to rt, diluted with EtOAc, filtered through a Celite pad and washed with EtOAc. The filtrate was concentrated. Purification by preparative reverse phase Gilson HPLC and subsequent neutralization of the combined fractions over PL-SO3H MP gave the title compound (48 mg, 47% yield) as a white powder. ¹H-NMR (400 MHz, DMSO-d₆, 298 K): δ ppm 1.91-2.03 (br.s., 3 H) 3.36-3.70 (m, 8 H) 3.91 (s, 3 H) 6.98 (d, 1 H) 8.06 (br.s., 1 H) 8.14 (d, 1 H) 8.25 (d, 3 H) 8.30 (br.s., 1 H) 8.44 (d, 1 H) 8.63 (br.s., 1 H) 9.42 (s, 1 H). MS: 536.6 [M+1]⁺, Rt$^{(2')}$=1.18 min.

Examples 102' to 109', were prepared using procedures analogous to those used for example 101', using appropriate starting materials.

| Example | Structure/Name | Rt (min.) | MS (ES): [M + H]⁺ | 1H-NMR |
|---|---|---|---|---|
| 102' | ![structure] 1-(4-{5-[6-(2-Methoxy-pyrimidin-5-yl)-quinazolin-4-yl]-2-methyl-benzoyl}-piperazin-1-yl)-ethanone | 0.89 $^{(1')}$ | 483.3 | ¹H-NMR (400 MHz, DMSO-d₆, 298K): δ ppm 1.90-2.06 (m, 3 H) 2.37 (s, 3 H) 3.20-3.80 (br. m., 8 H) 3.98 (s, 3 H) 7.57 (d, 1 H) 7.75 (s, 1 H) 7.88 (d, 1 H) 8.21 (d, 1 H) 8.32 (s, 1 H) 8.41 (d, 1 H) 9.04 (d, 2 H) 9.37 (s, 1 H) |
| 103' | ![structure] 5-{4-[3-(4-Acetyl-piperazine-1-carbonyl)-5-trifluoromethyl-phenyl]-quinazolin-6-yl}-2-methoxy-nicotinonitrile | 1.22 $^{(1')}$ | 561.3 | ¹H-NMR (400 MHz, DMSO-d₆, 298K): δ ppm 1.87-2.07 (br. s., 3) 3.34-3.74 (m, 8 H) 4.06 (s, 3 H) 8.07 (br. s, 1 H) 8.21 (br. s., 1 H) 8.23 (d, 1 H) 8.30 (br. s., 1 H) 8.35 (d, 1 H) 8.46 (d, 1 H) 8.79 (br. s., 1 H) 8.92 (br. s., 1 H) 9.43 (s, 1 H) |

-continued

| Example | Structure/Name | Rt (min.) | MS (ES): [M + H]+ | 1H-NMR |
|---|---|---|---|---|
| 104' | 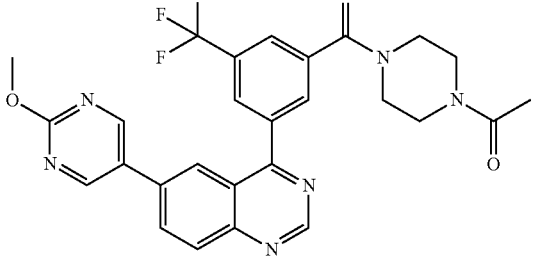<br>1-(4-{3-[6-(2-Methoxy-pyrimidin-5-yl)-quinazolin-4-yl]-5-trifluoromethyl-benzoyl}-piperazin-1-yl)-ethanone | 1.06 (2') | 537.6 | 1H-NMR (400 MHz, DMSO-d6, 298K): δ ppm 1.94-2.06 (br. s. 3 H) 3.35-3.71 (m, 8 H) 3.99 (s, 3 H) 8.06 (br. s., 1 H) 8.23 (br. s., 1 H) 8.27 (d, 1 H) 8.30 (br. s., 1 H) 8.35 (br. s., 1 H) 8.49 (dd, 1 H) 9.08 (br. s., 2 H) 9.45 (s, 1 H) |
| 105' | 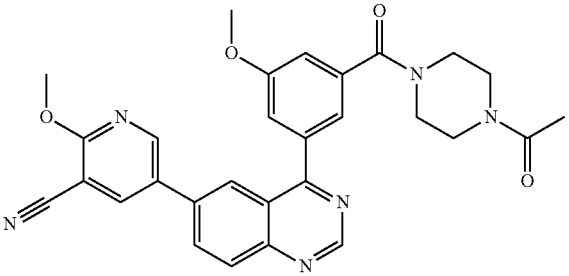<br>5-{4-[3-(4-Acetyl-piperazine-1-carbonyl)-5-methoxy-phenyl]-quinazolin-6-yl}-2-methoxy-nicotinonitrile | 1.13 (1') | 523.3 | 1H-NMR (400 MHz, DMSO-d6, 298K): δ ppm 1.91-2.02 (m, 3 H) 3.39-3.64 (m, 8 H) 3.90 (s, 3 H) 4.06 (s, 3 H) 7.23 (s, 1 H) 7.42 (s, 1 H) 7.50 (s, 1 H) 8.22 (d, 1 H) 8.36 (d, 1 H) 8.43 (d, 1 H) 8.79 (br. s., 1 H) 8.90 (s, 1 H) 9.40 (s, 1 H) |
| 106' | 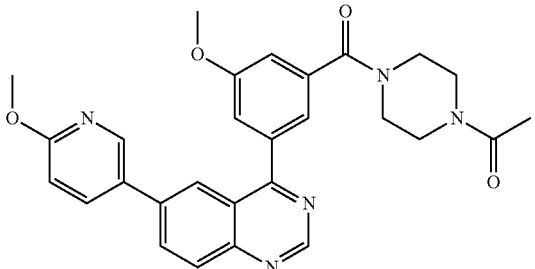<br>1-(4-{3-Methoxy-5-[6-(6-methoxy-pyridin-3-yl)-quinazolin-4-yl]-benzoyl}-piperazin-1-yl)-ethanone | 1.09 (1') | 498.3 | 1H-NMR (400 MHz, DMSO-d6, 298K): δ ppm 1.89-2.08 (m, 3 H) 3.39-3.69 (m, 8 H) 3.90 (s, 3 H) 3.91 (s, 3 H) 6.96 (d, 1 H) 7.23 (s, 1 H) 7.42 (s, 1 H) 7.49 (s, 1 H) 8.12 (d, 1 H) 8.20 (d, 1 H) 8.25 (s, 1 H) 8.40 (dd, 1 H) 8.59 (d, 1 H) |
| 107' | 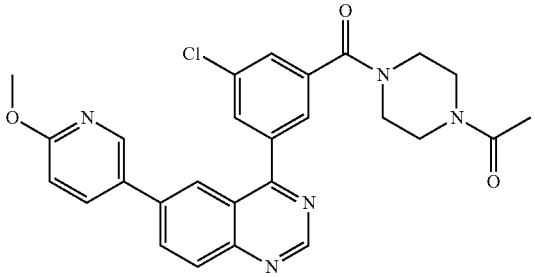 [SMILES: COc1ccc(-c2ccc3ncnc(-c4cc(F)cc(C(=O)N5CCN(C(C)=O)CC5)c4)c3c2)cn1]<br>1-(4-{3-Chloro-5-[6-(6-methoxy-pyridin-3-yl)-quinazolin-4-yl]-benzoyl}-piperazin-1-yl)-ethanone | 1.18 (1') | 502.3 | 1H-NMR (400 MHz, DMSO-d6, 298K): δ ppm 1.88-2.07 (m, 3 H) 3.39-3.69 (m, 8 H) 3.92 (s, 3 H) 6.97 (d, 1 H) 7.77 (s, 1 H) 7.85 (s, 1 H) 8.02 (s, 1 H) 8.15 (d, 1 H) 8.19-8.25 (m, 2 H) 8.42 (dd, 1 H) 8.62 (d, 1 H) 9.39 (s, 1 H) |

| Example | Structure/Name | Rt (min.) | MS (ES): [M + H]+ | 1H-NMR |
|---|---|---|---|---|
| 108' | 1-(4-{3-[6-(6-Methoxy-pyridin-3-yl)-quinazolin-4-yl]-5-methyl-benzoyl}-piperazin-1-yl)-ethanone | 1.12 (1') | 482.3 | $^1$H-NMR (400 MHz, DMSO-$d_6$, 298K): δ ppm 1.87-2.06 (m, 3 H) 3.36-3.71 (m, 8 H) 3.91 (s, 3 H) 6.96 (d, 1 H) 7.50 (s, 1 H) 7.67 (s, 1 H) 7.79 (s, 1 H) 8.11 (dd, 1 H) 8.16-8.24 (m, 2 H) 8.38 (dd, 1 H) 8.59 (d, 1 H) 9.36 (s, 1 H) |
| 109' | 5-{4-[3-(4-Acetyl-piperazine-1-carbonyl)-5-methyl-phenyl]-quinazolin-6-yl}-2-methoxy-nicotinonitrile | 1.16 (1') | 507.3 | $^1$H-NMR (400 MHz, DMSO-$d_6$, 298K): δ ppm 1.88-2.06 (m, 3 H) 3.35-3.69 (m, 8 H) 4.07 (s, 3 H) 7.51 (s, 1 H) 7.67 (s, 1 H) 7.81 (s, 1 H) 8.23 (d, 1 H) 8.34 (d, 1 H) 8.43 (dd, 1 H) 8.79 (d, 1 H) 8.90 (d, 1 H) 9.39 (s, 1 H) |

(1') LC methode 1', (2') LC methode 2'

Scheme 8'

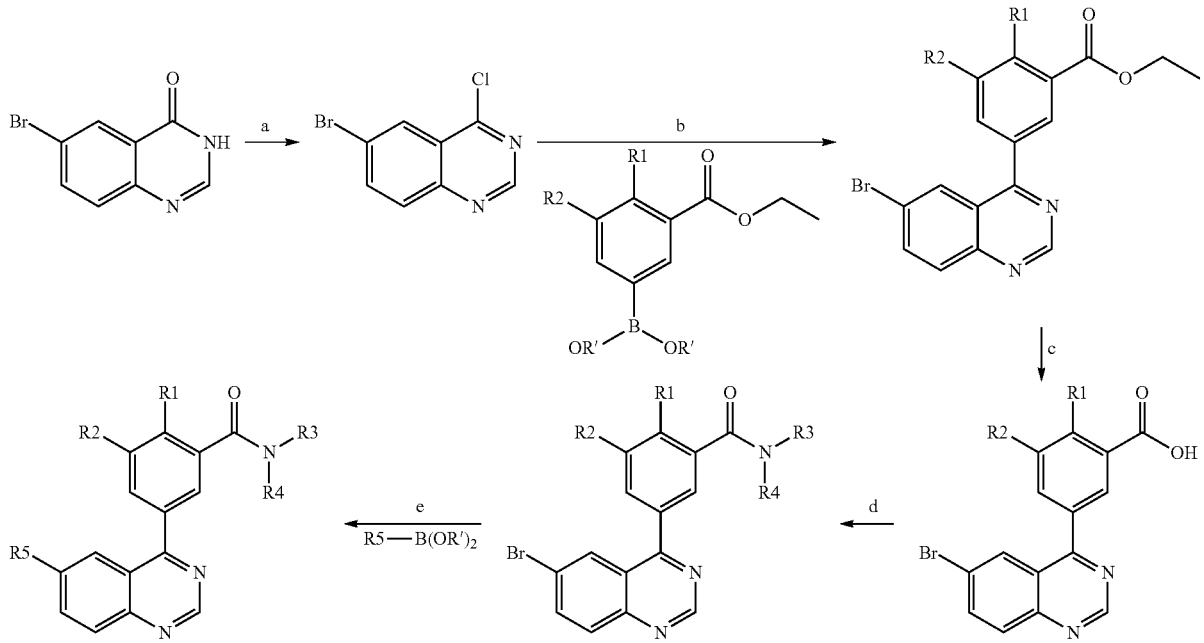

a) Chloronation of 6-Bromo-3H-quinazolin-4-one is performed under customary phosphorus oxychoride condition by heating at reflux or 130° C. in diluted (such as in CH2Cl2) or neat phosphorus oxychoride. b) Suzuki cross-coupling between 6-Bromo-4-chloro-quinazoline and 3-(ethoxycarbonyl)phenyl-boronic acid or 3-(ethoxycarbonyl)phenyl-boronate is performed under customary Suzuki conditions using palladium catalyst such as preferably Dichlorodiphenylphosphine palladium (PdCl₂(PPh₃)₂), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. c) Saponification of the carboxylic ester was performed under customary saponification conditions, using among the possible aqueous bases lithium hydroxyide is preferred and organic solvent such a preferably dioxane. The reaction may preferably be carried out at room temperature. d) Condenation of a carboxylic acid with amines of the formula R3NHR4 preferably takes place under customary condensation conditions. The reaction can be carried on by dissolving the carboxylic acid and the amine of formula R3NHR4 in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example and preferably (2-(1H-Benzotriazole-1-yl)-1,1,3,3-tetramethyluronium hexafluorophosphate (HBTU). The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon. e) Suzuki cross-coupling between aryl bromide and boronic acid or boronic acid derivatives such as boronate of formula R5-B(OR')₂ is performed under customary Suzuki conditions using palladium catalyst such as preferably palladium tetrakis(triphenylphosphine) palladium (Pd(PPh₃)₄), aqueous base and organic solvent such as preferably acetonitrile. The reaction is preferably stirred at a temperature of approximately 100-120° C. in preferably a microwaves oven. The reaction may preferably be carried out under an inert gas such as nitrogen or argon.

The final compounds described herein were according the general procedure described in scheme 8'.

Example 110'

1-(4-{3-Fluoro-5-[6-(6-methoxy-pyridin-3-yl)-quinazolin-4-yl]-benzoyl}-piperazin-1-yl)-ethanone

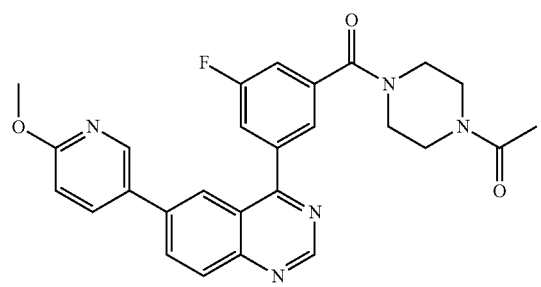

A mixture of 1-{4-[3-(6-bromo-quinazolin-4-yl)-5-fluoro-benzoyl]-piperazin-1-yl}-ethanone (150 mg, 0.328 mmol), 6-methoxypyridin-3-ylboronic acid (50.2 mg, 0.328 mmol), K₃PO₄ (104 mg, 0.492 mmol) and PdCl₂(PPh₃)₂ (11.51 mg, 0.016 mmol) was flushed with argon for few minutes. To the mixture was then added 3 ml of Acetonitrile followed by 0.3 ml of water. The vial was capped and the reaction mixture was heated to 120° C. for 10 min using a microwave oven. The mixture was then cooled down to rt, diluted with CH₂Cl₂ and filtered through a Celite pad. The organic layer was washed with sat. Bicarbonate solution, dried by passing through a phase separating cartridge and evaporated. Purification by preparative reverse phase Gilson HPLC and subsequent neutralization of the combined fractions over SCx-2 cartridge gave the title compound (68 mg, 41% yield) as a powder. ¹H-NMR (400 MHz, DMSO-d₆, 298 K): δ ppm 1.88-2.06 (m, 3 H) 3.34-3.69 (m, 8 H) 3.91 (s, 3 H) 6.97 (d, 1 H) 7.58 (d, 1 H) 7.73 (s, 1 H) 7.85 (dd, 1 H) 8.15 (d, 1 H) 8.19-8.26 (m, 2 H) 8.42 (dd, 1 H) 8.62 (d, 1 H) 9.39 (s, 1 H). MS: 485.0 [M+1]⁺, Rt$^{(1')}$=1.04 min.

1-{4-[3-(6-Bromo-quinazolin-4-yl)-5-fluoro-benzoyl]-piperazin-1-yl}-ethanone

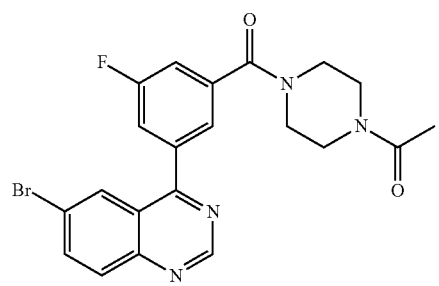 [SMILES: CC(=O)N1CCN(C(=O)c2cc(F)cc(-c3ncnc4ccc(Br)cc34)c2)CC1]

To a mixture of 3-(6-bromo-quinazolin-4-yl)-5-fluoro-benzoic acid (1.36 g, 3.72 mmol) in CH₂Cl₂ (15 mL) was added DIPEA (1.30 mL, 7.44 mmol) and HBTU (1.694 g, 4.47 mmol) at rt. The reaction mixture was stirred at rt for 20 min. To the mixture was then added 1-(piperazin-1-yl)ethanone (0.572 g, 4.47 mmol) and the reaction mixture was stirred at rt for 1 h. The reaction was quenched with a saturated aqueous solution of NaHCO₃ and extracted with CH₂Cl₂. The organic layer was washed twice with brine, dried by passing through a phase separating cartridge and evaporated. Purification by Flash chromatography using Biotage Isolera system (amine functionalized silica KP-NH, eluting with Cyclohexane/EtOAc 0 to 100%) gave the title compound (1.20 g, 68% yield) as a beige foam. MS: 457.4-459.3 [M+1]⁺, Rt$^{(2')}$=1.03 min.

3-(6-Bromo-quinazolin-4-yl)-5-fluoro-benzoic acid

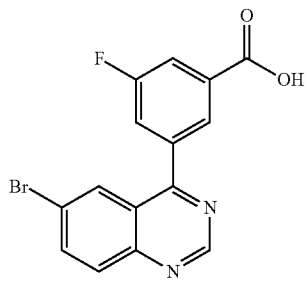 [SMILES: O=C(O)c1cc(F)cc(-c2ncnc3ccc(Br)cc23)c1]

To a solution of 3-(6-bromo-quinazolin-4-yl)-5-fluoro-benzoic acid ethyl ester (1.417 g, 3.78 mmol) in dioxane (15 mL) was added at rt a 2M aqueous solution of LiOH.H₂O (7.55 mL, 7.55 mmol) and the reaction mixture was stirred 2 h at rt. The reaction was quenched with a 2M aqueous solution of HCl (5 mL), the formed precipitate was filtered and dried under vacuum to give the title compound (1.36 g, 99% yield) as a white solid. MS: 349.0 [M+1]⁺, Rt$^{(1')}$=1.17 min.

3-(6-Bromo-quinazolin-4-yl)-5-fluoro-benzoic acid ethyl ester

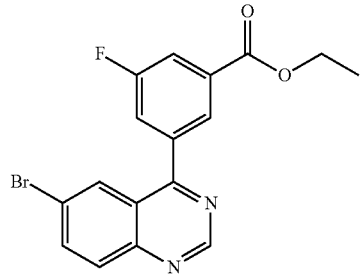 [SMILES: CCOC(=O)c1cc(F)cc(-c2ncnc3ccc(Br)cc23)c1]

A mixture of 6-bromo-4-chloroquinazoline (1.5 g, 6.16 mmol), 3-(ethoxycarbonyl)-5-fluorophenylboronic acid (1.306 g, 6.16 mmol), K₃PO₄ (1.961 g, 9.24 mmol) and PdCl₂(PPh₃)₂ (216 mg, 0.308 mmol) was flushed with argon for few minutes. To the mixture was then added 24 ml of Acetonitrile followed by 2.4 ml of water. The vial was capped and the reaction mixture was heated to 120° C. for 10 min using a microwave oven. The mixture was then cooled down to rt, diluted with CH₂Cl₂ and filtered through a Celite pad. The organic layer was washed with sat. Bicarbonate solution, dried by passing through a phase separating cartridge and evaporated. Purification by Flash chromatography using Biotage Isolera system (amine functionalized silica KP-NH, eluting with Cyclohexane/EtOAc 0 to 30%) gave the title compound (1.417 g, 61% yield) as a solid. MS: 375.1-377.1 [M+1]⁺, Rt$^{(1')}$=1.54 min.

The compound of example 111' was prepared using procedures analogous to those used for example 110', using appropriate starting materials.

Example 112'

1-(4-{4-[6-(2-Methoxy-pyrimidin-5-yl)-quinazolin-4-yl]-pyridine-2-carbonyl}-piperazin-1-yl)-ethanone

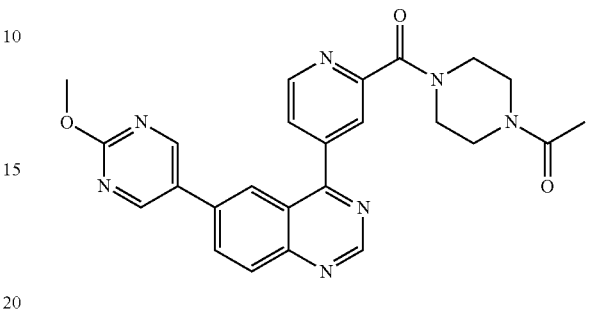

To a mixture of 2-methoxypyrimidin-5-yl boronic acid (36.9 mg, 0.240 mmol) and Pd(PPh₃)₄ (11.56 mg, 0.010 mmol) was added a solution of 1-{4-[4-(6-Bromo-quinazolin-4-yl)-pyridine-2-carbonyl]-piperazin-1-yl}-ethanone (88 mg, 0.200 mmol) in 2 mL of acetonitrile. The reaction mixture was flushed with argon and a 1M aqueous solution of Na2CO3 (0.400 mL, 0.400 mmol) was added and the vial capped. The reaction mixture was heated to 120° C. for 10 min using a microwave oven then cooled down to rt, diluted with EtOAc, filtered through a Celite pad and concentrated. Purification by preparative reverse phase Gilson HPLC and subsequent neutralization of the combined fractions over PL-HCO₃ MP gave the title compound (40 mg, 43% yield) as a white powder. ¹H-NMR (400 MHz, DMSO-d₆, 298 K): δ ppm 2.01-2.06 (d, 3 H) 3.48 (br.s., 3 H) 3.58 (br.s., 3 H) 3.65 (br.s., 1 H) 3.73 (br.s., 1 H) 3.99 (s, 3 H) 8.01 (dd, 1 H) 8.06 (br.s., 1 H) 8.28 (d, 1 H) 8.34 (d, 1 H) 8.49 (dd, 1 H) 8.87 (d, 1 H) 9.09 (s, 2 H) 9.47 (s, 1 H). MS: 470.6 [M+1]⁺, Rt$^{(2')}$=0.78 min.

The compounds of examples 113' and 114' were prepared using procedures analogous to those used for example 112', using appropriate starting materials.

| Example | Structure/Name | Rt (min.) | MS (ES): [M + H]⁺ | 1H-NMR |
|---|---|---|---|---|
| 111' | ![structure] 1-(4-{3-Fluoro-5-[6-(2-methoxy-pyrimidin-5-yl)-quinazolin-4-yl]-benzoyl}-piperazin-1-yl)-ethanone | 0.91 $^{(1')}$ | 487.3 | ¹H-NMR (400 MHz, DMSO-d₆, 298K): δ ppm 2.00 (d, 3 H) 3.35-3.74 (m, 8 H) 3.99 (s, 3 H) 7.58 (d, 1 H) 7.74 (s, 1 H) 7.85 (d, 1 H) 8.24 (d, 1 H) 8.35 (s, 1 H) 8.46 (d, 1 H) 9.07 (s, 2 H) 9.41 (s, 1 H) |

$^{(1')}$ LC methode 1'

| Example | Structure/Name | Rt (min.) | MS (ES): [M + H]+ | 1H-NMR |
|---|---|---|---|---|
| 113' | 5-{4-[2-(4-Acetyl-piperazine-1-carbonyl)-pyridin-4-yl]-quinazolin-6-yl}-2-methoxy-nicotinonitrile | 0.97 (2') | 494.6 | 1H-NMR (400 MHz, DMSO-$d_6$, 298K): δ ppm 2.00-2.05 (br. s., 3 H) 3.44-3.75 (m, 8 H) 4.07 (s, 3 H) 8.01 (d, 1 H) 8.06 (br. s., 1 H) 8.27 (d, 1 H) 8.35 (d, 1 H) 8.46-8.51 (m, 1 H) 8.82 (br. s., 1 H) 8.88 (d, 1 H) 8.95 (br. s., 1 H) 9.47 (s, 1 H) |
| 114' | 1-(4-{4-[6-(6-Methoxy-5-trifluoromethyl-pyridin-3-yl)-quinazolin-4-yl]-pyridine-2-carbonyl}-piperazin-1-yl)-ethanone | 1.13 (2') | 537.6 | 1H-NMR (400 MHz, DMSO-$d_6$, 298K): δ ppm 1.96-2.08 (d, 3 H) 3.44-3.75 (m, 8 H) 4.06 (s, 3 H) 8.02 (dd, 1 H) 8.08 (br. s., 1 H) 8.26 (d, 1 H) 8.34 (d, 1 H) 8.50-8.53 (dd, 2 H) 8.87 (d, 1 H) 8.90 (d, 1 H) 9.47 (s, 1 H) |

(2')LC methode 2'

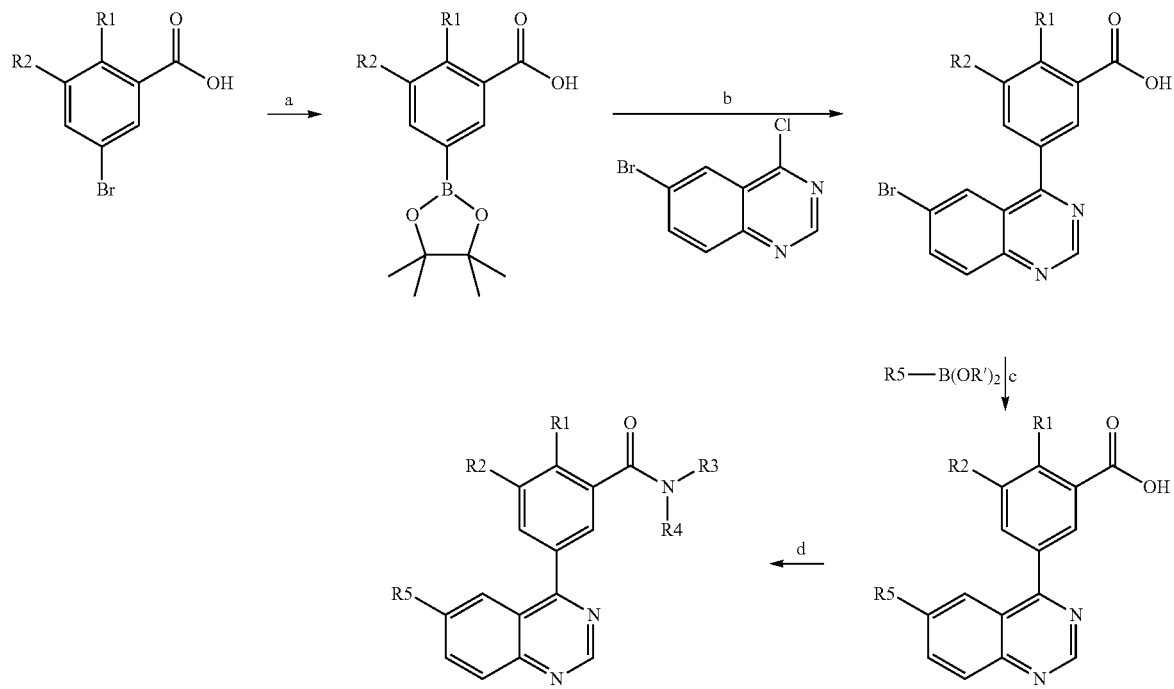

Scheme 9' a) Formation of the boronate ester was performed using palladium catalyst such as preferably 1,1-Bis(diphenylphosphino)-ferrocene]-dichloropalladium (PdCl2(dppf)-CH$_2$Cl$_2$), aqueous base such as preferably potassium acetate organic solvent such as preferably dioxane and Bis-(pinacolato)-diboron. The reaction is preferably stirred at approximately 80° C. for several hours. b) Suzuki cross-coupling between 6-Bromo-4-chloro-quinazoline and the boronate is performed under customary Suzuki conditions using Dichlorodiphenylphosphine palladium (PdCl$_2$(PPh$_3$)

2), aqueous base and organic solvent such as preferably acetonitrile. The reaction is preferably stirred at a temperature of approximately 100-120° C. in preferably a microwaves oven. The reaction may preferably carried out under an inert gas such as nitrogen or atrgon. d) Suzuki cross-coupling between aryl bromide and boronic acid or boronic acid derivatives such as boronate of formula R5-B(OR')$_2$ is performed under customary Suzuki conditions using palladium catalyst such as preferably Dichlorodiphenylphosphine palladium (PdCl$_2$(PPh$_3$)$_2$), aqueous base and organic solvent such as preferably acetonitrile. The reaction is preferably stirred at a temperature of approximately 100-120° C. in preferably a microwaves oven. The reaction may preferably carried out under an inert gas such as nitrogen or argon. c) Suzuki cross-coupling between aryl bromide and boronic acid or boronic acid derivatives such as boronate of formula R5-B(OR')$_2$ is performed under customary Suzuki conditions using palladium catalyst such as preferably palladium tetrakis(triphenylphosphine) palladium (Pd(PPh$_3$)$_4$), aqueous base and organic solvent such as preferably acetonitrile. The reaction is preferably stirred at a temperature of approximately 100-120° C. The reaction may preferably carried out under an inert gas such as nitrogen or argon. d) Condenation of a carboxylic acid with amines of the formula R3NHR4 preferably takes place under customary condensation conditions. The reaction can be carried on by dissolving the carboxylic acid and the amine of formula R3NHR4 in a suitable solvent, for example halogenated hydrocarbon, such as methylene chloride, N,N-dimethylformamide, N,N-dimethylacetamide, N-2-methyl-pyrrolidone, methylene chloride, or a mixture of two or more such solvents, and by the addition of a suitable base, for example triethylamine, diisopropylethylamine (DIPEA) or N-methylmorpholine and a suitable coupling agent that forms a reactive derivative of the carboxylic acid in situ, for example (2-(1H-Benzotriazole-1-yl)-1,1,3,3-tetramethyluronium hexafluorophosphate (HBTU) and preferably Propylphosphonic anhydride. The reaction mixture is preferably stirred at a temperature of from approximately −20 to 50° C., especially from −5° C. to 30° C., e.g at 0° C. to room temperature. The reaction my preferably be carried out under an inert gas, e.g. nitrogen or argon.

The final compounds described herein were according the general procedure described in scheme 9'.

Example 115'

{5-[6-(6-Methoxy-pyridin-3-yl)-quinazolin-4-yl]-2-methyl-phenyl}-(4-methyl-piperazin-1-yl)-methanone

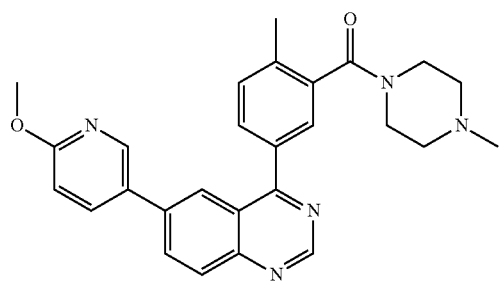 [SMILES: COc1ccc(-c2ccc3ncnc(-c4ccc(C)c(C(=O)N5CCN(C)CC5)c4)c3c2)cn1]

To a mixture of 5-[6-(6-methoxy-pyridin-3-yl)-quinazolin-4-yl]-2-methyl-benzoic acid (55 mg, 0.148 mmol) in CH$_2$Cl$_2$ (2 mL) was added DIPEA (0.039 mL, 0.222 mmol) and propylphosphonic anhydride sol. 50% in DMF (0.065 mL, 0.222 mmol) at rt. The reaction mixture was stirred at rt for 30 min. To the mixture was then added 1-methylpiperazine (0.016 mL, 0.148 mmol) and the reaction mixture was stirred at rt for 12 h. The reaction was quenched with a saturated aqueous solution of NaHCO$_3$ and extracted with CH$_2$Cl$_2$. The organic layer was then dried by passing through a phase separating cartridge and evaporated. Purification by preparative reverse phase HPLC and subsequent neutralization of the combined fractions over SCx-2 cartridge gave the title compound (32 mg, 46% yield) as a yellow powder. $^1$H-NMR (400 MHz, DMSO-d$_6$, 298 K): δ ppm 2.13 (s, 3 H) 2.17 (br. s., 2H) 2.34 (d, 2 H) 2.36 (s, 3 H) 3.26 (t, 2 H) 3.65 (br. s., 2H) 3.92 (s, 3 H) 6.96 (d, 1 H) 7.56 (d, 1 H) 7.64 (d, 1 H) 7.87 (dd, 1 H) 8.12 (dd, 1 H) 8.19 (d, 1 H) 8.23 (d, 1 H) 8.38 (dd, 1 H) 8.59 (d, 1 H) 9.36 (s, 1 H). MS: 454.3 [M+1]$^+$, Rt$^{(1')}$=: 0.87 min.

5-[6-(6-Methoxy-pyridin-3-yl)-quinazolin-4-yl]-2-methyl-benzoic acid

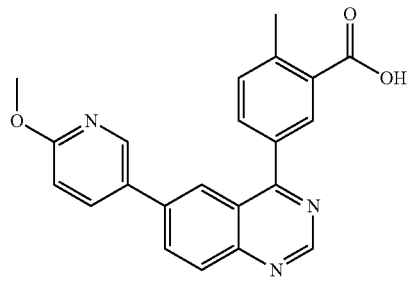 [SMILES: COc1ccc(-c2ccc3ncnc(-c4ccc(C)c(C(=O)O)c4)c3c2)cn1]

A mixture of 5-(6-bromo-quinazolin-4-yl)-2-methyl-benzoic acid (318 mg, 0.741 mmol), 6-methoxypyridin-3-ylboronic acid (113 mg, 0.741 mmol), K$_3$PO$_4$ (236 mg, 1.112 mmol) and PdCl$_2$(PPh$_3$)$_2$ (26.0 mg, 0.037 mmol) was flushed with argon for few minutes. To the mixture was then added 6 ml of Acetonitrile followed by 0.8 ml of water. The vial was capped and the reaction mixture was heated to 120° C. for 5 min using a microwave oven. The mixture was then cooled down to rt, diluted with EtOAc and filtered through a Celite pad. The organic layer was washed with a solution of HCl 2M. As a part of the compound remains into the aqueous phase, the pH was basified around 8 and the compound was extracted again with EtOAc. The combined organic layers were dried over Na$_2$SO$_4$, filtered and evaporated. Precipitation in EtOAc/Cyclohexane gave the title compound (168 mg, 61% yield) as a yellow powder. MS: 372.2 [M+1]$^+$. Rt$^{(1')}$=1.22 min.

5-(6-Bromo-quinazolin-4-yl)-2-methyl-benzoic acid

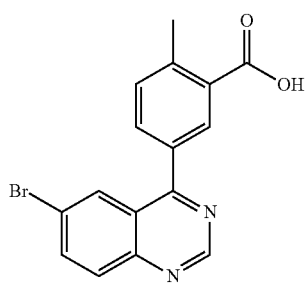 [SMILES: Cc1ccc(-c2ncnc3ccc(Br)cc23)cc1C(=O)O]

A mixture of 6-bromo-4-chloroquinazoline (300 mg, 1.232 mmol), 2-methyl-5-(4,4,5,5-tetramethyl-[1,3,2]dioxaborolan-2-yl)-benzoic acid (497 mg, 1.232 mmol, purity 65% by UPLC), $K_3PO_4$ (392 mg, 1.848 mmol) and $PdCl_2(PPh_3)_2$ (43.2 mg, 0.062 mmol) was flushed with argon for few minutes. To the mixture was then added 8 ml of Acetonitrile followed by 0.8 ml of water. The vial was capped and the reaction mixture was heated to 120° C. for 5 min using a microwave oven. The mixture was then cooled down to rt, diluted with EtOAc and filtered through a Celite pad. The organic layer was washed with a solution of HCl 2M, dried over $Na_2SO_4$, filtered and evaporated. Precipitation in EtOAc/Cyclohexane gave the title compound (318 mg, 80% purity, 60% yield) as a beige powder. MS: 345.0 [M+1]$^+$, Rt$^{(1')}$=1.23 min.

Examples 116' to 117', were prepared using procedures analogous to those used for example 115', using appropriate starting materials.

are 5 μM and 6 μg/mL, respectively. The reaction is started by the addition of PI3 kinase, e.g. PI3 kinase δ. p110δ. The components of the assay are added per well as follows:

10 μl test compound in 5% DMSO per well in columns 2-1.

Total activity is determined by addition 10 μl of 5% vol/vol DMSO in the first 4 wells of column 1 and the last 4 wells of column 12.

The background is determined by addition of 10 μM control compound to the last 4 wells of column 1 and the first 4 wells of column 12.

2 mL 'Assay mix' are prepared per plate:
1.912 mL of HEPES assay buffer
8.33 μl of 3 mM stock of ATP giving a final concentration of 5 μM per well
1 μl of [$^{33}$P]ATP on the activity date giving 0.05 μCi per well

| Example | Structure/Name | Rt (min.) | MS (ES): [M + H]$^+$ | 1H-NMR |
|---|---|---|---|---|
| 116' | 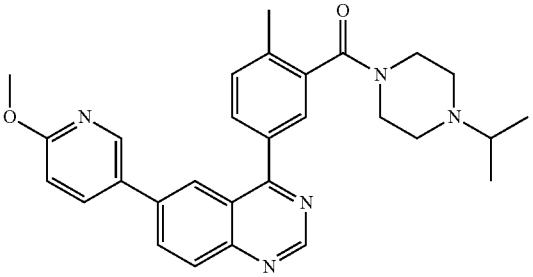<br>(4-Isopropyl-piperazin-1-yl)-{5-[6-(6-methoxy-pyridin-3-yl)-quinazolin-4-yl]-2-methyl-phenyl}-methanone | 0.92 $^{(1')}$ | 482.4 | $^1$H-NMR (400 MHz, DMSO-d$_6$, 298K): δ ppm 0.89 (d, 6 H) 2.28 (t, 2 H) 2.35 (s, 3 H) 2.42-2.48 (m, 2 H) 3.25 (d, 2 H) 3.47-3.76 (m, 2 H) 3.91 (s, 3 H) 6.95 (d, 1 H) 7.56 (d, 1 H) 7.62 (d, 1 H) 7.85 (d, 1 H) 8.08-8.15 (m, 1 H) 8.17-8.24 (m, 2 H) 8.34-8.41 (m, 1 H) 8.59 (d, 1 H) 9.36 (s, 1 H) |
| 117' | 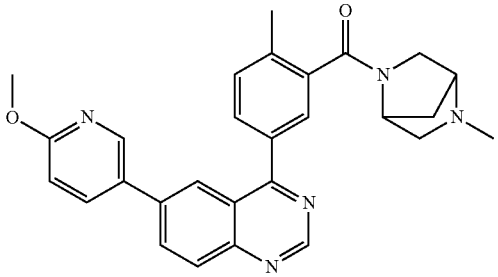<br>(2,5-Diaza-bicyclo[2.2.1]hept-2-yl)-{5-[6-(6-methoxy-pyridin-3-yl)-quinazolin-4-yl]-2-methyl-phenyl}-methanone | 0.88 $^{(1')}$ | 466.3 | $^1$H-NMR (400 MHz, DMSO-d$_6$, 298K): δ ppm 1.65-1.88 (m, 2 H) 2.21-2.27 (m, 3 H) 2.36-2.40 (m, 3 H) 2.53-3.23 (m, 4 H) 3.40-3.55 (m, 2 H) 3.90-3.93 (m, 3 H) 6.93-7.00 (m, 1 H) 7.52-7.61 (m, 1 H) 7.67-7.73 (m, 1 H) 7.82-7.90 (m, 1 H) 8.08-8.15 (m, 1 H) 8.17-8.24 (m, 1 H) 8.33-8.41 (m, 1 H) 8.56-8.61 (m, 1 H) 9.34-9.38 (m, 1 H) |

$^{(1')}$ LC/MS methode 1'

Biological Evaluation

The activity of a PI3K inhibitor, wherein said inhibitor has an inhibitory action on the PI3K isoform delta, can be assessed by the following in vitro & in vivo methods.

Biological Assays

1 Determination of Enzymatic PI3K Alpha and PI3K Delta Isoform Inhibition 1.1 Test of Lipid Kinase Activity The efficacy of the PI3K inhibitors, wherein said inhibitor has an inhibitory action on the PI3K isoform delta, can be demonstrated as follows:

The kinase reaction is performed in a final volume of 50 μl per well of a half area COSTAR, 96 well plate. The final concentrations of ATP and phosphatidyl inositol in the assay 30 μl of 1 mg/mL PI stock giving a final concentration of 6 μg/mL per well 5 μl of 1 M stock $MgCl_2$ giving a final concentration of 1 mM per well 20 μl of the assay mix are added per well.

2 mL 'Enzyme mix' are prepared per plate (x* μl PI3 kinase p110β in 2 mL of kinase buffer). The 'Enzyme mix' is kept on ice during addition to the assay plates.

The volume of enzyme is dependent on the enzymatic activity of the batch in use.

20 μl 'Enzyme mix' are added/well to start the reaction.

The plate is then incubated at room temperature for 90 minutes.

The reaction is terminated by the addition of 50 µl WGA-SPA bead (wheat germ agglutinin-coated Scintillation Proximity Assay beads) suspension per well.

The assay plate is sealed using TopSeal-S (heat seal for polystyrene microplates, PerkinElmer LAS [Deutschland] GmbH, Rodgau, Germany) and incubated at room temperature for at least 60 minutes.

The assay plate is then centrifuged at 1500 rpm for 2 minutes using the Jouan bench top centrifuge (Jouan Inc., Nantes, France).

The assay plate is counted using a Packard TopCount, each well being counted for 20 seconds.

In a more preferred assay, the kinase reaction is performed in a final volume of 10 µl per well of a low volume non-binding CORNING, 384 well black plate (Cat. No. #3676). The final concentrations of ATP and phosphatidyl inositol (PI) in the assay are 1 µM and 10 µg/mL, respectively. The reaction is started by the addition of ATP.

The components of the assay are added per well as follows:

50 nl test compounds in 90% DMSO per well, in columns 1-20, 8 concentrations (⅓ and 1/3.33 serial dilution step) in single.

Low control: 50 nl of 90% DMSO in half the wells of columns 23-24 (0.45% in final).

High control: 50 nl of reference compound (e.g. compound of Example 7 in WO 2006/122806) in the other half of columns 23-24 (2.5 µM in final).

Standard: 50 nl of reference compound as just mentioned diluted as the test compounds in columns 21-22.

20 mL 'buffer' are prepared per assay:
  200 µl of 1M TRIS HCl pH7.5 (10 mM in final)
  60 µl of 1M $MgCl_2$ (3 mM in final)
  500 µl of 2M NaCl (50 mM in final)
  100 µl of 10% CHAPS (0.05% in final)
  200 µl of 100 mM DTT (1 mM in final)
  18.94 mL of nanopure water 10 mL 'PI' are prepared per assay:
  200 µl of 1 mg/mL I-alpha-Phosphatidylinositol (Liver Bovine, Avanti Polar Lipids Cat. No. 840042C MW=909.12) prepared in 3% OctylGlucoside (10 µg/mL in final)
  9.8 mL of 'buffer'

10 mL 'ATP' are prepared per assay:
  6.7 µl of 3 mM stock of ATP giving a final concentration of 1 µM per well 10 mL of 'buffer'

2.5 mL of each PI3K construct are prepared per assay in 'PI' with the following final concentration:
  10 nM PI3K alfa EMV B1075
  25 nM beta EMV BV949
  10 nM delta EMV BV1060
  150 nM gamma EMV BV950

5 µl of 'PI/PI3K' are added per well.

5 µl 'ATP' are added per well to start the reaction.

The plates are then incubated at room temperature for 60 minutes (alfa, beta, delta) or 120 minutes (gamma).

The reaction is terminated by the addition of 10 µl Kinase-Glo (Promega Cat. No. #6714).

The assay plates are read after 10 minutes in Synergy 2 reader (BioTek, Vermont USA) with an integration time of 100 milliseconds and sensitivity set to 191.

Output: The High control is around 60'000 counts and the Low control is 30'000 or lower This luminescence assay gives a useful Z'ratio between 0.4 and 0.7

The Z' value is a universal measurement of the robustness of an assay. A Z' between 0.5 and 1.0 is considered an excellent assay.

For this assay, the PI3K constructs mentioned are prepared as follows:

1.2 Generation of Gene Constructs

Two different constructs, BV 1052 and BV 1075, are used to generate the PI3 Kinase α proteins for compound screening.

PI3Kα BV-1052 p85(iSH2)-Gly Linker-p110a(D20aa)-C-Term his Tag

PCR products for the inter SH2 domain (iSH2) of the p85 subunit and for the p110-a subunit (with a deletion of the first 20 amino acids) are generated and fused by overlapping PCR. The iSH2 PCR product is generated from first strand cDNA using initially primers gwG130-p01 (5'-CGA-GAATATGATAGATTATATGAAGAAT-3') (SEQ ID NO: 1) and gwG130-p02 (5'-TGGTTT-AATGCTGTTCAT-ACGTTTGTCAAT-3') (SEQ ID NO: 2). Subsequently in a secondary PCR reaction, Gateway (Invitrogen AG, Basel, Switzerland) recombination AttB1 sites and linker sequences are added at the 5'end and 3'end of the p85 iSH2 fragment respectively, using primers gwG130-p03 (5'-GGGACAAGTTTGTACAAAAAAGCAGGCTAC-GAAGGAGATATACATAT-GCGAGAATATGATAGAT-TATATGAAGAAT-3') (SEQ ID NO: 3) and gwG152-p04 (5'-TACCATAATTCCACCACCACCACCGGAAATTC-CCCCTGGTTT-AATGCTGTTCATACGTTTGTCAAT-3') (SEQ ID NO: 4).

The p110-a fragment is also generated from first strand cDNA, initially using primers gwG152-p01 (5'-CTAGTG-GAATGTTTACTACCAAATGG-3') (SEQ ID NO: 5) and gwG152-p02 (5'-GTTCAATG-CATGCTGTTTAATT-GTGT-3') (SEQ ID NO: 6).

In a subsequent PCR reaction, linker sequence and a Histidine tag are added at the 5'end and 3'end of the p110-a fragment respectively, using primers gw152-p03 (5'-GGGGGAATTTCCGGTGGTGGTGGTGGAATTATGG-TAC-TAGTGGAATGTTTACTACC-AAATGGA-3') (SEQ ID NO: 7) and gwG152-p06 (5'-AGCTCCGTGATGGT-GATGGTGATGTGCTCCGTTCAATG-CATGCTGTT-TAATTGTGT-3') (SEQ ID NO: 8).

The p85-iSH2/p110-a fusion protein is assembled in a third PCR reaction by the overlapping linkers at the 3'end of the iSH2 fragment and the 5'end of the p110-a fragment, using the above mentioned gwG130-p03 primer and a primer containing an overlapping Histidine tag and the AttB2 recombination sequences (5'-GGGACCACTTTGTA-CAAGAAAGCTGGGTTTAAGCTCCGTGATGGT-GATGGTGAT-GTGCTCC-3') (SEQ ID NO: 9).

This final product is recombined in a (Invitrogen) OR reaction into the donor vector pDONR201 to generate the ORF318 entry clone. This clone is verified by sequencing and used in a Gateway LR reaction to transfer the insert into the Gateway adapted pBlueBac4.5 (Invitrogen) vector for generation of the baculovirus expression vector LR410.

PI3Kα BV-1075 p85(iSH2)-12 XGly Linker-p110a(D20aa)-C-Term his Tag

The construct for Baculovirus BV-1075 is generated by a three-part ligation comprised of a p85 fragment and a p110-a fragment cloned into vector pBlueBac4.5. The p85 fragment is derived from plasmid p1661-2 digested with Nhe/Spe. The p110-a fragment derived from LR410 (see above) as a SpeI/HindIII fragment. The cloning vector pBlueBac4.5 (Invitrogen) is digested with Nhe/HindIII. This results in the construct PED 153.8

The p85 component (iSH2) is generated by PCR using ORF 318 (described above) as a template and one forward primer KAC1028 (5'-GCTAGCATGCGAGAATATGATA-GATTATATGAAGAATATACC) (SEQ ID NO: 10) and two reverse primers, KAC1029 (5'-GCCTCCACCACCTC-CGCCTGGTTTAATGCTGTTCATACGTTTGTC) (SEQ ID NO: 11) and KAC1039 (5'-TACTAGTCCGCCTCCAC-CACCTCCGCCTCCACCACCTCCGCC) (SEQ ID NO: 12).

The two reverse primers overlap and incorporate the 12× Gly linker and the N-terminal sequence of the p110a gene to the SpeI site. The 12× Gly linker replaces the linker in the BV1052 construct. The PCR fragment is cloned into pCR2.1 TOPO (Invitrogen). Of the resulting clones, p1661-2 is determined to be correct. This plasmid is digested with Nhe and SpeI and the resulting fragment is gel-isolated and purified for sub-cloning.

The p110-a cloning fragment is generated by enzymatic digest of clone LR410 (see above) with Spe I and HindIII. The SpeI site is in the coding region of the p110a gene. The resulting fragment is gel-isolated and purified for sub-cloning.

The cloning vector, pBlueBac4.5 (Invitrogen) is prepared by enzymatic digestion with Nhe and HindIII. The cut vector is purified with Qiagen (Quiagen N.V, Venlo, Netherlands) column and then dephosphorylated with Calf Intestine alkaline phosphatase (CIP) (New England BioLabs, Ipswich, Mass.). After completion of the CIP reaction the cut vector is again column purified to generate the final vector. A 3 part ligation is performed using Roche Rapid ligase and the vendor specifications.

PI3Kβ BV-949 p85(iSH2)-Gly Linker-p110b(Full-Length)-C-Term his Tag

PCR products for the inter SH2 domain (iSH2) of the p85 subunit and for the full-length p110-b subunit are generated and fused by overlapping PCR.

The iSH2 PCR product is generated from first strand cDNA initially using primers gwG130-p01 (5'-CGA-GAATATGATAGATTATATGAAGAAT-3') (SEQ ID NO: 1) and gwG130-p02 (5'-TGGTTT-AATGCTGTTCAT-ACGTTTGTCAAT-3') (SEQ ID NO: 2). Subsequently, in a secondary PCR reaction Gateway (Invitrogen) recombination AttB1 sites and linker sequences are added at the 5'end and 3'end of the p85 iSH2 fragment respectively, using primers gwG130-p03 (5'-GGGACAAGTTTGTA-CAAAAAAGCAGGCTACGAAGGAGATA-TACATAT-GCGAGAATATGATAGATTATATGAAGAAT-3') (SEQ ID NO: 3) and gwG130-p05 (5'-ACTGAAGCATCCTCCTC-CTCCTCCTCCTGGTTTAAT-GCTGTTCATACGTTT-GTC-3') (SEQ ID NO: 13).

The p110-b fragment is also generated from first strand cDNA initially using primers gwG130-p04 (5'-ATTAAAC-CAGGAGGAGGAGGAGGAGGATGCTTCA-GTTTCATAATGCC-TCCTGCT-3') (SEQ ID NO: 4) which contains linker sequences and the 5'end of p110-b and gwG130-p06 (5'-AGCTCCGTGATGGTGATGGTGATGT-GCTCCAGATCTGTAGTCTTT-CCGAACTGTGTG-3') (SEQ ID NO: 14) which contains sequences of the 3'end of p110-b fused to a Histidine tag.

The p85-iSH2/p110-b fusion protein is assembled by an overlapping PCR a reaction of the linkers at the 3'end of the iSH2 fragment and the 5'end of the p110-b fragment, using the above mentioned gwG130-p03 primer and a primer containing an overlapping Histidine tag and the AttB2 recombination sequences (5'-GGGACCACTTTGTA-CAAGAAAGCTGGGTTT-AAGCTCCGTGATGGT-GATGGTGATGTGCTCC-3') (SEQ ID NO: 15).

This final product is recombined in a Gateway (Invitrogen) OR reaction into the donor vector pDONR201 to generate the ORF253 entry clone. This clone is verified by sequencing and used in a Gateway LR reaction to transfer the insert into the Gateway adapted pBlueBac4.5 (Invitrogen) vector for generation of the baculovirus expression vector LR280.

PI3Kδ BV-1060 p85(iSH2)-Gly Linker-p110d(Full-Length)-C-Term his Tag

PCR products for the inter SH2 domain (iSH2) of the p85 subunit and for the full-length p110-d subunit are generated and fused by overlapping PCR.

The iSH2 PCR product is generated from first strand cDNA using initially primers gwG130-p01 (5'-CGA-GAATATGATAGATTATATGAAGAAT-3') (SEQ ID NO: 1) and gwG130-p02 (5'-TGGTTT-AATGCTGTTCAT-ACGTTTGTCAAT-3') (SEQ ID NO: 2). Subsequently, in a secondary PCR reaction Gateway (Invitrogen) recombination AttB1 sites and linker sequences are added at the 5'end and 3'end of the p85 iSH2 fragment respectively, using primers gwG130-p03 (5'-GGGACAAGTTTGTA-CAAAAAAGCAGGCTACGAAGGAGATATACAT-AT-GCGAGAATATGATAGATTATATGAAGAAT-3') (SEQ ID NO: 3) and gwG154-p04 (5'-TCCTCCTCCTCCTCCTC-CTGGTTTAATGCTGTTCATACGTTTGTC-3') (SEQ ID NO: 16).

The p110-a fragment is also generated from first strand cDNA using initially primers gwG154-p01 (5'-ATGC-CCCCTGGGGTGGACTGCCCCAT-3') (SEQ ID NO: 17) and gwG154-p02 (5'-CTACTG-CCTGTTGTCTTTGGA-CACGT-3') (SEQ ID NO: 18).

In a subsequent PCR reaction linker sequences and a Histidine tag is added at the 5'end and 3'end of the p110-d fragment respectively, using primers gw154-p03 (5'-AT-TAAACCAGGAGGAGGAGGAGGAGGAC-CCCCTGGGGTGGAC-TGCCCCATGGA-3') (SEQ ID NO: 19) and gwG154-p06 (5'-AGCTCCGTGATGGTGAT-GGTGATGTGCT-CCCTGCCTGTTGTCTTTGGA-CACGTTGT-3') (SEQ ID NO: 20).

The p85-iSH2/p110-d fusion protein is assembled in a third PCR reaction by the overlapping linkers at the 3'end of the iSH2 fragment and the 5'end of the p110-d fragment, using the above mentioned gwG130-p03 primer and a primer containing an overlapping Histidine tag and the Gateway (Invitrogen) AttB2 recombination sequences (5'-GGGACCACTTTGTA-CAAGAAAGCTGGGTTT-AAGCTCCGTGATGGTGATGGTGATGTGCTCC-3') (SEQ ID NO: 21).

This final product is recombined in a Gateway (Invitrogen) OR reaction into the donor vector pDONR201 to generate the ORF319 entry clone. This clone is verified by sequencing and used in a Gateway LR reaction to transfer the insert into the Gateway adapted pBlueBac4.5 (Invitrogen) vector for generation of the baculovirus expression vector LR415.

PI3Kγ BV-950 p110g(D144aa)-C-Term his Tag

This construct is obtained from Roger Williams lab, MRC Laboratory of Molecular Biology, Cambridge, UK (November, 2003). Description of the construct in: Pacold M. E. et al. (2000) Cell 103, 931-943.

1.3 Protein Expression and Purification

Methods to generate recombinant baculovirus and protein for PI3K isoforms:

The pBlue-Bac4.5 (for a, b, and d isoforms) or pVL1393 (for g) plasmids containing the different PI3 kinase genes are co-transfected with BaculoGold WT genomic DNA (BD Biosciences, Franklin Lakes, N.J., USA) using methods recommended by the vendor. Subsequently, the recombinant baculovirus obtained from the transfection is plaque-purified on Sf9 insect cells to yield several isolates expressing recombinant protein. Positive clones are selected by anti-HIS or anti-isoform antibody western. For PI3K alpha and delta isoforms, a secondary plaque-purification is performed on the first clonal virus stocks of PI3K. Amplification of all baculovirus isolates is performed at low multiplicity of infection (moi) to generate high-titer, low passage stock for protein production. The baculoviruses are designated BV1052 ($\alpha$) and BV1075 ($\alpha$), BV949 ($\beta$), BV1060 ($\delta$) and BV950 ($\gamma$).

Protein production involves infection (passage 3 or lower) of suspended Tn5 (*Trichoplusia ni*) or TiniPro (Expression Systems, LLC, Woodland, Calif., USA) cells in protein-free media at moi of 2-10 for 39-48 hours in 2 l glass Erlenmyer flasks (110 rpm) or wave-bioreactors (22-25 rpm). Initially, 10 l working volume wave-bioreactors are seeded at a density of 3e5 cells/mL at half capacity (5 L). The reactor is rocked at 15 rpm during the cell growth phase for 72 hours, supplemented with 5% oxygen mixed with air (0.2 l per minute). Immediately prior to infection, the wave-reactor cultures are analyzed for density, viability and diluted to approximately 1.5e6 cell/mL. 100-500 mL of high titer, low passage virus is added following 2-4 hours of additional culture. Oxygen is increased to 35% for the 39-48 hour infection period and rocking platform rpm increased to 25. During infection, cells are monitored by Vicell viability analyzer (Beckman Coulter, Inc, Fullerton, Calif., USA) bioprocess for viability, diameter and density. Nova Bioanalyzer (NOVA Biomedical Corp., Waltham, Mass., USA) readings of various parameters and metabolites (pH, $O_2$ saturation, glucose, etc.) are taken every 12-18 hours until harvest. The wave-bioreactor cells are collected within 40 hours post infection. Cells are collected by centrifugation (4 degrees C at 1500 rpm), and subsequently maintained on ice during pooling of pellets for lysis and purification. Pellet pools are made with small amounts of cold, un-supplemented Grace's media (w/o protease inhibitors).

PI3K Alpha Purification Protocol for HTS (BV1052)

PI3K alpha is purified in three chromatographic steps: immobilized metal affinity chromatography on a Ni Sepharose resin (GE Healthcare, belonging to General Electric Company, Fairfield, Conn., USA), gel filtration utilizing a Superdex 200 26/60 column (GE Healthcare), and finally a cation exchange step on a SP-XL column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The pool from the GFC column is diluted into a low salt buffer and applied to a prepared SP-XL column. The column is washed with low salt buffer until a stable A280 baseline absorbance is achieved, and eluted using a 20 column volume gradient from 0 mM NaCl to 500 mM NaCl. Again, fractions from the SP-XL column are analyzed by Coomassie stained SDS-PAGE gels, and fractions containing the target protein are pooled. The final pool is dialyzed into a storage buffer containing 50% glycerol and stored at −20° C. The final pool is assayed for activity in a phosphoinosititol kinase assay.

PI3K Beta Purification Protocol for HTS (BV949)

PI3K beta is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinostitol kinase assay.

PI3K Gamma Purification Protocol for HTS (BV950)

PI3K gamma is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinostitol kinase assay.

PI3K Delta Purification Protocol for HTS (BV1060)

PI3K delta is purified in three chromatographic steps: immobilized metal affinity chromatography on a Ni Sepharose resin (GE Healthcare), gel filtration utilizing a Superdex 200 26/60 column (GE Healthcare), and finally a anion exchange step on a Q-HP column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing the target protein are pooled and applied to a prepared GFC column. Fractions from the GFC column are analyzed by Coomassie stained SDS-PAGE gels, and fractions containing the target protein are pooled. The pool from the GFC column is diluted into a low salt buffer and applied to a prepared Q-HP column. The column is washed with low salt buffer until a stable A280 baseline absorbance is achieved, and eluted using a 20 column volume gradient from 0 mM NaCl to 500 mM NaCl. Again, fractions from the Q-HP column are analyzed by Coomassie stained SDS-PAGE gels, and fractions containing the target protein are pooled. The final pool is dialyzed into a storage buffer containing 50% glycerol and stored at −20° C. The final pool is assayed for activity in the phosphoinostitol kinase assay.

$IC_{50}$ is determined by a four parameter curve fitting routine that comes along with "excel fit". A four parameter logistic equation is used to calculate $IC_{50}$ values (IDBS XLfit) of the percentage inhibition of each compound at 8 concentrations (usually 10, 3.0, 1.0, 0.3, 0.1, 0.030, 0.010 and 0.003 µM). Alternatively, $IC_{50}$ values are calculated using idbsXLfit model 204, which is a 4 parameter logistic model.

Yet alternatively, for an ATP depletion assay, the PI3K inhibitors, wherein said inhibitors have an inhibitory action on the PI3K isoform delta, to be tested are dissolved in DMSO and directly distributed into a white 384-well plate at 0.5 µl per well. To start the reaction, 10 µl of 10 nM PI3 kinase and 5 µg/mL 1-alpha-phosphatidylinositol (PI) are added into each well followed by 10 µl of 2 µM ATP. The reaction is performed until approx 50% of the ATP is depleted, and then stopped by the addition of 20 µl of Kinase-Glo solution (Promega Corp., Madison, Wis., USA). The stopped reaction is incubated for 5 minutes and the remaining ATP is then detected via luminescence. $IC_{50}$ values are then determined.

Some of the compounds of examples 1-49 and 51-95 show a certain level of selectivity against the different paralogs PI3K α, β, γ and δ.

Suitably, the compounds of examples 1-49 and 51-95 show a certain level of selectivity for the isoform PI3Kδ, e.g. as indicated in in vitro and in vivo tests against the different paralogs PI3K α and β.

Some of the compounds of examples 1'-117' show a certain level of selectivity against the different paralogs PI3K α, β, γ and δ.

Suitably, the compounds of examples 1'-117' show a certain level of selectivity for the isoform PI3Kδ e.g as indicated in in vitro and in vivo tests with selectivity of at least 10-fold, and more preferably at least 30-fold against the different paralogs PI3K α and β.

The range of activity, expressed as $IC_{50}$, in these assays, is preferably between 1 nM and 5000 nM, more preferably between 1 nM and about 1000 nM.

2. Cellular Assays
2.1 Determination of PI3K Alpha, PI3K Beta and PI3K Delta Inhibition in Rat1 Cells The efficacy of the compounds in blocking the activation of the PI3K/Akt pathway was demonstrated in cellular settings using a homogeneous sandwich phospho-ELISA based on the ALPHA technology of Perkin Elmer for a sensitive quantification of compound of mediated inhibition of Akt Ser473 phosphorylation in Rat1 cells stably transfected with activated versions of PI3-kinase isoforms alpha, beta or delta:

2.1.1 Cells and Cell Culture Conditions

Rat1 cell lines stably expressing a myr-HA-tagged, constitutively active subunit of the human catalytic PI3K class I p110 isoform α, β or δ (addition of a myristylation signal at the N-terminus of p110 isoforms has been shown to lead to constitutive activation of PI3K and corresponding downstream signals, such as phosphorylation of Akt at Ser473) were cultivated in Dulbecco's modified Eagle's medium (DMEM high Glucose, GIBCO, cat. No. 41956-039) supplemented with 10% heat inactivated fetal bovine calf serum (Amimed, cat. No. 2-01F16-I), 1% L-Glutamine (Invitrogen, cat. No. 25030-02), 1% penicillin-streptomycin (GIBCO, cat. No. 15140-114) and 10 µg/ml Puromycin (Sigma, cat. No. P9620).

2.1.2 Compound Treatment of Cells and Preparation of Samples

The Rat1-myr-HA-p110 alpha, beta and delta cells were trypsinized and counted with a CASY TT cell counter (Schärfe System GmbH, Reutlingen Germany). Rat cell expressing the the catalytic subunit of human phosphoinositide-3 kinase (PI3K) myr-HA-p 10 alpha, beta and delta were seeded in 384-well plates at a density of 7500 (PI3K alpha), 6200 (PI3K beta), or 4000 (PI3K delta) cells in 40 ul complete growth medium (Dulbecco's modified Eagle's medium (DMEM high glucose) supplemented with 10% (v/v) fetal bovine serum, 1% (v/v) MEM non essential amino acids, 10 mM HEPES, 2 mM L-glutamine, 10 µg/mL puromycin and 1% (v/v) Penicillin/Streptomycin) and were incubated at 37% C/5% $CO_2$/95% humidity for 48-72 h before exposing them to test compounds.

The compounds were prepared as 10 mM stock solutions in 90% DMSO (Merck, #8.02912.2500) in 384 well plates (Greiner PP-Microplate, #781201) in 3-fold serial dilutions in 90% DMSO (Merck, #8.02912.2500) with 8 concentrations starting at 10 mM. Compounds were diluted in 384-well compound plates to obtain 8-point serial dilutions for 40 test, as well as 4 reference compounds plus 16 high controls and 16 low (inhibited) controls. Predilution plates were prepared by dispensing 250 nl of each compound solutions into 384-well polypropylen plates using a Hummingwell nanoliter dispensor. Compounds were then further diluted by the addition of 49.75 ul complete growth medium. 10 ul of prediluted compound solution were transferred to the cell plate using a 384-well pipettor, resulting in a final volume of 50 ul and a DMSO concentration of 0.11% including for the control cells (high and low control). The compound dilution resulted in the above specified 8 final concentrations of 10, 3.333, 1.111, 0.370, 0.123, 0.041, 0.014 and 0.005 µM 2.1.3 Phosphoinositide-3 Kinase (PI3K)-Mediated Akt ½ (S473) Phosphorylation in Rat-1 Cells For detection of p-Akt(Ser473), the SureFire® p-Akt ½ (Ser473) Assay Kit (PerkinElmer, U.S.A) was used. Untreated cells were used as low controls, cells stimulated in absence of compounds were used as high controls. After an incubation of 1 h with compounds at 37% C/5% $CO_2$/ 95% humidity, cells were lysed by addition of 20 ul of lysis buffer for AlphaScreen® SureFire® detection enriched with 0.72% BSA. Cell lysates were either used immediately of stored frozen (in sealed plates) at −20° C. until use.

Five ul of cell lysate was transferred to 384-well low volume Proxiplates for detection using a 384-well pipettor. Addition of AlphaScreen® SureFire® reagents was done according to the manufacturer's protocol. First, 5 ul of reaction buffer plus activation buffer mix containing AlphaScreen® acceptor beads was added, the plate was sealed, and incubated on a plate shaker for 2 hours at room temperature. Second, 2 ul of dilution buffer containing AlphaScreen® donor beads was added, and the plate was incubated on plate shaker as above for a further 2 hours in the dark at RT. Then light emission was measured using the EnVision Reader (Perkin Elmer). The difference between high and low controls was taken as 100% and compound effects were expressed as percent inhibition. $IC_{50}$ values were determined from the dose response curves by graphical extrapolation.

2.2 Determination of TLR9-Induced IL-6 in Murine Splenocytes 2.2.1 Preparation of Single Cell Suspension from Mouse Spleen Spleens were dissected from C57BL/6 mice immediately following euthanasia. Excess fat was trimmed from the spleens prior to mashing the spleen through a 0.4 µM cell strainer using a plunger from a 5 ml syringe. A single cell suspension was prepared and the volume was adjusted to 15 ml in a 50 ml Falcon tube using cold PBS. Cells were centrifuged at 1500 rpm for 5 minutes at 4° C. degrees prior to removal of supernatant and re-suspension in 5 ml of red blood cell lysis buffer per spleen and incubation for 5 minutes at room temperature. Ice cold PBS (30 ml) was added to the cells prior to centrifugation at 1500 rpm for 5 minutes at 4° C. The supernatant was removed and the cells were washed twice with 40 ml of murine splenocyte culture media (MSCM). MSCM consisted of RPMI supplemented with 100 units/ml Penicillin and 100 µg/ml Streptomycin, 1×nonessential amino acids, 1 mM Sodium Pyruvate, 0.05 mM β-mercaptoethanol, and 10% heatinactivated Fetal Bovine Serum (FBS). Cells were re-suspended in 10-20 ml of MSCM and counted using a Countess cell counter. Approximately $60 \times 10^6$ splenocytes were obtained from a single C57BL/6 mouse spleen.

2.2.2 Stimulation of C57BL/6 Murine Splenocytes and Treatment with Specific Inhibitor Splenocytes were plated at a final density of $2 \times 10^5$ cells/well in a volume of 100 µl in 96 well flat bottomed plates and incubated in a humidified 37° C. incubator for 2-4 hours. Afterwards, compounds to be tested were dispensed using an automated liquid handling machine using previously prepared compound stock plates. Stock plates consisted of compounds (in 90%/10% DMSO/ddH$_2$O) arrayed in 9 point using 3-fold dilutions. The liquid handling machine dispensed 1 µl of each dilution from the previously prepared compound source plate into the appropriate destination well in the 96-well plate. The final starting concentration of the compounds in the cell culture was 10 µM. The final concentration of DMSO in the cell cultures was 0.5%. Cells were incubated with compounds for 1 hour prior to addition of TLR ligand. Then, a $10 \times EC_{80}$ concentration of CpG1826 was added in a volume of 20 µl (for a final culture volume of 200 µl) whereupon cultures were incubated overnight in a humidified 37° C. incubator.

2.2.3 Determination of Interleukin-6 by ELISA

After overnight culture, cells were transferred to 96-well V-bottomed plates and centrifuged at 2000 rpm for 5 minutes at room temperature. Subsequently 150 µl of each culture supernatant was transferred to 96-well flat-bottomed plates and IL-6 levels were measured using commercially available mouse IL-6 sandwich ELISA kit (R&D systems). Briefly, plates were coated overnight with the capture antibody prior to blocking for 1 hour with PBS/0.1% BSA. Samples and standards were added in a volume of 50 µl and the plate was incubated for 2 hours at room temperature. After removal of the standards/samples, the plate was washed using PBS/0.05% Tween prior to addition of 50 µl of the biotinylated detection antibody whereupon the plate was incubated for 2 hours at room temperature with agitation. Plates were washed again using PBS/0.05% Tween prior to addition of 50 µl streptavidin-horseradish peroxidase per well for 20 minutes. Following additional plate washes 50 µl TMB substrate was added to each well and plates were incubated for 20 minutes prior addition of 25 µl/well stop solution. IL-6 levels were measured using a SpectraMax 190 Plate Reader (450 nm) and analyzed using SoftMax Pro and GraphPad Prism software.

2.3 Determination of TLR9-Induced IFN-Alpha in Murine Splenocytes 2.3.1 Preparation of Single Cell Suspension from Mouse Spleen Spleens were dissected from 129/Sv mice immediately following euthanasia. Excess fat was trimmed from the spleens prior to mashing the spleen through a 0.4 µM cell strainer using a plunger from a 5 ml syringe. A single cell suspension was prepared and the volume was adjusted to 15 ml in a 50 ml Falcon tube using cold PBS. Cells were centrifuged at 1500 rpm for 5 minutes at 4° C. degrees prior to removal of supernatant and re-suspension in 5 ml of red blood cell lysis buffer per spleen and incubation for 5 minutes at room temperature. Ice cold PBS (30 ml) was added to the cells prior to centrifugation at 1500 rpm for 5 minutes at 4° C. The supernatant was removed and the cells were washed twice with 40 ml of murine splenocyte culture media (MSCM). MSCM consisted of RPMI supplemented with 100 units/ml Penicillin and 100 µg/ml Streptomycin, 1×nonessential amino acids, 1 mM Sodium Pyruvate, 0.05 mM β-mercaptoethanol, and 10% heatinactivated Fetal Bovine Serum (FBS). Cells were re-suspended in 10-20 ml of MSCM and counted using a Countess cell counter. Approximately $60 \times 10^6$ splenocytes were obtained from a single C57BL/6 mouse spleen.

2.3.2 Stimulation of 129/Sv Murine Splenocytes and Treatment with Specific Inhibitor Splenocytes were plated at a final density of $2 \times 10^5$ cells/well in a volume of 100 µl in 96 well flat bottomed plates and incubated in a humidified 37° C. incubator for 2-4 hours. Afterwards, compounds to be tested were dispensed using an automated liquid handling machine using previously prepared compound stock plates. Stock plates consisted of compounds (in 90%/10% DMSO/ddH$_2$O) arrayed in 9 point using 3-fold dilutions. The liquid handling machine dispensed 1 µl of each dilution from the previously prepared compound source plate into the appropriate destination well in the 96-well plate. The final starting concentration of the compounds in the cell culture was 10 µM. The final concentration of DMSO in the cell cultures was 0.5%. Cells were incubated with compounds for 1 hour prior to addition of TLR ligand. Then, a $10 \times EC_{80}$ concentration of CpG1585 was added in a volume of 20 µl (for a final culture volume of 200 µl) whereupon cultures were incubated overnight in a humidified 37° C. incubator.

2.3.3 Determination of IFN-Alpha by ELISA

After overnight culture, cells were transferred to 96-well V-bottomed plates and centrifuged at 2000 rpm for 5 minutes at room temperature. Subsequently 150 µl of each culture supernatant was transferred to 96-well flat-bottomed plates and IL-6 levels were measured using commercially available mouse IFN-alpha sandwich ELISA kit (PBL Interferon Source). Briefly, pre-coated plates were incubated 1 hour with 100 µl standards/samples and 50 µl detection antibody solution under gently shaking, prior 24 hours incubation at 4 degrees without shaking. The plates were then washed using PBS/0.05% Tween prior to addition of 100 µl streptavidin-horseradish peroxidase per well for 2 hours at room temperature with gently shaking. Following a new washing step, 100 µl TMB substrate was added to each well and plates were incubated for 15 minutes (in the dark and without shaking), prior addition of 100 µl/well stop solution. IFN-alpha levels were measured within 5 minutes using a SpectraMax 190 Plate Reader (450 nm) and analyzed using SoftMax Pro and GraphPad Prism software.

2.4 Determination of TLR9-Induced IFNalpha in Human Peripheral Blood Mononuclear Cells (PBMCs) and Isolated Plasmacytoid Dendritic Cells (pDCs)

2.4.1 Preparation of PBMC from Fresh Human Blood

Human blood (ca. 75 ml) was collected in 10 S-Monovette tubes containing Heparin (S-Monovette 7.5 mL NH Heparin 16 IU/mL blood; Starstedt). Leucosep™ tubes (30 mL #227290; Greiner Bio-one) were prepared by addition of 15 ml lymphocyte separation medium LSM1077™ per tube (#J15-004; PAA Laboratories) and centrifugation for 30 sec at 1000 g. Some 25 ml blood was transferred to Leucosep™ tubes following dilution with equal parts of PBS (without Ca2+/Mg2+; #14190-094). Samples were centrifuged at 800 g for 20 min at 22° C. using an Eppendorf 5810R centrifuge without brake. The PBMC layer was carefully removed from plasma:separation medium interface and transferred into clean 50 ml tube. Cells were washed once by addition of PBS (up to 45 ml) and centrifugated (1400 rpm, 10 min at 22° C.) with brake (set at speed 9) using an Eppendorf 5810R. Pelleted cells were carefully resuspended in Media (RPMI 1640+GlutaMAX-I, 0.05 mM 2-mercaptoethanol, 10 mM HEPES and 5% v/v FCS) and samples pooled. The medium components 2-mercaptoethanol (#31350-010; 50 mM), Hepes (#15630-056, 1M) and RPMI 1640 (1×)+GlutaMAX-I (#61870-010) were obtained from Gibco. FCS (#2-01F36-1) was obtained from Amimed. The PBMC were counted using a Countess® Automated cell counter (sample was pre-diluted 1:10 in Media, prior to the addition of equal volume (10 μl) of Trypan Blue). Cells were diluted to $4\times10^6$ cells/ml and seeded in 384-well plates (#353962; Becton Dickinson AG) to give a final volume of 25 μl (i.e. $1\times10^5$ cells/well).

2.4.2 Isolation of Fresh Human pDCs from Buffy Coats/PBMCs

Human PBMCs were prepared using Buffy Coats as source material from healthy donations (approx. 50 ml obtained from Blutspendezentrum SRK Basel) and processed as indicated above. Fresh PBMCs were resuspended and diluted in RoboSep™ buffer (PBS containing 2% v/v FBS, 1 mM EDTA (Gibco #15575-038) to obtain a final concentration of $50\times10^6$ PBMCs/ml. Human pDCs (negative selection) were isolated using plasmacytoid DC Enrichment kit (Stemcell, #19062) using an automation RobSep™ station as described according to manufacturer protocols. Typical pDC yields were approx. 0.1% of total PBMCs and with a purity>90%. Isolated pDCs were diluted to $4\times10^5$ cells/ml and seeded in 384-well plates (#353962; Becton Dickinson AG) to give a final volume of 25 μl (i.e. $1\times10^4$ cells/well). For stimulation using malaria nuclear extact (see below), pDCs were seeded at a final concentration of $5\times10^4$ cells/well.

2.4.3 Preparation of *Plasmodium falciparum* Nuclear Extract

The preparation of the nuclear extract of *plasmodium falciparum* was performed according to Gowda et al [Gowda et al. "The Nucleosome (Histone-DNA Complex) Is the TLR9-Specific Immunostimulatory Component of *Plasmodium falciparum* That Activates DCs", PLoS ONE 2011]. In brief, *Plasmodium falciparum* 3D7 parasites were cultured in human red blood cell at 2% hematocrit. When the parasite was at late trophozoite and schizont stages, the infected red blood cells (IRBCs) were harvested by centrifugation and the pellets were re-suspended in 20 volumes of 0.1% saponin (m/v) in PBS, pH 7.2. The re-suspension was incubated on ice for 10 minutes and centrifuged at 2,500 g at 4° C. for 15 min. The pellet was re-suspended in the above solution, incubated on ice for 10 min and centrifuged at 2,500 g at 4° C. for 15 min. The parasite pellet thus obtained was washed 3 times with cold PBS, pH 7.2, by centrifugation. Each time 35 ml of cold PBS was used. The pellet obtained after the last centrifugation was suspended in 10 volumes of lysis buffer (20 mM HEPES, pH 7.5, 10 mM KCl, 1 mM EDTA, 1 mM dithiothreitol, 1 mM phenylmethylsulfonyl fluoride (PMSF) and 1% Triton X-100) and incubated on ice for 5 min. The suspension was centrifuged at 5,000 g at 4° C. for 10 min, and nuclear material was washed three times with the lysis buffer to remove membrane components. The nuclear material was re-suspended in PBS, pH 7.2. Insoluble material was subsequently solubilized by using a water-bath sonicator.

2.4.4 Stimulation of PBMC or pDCs and Treatment with Specific Inhibitor

Compounds were pre-diluted in 100% v/v DMSO (#41640-100 mL; Sigma-Aldrich), followed by transfer in Media (to achieve a final DMSO concentration of 0.25%). Cells were treated with appropriate compound dilution (5 μl) or vehicle control (5 μl) and incubated for 30 min at 37° C. in a humidified incubator in air with 5% (v/v) $CO_2$. Cells were stimulated with CpG2216 (0.3 μM; #tlrl-hodna; Invivogen), malaria nuclear extract (2.5 μg/ml; see above for preparation) or vehicle control (10 μl/well) and incubated for 20 h. Plates were briefly centrifuged (200×g for 2 min at 22° C.) and supernatant samples (30 μl) removed for quantification of IFNα levels.

2.4.5 Quantification of IFNα Using AlphaLisa Technology

For quantification of IFNalpha the human interferon AlphaLISA Kit (#AL264F) from PerkinElmer was used. An antibody mix containing anti-IFNα acceptor beads (5 μg/ml final) and biotinylated antibody anti-IFNα(0.5 nM final) is prepared fresh and dispensed (5 μl) into 384-well Optiplates™ (#6007299; PerkinElmer). Dilution of known IFNα standards (human IFNα B (2b)) were prepared and together with cell supernatants (5 μl) were added to plates above. Plates were briefly centrifuged (pulse at 200 g), covered with adhesive sealing film, vortexed and incubated 1 h at room temperature in the dark. Streptavidin-coated donor beads (20 μg/ml final) was prepared and added to each well (5 μl) in a dark lit area (light sensitive mix). Plates were incubated 30 min at room temperature (Plates must not be centrifuged or covered). After incubation, the plates were read with an EnVision™ multiplate reader equipped with the ALPHA option using the instrument's own "AlphaScreen standard settings" (e.g. total measurement time: 550 ms, Laser 680 nm excitation time: 180 ms, mirror: D640 as, emission filter: M570w, center wavelength 570 nm, bandwidth 100 nm, transmittance 75%). Data were collected for analysis and quantification of IFNα levels.

2.4.6 Data Evaluation and Analysis

Data were analysed using Excel XL fit 4.0 (Microsoft) with XLfit add-in (IDBS; version 4.3.2). Specific IFNα concentrations were determined following extrapolation to standard curves using human IFNα B (2b). Individual $IC_{50}$ values of compounds were determined by nonlinear regression after fitting of curves to the experimental data.

Biological Data

| Enzymatic Assay | | |
|---|---|---|
| Example | PI3K alpha (uM) | PI3K delta (uM) |
| 1 | 2.0378 | 0.015 |
| 2 | 3.391 | 0.009 |
| 3 | 2.386 | 0.015 |
| 4 | 1.764 | 0.033 |

| Enzymatic Assay | | | Enzymatic Assay | | |
|---|---|---|---|---|---|
| Example | PI3K alpha (uM) | PI3K delta (uM) | Example | PI3K alpha (uM) | PI3K delta (uM) |
| 5 | 0.749 | 0.020 | 81 | 0.651 | 0.02 |
| 6 | 0.987 | 0.044 | 82 | 0.066 | 0.003 |
| 7 | 1.973 | 0.013 | 83 | 0.432 | 0.017 |
| 8 | 2.494 | 0.027 | 84 | 0.058 | 0.009 |
| 9 | 2.906 | 0.009 | 85 | 0.569 | 0.021 |
| 10 | 0.668 | 0.009 | 86 | 1.330 | 0.020 |
| 11 | 1.199 | 0.011 | 87 | 0.452 | 0.012 |
| 12 | 0.952 | 0.012 | 88 | 1.336 | 0.034 |
| 13 | 1.802 | 0.013 | 89 | 1.189 | 0.029 |
| 14 | 1.832 | 0.013 | 90 | 1.991 | 0.038 |
| 15 | 1.631 | 0.014 | 91 | 0.924 | 0.011 |
| 16 | 1.684 | 0.016 | 92 | 2.545 | 0.009 |
| 17 | 7.678 | 0.017 | 93 | 0.872 | 0.024 |
| 18 | 0.871 | 0.033 | 94 | 1.714 | 0.021 |
| 19 | 3.056 | 0.033 | 95 | 0.757 | 0.053 |
| 20 | 1.839 | 0.048 | 1' | 0.294 | 0.0072 |
| 21 | 0.320 | 0.008 | 2' | 0.779 | 0.0095 |
| 22 | 0.580 | 0.008 | 3' | 0.062 | <0.003 |
| 23 | 0.129 | 0.010 | 4' | 1.1585 | 0.009 |
| 24 | 0.374 | 0.009 | 5' | 1.3215 | 0.0085 |
| 25 | 0.820 | 0.026 | 6' | 0.589 | 0.008625 |
| 26 | 0.368 | 0.021 | 7' | 0.712 | 0.006 |
| 27 | 3.410 | 0.040 | 8' | 0.268 | 0.0095 |
| 28 | 1.214 | 0.004 | 9' | 1.398 | 0.01004 |
| 29 | 2.585 | 0.011 | 10' | >9.1 | 0.027 |
| 30 | 2.831 | 0.040 | 11' | 1.0735 | 0.028 |
| 31 | 3.024 | 0.021 | 12' | 0.4175 | 0.02025 |
| 32 | 2.036 | 0.023 | 13' | 1.328 | 0.034 |
| 33 | 1.967 | 0.018 | 14' | 0.0785 | <0.003 |
| 34 | 1.648 | 0.014 | 15' | 1.2315 | 0.017 |
| 35 | 4.232 | 0.049 | 16' | 0.695 | 0.0125 |
| 36 | 4.103 | 0.025 | 17' | 0.3525 | 0.006375 |
| 37 | 7.021 | 0.031 | 18' | 1.2855 | 0.0421429 |
| 38 | 3.306 | 0.016 | 19' | 0.678 | 0.0115 |
| 39 | 0.434 | 0.009 | 20' | 2.483 | 0.024 |
| 40 | 0.260 | 0.006 | 21' | 2.2676667 | 0.0145 |
| 41 | 0.515 | 0.014 | 22' | 0.7895 | 0.0115 |
| 42 | 0.863 | 0.013 | 23' | 0.931 | 0.0125 |
| 43 | 0.728 | 0.016 | 24' | 0.4 | 0.015 |
| 44 | 1.189 | 0.016 | 25' | 0.1835 | 0.007 |
| 45 | 0.860 | 0.018 | 26' | 0.6136 | 0.01775 |
| 46 | 0.803 | 0.027 | 27' | 0.4035 | 0.0185 |
| 47 | 0.656 | 0.025 | 28' | 0.418 | 0.009 |
| 48 | 0.518 | 0.029 | 29' | 0.075 | 0.003 |
| 49 | 0.388 | 0.034 | 30' | 0.3866667 | 0.0066667 |
| 51 | 0.912 | 0.044 | 31' | 0.631 | 0.006 |
| 52 | 1.024 | 0.046 | 32' | 0.174 | 0.007 |
| 53 | 0.504 | 0.006 | 33' | 0.639 | 0.012 |
| 54 | 0.384 | 0.005 | 34' | 0.488 | 0.0225 |
| 55 | 0.661 | 0.005 | 35' | 0.262 | 0.007 |
| 56 | 0.860 | 0.013 | 36' | 0.21725 | 0.0045 |
| 57 | 0.590 | 0.025 | 37' | 0.426 | 0.004 |
| 58 | 3.060 | 0.030 | 38' | 0.3725 | 0.007 |
| 59 | 9.100 | 0.028 | 39' | 0.77 | 0.0115 |
| 60 | 3.333 | 0.045 | 40' | 0.2695 | 0.003 |
| 61 | 0.589 | 0.012 | 41' | 0.7075 | 0.0205 |
| 62 | 0.489 | 0.023 | 42' | 0.152 | 0.006 |
| 63 | 0.791 | 0.051 | 43' | 0.3745 | 0.011 |
| 64 | 2.331 | 0.032 | 44' | 0.2825 | <0.003 |
| 65 | 0.738 | 0.023 | 45' | 1.1975 | 0.0365 |
| 66 | 1.280 | 0.014 | 46' | 5.295 | 0.0235 |
| 67 | 0.262 | 0.023 | 47' | >9.1 | 0.027 |
| 68 | 0.043 | 0.007 | 48' | 3.7995 | 0.0475 |
| 69 | 0.056 | 0.003 | 49' | 8.9455 | 0.0355 |
| 70 | 0.121 | 0.006 | 50' | 0.319 | 0.0105 |
| 71 | 0.057 | 0.003 | 51' | 0.1175 | 0.0035 |
| 72 | 0.093 | 0.004 | 52' | 0.189 | 0.0075 |
| 73 | 0.054 | 0.004 | 53' | 0.472 | 0.007 |
| 74 | 0.113 | 0.004 | 54' | 0.069 | 0.003 |
| 75 | 0.118 | 0.004 | 55' | 0.19275 | 0.00925 |
| 76 | 0.106 | 0.007 | 56' | 0.5425 | 0.011 |
| 77 | 1.290 | 0.044 | 57' | 0.4615 | 0.02175 |
| 78 | 0.384 | 0.012 | 58' | 0.6455 | 0.0055 |
| 79 | 0.781 | 0.017 | 59' | 1.7095 | 0.0315 |
| 80 | 0.430 | 0.016 | 60' | 0.657 | 0.0195 |

| Enzymatic Assay | | |
|---|---|---|
| Example | PI3K alpha (uM) | PI3K delta (uM) |
| 61' | 0.39 | 0.003 |
| 62' | 1.151 | 0.007 |
| 63' | 0.505 | 0.006 |
| 64' | 0.583 | 0.011 |
| 65' | 0.64 | 0.01 |
| 66' | 0.763 | 0.0095 |
| 67' | 0.306 | 0.007 |
| 68' | 0.097 | 0.003 |
| 69' | 0.88 | 0.008 |
| 70' | 1.026 | 0.03 |
| 71' | 0.5505 | 0.008 |
| 72' | 0.0695 | 0.003 |
| 73' | 0.0605 | <0.003 |
| 74' | 0.1496667 | 0.005 |
| 75' | 0.3195 | 0.012 |
| 76' | 0.5775 | 0.0235 |
| 77' | 0.573 | 0.014 |
| 78' | 0.123 | 0.0045 |
| 79' | 0.3595 | 0.01 |
| 80' | 0.717 | 0.0105 |
| 81' | 0.401 | 0.003625 |
| 82' | 1.334 | 0.0215 |
| 83' | 0.904 | 0.021 |
| 84' | 0.5585 | 0.0095 |
| 85' | 0.793 | 0.007 |
| 86' | 0.3805 | 0.0155 |
| 87' | 0.126 | <0.003 |
| 88' | 0.1 | 0.002675 |
| 89' | 0.099 | 0.004 |
| 90' | 0.181 | 0.00575 |
| 91' | 0.1465 | <0.003 |
| 92' | 0.1955 | 0.00375 |
| 93' | 0.12 | <0.003 |
| 94' | 0.174 | 0.006 |
| 95' | 0.281 | 0.009 |
| 96' | 0.316 | 0.006 |
| 97' | 0.463 | 0.023 |
| 98' | 0.1015 | 0.0035 |
| 99' | 0.237 | 0.0045 |
| 100' | 0.188 | 0.005 |
| 101' | 1.271 | 0.016 |
| 102' | 0.77 | 0.011 |
| 103' | 2.121 | 0.008 |
| 104' | 3.293 | 0.038 |
| 105' | 0.72 | 0.007 |
| 106' | 0.44 | 0.005 |
| 107' | 0.716 | 0.005 |
| 108' | 0.158 | 0.007 |
| 109' | 0.435 | 0.014 |
| 110' | 0.366 | 0.008 |
| 111' | 1.357 | 0.01 |
| 112' | 2.316 | 0.049 |
| 113' | 0.979 | 0.018 |
| 114' | 0.071 | 0.003 |
| 115' | 0.888 | 0.0425 |
| 116' | 0.306 | 0.014 |
| 117' | 0.238 | 0.009 |

Cellular Assays
PI3K delta inhibition in Rat1-myr-HA-p110 delta cells

| Example | Cell PI3Kδ/ IC$_{50}$ [umol l−1] |
|---|---|
| 1 | 0.153 |
| 5 | 0.455 |
| 20 | 0.254 |
| 28 | 0.268 |
| 65 | 0.191 |
| 67 | 0.047 |
| 68 | 0.053 |
| 71 | 0.035 |
| 81 | 0.246 |
| 82 | 0.116 |

| Example | Cell PI3Kd/ IC$_{50}$ [umol l−1] |
|---|---|
| 1' | 0.02735 |
| 2' | 0.0275 |
| 7' | 0.083 |
| 12' | 0.0535 |
| 44' | 0.037 |
| 75' | 0.014 |
| 81' | 0.0195 |
| 91' | 0.0323333 |
| 110' | 0.103 |
| 117' | 0.043 |

Inhibition of TLR9-induced cytokine production in murine splenocytes

| Example | TLR9-ligand induced IL-6 in murine splenocytes IC$_{50}$ [microM] | TLR9-ligand induced IFNα in murine splenocytes IC$_{50}$ [microM] |
|---|---|---|
| 1 | 0.327 (n = 2) | nd |
| 67 | 0.096 (n = 2) | >2.220 (n = 2) |

Inhibition of TLR9-induced cytokine production in human PBMC and pDCs

| Example | TLR9-ligand induced IFNα in human PBMC IC$_{50}$ [umol l−1] | TLR9-ligand induced IFNα in human pDCs IC$_{50}$ [umol l−1] |
|---|---|---|
| 1 | 0.211 (n = 3) | 0.050 (n = 4) |
| 67 | 0.109 (n = 3) | 0.033 (n = 4) |

Inhibition of P. falciparum nuclear extract-induced cytokine production in human pDCs

| Example | Condition (isolated human pDCs) | IFNα level [pg/ml] | % inh. of IFNα by nuclear extract |
|---|---|---|---|
| | vehicle control | 336 | |
| | nuclear extract only | 5301 | |
| 67 | 1 μM | 1483 | 77 |
| 67 | 0.1 μM | 2110 | 64 |
| 67 | 0.01 μM | 4084 | 25 |

The invention claimed is:

1. A method of treating a host-mediated immunopathology caused by acute or cerebral malaria in a subject suffering from acute or cerebral malaria, the method comprising the step of administering to the subject a PI3K inhibitor, wherein said PI3K inhibitor has an inhibitory action on the host PI3K isoform delta, wherein inhibition of host PI3K isoform delta causes a reduction of the host immune response to the acute or cerebral malaria, and wherein the PI3K inhibitor is a compound of formula (I) or a tautomer and/or N-oxide and/or pharmaceutically acceptable salt or solvate thereof:

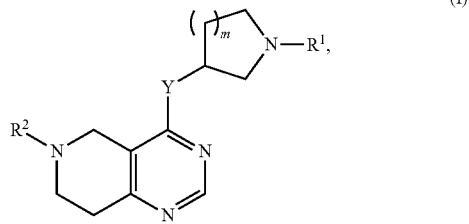

wherein
Y is selected from O and $NR^3$;
$R^1$ is —C(O)—$R^4$;
$R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, $C_1$-$C_8$-alkyl-sulfonyl-$C_1$-$C_8$-alkyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino, and N,N-di-$C_1$-$C_8$-alkyl-amino,
wherein '$C_1$-$C_8$-alkyl' in N—$C_1$-$C_8$-alkyl-amino and N,N-di-$C_1$-$C_8$-alkyl-amino may be unsubstituted or substituted by halogen, hydroxyl, or $C_1$-$C_4$-alkoxy;
wherein '$C_3$-$C_{12}$-cycloalkyl' in $C_3$-$C_{12}$-cycloalkyl and $C_3$-$C_{12}$-cycloalkyl-$C_1$-$C_8$-alkyl may be unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl, and $C_1$-$C_8$-alkoxy-$C_1$-$C_8$-alkyl-carbonyl;
wherein 'heterocyclyl' is selected from oxiranyl, aziridinyl, oxetanyl, thiethanyl, acetitinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl, thiomorpholinyl, piperazinyl, azepanyl, thiepanyl, and oxepanyl; each of which is unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl, and $C_1$-$C_8$-alkoxy-$C_1$-$C_8$-alkyl-carbonyl;
wherein 'heterocyclyl' can be attached at a heteroatom or a carbon atom and wherein the N and/or S heteroatoms can also optionally be oxidized to various oxidation states; and
wherein 'heteroaryl' is selected from furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl, 1,3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl, and 1,3,5-triazinyl; each of which is unsubstituted or substituted by 1-5 substituents independently selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl, and $C_1$-$C_8$-alkoxy-$C_1$-$C_8$-alkyl-carbonyl; wherein 'heteroaryl' can be attached at a heteroatom or a carbon atom and wherein the N and/or S heteroatoms can also optionally be oxidized to various oxidation states;

$R^2$ is selected from phenyl, naphthyl, pyridyl, pyrimidinyl, pyrazinyl, pyridazinyl, quinoliny, and isoquinolinyl, each of which is unsubstituted or substituted by 1-5 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl, and $C_1$-$C_8$-alkoxy-$C_1$-$C_8$-alkyl-carbonyl;

$R^3$ is selected from H, $C_1$-$C_4$-alkyl, and halo-$C_1$-$C_4$-alkyl; and m is selected from 0 and 1.

2. The method of claim 1, wherein the PI3K inhibitor is a compound of formula (Id')

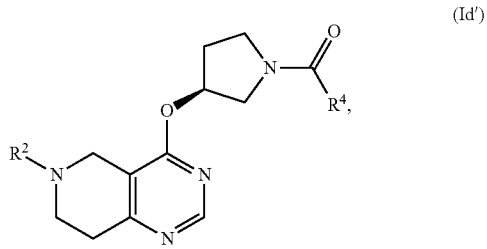

(Id')

and/or tautomers and/or N-oxides and/or pharmaceutically acceptable salts thereof.

3. The method of claim 1, wherein the PI3K inhibitor is a compound of formula (Ie')

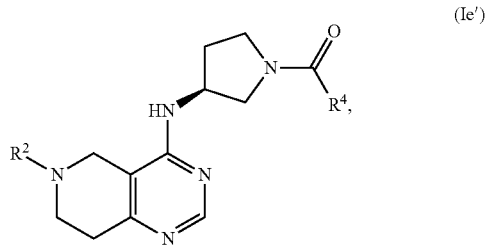

(Ie')

and/or tautomers and/or N-oxides and/or pharmaceutically acceptable salts thereof.

4. The method of claim 1, wherein the PI3K inhibitor is a compound in which $R^2$ is selected from naphthyl, pyridyl, and pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl, and $C_1$-$C_8$-alkoxy-$C_1$-$C_8$-alkyl-carbonyl.

5. The method of claim 1, wherein the PI3K inhibitor is a compound in which $R^1$ is —C(O)—$R^4$, and $R^4$ is selected from heterocyclyl, $C_4$-$C_8$-cycloalkyl or heteroaryl;

wherein '$C_3$-$C_{12}$-cycloalkyl' may be unsubstituted or substituted by 1-3 substituents independently selected from fluoro, $C_1$-$C_4$-alkyl, hydroxyl, and $C_1$-$C_4$-alkoxy;

wherein 'heterocyclyl' is selected from pyrrolidinyl, tetrahydropyranyl, piperidinyl, tetrahydrothiopyranyl, morpholinyl, and piperazinyl; each of which is unsubstituted or substituted by 1-3 substituents independently selected from oxo, halogen, $C_1$-$C_4$-alkyl, hydroxyl, and $C_1$-$C_4$-alkyl-carbonyl;

wherein 'heterocyclyl' can be attached at a heteroatom or a carbon atom and wherein the N and/or S heteroatoms can also optionally be oxidized to various oxidation states;

wherein 'heteroaryl' is selected from furanyl, imidazolyl, pyrazolyl, thiazolyl, oxazolyl, isoxazolyl, 1,3,4-oxadiazolyl, pyridyl, and pyrazinyl; each of which is unsubstituted or substituted by 1-3 substituents independently selected from $C_1$-$C_4$-alkyl, and hydroxyl; and wherein 'heteroaryl' can be attached at a heteroatom or a carbon atom and wherein the N and/or S heteroatoms can also optionally be oxidized to various oxidation states.

6. The method of claim 1, wherein the PI3K inhibitor is a compound in which $R^1$ is —C(O)—$R^4$, and $R^4$ is selected from $C_1$-$C_8$-alkyl, $C_1$-$C_8$-alkoxy-$C_1$-$C_8$-alkyl, $C_1$-$C_8$-alkoxy, and N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxyl, or $C_1$-$C_4$-alkoxy.

7. The method of claim 1, wherein the PI3K inhibitor is selected from the group consisting of {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

(S)-1-(3-(6-(6-Methoxy-5-(trifluoromethyl)pyridin-3-yl)-5,6,7,8-tetrahydropyrido[4,3-d]pyrimidin-4-ylamino) pyrrolidin-1-yl)propan-1-one; and 1-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)propan-1-one.

8. The method of claim 1, wherein the PI3K inhibitor is a pharmaceutically acceptable salt selected from citrate, fumarate, napadisylate, phosphate, hydrochloride, and hippurate.

9. The method of claim 1, wherein the subject is a human.

* * * * *

SEQUENCE LISTING

<160> NUMBER OF SEQ ID NOS: 21

<210> SEQ ID NO 1
<211> LENGTH: 28
<212> TYPE: DNA
<213> ORGANISM: Artificial
<220> FEATURE:
<223> OTHER INFORMATION: Primer

<400> SEQUENCE: 1
cgagaatatg atagattata tgaagaat                                    28

<210> SEQ ID NO 2
<211> LENGTH: 30
<212> TYPE: DNA
<213> ORGANISM: Artificial
<220> FEATURE:
<223> OTHER INFORMATION: Primer

<400> SEQUENCE: 2
tggtttaatg ctgttcatac gtttgtcaat                                  30

<210> SEQ ID NO 3
<211> LENGTH: 76
<212> TYPE: DNA
<213> ORGANISM: Artificial
<220> FEATURE:
<223> OTHER INFORMATION: Primer

<400> SEQUENCE: 3
gggacaagtt tgtacaaaaa agcaggctac gaaggagata tacatatgcg agaatatgat    60
agattatatg aagaat                                                 76

<210> SEQ ID NO 4
<211> LENGTH: 66
<212> TYPE: DNA
<213> ORGANISM: Artificial
<220> FEATURE:
<223> OTHER INFORMATION: Primer

<400> SEQUENCE: 4
taccataatt ccaccaccac caccggaaat tcccctggt ttaatgctgt tcatacgttt     60
gtcaat                                                            66

<210> SEQ ID NO 5
<211> LENGTH: 26
<212> TYPE: DNA
<213> ORGANISM: Artificial
<220> FEATURE:
<223> OTHER INFORMATION: Primer

<400> SEQUENCE: 5
ctagtggaat gtttactacc aaatgg                                      26

<210> SEQ ID NO 6
<211> LENGTH: 26
<212> TYPE: DNA
<213> ORGANISM: Artificial
<220> FEATURE:
<223> OTHER INFORMATION: Primer

<400> SEQUENCE: 6
gttcaatgca tgctgtttaa ttgtgt                                      26

<210> SEQ ID NO 7
<211> LENGTH: 63
<212> TYPE: DNA
<213> ORGANISM: Artificial
<220> FEATURE:
<223> OTHER INFORMATION: Primer

<400> SEQUENCE: 7
gggggaattt ccgtggtgg tggtggaatt atggtactag tggaatgttt actaccaaat    60
gga                                                                63

<210> SEQ ID NO 8
<211> LENGTH: 56
<212> TYPE: DNA
<213> ORGANISM: Artificial
<220> FEATURE:
<223> OTHER INFORMATION: Primer

<400> SEQUENCE: 8
agctccgtga tggtgatggt gatgtgctcc gttcaatgca tgctgtttaa ttgtgt       56

<210> SEQ ID NO 9
<211> LENGTH: 61
<212> TYPE: DNA
<213> ORGANISM: Artificial
<220> FEATURE:
<223> OTHER INFORMATION: Primer

<400> SEQUENCE: 9
gggaccactt tgtacaagaa agctgggttt aagctccgtg atggtgatgg tgatgtgctc    60
c                                                                  61

<210> SEQ ID NO 10
<211> LENGTH: 42
<212> TYPE: DNA
<213> ORGANISM: Artificial
<220> FEATURE:
<223> OTHER INFORMATION: Primer

<400> SEQUENCE: 10
gctagcatgc gagaatatga tagattatat gaagaatata cc                     42

<210> SEQ ID NO 11
<211> LENGTH: 45
<212> TYPE: DNA
<213> ORGANISM: Artificial
<220> FEATURE:
<223> OTHER INFORMATION: Primer

<400> SEQUENCE: 11
gcctccacca cctccgcctg gtttaatgct gttcatacgt ttgtc                  45

<210> SEQ ID NO 12
<211> LENGTH: 42
<212> TYPE: DNA
<213> ORGANISM: Artificial
<220> FEATURE:
<223> OTHER INFORMATION: Primer

<400> SEQUENCE: 12
tactagtccg cctccaccac ctccgcctcc accacctccg cc                     42

<210> SEQ ID NO 13
<211> LENGTH: 54
<212> TYPE: DNA

```
<213> ORGANISM: Artificial
<220> FEATURE:
<223> OTHER INFORMATION: Primer

<400> SEQUENCE: 13
actgaagcat cctcctcctc ctcctcctgg tttaatgctg ttcatacgtt tgtc          54

<210> SEQ ID NO 14
<211> LENGTH: 57
<212> TYPE: DNA
<213> ORGANISM: Artificial
<220> FEATURE:
<223> OTHER INFORMATION: Primer

<400> SEQUENCE: 14
agctccgtga tggtgatggt gatgtgctcc agatctgtag tctttccgaa ctgtgtg       57

<210> SEQ ID NO 15
<211> LENGTH: 61
<212> TYPE: DNA
<213> ORGANISM: Artificial
<220> FEATURE:
<223> OTHER INFORMATION: Primer

<400> SEQUENCE: 15
gggaccactt tgtacaagaa agctgggttt aagctccgtg atggtgatgg tgatgtgctc    60
c                                                                    61

<210> SEQ ID NO 16
<211> LENGTH: 45
<212> TYPE: DNA
<213> ORGANISM: Artificial
<220> FEATURE:
<223> OTHER INFORMATION: Primer

<400> SEQUENCE: 16
tcctcctcct cctcctcctg gtttaatgct gttcatacgt ttgtc                    45

<210> SEQ ID NO 17
<211> LENGTH: 26
<212> TYPE: DNA
<213> ORGANISM: Artificial
<220> FEATURE:
<223> OTHER INFORMATION: Primer

<400> SEQUENCE: 17
atgccccctg gggtggactg ccccat                                         26

<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
ctactgcctg ttgtctttgg acacgt                                         26

<210> SEQ ID NO 19
<211> LENGTH: 53
<212> TYPE: DNA
<213> ORGANISM: Artificial
<220> FEATURE:
<223> OTHER INFORMATION: Primer

<400> SEQUENCE: 19
```

```
attaaaccag gaggaggagg aggaggaccc cctggggtgg actgccccat gga            53

<210> SEQ ID NO 20
<211> LENGTH: 56
<212> TYPE: DNA
<213> ORGANISM: Artificial
<220> FEATURE:
<223> OTHER INFORMATION: Primer

<400> SEQUENCE: 20
agctccgtga tggtgatggt gatgtgctcc ctgcctgttg tctttggaca cgttgt        56

<210> SEQ ID NO 21
<211> LENGTH: 61
<212> TYPE: DNA
<213> ORGANISM: Artificial
<220> FEATURE:
<223> OTHER INFORMATION: Primer

<400> SEQUENCE: 21
gggaccactt tgtacaagaa agctgggttt aagctccgtg atggtgatgg tgatgtgctc    60
c                                                                    61
```